United States Patent
Ozsolak et al.

(10) Patent No.: US 12,318,489 B2
(45) Date of Patent: Jun. 3, 2025

(54) NANOPARTICLE FORMULATIONS FOR DELIVERY OF NUCLEIC ACID COMPLEXES

(71) Applicant: Translate Bio MA, Inc., Lexington, MA (US)

(72) Inventors: Fatih Ozsolak, Boston, MA (US); Balkrishen Bhat, Carlsbad, CA (US)

(73) Assignee: Translate Bio MA, Inc., Lexington, MA (US)

( * ) Notice: Subject to any disclaimer, the term of this patent is extended or adjusted under 35 U.S.C. 154(b) by 1260 days.

(21) Appl. No.: 15/771,321

(22) PCT Filed: Oct. 26, 2016

(86) PCT No.: PCT/US2016/058842
§ 371 (c)(1),
(2) Date: Apr. 26, 2018

(87) PCT Pub. No.: WO2017/075038
PCT Pub. Date: May 4, 2017

(65) Prior Publication Data
US 2018/0311176 A1     Nov. 1, 2018

Related U.S. Application Data

(60) Provisional application No. 62/288,154, filed on Jan. 28, 2016, provisional application No. 62/288,128, (Continued)

(51) Int. Cl.
*A61K 9/51*     (2006.01)
*A61K 9/00*     (2006.01)
(Continued)

(52) U.S. Cl.
CPC .......... *A61K 9/5153* (2013.01); *A61K 9/0014* (2013.01); *A61K 9/0019* (2013.01);
(Continued)

(58) Field of Classification Search
CPC .................................. A61K 9/51; A61K 48/00
See application file for complete search history.

(56) References Cited

U.S. PATENT DOCUMENTS 5,534,499 A    7/1996   Ansell
5,580,859 A    12/1996  Felgner et al.
(Continued)

FOREIGN PATENT DOCUMENTS

EP    3315125 A1      5/2018
JP    2008-044958 A   2/2008
(Continued)

OTHER PUBLICATIONS

Yeom et al. Inhibition of xenograft tumor growth by gold nanoparticle-DNA oligonucleotide conjugates-assisted delivery of BAX mRNA. PLoS ONE 2013, 8;9:e75369. (Year: 2013).*

(Continued)

*Primary Examiner* — Allison M Fox
*Assistant Examiner* — Jennifer S Spence

(57) ABSTRACT

Aspects of the disclosure relate to particle formulations, e.g., nanoparticle formulations, methods of making particle formulations, and methods for delivery of oligonucleotides and/or synthetic RNA, e.g., for increasing gene expression in a targeted manner. In some embodiments, compositions and methods are provided that are useful for posttranscriptionally altering protein and/or RNA levels in a targeted manner. Aspects of the disclosure described herein provide compositions and methods that are useful for protecting RNAs from degradation (e.g., exonuclease mediated degradation).

18 Claims, 4 Drawing Sheets

Specification includes a Sequence Listing.

Oligo Design to 3' RNA ends

Related U.S. Application Data filed on Jan. 28, 2016, provisional application No. 62/246,290, filed on Oct. 26, 2015, provisional application No. 62/246,305, filed on Oct. 26, 2015.

(51) Int. Cl.

| | | |
|---|---|---|
| A61K 9/127 | (2025.01) | |
| A61K 9/16 | (2006.01) | |
| A61K 9/19 | (2006.01) | |
| A61K 47/10 | (2017.01) | |
| A61K 47/14 | (2017.01) | |
| A61L 24/04 | (2006.01) | |
| B82Y 5/00 | (2011.01) | |
| C07K 14/705 | (2006.01) | |
| C07K 14/775 | (2006.01) | |
| C12N 15/11 | (2006.01) | |

(52) U.S. Cl.
CPC .......... *A61K 9/0053* (2013.01); *A61K 9/0073* (2013.01); *A61K 9/127* (2013.01); *A61K 9/1647* (2013.01); *A61K 9/19* (2013.01); *A61K 9/5123* (2013.01); *A61K 47/10* (2013.01); *A61K 47/14* (2013.01); *A61L 24/046* (2013.01); *B82Y 5/00* (2013.01); *C07K 14/705* (2013.01); *C07K 14/775* (2013.01); *C12N 15/111* (2013.01); *C12N 2310/11* (2013.01); *C12N 2310/315* (2013.01); *C12N 2310/3231* (2013.01); *C12N 2310/346* (2013.01); *C12N 2320/00* (2013.01)

(56) References Cited

U.S. PATENT DOCUMENTS

| | | | |
|---|---|---|---|
| 5,582,972 A | 12/1996 | Lima et al. | |
| 5,728,527 A | 3/1998 | Singer et al. | |
| 5,766,903 A | 6/1998 | Sarnow et al. | |
| 5,773,244 A | 6/1998 | Ares et al. | |
| 5,820,873 A | 10/1998 | Choi et al. | |
| 5,885,613 A | 3/1999 | Holland et al. | |
| 5,962,675 A | 10/1999 | Beigelman et al. | |
| 6,015,710 A | 1/2000 | Shay et al. | |
| 6,046,307 A | 4/2000 | Shay et al. | |
| 6,063,400 A | 5/2000 | Geho et al. | |
| 6,111,094 A | 8/2000 | Bennet et al. | |
| 6,146,829 A | 11/2000 | Cook et al. | |
| 6,197,944 B1 | 3/2001 | Walder et al. | |
| 6,210,892 B1 | 4/2001 | Bennett et al. | |
| 6,210,931 B1 | 4/2001 | Feldstein et al. | |
| 6,261,836 B1 | 7/2001 | Cech et al. | |
| 6,277,981 B1 | 8/2001 | Tu et al. | |
| 6,287,825 B1 | 9/2001 | Weissman et al. | |
| 6,291,637 B1 | 9/2001 | Das et al. | |
| 6,320,017 B1 | 11/2001 | Ansell | |
| 6,322,978 B1 | 11/2001 | Kahn et al. | |
| 6,503,756 B1 | 1/2003 | Freier et al. | |
| 6,586,559 B2 | 7/2003 | Ansell | |
| 6,727,355 B2 | 4/2004 | Matsuo et al. | |
| 7,399,845 B2 | 7/2008 | Seth et al. | |
| 8,092,992 B2 | 1/2012 | Kuwabara et al. | |
| 8,309,705 B2 | 11/2012 | Zamore et al. | |
| 8,846,631 B2 * | 9/2014 | Marcusson ............ A61K 48/00 514/44 A | |
| 2003/0083272 A1 | 5/2003 | Wiederholt et al. | |
| 2003/0113914 A1 | 6/2003 | Graham | |
| 2003/0125241 A1 | 7/2003 | Wissenbach et al. | |
| 2003/0125273 A1 | 7/2003 | Bennet et al. | |
| 2003/0125274 A1 | 7/2003 | Gaarde | |
| 2003/0211606 A1 | 11/2003 | Dobie | |
| 2004/0005565 A1 | 1/2004 | Bennett et al. | |
| 2004/0023378 A1 | 2/2004 | Chiang | |
| 2004/0033977 A1 | 2/2004 | Bennett et al. | |
| 2004/0110153 A1 | 6/2004 | Dong et al. | |
| 2004/0115674 A1 | 6/2004 | Knott et al. | |
| 2004/0171047 A1 | 9/2004 | Dahl et al. | |
| 2004/0209838 A1 | 10/2004 | Monia et al. | |
| 2005/0014168 A1 | 1/2005 | Erlander et al. | |
| 2005/0112631 A1 | 5/2005 | Piepenburg et al. | |
| 2005/0261216 A1 | 10/2005 | Gozzini | |
| 2005/0261217 A1 | 11/2005 | Dobie et al. | |
| 2005/0287539 A1 | 12/2005 | Labourier | |
| 2006/0205635 A1 | 9/2006 | Corey et al. | |
| 2006/0211640 A1 | 9/2006 | Kane | |
| 2006/0223098 A1 | 10/2006 | Lane et al. | |
| 2006/0269530 A1 | 11/2006 | Clawson et al. | |
| 2007/0066549 A1 | 3/2007 | Freier et al. | |
| 2007/0123484 A1 | 5/2007 | Bhat et al. | |
| 2007/0123485 A1 | 5/2007 | Honigman et al. | |
| 2008/0299662 A1 | 12/2008 | Ferrandez | |
| 2009/0092988 A1 | 4/2009 | Schwartz et al. | |
| 2009/0155910 A1 | 6/2009 | McGonigle | |
| 2009/0181916 A1 | 7/2009 | Worm | |
| 2009/0203765 A1 | 8/2009 | Bhanot et al. | |
| 2010/0184833 A1 | 7/2010 | De Kimpe et al. | |
| 2010/0249214 A1 | 9/2010 | Brown | |
| 2010/0256223 A1 | 10/2010 | Moeller et al. | |
| 2011/0184050 A1 | 7/2011 | De Kimpe et al. | |
| 2011/0190222 A1 | 8/2011 | Corey et al. | |
| 2011/0190370 A1 | 8/2011 | Ward et al. | |
| 2011/0245327 A1 | 10/2011 | Wengel et al. | |
| 2011/0269818 A1 | 11/2011 | Bennett et al. | |
| 2011/0305769 A1 | 12/2011 | Zhao et al. | |
| 2011/0306653 A1 | 12/2011 | Hirao et al. | |
| 2012/0052487 A9 | 3/2012 | Khvorova et al. | |
| 2012/0065252 A1 | 3/2012 | Schrum et al. | |
| 2012/0071418 A1 | 3/2012 | Copeland et al. | |
| 2012/0157333 A1 | 6/2012 | Kauppinen et al. | |
| 2012/0288869 A1 | 11/2012 | Schwartz et al. | |
| 2012/0295952 A1 | 11/2012 | Collard et al. | |
| 2013/0096183 A1 | 4/2013 | Collard et al. | |
| 2013/0164846 A1 | 6/2013 | Saestrom | |
| 2013/0177909 A1 | 7/2013 | Okumura et al. | |
| 2013/0184325 A9 | 7/2013 | Collard et al. | |
| 2013/0244282 A1 | 9/2013 | Schrum et al. | |
| 2013/0252281 A1 | 9/2013 | de Fougerolles et al. | |
| 2013/0280713 A1 | 10/2013 | Park et al. | |
| 2014/0128455 A1 | 5/2014 | Zain-Luqman et al. | |
| 2014/0187606 A1 | 7/2014 | Collard et al. | |
| 2014/0294929 A1 * | 10/2014 | Cunningham ........ C12N 15/113 424/450 | |
| 2014/0371293 A1 | 12/2014 | Brown et al. | |
| 2015/0005364 A1 | 1/2015 | Chae et al. | |
| 2015/0050738 A1 | 2/2015 | Ozsolak et al. | |
| 2018/0125989 A1 | 5/2018 | DeRosa et al. | |
| 2023/0062603 A1 | 3/2023 | Bhat et al. | |

FOREIGN PATENT DOCUMENTS

| | | |
|---|---|---|
| JP | 4236812 B2 | 3/2009 |
| WO | WO 92/01813 A1 | 2/1992 |
| WO | WO 94/001550 A1 | 1/1994 |
| WO | WO 97/38013 A1 | 10/1997 |
| WO | WO 99/10509 A1 | 3/1999 |
| WO | WO 2001/000821 A1 | 1/2000 |
| WO | WO 2006/108423 A2 | 10/2006 |
| WO | WO 2007/133812 A2 | 11/2007 |
| WO | WO 2009/032083 A1 | 3/2009 |
| WO | WO 2010/093860 A2 | 8/2010 |
| WO | WO 2010/115993 A1 | 10/2010 |
| WO | WO 2010/120803 A2 | 10/2010 |
| WO | WO 2010/120820 A1 | 10/2010 |
| WO | WO 2011/053994 A1 | 5/2011 |
| WO | WO 2011/057350 A1 | 5/2011 |
| WO | WO 2011/119058 A2 | 9/2011 |
| WO | WO 2011/159836 A2 | 12/2011 |
| WO | WO 2011/161460 A2 | 12/2011 |
| WO | WO 2012/050975 A1 | 4/2012 |
| WO | WO 2012/109476 A2 | 8/2012 |
| WO | WO 2012/122645 A1 | 9/2012 |
| WO | WO 2012/158736 A1 | 11/2012 |
| WO | WO 2013/039857 A1 | 3/2013 |
| WO | WO 2013/039861 A2 | 3/2013 |

(56) References Cited

FOREIGN PATENT DOCUMENTS

| | | |
|---|---|---|
| WO | WO 2013/090186 A1 | 6/2013 |
| WO | WO 2013/101690 A1 | 7/2013 |
| WO | WO 2013/106496 A1 | 7/2013 |
| WO | WO 2013/130161 A1 | 9/2013 |
| WO | WO 2013/173599 A1 | 11/2013 |
| WO | WO 2013/173605 A1 | 11/2013 |
| WO | WO 2013/173608 A1 | 11/2013 |
| WO | WO 2013/185067 A1 | 12/2013 |
| WO | WO 2015/023975 A1 | 2/2015 |
| WO | WO 2015/034925 A1 | 3/2015 |

OTHER PUBLICATIONS

Conforto et al. Impact of CUX2 on the female mouse liver transcriptome: Activation of female-biased genes and repression of male-biased genes. Molecular and Cellular Biology 2012, 32;22:4611-4627. (Year: 2012).*
Kormann et al. Expression of therapeutic proteins after delivery of chemically modified mRNA in mice. Nature Biotechnology 2011, 29;2:154-159. (Year: 2011).*
Zheng et al. Topical delivery of siRNA-based spherical nucleic acid nanoparticle conjugates for gene regulation. Proceedings of the National Academy Sciences 2012, 109;30:11975-11980. (Year: 2012).*
Mo et al. Surfactant protein expression in human skin: Evidence and implications. Journal of investigative Dermatology 2007, 127:381-386. (Year: 2007).*
Xhang et al. Antibody-linked spherical nucleic acids for cellular targeting. Journal of the American Chemical Society 2012, 134;40:16488-16491. (Year: 2012).*
Koshkin et al. LNA (locked nucleic acids): Synthesis of the adenine, cytosine, guanine, 5-methylcytosine, thymine, and uracil bicyclonucleoside monomers, oligomerization, and unprecedented nucleic acid recognition. Tetrahedron 1998, 54:3607-3630. (Year: 1998).*
Akinc et al. Targeted delivery of RNAi therapeutics with endogenous and exogenous ligand-based mechanisms. Molecular Therapy 2010, 18;7:1357-1364. (Year: 2010).*
PCT/US2016/058842, Feb. 3, 2017, International Search Report and Written Opinion.
PCT/US2016/058842, May 11, 2018, International Preliminary Report on Patentability.
[No Author Listed], Anchored Oligo(dT)20 Primer. Invitrogen Life Technologies. Rev. date: Jun. 19, 2003. 1 page.
Baker et al., 2'-O-(2-Methoxy)ethyl-modified anti-intercellular adhesion molecule 1 (ICAM-1) oligonucleotides selectively increase the ICAM-1 mRNA level and inhibit formation of the ICAM-1 translation initiation complex in human umbilical vein endothelial cells. J Biol Chem. May 2, 1997;272(18):11994-2000.
Bandiera et al., Genetic variations creating microRNA target sites in the Fxn 3'-UTR affect frataxin expression in Friedreich ataxia. PLoS One. 2013;8(1):e54791. doi:10.1371/journal.pone.0054791. Epub Jan. 30, 2013.
Carr et al., Isolation and characterization of the rat thyrotropin beta-subunit gene. Differential regulation of two transcriptional start sites by thyroid hormone. J Biol Chem. Jan. 25, 1987;262(3):981-7.
Carthew et al., Origins and Mechanisms of miRNAs and siRNAs. Cell. Feb. 20, 2009;136(4):642-55. doi: 10.1016/j.cell.2009.01.035. Review.
Chahrour et al., MeCP2, a key contributor to neurological disease, activates and represses transcription. Science. May 30, 2008;320(5880):1224-9.
Cook et al., The use of antisense oligonucleotides to establish autocrine angiotensin growth effects in human neuroblastoma and mesangial cells. Antisense Res Dev. 1992 Fall;2(3):199-210.
Crooke, Antisense drug technology. Principles, strategies, and applications. $2^{nd}$ edition. CRC Press. 2007. 120-123.
Dahl et al., Circle-to-circle amplification for precise and sensitive DNA analysis. Proc Natl Acad Sci U S A. Mar. 30, 2004;101(13):4548-53.
Daughters et al., RNA gain-of-function in spinocerebellar ataxia type 8. PLoS Genet. Aug. 2009;5(8):e1000600. doi: 10.1371/journal.pgen.1000600. Epub Aug. 14, 2009.
Davidson et al., Singles engage the RNA interference pathway. Cell. Aug. 31, 2012;150(5):873-5. doi: 10.1016/j.cell.2012.08.008.
Delgado et al., β-Catenin knockdown in liver tumor cells by a cell permeable gamma guanidine-based peptide nucleic acid. Curr Cancer Drug Targets. Oct. 2013;13(8):867-78.
Dinger et al., NRED: a database of long noncoding RNA expression. Nucleic Acids Res. Jan. 2009;37(Database issue):D122-6. doi: 10.1093/nar/gkn617. Epub Oct. 1, 2008.
Dominski et al., Identification and characterization by antisense oligonucleotides of exon and intron sequences required for splicing. Mol Cell Biol. Nov. 1994; 14(11): 7445-7454.
Doyle et al., Inhibition of gene expression inside cells by peptide nucleic acids: effect of mRNA target sequence, mismatched bases, and PNA length. Biochemistry. Jan. 9, 2001;40(1):53-64.
Dragulescu-Andrasi et al., Cell-permeable peptide nucleic acid designed to bind to the 5'-untranslated region of E-cadherin transcript induces potent and sequence-specific antisense effects. J Am Chem Soc. Dec. 20, 2006;128(50):16104-12.
Eddy, Non-coding RNA genes and the modern RNA world. Nat Rev Genet. Dec. 2001;2(12):919-29.
Efthymiou et al., Chemical architecture and applications of nucleic acid derivatives containing 1, 2, 3-triazole functionalities synthesized via click chemistry. Molecules. 2012;17(11):12665-12703.
Fratczak et al., LNA-modified primers drastically improve hybridization to target RNA and reverse transcription. Biochemistry. Jan. 27, 2009;48(3):514-6. doi: 10.1021/bi8021069.
Frith et al., A code for transcription initiation in mammalian genomes. Genome Res. Jan. 2008;18(1):1-12.
Fu et al., Mir-144 selectively regulates embryonic alpha-hemoglobin synthesis during primitive erythropoiesis. Blood. Feb. 5, 2009;113(6):1340-9.
Genbank Submission; NCBI, Accession No. AF106693. Ristow et al., Jul. 26, 2016.
Genbank Submission; NCBI, Accession No. BX572607.1; 2015.
Genbank Submission; NCBI, Accession No. LA219700. Peng et al., Jun. 7, 2014.
Genbank Submission; NCBI, Accession No. NG_009361.1; Salomons et al.; Jun. 27, 2016.
Genbank Submission; NCBI, Accession No. XM_006715245.3; Jun. 6, 2016.
Genbank Submission; NCBI, Accession No. NM_007294.3; Orban et al.; May 25, 2016.
Genbank Submission; NCBI, Accession No. NM_199461.3; Miles et al.; Jun. 4, 2016.
Genbank Submission; NCBI; Accession No. NM_01099771.2.; Sep. 1, 2016. Pieragostino et al.
Genbank Submission; NCBI; Accession No. NM_013402.4; Oct. 6, 2016. Barman et al.
Genbank Submission; NCBI; Accession No. XM_017012145.1; Jun. 6, 2016.
Genbank Submission; NCBI; Accession No. XR_001732682.1; Jun. 6, 2016.
Genbank Submission; NCBI; Accession No. XR_001759365.1.; Jun. 6, 2016.
Genbank Submission; NIH Accession No. AF024710.1 May 20, 2016.
Genbank Submission; NIH, Accession No. AF095785.1 May 29, 2002.
Genbank Submission; NIH, Accession No. J03132.1 Sep. 28, 2008.
Genbank Submission; NIH, Accession No. NM_000144.4. Pandey et al., Mar. 15, 2015. 6 pages.
Genbank Submission; NIH, Accession No. NM_000314.5. Singh et al., Mar. 15, 2015. 9 pages.
Genbank Submission; NIH, Accession No. NM_000546.2. Dec. 24, 2006.
Genbank Submission; NIH, Accession No. NM_001161706. Pandey et al., Mar. 15, 2015.
Genbank Submission; NIH, Accession No. NM_002155.4. Khalouei et al., Dec. 11, 2014. 3 pages.

(56) References Cited

OTHER PUBLICATIONS

Genbank Submission; NIH, Accession No. NM_021020.1 Sep. 28, 2008.
Genbank Submission; NIH, Accession No. NM_181425.2. Pandey et al., Mar. 15, 2015.
Genbank Submission; NIH, Accession No. XM_004398354.1. Mar. 31, 2013. 2 pages.
Ghisolfi et al., Increased Bcl2 expression by antisense oligoribonucleotides targeting the adenine-uridine-rich element motif. Mol Pharmacol. Sep. 2005;68(3):816-21. Epub Jun. 13, 2005.
Gogliotti et al., The DcpS inhibitor RG3039 improves survival, function and motor unit pathologies in two SMA mouse models. Hum Mol Genet. Jun. 4, 2013. [Epub ahead of print].
Greiner et al., Identification of a specific inhibitor of the histone methyltransferase SU(VAR)3-9. Nature Chem Biol. Aug. 2005;1(3):143-5.
Houseley et al., RNA-quality control by the exosome. Nat Rev Mol Cell Biol. Jul. 2006;7(7):529-39.
Jan et al., Formation, regulation and evolution of Caenorhabditis elegans 3'UTRs. Nature. Jan. 6, 2011;469(7328):97-101. doi:10.1038/nature09616. Epub Nov. 17, 2010.
Janowski et al., Inhibiting gene expression at transcription start sites in chromosomal DNA with antigene RNAs. Nat Chem Biol. Sep. 2005;1(4):216-22. Epub Jul. 31, 2005.
Jepsen et al., Locked nucleic acid: a potent nucleic acid analog in therapeutics and biotechnology. Oligonucleotides. 2004;14(2):130-46. Review.
Khalil et al., Many human large intergenic noncoding RNAs associate with chromatin-modifying complexes and affect gene expression. Proc Natl Acad Sci U S A. Jul. 14, 2009;106(28):11667-72.
Kim et al., Self-assembled Messenger RNA Nanoparticles (mRNA-NPs) for Efficient Gene Expression. Sci Rep. Aug. 3, 2015;5:12737. doi:10.1038/srep12737.
Kim, MicroRNA biogenesis: coordinated cropping and dicing. Nat Rev Mol Cell Biol. May 2005;6(5):376-85.
Kukis et al., Cleavable linkers to enhance selectivity of antibody-targeted therapy of cancer. Cancer Biother Radiopharm. Dec. 2001;16(6):457-67. Review.
Kurreck et al. Design of antisense oligonucleotides stabilized by locked nucleic acids. Nucleic Acids Res. May 1, 2002; 30(9):1911-1918.
Larimer et al., Complete genome sequence of the metabolically versatile photosynthetic bacterium Rhodopseudomonas palustris. Nat Biotechnol. Jan. 2004;22(1):55-61. Epub Dec. 14, 2003.
Ledebur et al., Transcriptional regulation of the intercellular adhesion molecule-1 gene by inflammatory cytokines in human endothelial cells. Essential roles of a variant NF-kappa B site and p65 homodimers. J Biol Chem. Jan. 13, 1995;270(2):933-43.
Li et al., Expression of human frataxin is regulated by transcription factors SRF and TFAP2. PLoS One. Aug. 20, 2010;5(8):e12286. doi: 10.1371/journal.pone.0012286. 8 pages.
Liang et al., B1-induced caspase-independent apoptosis in MCF-7 cells is mediated by down-regulation of Bcl-2 via p53 binding to P2 promoter TATA box. Toxicol Appl Pharmacol. Oct. 1, 2011;256(1):52-61. doi:10.1016/j.taap.2011.07.010. Epub Jul. 23, 2011.
Majlessi et al., Advantages of 2'-O-methyl oligoribonucleotide probes for detecting RNA targets. Nucleic Acids Res. May 1, 1998;26(9):2224-9.
Merienne et al., SCA8 CAG/CTG expansions, a tale of two TOXICities: a unique or common case? PLoS Genet. Aug. 2009;5(8):e1000593. doi: 10.1371/journal.pgen.1000593. Epub Aug. 14, 2009.
Miller et al., A TALE nuclease architecture for efficient genome editing. Nat Biotechnol. Feb. 2011;29(2):143-8. doi: 10.1038/nbt.1755. Epub Dec. 22, 2010.
Minet et al., HIF1A gene transcription is dependent on a core promoter sequence encompassing activating and inhibiting sequences located upstream from the transcription initiation site and cis elements located within the 5'UTR. Biochem Biophys Res Commun. Aug. 2, 1999;261(2):534-40.
Nam et al., Oligo(dT) primer generates a high frequency of truncated cDNAs through internal poly(A) priming during reverse transcription. Proc Natl Acad Sci U S A. Apr. 30, 2002;99(9):6152-6. Epub Apr. 23, 2002.
Paro et al., Extending the frontiers of epigenetic regulation. Curr Opin Genet Dev. Apr. 2010;20(2):107-9. doi: 10.1016/j.gde.2010.03.011.
Ruan et al., Genome wide full-length transcript analysis using 5' and 3' paired-end-tag next generation sequencing (RNA-PET). Methods Mol Biol. 2012;809:535-62. doi: 10.1007/978-1-61779-376-9_35.
Sankaran et al., MicroRNA-15a and -16-1 act via MYB to elevate fetal hemoglobin expression in human trisomy 13. Proc Natl Acad Sci U S A. Jan. 25, 2011;108(4):1519-24.
Scaringe, Advanced 5'-Silyl-2'-Orthoester Approach to RNA Oligonucleotide Synthesis. Meth Enzym. 2000;317:3-18.
Sciabola et al., Improved nucleic acid descriptors for siRNA efficacy prediction. Nucleic Acids Res. Feb. 1, 2013;41(3):1383-94. doi: 10.1093/nar/gks1191.
Shepard et al., Complex and dynamic landscape of RNA polyadenylation revealed by PAS—Seq. RNA. Apr. 2011;17(4):761-72. doi: 10.1261/rna.2581711. Epub Feb. 22, 2011.
Silahtaroglu et al., FISHing with locked nucleic acids (LNA): evaluation of different LNA/DNA mixmers. Mol Cell Probes. Aug. 2003;17(4):165-9.
Skerra, Phosphorothioate primers improve the amplification of DNA sequences by DNA polymerases with proofreading activity. Nucleic Acids Res. Jul. 25, 1992;20(14):3551-4.
Sonenberg et al., Eukaryotic translation initiation factors and regulators. Curr Opin Struct Biol. Feb. 2003;13(1):56-63.
Tam et al., Advances in Lipid Nanoparticles for siRNA Delivery. Pharmaceutics. Sep. 18, 2013;5(3):498-507. doi: 10.3390/pharmaceutics5030498.
Taylor et al., Antisense oligonucleotides: a systematic high-throughput approach to target validation and gene function determination. Drug Discov Today. Dec. 1999;4(12):562-567.
Vedernikov et al., Hepatitis C virus genotyping using 5' nuclease real-time PCR and probes with oligodeoxyinosine linkers. Mol Gen Micro Virol. Dec. 2009;24(2):200-206.
Wahlestedt, Natural antisense and noncoding RNA transcripts as potential drug targets. Drug Discov Today. Jun. 2006;11(11-12):503-8.
Yoshizawa et al., Nuclease resistance of an extraordinarily thermostable mini-hairpin DNA fragment, d(GCGAAGC) and its application to in vitro protein synthesis. Nucleic Acids Res. Jun. 25, 1994;22(12):2217-21.
Zhao et al., Systematic clustering of transcription start site landscapes. PLoS One. 2011;6(8):e23409. doi:10.1371/journal.pone.0023409. Epub Aug. 24, 2011.
Extended European Search Report for EP 16860675.4 mailed Apr. 29, 2019.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008. Author Manuscript, 20 pages.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Lächelt et al., Nucleic Acid Therapeutics Using Polyplexes: A Journey of 50 Years (and Beyond). Chem Rev. Oct. 14, 2015;115(19):11043-78. doi: 10.1021/cr5006793. Epub Apr. 15, 2015.
Love et al., Lipid-like materials for low-dose, in vivo gene silencing. Proc Natl Acad Sci U S A. Feb. 2, 2010;107(5):1864-9. doi: 10.1073/pnas.0910603106. Epub Jan. 11, 2010. Erratum in: Proc Natl Acad Sci U S A. May 25, 2010;107(21):9915.
Mahon et al., A combinatorial approach to determine functional group effects on lipidoid—mediated siRNA delivery. Bioconjug Chem. Aug. 18, 2010;21(8):1448-54. doi: 10.1021/bc100041r. Author Manuscript, 17 pages.

(56) References Cited

OTHER PUBLICATIONS

Phua et al., Transfection efficiency and transgene expression kinetics of mRNA delivered in naked and nanoparticle format. J Control Release. Mar. 28, 2013;166(3):227-33. doi: 10.1016/j.jconrel.2012.12.029. Epub Jan. 7, 2013.

Schroeder et al., Lipid-based nanotherapeutics for siRNA delivery. J Intern Med. Jan. 2010;267(1):9-21. doi: 10.1111/j.1365-2796.2009.02189.x. Author Manuscript, 21 pages.

Siegwart et al., Combinatorial synthesis of chemically diverse core-shell nanoparticles for intracellular delivery. Proc Natl Acad Sci U S A. Aug. 9, 2011;108(32):12996-13001. doi: 10.1073/pnas.1106379108. Epub Jul. 22, 2011.

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015. PMID: 26469188.

Lächelt et al., Nucleic Acid Therapeutics Using Polyplexes: A Journey of 50 Years (and Beyond). Chem Rev. Oct. 14, 2015;115(19):11043-78. doi: 10.1021/cr5006793. Epub Apr. 15, 2015. PMID: 25872804.

Phua et al., Transfection efficiency and transgene expression kinetics of mRNA delivered in naked and nanoparticle format. J Control Release. Mar. 28, 2013;166(3):227-33. doi: 10.1016/j.jconrel.2012.12.029. Epub Jan. 7, 2013. PMID: 23306021; PMCID: PMC3594075.

International Search Report and Written Opinion mailed Apr. 22, 2021 in connection with International Application No. PCT/US2021/012251.

International Preliminary Report on Patentability mailed Jul. 12, 2022 in connection with International Application No. PCT/US2021/012251.

Cheng et al., Lipid Nanoparticles Loaded with an Antisense Oligonucleotide Gapmer Against Bcl-2 for Treatment of Lung Cancer. Pharm Res. Feb. 2017;34(2):310-320. doi: 10.1007/s11095-016-2063-5. Epub Nov. 28, 2016.

Lin et al., Influence of cationic lipid composition on uptake and intracellular processing of lipid nanoparticle formulations of siRNA. Nanomedicine: Nanotechnology, Biology, and Medicine. Feb. 2013;9(2):233-46. doi: 10.1016/j.nano.2012.05.019. Epub Jun. 12, 2012.

* cited by examiner

Oligo Design to 3' RNA ends
complementary to the 3' end of RNA, before the polyA-tail
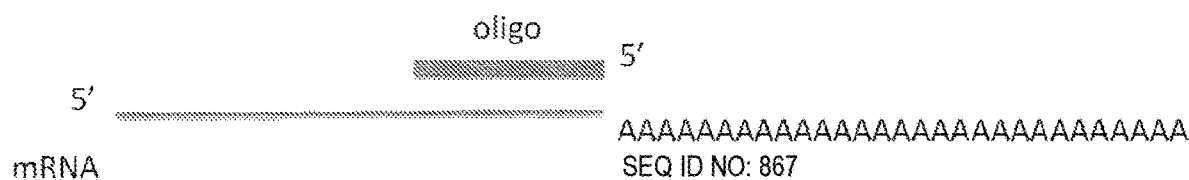
complementary to the 3' end of RNA with a 5' T-stretch to hybridize to the polyA tail
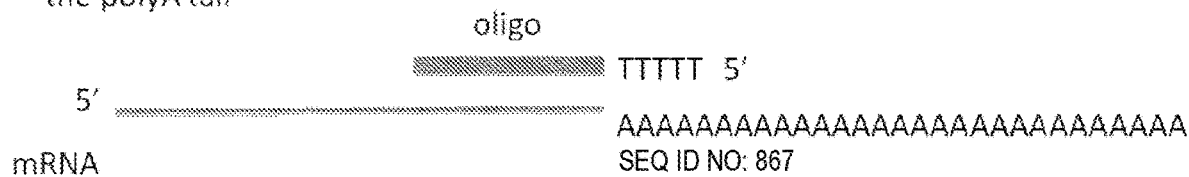
FIG. 1

Oligo design to 5' ends complementary to the 5' end of RNA

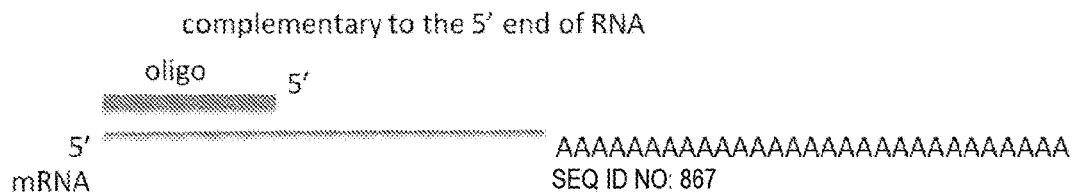

AAAAAAAAAAAAAAAAAAAAAAAAAAAAA
SEQ ID NO: 867 complementary to the 5' end of RNA, with 3'overhang residues to create a RNA-oligo duplex with a recessed end. Overhang can include a combination of nucleotides including, but not limited to, C to potentially interact with 5' methylguanosine cap and stabilize the cap further.

AAAAAAAAAAAAAAAAAAAAAAAAAAAAA
SEQ ID NO: 867

FIG. 2

Oligo design to 5' ends
5' oligos with loops to stabilize 5' RNA cap – Oligo 62
```
oligo      5'
                                                                    mRNA
                                AAAAAAAAAAAAAAAAAAAAAAAAAAAAA
   5' cap                       SEQ ID NO: 867
```
Oligo design to 5' and 3' ends
Circularization oligos protect both ends of RNA with one oligo to create a pseudo-circularized RNA
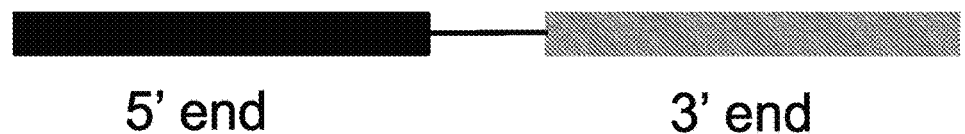
5' end             3' end
FIG. 3A

SEQUENCE LISTING

```
<160> NUMBER OF SEQ ID NOS: 868

<210> SEQ ID NO 1
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 1
tgacccaagg gagac                                                      15

<210> SEQ ID NO 2
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 2
tggccactgg ccgca                                                      15
```

```
<210> SEQ ID NO 3
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 3
cggcgacccc tggtg                                                     15

<210> SEQ ID NO 4
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 4
cgccctccag cgctg                                                     15

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 5
cgctccgccc tccag                                                     15

<210> SEQ ID NO 6
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 6
tgacccaagg gagaccc                                                   17

<210> SEQ ID NO 7
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 7
tggccactgg ccgcacc                                                   17

<210> SEQ ID NO 8
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 8
cggcgacccc tggtgcc                                                   17

<210> SEQ ID NO 9
<211> LENGTH: 17
<212> TYPE: DNA
<213> ORGANISM: Artificial Sequence
<220> FEATURE:
```

-continued

<223> OTHER INFORMATION: Synthetic Oligonucleotide

<400> SEQUENCE: 9
cgccctccag cgctgcc                                                17

<210> SEQ ID NO 10
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 10
cgctccgccc tccagcc                                                17

<210> SEQ ID NO 11
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 11
tgacccaagg gagacggaaa ccac                                        24

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 12
tggccactgg ccgcaggaaa ccac                                        24

<210> SEQ ID NO 13
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 13
cggcgacccc tggtgggaaa cctc                                        24

<210> SEQ ID NO 14
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 14
cgccctccag cgctgggaaa cctc                                        24

<210> SEQ ID NO 15
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 15
cgctccgccc tccagccaaa ggtc                                        24

```
<210> SEQ ID NO 16
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 16
ggtttttaag gcttt                                                          15

<210> SEQ ID NO 17
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 17
ggggtcttgg cctga                                                          15

<210> SEQ ID NO 18
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 18
cataatgaag ctggg                                                          15

<210> SEQ ID NO 19
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 19
aggaggcaac acatt                                                          15

<210> SEQ ID NO 20
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 20
attattttgc ttttt                                                          15

<210> SEQ ID NO 21
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 21
cattttccct cctgg                                                          15

<210> SEQ ID NO 22
<211> LENGTH: 15
<212> TYPE: DNA
<213> ORGANISM: Artificial Sequence
<220> FEATURE:
<223> OTHER INFORMATION: Synthetic Oligonucleotide
```

<400> SEQUENCE: 22
gtaggctacc cttta                                                        15

<210> SEQ ID NO 23
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 23
gaggcttgtt gcttt                                                        15

<210> SEQ ID NO 24
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 24
catgtatgat gttat                                                        15

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
tttttggttt ttaaggcttt                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
tttttggggt cttggcctga                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
tttttcataa tgaagctggg                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
tttttaggag gcaacacatt                                                   20

<210> SEQ ID NO 29
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 29
tttttattat tttgcttttt                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
tttttcattt tccctcctgg                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
tttttgtagg ctacccttta                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
tttttgaggc ttgttgcttt                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
tttttcatgt atgatgttat                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
cggcgcccga gagtccacat                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
```
ccaggaggcc ggctactgcg                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
ctgggctggg ctgggtgacg                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
acccgggtga gggtctgggc                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
ccaactctgc cggccgcggg                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
acggcggccg cagagtgggg                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
tcgatgtcgg tgcgcaggcc                                          20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
ggcggggcgt gcaggtcgca                                          20

<210> SEQ ID NO 42
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 42
acgttggttc gaacttgcgc                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
ttccaaatct ggttgaggcc                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
agacactctg cttttgaca                                                20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
tttcctcaaa ttcatcaaat                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
gggtggccca aagttccaga                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
tggtctcatc tagagagcct                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
ctctgctagt ctttcatagg                                               20
```

```
<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
gctaaagagt ccagcgtttc                                                    20

<210> SEQ ID NO 50
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 50
gcaaggtctt caaaaaactc t                                                  21

<210> SEQ ID NO 51
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 51
ctcaaacgtg tatggcttgt ct                                                 22

<210> SEQ ID NO 52
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 52
cccaaaggag acatcatagt c                                                  21

<210> SEQ ID NO 53
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 53
cagtttgaca gttaagacac cact                                               24

<210> SEQ ID NO 54
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 54
ataggttcct agatctccac c                                                  21

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 55
ggcgtctgct tgttgatcac                                                    20

<210> SEQ ID NO 56
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 56
aagatagcca gatttgcttg ttt                                                23

<210> SEQ ID NO 57
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 57
ggtccactac atacctggat ggag                                               24

<210> SEQ ID NO 58
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 58
cccagtccag tcataacgct t                                                  21

<210> SEQ ID NO 59
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 59
cgtgggagta cacccagttt tt                                                 22

<210> SEQ ID NO 60
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 60
catggaggga cacgccgt                                                      18

<210> SEQ ID NO 61
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 61
gtgagctctg cggccagcag ct                                                 22

<210> SEQ ID NO 62

```
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 62
agtttggttt ttaaggcttt a                                              21

<210> SEQ ID NO 63
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 63
taggccaagg aagacaagtc c                                              21

<210> SEQ ID NO 64
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 64
tcaagcatct tttccggaa                                                 19

<210> SEQ ID NO 65
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 65
tccttaaaac ggggctgggc a                                              21

<210> SEQ ID NO 66
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 66
ttggcctgat agcttttaat g                                              21

<210> SEQ ID NO 67
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 67
cctcagctgc ataatgaagc tggggtc                                        27

<210> SEQ ID NO 68
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 68
```
aacaacaaca acaacaaaaa acaga 25

<210> SEQ ID NO 69
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 69
cctcaaaagc aggaataaaa aaaata 26

<210> SEQ ID NO 70
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 70
gctgtgacac atagcccaac tgt 23

<210> SEQ ID NO 71
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 71
ggaggcaaca cattctttct acaga 25

<210> SEQ ID NO 72
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 72
ctattaatat tactg 15

<210> SEQ ID NO 73
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 73
cattatgtgt atgtat 16

<210> SEQ ID NO 74
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 74
tttatctatg ttatt 15

<210> SEQ ID NO 75
<211> LENGTH: 15
<212> TYPE: DNA

```
<213> ORGANISM: Artificial Sequence
<220> FEATURE:
<223> OTHER INFORMATION: Synthetic Oligonucleotide

<400> SEQUENCE: 75
ctaatttgaa gttct                                                    15

<210> SEQ ID NO 76
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 76
ttcgaacttg cgcgg                                                    15

<210> SEQ ID NO 77
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 77
tagagagcct gggt                                                     14

<210> SEQ ID NO 78
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 78
acaccactcc caaag                                                    15

<210> SEQ ID NO 79
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 79
aggtccacta catac                                                    15

<210> SEQ ID NO 80
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 80
cgttaacctg gatgg                                                    15

<210> SEQ ID NO 81
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 81
aaagccttaa aaacc                                                    15
```

```
<210> SEQ ID NO 82
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 82
tcaggccaag acccc                                                    15

<210> SEQ ID NO 83
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 83
cccagcttca ttatg                                                    15

<210> SEQ ID NO 84
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 84
aatgtgttgc ctcct                                                    15

<210> SEQ ID NO 85
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 85
aaaaagcaaa ataat                                                    15

<210> SEQ ID NO 86
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 86
ccaggaggga aaatg                                                    15

<210> SEQ ID NO 87
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 87
taaagggtag cctac                                                    15

<210> SEQ ID NO 88
<211> LENGTH: 15
<212> TYPE: DNA
<213> ORGANISM: Artificial Sequence
<220> FEATURE:
```

<223> OTHER INFORMATION: Synthetic Oligonucleotide

<400> SEQUENCE: 88
aaagcaacaa gcctc                                                    15

<210> SEQ ID NO 89
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 89
ataacatcat acatg                                                    15

<210> SEQ ID NO 90
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 90
gatactatct tcctc                                                    15

<210> SEQ ID NO 91
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 91
atgggggacg gggca                                                    15

<210> SEQ ID NO 92
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 92
ggttgagact gggtg                                                    15

<210> SEQ ID NO 93
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 93
agactgaaga ggtgc                                                    15

<210> SEQ ID NO 94
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 94
cgggacggct gtgtt                                                    15

```
<210> SEQ ID NO 95
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 95
tctgtgtggg cagca                                                    15

<210> SEQ ID NO 96
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 96
aaagccttaa aaacc                                                    15

<210> SEQ ID NO 97
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 97
tcaggccaag acccc                                                    15

<210> SEQ ID NO 98
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 98
cccagcttca ttatg                                                    15

<210> SEQ ID NO 99
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 99
aatgtgttgc ctcct                                                    15

<210> SEQ ID NO 100
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 100
aaaaagcaaa ataat                                                    15

<210> SEQ ID NO 101
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 101
ccaggaggga aaatg                                                    15

<210> SEQ ID NO 102
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 102
taaagggtag cctac                                                    15

<210> SEQ ID NO 103
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 103
aaagcaacaa gcctc                                                    15

<210> SEQ ID NO 104
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 104
ataacatcat acatg                                                    15

<210> SEQ ID NO 105
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 105
gatactatct tcctc                                                    15

<210> SEQ ID NO 106
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 106
atgggggacg gggca                                                    15

<210> SEQ ID NO 107
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 107
ggttgagact gggtg                                                    15

<210> SEQ ID NO 108
<211> LENGTH: 15
```

```
<212> TYPE: DNA
<213> ORGANISM: Artificial Sequence
<220> FEATURE:
<223> OTHER INFORMATION: Synthetic Oligonucleotide

<400> SEQUENCE: 108
agactgaaga ggtgc                                                      15

<210> SEQ ID NO 109
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 109
cgggacggct gtgtt                                                      15

<210> SEQ ID NO 110
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 110
tctgtgtggg cagca                                                      15

<210> SEQ ID NO 111
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 111
gaagaagaag aagaa                                                      15

<210> SEQ ID NO 112
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 112
ttcttcttct tcttc                                                      15

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
cggcgcccga gagtccacat                                                 20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
```

-continued

```
acggcggccg cagagtgggg                                        20

<210> SEQ ID NO 115
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 115
cctcaaaagc aggaataaaa aaaata                                 26

<210> SEQ ID NO 116
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 116
atgggggacg gggca                                             15

<210> SEQ ID NO 117
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 117
ggttgagact gggtg                                             15

<210> SEQ ID NO 118
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 118
atgggggacg gggca                                             15

<210> SEQ ID NO 119
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 119
tgacccaagg gagactttt ggtttttaag gcttt                        35

<210> SEQ ID NO 120
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 120
tggccactgg ccgcattttt ggtttttaag gcttt                       35

<210> SEQ ID NO 121
<211> LENGTH: 35
<212> TYPE: DNA
<213> ORGANISM: Artificial Sequence
```

```
<220> FEATURE:
<223> OTHER INFORMATION: Synthetic Oligonucleotide

<400> SEQUENCE: 121
cggcgacccc tggtgttttt ggtttttaag gcttt                              35

<210> SEQ ID NO 122
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 122
cgccctccag cgctgttttt ggtttttaag gcttt                              35

<210> SEQ ID NO 123
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 123
cgctccgccc tccagttttt ggtttttaag gcttt                              35

<210> SEQ ID NO 124
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 124
tgacccaagg gagactttttt ggggtcttgg cctga                             35

<210> SEQ ID NO 125
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 125
tggccactgg ccgcattttt ggggtcttgg cctga                              35

<210> SEQ ID NO 126
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 126
cggcgacccc tggtgttttt ggggtcttgg cctga                              35

<210> SEQ ID NO 127
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 127
cgccctccag cgctgttttt ggggtcttgg cctga                              35
```

<210> SEQ ID NO 128
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 128
cgctccgccc tccagttttt ggggtcttgg cctga                                35

<210> SEQ ID NO 129
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 129
tgacccaagg gagactttt cataatgaag ctggg                                 35

<210> SEQ ID NO 130
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 130
tggccactgg ccgcattttt cataatgaag ctggg                                35

<210> SEQ ID NO 131
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 131
cggcgacccc tggtgttttt cataatgaag ctggg                                35

<210> SEQ ID NO 132
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 132
cgccctccag cgctgttttt cataatgaag ctggg                                35

<210> SEQ ID NO 133
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 133
cgctccgccc tccagttttt cataatgaag ctggg                                35

<210> SEQ ID NO 134
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 134
tgacccaagg gagactttt aggaggcaac acatt                    35

<210> SEQ ID NO 135
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 135
tggccactgg ccgcattttt aggaggcaac acatt                    35

<210> SEQ ID NO 136
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 136
cggcgacccc tggtgttttt aggaggcaac acatt                    35

<210> SEQ ID NO 137
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 137
cgccctccag cgctgttttt aggaggcaac acatt                    35

<210> SEQ ID NO 138
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 138
cgctccgccc tccagttttt aggaggcaac acatt                    35

<210> SEQ ID NO 139
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 139
tgacccaagg gagactttt attattttgc ttttt                    35

<210> SEQ ID NO 140
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 140
tggccactgg ccgcattttt attattttgc ttttt                    35

<210> SEQ ID NO 141

```
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 141
cggcgacccc tggtgttttt attattttgc ttttt                                35

<210> SEQ ID NO 142
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 142
cgccctccag cgctgttttt attattttgc ttttt                                35

<210> SEQ ID NO 143
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 143
cgctccgccc tccagttttt attattttgc ttttt                                35

<210> SEQ ID NO 144
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 144
tgacccaagg gagactttttt cattttccct cctgg                               35

<210> SEQ ID NO 145
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 145
tggccactgg ccgcattttt cattttccct cctgg                                35

<210> SEQ ID NO 146
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 146
cggcgacccc tggtgttttt cattttccct cctgg                                35

<210> SEQ ID NO 147
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 147
```
cgccctccag cgctgttttt cattttccct cctgg                35

<210> SEQ ID NO 148
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 148
cgctccgccc tccagttttt cattttccct cctgg                35

<210> SEQ ID NO 149
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 149
tgacccaagg gagacttttt gtaggctacc cttta                35

<210> SEQ ID NO 150
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 150
tggccactgg ccgcattttt gtaggctacc cttta                35

<210> SEQ ID NO 151
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 151
cggcgacccc tggtgttttt gtaggctacc cttta                35

<210> SEQ ID NO 152
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 152
cgccctccag cgctgttttt gtaggctacc cttta                35

<210> SEQ ID NO 153
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 153
cgctccgccc tccagttttt gtaggctacc cttta                35

<210> SEQ ID NO 154
<211> LENGTH: 35
<212> TYPE: DNA

```
<213> ORGANISM: Artificial Sequence
<220> FEATURE:
<223> OTHER INFORMATION: Synthetic Oligonucleotide

<400> SEQUENCE: 154
tgacccaagg gagactttt gaggcttgtt gcttt                    35

<210> SEQ ID NO 155
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 155
tggccactgg ccgcattttt gaggcttgtt gcttt                   35

<210> SEQ ID NO 156
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 156
cggcgacccc tggtgttttt gaggcttgtt gcttt                   35

<210> SEQ ID NO 157
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 157
cgccctccag cgctgttttt gaggcttgtt gcttt                   35

<210> SEQ ID NO 158
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 158
cgctccgccc tccagttttt gaggcttgtt gcttt                   35

<210> SEQ ID NO 159
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 159
tgacccaagg gagactttt catgtatgat gttat                    35

<210> SEQ ID NO 160
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 160
tggccactgg ccgcattttt catgtatgat gttat                   35
```

<210> SEQ ID NO 161
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 161
cggcgacccc tggtgttttt catgtatgat gttat                35

<210> SEQ ID NO 162
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 162
cgccctccag cgctgttttt catgtatgat gttat                35

<210> SEQ ID NO 163
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 163
cgctccgccc tccagttttt catgtatgat gttat                35

<210> SEQ ID NO 164
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 164
cgccctccag tttttggttt ttaag                25

<210> SEQ ID NO 165
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 165
cgccctccag tttttggggt cttgg                25

<210> SEQ ID NO 166
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 166
cgccctccag tttttcataa tgaag                25

<210> SEQ ID NO 167
<211> LENGTH: 25
<212> TYPE: DNA
<213> ORGANISM: Artificial Sequence
<220> FEATURE:

<223> OTHER INFORMATION: Synthetic Oligonucleotide

<400> SEQUENCE: 167
cgccctccag tttttaggag gcaac                                              25

<210> SEQ ID NO 168
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 168
cgccctccag tttttattat tttgc                                              25

<210> SEQ ID NO 169
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 169
cgccctccag tttttcattt tccct                                              25

<210> SEQ ID NO 170
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 170
cgccctccag tttttgtagg ctacc                                              25

<210> SEQ ID NO 171
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 171
cgccctccag tttttgaggc ttgtt                                              25

<210> SEQ ID NO 172
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 172
cgccctccag tttttcatgt atgat                                              25

<210> SEQ ID NO 173
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 173
tgacccaagg gagactttt ttttttt                                             27

```
<210> SEQ ID NO 174
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 174
tggccactgg ccgcattttt tttttt                                         27

<210> SEQ ID NO 175
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 175
cggcgacccc tggtgttttt tttttt                                         27

<210> SEQ ID NO 176
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 176
cgccctccag cgctgttttt tttttt                                         27

<210> SEQ ID NO 177
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 177
cgctccgccc tccagttttt tttttt                                         27

<210> SEQ ID NO 178
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 178
aaaataaaca acaac                                                     15

<210> SEQ ID NO 179
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 179
aggaataaaa aaaata                                                    16

<210> SEQ ID NO 180
<211> LENGTH: 15
<212> TYPE: DNA
<213> ORGANISM: Artificial Sequence
<220> FEATURE:
<223> OTHER INFORMATION: Synthetic Oligonucleotide
```

<400> SEQUENCE: 180
tcaaaagcag gaata					15

<210> SEQ ID NO 181
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 181
actgtcctca aaagc					15

<210> SEQ ID NO 182
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 182
agcccaactg tcctc					15

<210> SEQ ID NO 183
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 183
tgacacatag cccaa					15

<210> SEQ ID NO 184
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 184
gagctgtgac acata					15

<210> SEQ ID NO 185
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 185
tctgggcctg ggctg					15

<210> SEQ ID NO 186
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 186
ggtgagggtc tgggc					15

<210> SEQ ID NO 187
<211> LENGTH: 15

```
<212> TYPE: DNA
<213> ORGANISM: Artificial Sequence
<220> FEATURE:
<223> OTHER INFORMATION: Synthetic Oligonucleotide

<400> SEQUENCE: 187
gggacccggg tgagg                                                    15

<210> SEQ ID NO 188
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 188
ccggccgcgg gaccc                                                    15

<210> SEQ ID NO 189
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 189
caactctgcc ggccg                                                    15

<210> SEQ ID NO 190
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 190
agtggggcca actct                                                    15

<210> SEQ ID NO 191
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 191
ggccgcagag tgggg                                                    15

<210> SEQ ID NO 192
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 192
gccacggcgg ccgca                                                    15

<210> SEQ ID NO 193
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 193
```

```
gtgcgcaggc cacgg                                                    15

<210> SEQ ID NO 194
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 194
gggggacggg gcagg                                                    15

<210> SEQ ID NO 195
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 195
gggacggggc aggtt                                                    15

<210> SEQ ID NO 196
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 196
gacggggcag gttga                                                    15

<210> SEQ ID NO 197
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 197
cggggcaggt tgaga                                                    15

<210> SEQ ID NO 198
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 198
gggcaggttg agact                                                    15

<210> SEQ ID NO 199
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 199
gcaggttgag actgg                                                    15

<210> SEQ ID NO 200
<211> LENGTH: 15
<212> TYPE: DNA
<213> ORGANISM: Artificial Sequence
```

```
<220> FEATURE:
<223> OTHER INFORMATION: Synthetic Oligonucleotide

<400> SEQUENCE: 200
aggttgagac tgggt                                             15

<210> SEQ ID NO 201
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 201
ggaaaaattc cagga                                             15

<210> SEQ ID NO 202
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 202
aattccagga gggaa                                             15

<210> SEQ ID NO 203
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 203
gagggaaaat gaatt                                             15

<210> SEQ ID NO 204
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 204
gaaaatgaat tgtcttc                                           17

<210> SEQ ID NO 205
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 205
gggggacggg gcagg                                             15

<210> SEQ ID NO 206
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 206
gggacggggc aggtt                                             15
```

```
<210> SEQ ID NO 207
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 207
gacggggcag gttga                                                    15

<210> SEQ ID NO 208
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 208
cggggcaggt tgaga                                                    15

<210> SEQ ID NO 209
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 209
gggcaggttg agact                                                    15

<210> SEQ ID NO 210
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 210
gcaggttgag actgg                                                    15

<210> SEQ ID NO 211
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 211
aggttgagac tgggt                                                    15

<210> SEQ ID NO 212
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 212
ggaaaaattc cagga                                                    15

<210> SEQ ID NO 213
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 213
aattccagga gggaa                                                        15

<210> SEQ ID NO 214
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 214
gagggaaaat gaatt                                                        15

<210> SEQ ID NO 215
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 215
gaaaatgaat tgtcttc                                                      17

<210> SEQ ID NO 216
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 216
ggtggtttca gttct                                                        15

<210> SEQ ID NO 217
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 217
tttttggtgg tttcagttct                                                   20

<210> SEQ ID NO 218
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 218
agcgtgctat ctggg                                                        15

<210> SEQ ID NO 219
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 219
tggcccaggg actct                                                        15

<210> SEQ ID NO 220
```

```
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 220
tctgcggctc tggc                                                         14

<210> SEQ ID NO 221
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 221
cggtccggct ctggg                                                        15

<210> SEQ ID NO 222
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 222
tcatcccggg aagct                                                        15

<210> SEQ ID NO 223
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 223
ccccaagtcc ccgct                                                        15

<210> SEQ ID NO 224
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 224
ccaaccatgc aagca                                                        15

<210> SEQ ID NO 225
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 225
tggcccaggg actcttc                                                      17

<210> SEQ ID NO 226
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 226
```
cggtccggct ctgggttc                                          18

<210> SEQ ID NO 227
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 227
ccaaccatgc aagcacc                                           17

<210> SEQ ID NO 228
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 228
tggcccaggg actctcacaa agtgac                                 26

<210> SEQ ID NO 229
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 229
cggtccggct ctgggaagaa actttc                                 26

<210> SEQ ID NO 230
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 230
ccaaccatgc aagcactcaa agagtc                                 26

<210> SEQ ID NO 231
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 231
tggcccaggg actcttttttg gtggtttcag ttct                        34

<210> SEQ ID NO 232
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 232
cggtccggct ctgggttttt ggtggtttca gttct                       35

<210> SEQ ID NO 233
<211> LENGTH: 35
<212> TYPE: DNA

```
<213> ORGANISM: Artificial Sequence
<220> FEATURE:
<223> OTHER INFORMATION: Synthetic Oligonucleotide

<400> SEQUENCE: 233
ccaaccatgc aagcattttt ggtggtttca gttct                          35

<210> SEQ ID NO 234
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 234
cagggactct ttttggtggt ttca                                      24

<210> SEQ ID NO 235
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 235
cggctctggg tttttggtgg tttca                                     25

<210> SEQ ID NO 236
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 236
catgcaagca tttttggtgg tttca                                     25

<210> SEQ ID NO 237
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 237
tggcccaggg actcggtggt ttcagttct                                 29

<210> SEQ ID NO 238
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 238
cggtccggct ctggtggtgg tttcagttct                                30

<210> SEQ ID NO 239
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 239
ccaaccatgc aagcaggtgg tttcagttct                                30
```

<210> SEQ ID NO 240
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 240
tttttagata aaatattata                                              20

<210> SEQ ID NO 241
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 241
tttttattca gataaaata                                               19

<210> SEQ ID NO 242
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 242
tttttggttt atttaaaact                                              20

<210> SEQ ID NO 243
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 243
tttttaaatt tatattacat                                              20

<210> SEQ ID NO 244
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 244
tttttcttaa atttatatta                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 245
tttttcacaa aatgttcatt                                              20

<210> SEQ ID NO 246
<211> LENGTH: 15
<212> TYPE: DNA
<213> ORGANISM: Artificial Sequence
<220> FEATURE:

<223> OTHER INFORMATION: Synthetic Oligonucleotide

<400> SEQUENCE: 246
cctccgcctt ctccc                                               15

<210> SEQ ID NO 247
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 247
tctggtcggg aaact                                               15

<210> SEQ ID NO 248
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 248
gctacagcct tttcc                                               15

<210> SEQ ID NO 249
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 249
cctccgcctt ctcccc                                              16

<210> SEQ ID NO 250
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 250
tctggtcggg aaactcc                                             17

<210> SEQ ID NO 251
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 251
gctacagcct tttccc                                              16

<210> SEQ ID NO 252
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 252
cctccgcctt ctccctcttt gatc                                     24

```
<210> SEQ ID NO 253
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 253
tctggtcggg aaactcaatt attgtc                                          26

<210> SEQ ID NO 254
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 254
gctacagcct tttccacttt gttc                                            24

<210> SEQ ID NO 255
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 255
cctccgcctt ctccctttt agataaaata ttata                                 35

<210> SEQ ID NO 256
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 256
tctggtcggg aaactttta gataaaatat tata                                  34

<210> SEQ ID NO 257
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 257
gctacagcct tttccttttt agataaaata ttata                                35

<210> SEQ ID NO 258
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 258
cctccgcctt ctccctttt ggtttattta aaact                                 35

<210> SEQ ID NO 259
<211> LENGTH: 34
<212> TYPE: DNA
<213> ORGANISM: Artificial Sequence
<220> FEATURE:
<223> OTHER INFORMATION: Synthetic Oligonucleotide
```

```
<400> SEQUENCE: 259
tctggtcggg aaacttttg gtttatttaa aact                           34

<210> SEQ ID NO 260
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 260
gctacagcct tttccttttt ggtttattta aaact                          35

<210> SEQ ID NO 261
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 261
cctccgcctt ctccctttt aaatttatat tacat                           35

<210> SEQ ID NO 262
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 262
tctggtcggg aaactttta aatttatatt acat                            34

<210> SEQ ID NO 263
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 263
gctacagcct tttccttttt aaatttatat tacat                          35

<210> SEQ ID NO 264
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 264
gccttctccc ttttagata aaata                                      25

<210> SEQ ID NO 265
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 265
tcgggaaact ttttagataa aata                                      24

<210> SEQ ID NO 266
<211> LENGTH: 25
```

```
<212> TYPE: DNA
<213> ORGANISM: Artificial Sequence
<220> FEATURE:
<223> OTHER INFORMATION: Synthetic Oligonucleotide

<400> SEQUENCE: 266
agccttttcc tttttagata aaata                                            25

<210> SEQ ID NO 267
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 267
gccttctccc tttttggttt attta                                            25

<210> SEQ ID NO 268
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 268
tcgggaaact ttttggttta ttta                                             24

<210> SEQ ID NO 269
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 269
agccttttcc tttttggttt attta                                            25

<210> SEQ ID NO 270
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 270
gccttctccc tttttaaatt tatat                                            25

<210> SEQ ID NO 271
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 271
tcgggaaact ttttaaattt atat                                             24

<210> SEQ ID NO 272
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 272
```
agccttttcc tttttaaatt tatat          25

<210> SEQ ID NO 273
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 273
aggtgtgcac tttta          15

<210> SEQ ID NO 274
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 274
tcatttttaa ggtgt          15

<210> SEQ ID NO 275
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 275
tttttaggtg tgcactttta          20

<210> SEQ ID NO 276
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 276
tttttcattt ttaaggtgt          19

<210> SEQ ID NO 277
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 277
cgcggtctcg gcggt          15

<210> SEQ ID NO 278
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 278
atcatccatg gtgag          15

<210> SEQ ID NO 279
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 279
cgcggtctcg gcggtttttta ggtgtgcact ttta                              34

<210> SEQ ID NO 280
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 280
atcatccatg gtgagttttt aggtgtgcac tttta                              35

<210> SEQ ID NO 281
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 281
cgcggtctcg gcggttttc atttttaagg tgt                                 33

<210> SEQ ID NO 282
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 282
atcatccatg gtgagttttt catttttaag gtgt                               34

<210> SEQ ID NO 283
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 283
tctcggcggt ttttaggtgt gcac                                          24

<210> SEQ ID NO 284
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 284
ccatggtgag ttttaggtg tgcac                                          25

<210> SEQ ID NO 285
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 285
tctcggcggt ttttcatttt taa                                           23

<210> SEQ ID NO 286
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 286
ccatggtgag tttttcattt ttaa                                    24

<210> SEQ ID NO 287
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 287
cgcggtctcg gcggtaggtg tgcactttta                              30

<210> SEQ ID NO 288
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 288
atcatccatg gtgagaggtg tgcactttta                              30

<210> SEQ ID NO 289
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 289
cgcggtctcg gcggttcatt tttaaggtgt                              30

<210> SEQ ID NO 290
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 290
atcatccatg gtgagtcatt tttaaggtgt                              30

<210> SEQ ID NO 291
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 291
tggagccgag cgctg                                              15

<210> SEQ ID NO 292
<211> LENGTH: 15
<212> TYPE: DNA
<213> ORGANISM: Artificial Sequence
<220> FEATURE:
<223> OTHER INFORMATION: Synthetic Oligonucleotide

```
<400> SEQUENCE: 292
gggcctgccc ctttg                                              15

<210> SEQ ID NO 293
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 293
ccccaagtca cctga                                              15

<210> SEQ ID NO 294
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 294
gacatcaata cctaa                                              15

<210> SEQ ID NO 295
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 295
aaactttacc aagtc                                              15

<210> SEQ ID NO 296
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 296
tggagccgag cgctgcc                                            17

<210> SEQ ID NO 297
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 297
gggcctgccc ctttgcc                                            17

<210> SEQ ID NO 298
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 298
ccccaagtca cctgacc                                            17

<210> SEQ ID NO 299
```

```
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 299
gacatcaata cctaacc                                                    17

<210> SEQ ID NO 300
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 300
aaactttacc aagtccc                                                    17

<210> SEQ ID NO 301
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 301
tggagccgag cgctgggaaa ccac                                            24

<210> SEQ ID NO 302
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 302
gggcctgccc ctttgggaaa ccac                                            24

<210> SEQ ID NO 303
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 303
ccccaagtca cctgaggaaa ccac                                            24

<210> SEQ ID NO 304
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 304
gacatcaata cctaaggaaa ccac                                            24

<210> SEQ ID NO 305
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 305
```

```
aaactttacc aagtcggaaa ccac                                          24

<210> SEQ ID NO 306
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 306
actgcaatat atttc                                                    15

<210> SEQ ID NO 307
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 307
gtgttaaaat tactt                                                    15

<210> SEQ ID NO 308
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 308
tttttactgc aatatatttc                                               20

<210> SEQ ID NO 309
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 309
tttttgtgtt aaaattactt                                               20

<210> SEQ ID NO 310
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 310
ccgagcgctg tttttactgc aatat                                         25

<210> SEQ ID NO 311
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 311
tgcccctttg tttttactgc aatat                                         25

<210> SEQ ID NO 312
<211> LENGTH: 25
<212> TYPE: DNA
```

```
<213> ORGANISM: Artificial Sequence
<220> FEATURE:
<223> OTHER INFORMATION: Synthetic Oligonucleotide

<400> SEQUENCE: 312
agtcacctga tttttactgc aatat                                              25

<210> SEQ ID NO 313
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 313
caatacctaa tttttactgc aatat                                              25

<210> SEQ ID NO 314
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 314
ttaccaagtc tttttactgc aatat                                              25

<210> SEQ ID NO 315
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 315
ccgagcgctg tttttgtgtt aaaat                                              25

<210> SEQ ID NO 316
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 316
tgcccctttg tttttgtgtt aaaat                                              25

<210> SEQ ID NO 317
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 317
agtcacctga tttttgtgtt aaaat                                              25

<210> SEQ ID NO 318
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 318
caatacctaa tttttgtgtt aaaat                                              25
```

<210> SEQ ID NO 319
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 319
ttaccaagtc tttttgtgtt aaaat                                          25

<210> SEQ ID NO 320
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 320
tgtctgtagc tccag                                                     15

<210> SEQ ID NO 321
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 321
tagctccagt gaggc                                                     15

<210> SEQ ID NO 322
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 322
tttcttctcc cacca                                                     15

<210> SEQ ID NO 323
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 323
tgtctgtagc tccagcc                                                   17

<210> SEQ ID NO 324
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 324
tagctccagt gaggccc                                                   17

<210> SEQ ID NO 325
<211> LENGTH: 17
<212> TYPE: DNA
<213> ORGANISM: Artificial Sequence
<220> FEATURE:

<223> OTHER INFORMATION: Synthetic Oligonucleotide

<400> SEQUENCE: 325
tttcttctcc caccacc          17

<210> SEQ ID NO 326
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 326
tgtctgtagc tccagggaaa ccac          24

<210> SEQ ID NO 327
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 327
tagctccagt gaggcggaaa ccac          24

<210> SEQ ID NO 328
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 328
tttcttctcc caccaggaaa ccac          24

<210> SEQ ID NO 329
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 329
tttttgtgtg atctcttagc          20

<210> SEQ ID NO 330
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 330
tttttgtgat ctcttagcag          20

<210> SEQ ID NO 331
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 331 tttttttgatc tcttagcaga          20

```
<210> SEQ ID NO 332
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 332
atttctctca atcct                                                      15

<210> SEQ ID NO 333
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 333
ggcgtgtata ttttt                                                      15

<210> SEQ ID NO 334
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 334
ggttatcgcc ctccc                                                      15

<210> SEQ ID NO 335
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 335
acgacttccg ccgcc                                                      15

<210> SEQ ID NO 336
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 336
atttctctca atcctcc                                                    17

<210> SEQ ID NO 337
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 337
ggcgtgtata tttttcc                                                    17

<210> SEQ ID NO 338
<211> LENGTH: 17
<212> TYPE: DNA
<213> ORGANISM: Artificial Sequence
<220> FEATURE:
<223> OTHER INFORMATION: Synthetic Oligonucleotide
```

<400> SEQUENCE: 338
ggttatcgcc ctccccc                                                  17

<210> SEQ ID NO 339
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 339
acgacttccg ccgcccc                                                  17

<210> SEQ ID NO 340
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 340
atttctctca atcctggaaa ccac                                          24

<210> SEQ ID NO 341
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 341
ggcgtgtata tttttggaaa ccac                                          24

<210> SEQ ID NO 342
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 342
ggttatcgcc ctcccggaaa ccac                                          24

<210> SEQ ID NO 343
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 343
acgacttccg ccgccggaaa ccac                                          24

<210> SEQ ID NO 344
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 344 tttttaatt ttttttaaa                                                20

<210> SEQ ID NO 345
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 345
tttttatatg caaaaaagaa                                            20

<210> SEQ ID NO 346
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 346
tttttcaaaa tatgggccaa                                            20

<210> SEQ ID NO 347
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 347
ttcaccacat gtaaa                                                 15

<210> SEQ ID NO 348
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 348 tttttttcacc acatgtaaa                                            19

<210> SEQ ID NO 349
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 349
aaatcagggc agaatgt                                               17

<210> SEQ ID NO 350
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 350
aaatcagggc agaatgtcc                                             19

<210> SEQ ID NO 351
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 351
```
aaatcagggc agaatgtcca aaggtc                                    26

<210> SEQ ID NO 352
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 352
aaatcagggc agaatgtttt tttcaccaca tgtaaa                         36

<210> SEQ ID NO 353
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 353
ttattgtctg agccc                                                15

<210> SEQ ID NO 354
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 354
tttttattgt ctgagccc                                             18

<210> SEQ ID NO 355
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 355
tcaggtgacg gatgt                                                15

<210> SEQ ID NO 356
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 356
tcaggtgacg gatgtcc                                              17

<210> SEQ ID NO 357
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 357
tcaggtgacg gatgtccaaa ggtc                                      24

<210> SEQ ID NO 358
<211> LENGTH: 33
<212> TYPE: DNA
<213> ORGANISM: Artificial Sequence

```
<220> FEATURE:
<223> OTHER INFORMATION: Synthetic Oligonucleotide

<400> SEQUENCE: 358
tcaggtgacg gatgttttttt attgtctgag ccc                              33

<210> SEQ ID NO 359
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 359
tgtggggagc tcggc                                                   15

<210> SEQ ID NO 360
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 360
ggggagctcg gctgc                                                   15

<210> SEQ ID NO 361
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 361
tttttgtggg gagctcggc                                               19

<210> SEQ ID NO 362
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 362
ttttggggag ctcggctgc                                               19

<210> SEQ ID NO 363
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 363
ttgtccaagg gcagg                                                   15

<210> SEQ ID NO 364
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 364
tcgatgagtg tgtgc                                                   15
```

```
<210> SEQ ID NO 365
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 365
agaagaaaaa ccacg                                                    15

<210> SEQ ID NO 366
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 366
aatatgattt cttcc                                                    15

<210> SEQ ID NO 367
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 367
gagatggggg acatg                                                    15

<210> SEQ ID NO 368
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 368
ttcagtttat tcaag                                                    15

<210> SEQ ID NO 369
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 369
ctgtctccac ttttt                                                    15

<210> SEQ ID NO 370
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 370
tggaataaaa cggg                                                     14

<210> SEQ ID NO 371
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 371
acaattgaga aaaca                                                       15

<210> SEQ ID NO 372
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 372
cagttttaag tggag                                                       15

<210> SEQ ID NO 373
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 373
tgacaagaat gagac                                                       15

<210> SEQ ID NO 374
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 374
ccgggcgagg ggagg                                                       15

<210> SEQ ID NO 375
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 375
ccgccggcct gcccg                                                       15

<210> SEQ ID NO 376
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 376
cgagcgcgta tcctg                                                       15

<210> SEQ ID NO 377
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 377
ctgcttctcc tcagc                                                       15

<210> SEQ ID NO 378
```

<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 378
ttttcagttt attcaag					17

<210> SEQ ID NO 379
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 379
ttttctgtct ccacttttt					19

<210> SEQ ID NO 380
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 380
tttttggaat aaaacggg					18

<210> SEQ ID NO 381
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 381
ttttacaatt gagaaaaca					19

<210> SEQ ID NO 382
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 382
ttttcagttt taagtggag					19

<210> SEQ ID NO 383
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 383
tttttgacaa gaatgagac					19

<210> SEQ ID NO 384
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 384
aacagtcata ataat                                                         15

<210> SEQ ID NO 385
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 385
taatttaaca gtcat                                                         15

<210> SEQ ID NO 386
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 386
gcacgctata aagca                                                         15

<210> SEQ ID NO 387
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 387
cccggggctg ggctt                                                         15

<210> SEQ ID NO 388
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 388
ccccgctccg cctcc                                                         15

<210> SEQ ID NO 389
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 389
gcgcctccct gattt                                                         15

<210> SEQ ID NO 390
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 390
tcgccgcggt ggctg                                                         15

<210> SEQ ID NO 391
<211> LENGTH: 15
<212> TYPE: DNA

```
<213> ORGANISM: Artificial Sequence
<220> FEATURE:
<223> OTHER INFORMATION: Synthetic Oligonucleotide

<400> SEQUENCE: 391
cagcgaatgg tcgcg                                                     15

<210> SEQ ID NO 392
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 392
tttttaacag tcataataat                                                20

<210> SEQ ID NO 393
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 393
tttttaattt aacagtcat                                                 19

<210> SEQ ID NO 394
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 394
gcggcggctg ctcta                                                     15

<210> SEQ ID NO 395
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 395
ttatcggccg ctgcc                                                     15

<210> SEQ ID NO 396
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 396
gcgtcgggga cggct                                                     15

<210> SEQ ID NO 397
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 397
gcggaggaaa ctgcg                                                     15
```

<210> SEQ ID NO 398
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 398
gccgcacgcc cgaca                                              15

<210> SEQ ID NO 399
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 399
cctgacccac cctcc                                              15

<210> SEQ ID NO 400
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 400
agggcaggcc gcggc                                              15

<210> SEQ ID NO 401
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 401
ctgaatcacc ccgcg                                              15

<210> SEQ ID NO 402
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 402
ggccccgagc tccgc                                              15

<210> SEQ ID NO 403
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 403
gcggctgctc taata                                              15

<210> SEQ ID NO 404
<211> LENGTH: 15
<212> TYPE: DNA
<213> ORGANISM: Artificial Sequence
<220> FEATURE:

<223> OTHER INFORMATION: Synthetic Oligonucleotide

<400> SEQUENCE: 404
cgccgcggca tgtgg                                                    15

<210> SEQ ID NO 405
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 405
ccctcctcct cttgc                                                    15

<210> SEQ ID NO 406
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 406
ggccgcgggc tcgtg                                                    15

<210> SEQ ID NO 407
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 407
gttatttttc tctgt                                                    15

<210> SEQ ID NO 408
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 408
atttaaaatg tttta                                                    15

<210> SEQ ID NO 409
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 409
tctctgtcca tttaa                                                    15

<210> SEQ ID NO 410
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 410
tcatttggtc atgtg                                                    15

```
<210> SEQ ID NO 411
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 411
tagttctctg tacat                                                    15

<210> SEQ ID NO 412
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 412
tctgctggct caact                                                    15

<210> SEQ ID NO 413
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 413
atcatagaat agatt                                                    15

<210> SEQ ID NO 414
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 414
ttatcataga ataga                                                    15

<210> SEQ ID NO 415
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 415
aattgacatt tagca                                                    15

<210> SEQ ID NO 416
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 416
gacatttagc atttt                                                    15

<210> SEQ ID NO 417
<211> LENGTH: 15
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 417
ttaaccattc aacac                                                        15

<210> SEQ ID NO 418
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 418
cttggccggg gaact                                                        15

<210> SEQ ID NO 419
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 419
gccggggaac tgccg                                                        15

<210> SEQ ID NO 420
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 420
cgcccggagc cgcgc                                                        15

<210> SEQ ID NO 421
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 421
cttggccggg gaactcc                                                      17

<210> SEQ ID NO 422
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 422
gccggggaac tgccgc                                                       16

<210> SEQ ID NO 423
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 423
cgcccggagc cgcgcc                                                       16

<210> SEQ ID NO 424
<211> LENGTH: 24
```

<212> TYPE: DNA
<213> ORGANISM: Artificial Sequence
<220> FEATURE:
<223> OTHER INFORMATION: Synthetic Oligonucleotide

<400> SEQUENCE: 424
cttggccggg gaactataaa attc                                    24

<210> SEQ ID NO 425
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 425
cttggccggg gaactttttg tcgttcagat aaaa                         34

<210> SEQ ID NO 426
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 426
cttggccggg gaacttttc agataaaata tt                            32

<210> SEQ ID NO 427
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 427
cttggccggg gaactgtcgt tcagataaaa                              30

<210> SEQ ID NO 428
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 428
cttggccggg gaactttcag ataaaatatt                              30

<210> SEQ ID NO 429
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 429
ccggggaact ttttgtcgtt caga                                    24

<210> SEQ ID NO 430
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 430

```
cgqqqaactt tttcagataa a                                              21

<210> SEQ ID NO 431
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 431
cggggaactg tcgttcaga                                                 19

<210> SEQ ID NO 432
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 432
ccggggaact ttcagataaa                                                20

<210> SEQ ID NO 433
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 433
gtcgttcaga taaaa                                                     15

<210> SEQ ID NO 434
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 434
ttcagataaa atatt                                                     15

<210> SEQ ID NO 435
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 435
tttttgtcgt tcagataaaa                                                20

<210> SEQ ID NO 436
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 436
tttttcagat aaaatatt                                                  18

<210> SEQ ID NO 437
<211> LENGTH: 15
<212> TYPE: DNA
<213> ORGANISM: Artificial Sequence
```

<220> FEATURE:
<223> OTHER INFORMATION: Synthetic Oligonucleotide

<400> SEQUENCE: 437
ctccgcggcc gctcc                                               15

<210> SEQ ID NO 438
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 438
gcccacatgc tactc                                               15

<210> SEQ ID NO 439
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 439
tccgaacgcc cacat                                               15

<210> SEQ ID NO 440
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 440
cgaggactcg gtggt                                               15

<210> SEQ ID NO 441
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 441
ccagctccgc ggccg                                               15

<210> SEQ ID NO 442
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 442
ctccgcggcc gctccc                                              16

<210> SEQ ID NO 443
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 443
gcccacatgc tactcc                                              16

<210> SEQ ID NO 444
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 444
ctccgcggcc gctcctcaaa gatc    24

<210> SEQ ID NO 445
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 445
gcccacatgc tactcccaaa ggtc    24

<210> SEQ ID NO 446
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 446
ctccgcggcc gctccttttt gggagggaac acact    35

<210> SEQ ID NO 447
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 447
gcccacatgc tactcttttt gggagggaac acact    35

<210> SEQ ID NO 448
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 448
ctccgcggcc gctccgggag ggaacacact    30

<210> SEQ ID NO 449
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 449
gcccacatgc tactcgggag ggaacacact    30

<210> SEQ ID NO 450
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 450
cggccgctcc gggagggaac                                               20

<210> SEQ ID NO 451
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 451
catgctactc gggagggaac                                               20

<210> SEQ ID NO 452
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 452
gggagggaac acact                                                    15

<210> SEQ ID NO 453
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 453
ggggtcttca cctga                                                    15

<210> SEQ ID NO 454
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 454
ggctgttata tcatg                                                    15

<210> SEQ ID NO 455
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 455
ggcattttaa gatgg                                                    15

<210> SEQ ID NO 456
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 456 ttttgggag ggaacacact                                                20

<210> SEQ ID NO 457
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 457
tttttggctg ttatatcatg                                               20

<210> SEQ ID NO 458
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 458
tttttttttt ggttttcc                                                 18

<210> SEQ ID NO 459
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 459
tgtctcattt ggaga                                                    15

<210> SEQ ID NO 460
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 460
ataatgaagc tggg                                                     14

<210> SEQ ID NO 461
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 461
ttttccctcc tggaa                                                    15

<210> SEQ ID NO 462
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 462
tgcataatga agctg                                                    15

<210> SEQ ID NO 463
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 463
```
aaatccttca aagaa                    15

<210> SEQ ID NO 464
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 464
ttggaagatt ttttg                    15

<210> SEQ ID NO 465
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 465
gcattcttgt agcag                    15

<210> SEQ ID NO 466
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 466
acaacaaaaa acaga                    15

<210> SEQ ID NO 467
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 467
tgaagctggg gtctt                    15

<210> SEQ ID NO 468
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 468
cctgaaaaca tttgt                    15

<210> SEQ ID NO 469
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 469
ttcattttcc ctcct                    15

<210> SEQ ID NO 470
<211> LENGTH: 15
<212> TYPE: DNA

```
<213> ORGANISM: Artificial Sequence
<220> FEATURE:
<223> OTHER INFORMATION: Synthetic Oligonucleotide

<400> SEQUENCE: 470
ttattattat tatat                                                    15

<210> SEQ ID NO 471
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 471
taactttgca tgaat                                                    15

<210> SEQ ID NO 472
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 472
atacaaacat gtatg                                                    15

<210> SEQ ID NO 473
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 473
attgtaaacc tataa                                                    15

<210> SEQ ID NO 474
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 474
tggagttggg gttat                                                    15

<210> SEQ ID NO 475
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 475
gttggggtta tttag                                                    15

<210> SEQ ID NO 476
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 476
ctccgccctc cag                                                      13
```

<210> SEQ ID NO 477
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 477
ccgccctcca g                                                          11

<210> SEQ ID NO 478
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 478 gccctccag                                                              9

<210> SEQ ID NO 479
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 479
cccgctccgc cctcc                                                      15

<210> SEQ ID NO 480
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 480
cgctccgccc tcc                                                        13

<210> SEQ ID NO 481
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 481
ctccgccctc c                                                          11

<210> SEQ ID NO 482
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 482 ccgccctcc                                                              9

<210> SEQ ID NO 483
<211> LENGTH: 13
<212> TYPE: DNA
<213> ORGANISM: Artificial Sequence
<220> FEATURE:

<223> OTHER INFORMATION: Synthetic Oligonucleotide

<400> SEQUENCE: 483
gccactggcc gca                                                              13

<210> SEQ ID NO 484
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 484
cactggccgc a                                                                11

<210> SEQ ID NO 485
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 485
gcgacccctg gtg                                                              13

<210> SEQ ID NO 486
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 486
gacccctggt g                                                                11

<210> SEQ ID NO 487
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 487
ctggccgcag gca                                                              13

<210> SEQ ID NO 488
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 488
ggccactggc cgc                                                              13

<210> SEQ ID NO 489
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 489
ctggtggcca ctg                                                              13

```
<210> SEQ ID NO 490
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 490
gacccctggt ggc                                                          13

<210> SEQ ID NO 491
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 491
gcggcgaccc ctg                                                          13

<210> SEQ ID NO 492
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 492
gtgctgcggc gac                                                          13

<210> SEQ ID NO 493
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 493
gctgggtgct gcg                                                          13

<210> SEQ ID NO 494
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 494
ccagcgctgg gtg                                                          13

<210> SEQ ID NO 495
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 495
gccctccagc gct                                                          13

<210> SEQ ID NO 496
<211> LENGTH: 13
<212> TYPE: DNA
<213> ORGANISM: Artificial Sequence
<220> FEATURE:
<223> OTHER INFORMATION: Synthetic Oligonucleotide
```

-continued

<400> SEQUENCE: 496
cgcccgctcc gcc                                                          13

<210> SEQ ID NO 497
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 497
cgccctccag cgctgttttt attattttgc ttttt                                  35

<210> SEQ ID NO 498
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 498
cgctccgccc tccagttttt attattttgc ttttt                                  35

<210> SEQ ID NO 499
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 499
caagtccagt ttggttt                                                      17

<210> SEQ ID NO 500
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 500
gaataggcca aggaaga                                                      17

<210> SEQ ID NO 501
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 501
atcaagcatc ttttccg                                                      17

<210> SEQ ID NO 502
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 502
ttaaaacggg gctgggc                                                      17

<210> SEQ ID NO 503
<211> LENGTH: 17

```
<212> TYPE: DNA
<213> ORGANISM: Artificial Sequence
<220> FEATURE:
<223> OTHER INFORMATION: Synthetic Oligonucleotide

<400> SEQUENCE: 503
gatagctttt aatgtcc                                                    17

<210> SEQ ID NO 504
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 504
agctggggtc ttggcct                                                    17

<210> SEQ ID NO 505
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 505
cctcagctgc ataatga                                                    17

<210> SEQ ID NO 506
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 506
caacaacaaa aaacaga                                                    17

<210> SEQ ID NO 507
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 507
aaaaaaataa acaacaa                                                    17

<210> SEQ ID NO 508
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 508
cctcaaaagc aggaata                                                    17

<210> SEQ ID NO 509
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 509
```
acacatagcc caactgt                                       17

<210> SEQ ID NO 510
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 510
ctttctacag agctgtg                                       17

<210> SEQ ID NO 511
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 511
gtaggaggca acacatt                                       17

<210> SEQ ID NO 512
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 512
cagaacttgg gggcaag                                       17

<210> SEQ ID NO 513
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 513
ccatagaaat taaaaat                                       17

<210> SEQ ID NO 514
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 514
acaatccaaa aaatctt                                       17

<210> SEQ ID NO 515
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 515
gtgagggagg aaatccg                                       17

<210> SEQ ID NO 516
<211> LENGTH: 17
<212> TYPE: DNA
<213> ORGANISM: Artificial Sequence

```
<220> FEATURE:
<223> OTHER INFORMATION: Synthetic Oligonucleotide

<400> SEQUENCE: 516
aagataaggg gtatcat                                                17

<210> SEQ ID NO 517
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 517
ggcataagac attataa                                                17

<210> SEQ ID NO 518
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 518
tgttatattc aggtata                                                17

<210> SEQ ID NO 519
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 519 tttgctttt taaaggt                                                 17

<210> SEQ ID NO 520
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 520
tttttccttc ttattat                                                17

<210> SEQ ID NO 521
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 521
cattttccct cctggaa                                                17

<210> SEQ ID NO 522
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 522
gaagagtgaa gacaatt                                                17
```

<210> SEQ ID NO 523
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 523
taaatccttc aaagaat                                                17

<210> SEQ ID NO 524
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 524
tcatgtactt cttgcag                                                17

<210> SEQ ID NO 525
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 525
ggttgaccag ctgctct                                                17

<210> SEQ ID NO 526
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 526
agatagaaca gtgagca                                                17

<210> SEQ ID NO 527
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 527
taatgtgtct catttgg                                                17

<210> SEQ ID NO 528
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 528
atttgtaggc taccctt                                                17

<210> SEQ ID NO 529
<211> LENGTH: 17
<212> TYPE: DNA
<213> ORGANISM: Artificial Sequence
<220> FEATURE:
<223> OTHER INFORMATION: Synthetic Oligonucleotide -continued

<400> SEQUENCE: 529
gaaagaagcc tgaaaac                                                      17

<210> SEQ ID NO 530
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 530
agaagtgctt acacttt                                                      17

<210> SEQ ID NO 531
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 531
tcaatgctaa agagctc                                                      17

<210> SEQ ID NO 532
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 532
agtctgggtg tcc                                                          13

<210> SEQ ID NO 533
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 533
ccgacagtct ggg                                                          13

<210> SEQ ID NO 534
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 534
ctccgacagt ctg                                                          13

<210> SEQ ID NO 535
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 535
gacagtctgg gtg                                                          13

<210> SEQ ID NO 536

```
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 536
cagtctgggt g                                                      11

<210> SEQ ID NO 537
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 537
ctcagcctgg ccctg                                                  15

<210> SEQ ID NO 538
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 538
agttcaagga tcagc                                                  15

<210> SEQ ID NO 539
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 539
gctctccgac agtct                                                  15

<210> SEQ ID NO 540
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 540
tctccgacag tct                                                    13

<210> SEQ ID NO 541
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 541
tccgacagtc t                                                      11

<210> SEQ ID NO 542
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 542
```
cggagctctc cgaca                                                     15

<210> SEQ ID NO 543
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 543
gagctctccg aca                                                       13

<210> SEQ ID NO 544
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 544
gctctccgac a                                                         11

<210> SEQ ID NO 545
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 545
ctattccatt ttgga                                                     15

<210> SEQ ID NO 546
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 546
ctattccatt ttg                                                       13

<210> SEQ ID NO 547
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 547
attccatttt ggaaa                                                     15

<210> SEQ ID NO 548
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 548
ccattttgga aaggt                                                     15

<210> SEQ ID NO 549
<211> LENGTH: 13
<212> TYPE: DNA

```
<213> ORGANISM: Artificial Sequence
<220> FEATURE:
<223> OTHER INFORMATION: Synthetic Oligonucleotide

<400> SEQUENCE: 549
ccattttgga aag                                                          13

<210> SEQ ID NO 550
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 550
cattttggaa aggtt                                                        15

<210> SEQ ID NO 551
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 551
cattttggaa agg                                                          13

<210> SEQ ID NO 552
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 552
ggaaaggttt attgt                                                        15

<210> SEQ ID NO 553
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 553
tccgacagtc tccattttgg aa                                                22

<210> SEQ ID NO 554
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 554
gctctccgac accattttgg aa                                                22

<210> SEQ ID NO 555
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 555
tccgacagtc tcattttgga aa                                                22
```

<210> SEQ ID NO 556
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 556
gctctccgac acattttgga aa                                           22

<210> SEQ ID NO 557
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 557
cctcaaaagc aggaa                                                   15

<210> SEQ ID NO 558
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 558
cctcaaaagc agg                                                     13

<210> SEQ ID NO 559
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 559
cctcaaaagc a                                                       11

<210> SEQ ID NO 560
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 560
tcaaaagcag gaa                                                     13

<210> SEQ ID NO 561
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 561
caaaagcagg a                                                       11

<210> SEQ ID NO 562
<211> LENGTH: 27
<212> TYPE: DNA
<213> ORGANISM: Artificial Sequence
<220> FEATURE:

<223> OTHER INFORMATION: Synthetic Oligonucleotide

<400> SEQUENCE: 562
ccgccctcca gcctcaaaag caggaat                                    27

<210> SEQ ID NO 563
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 563
ccgccctcca gcctcaaaag cagga                                      25

<210> SEQ ID NO 564
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 564
ccgccctcca gcctcaaaag cag                                        23

<210> SEQ ID NO 565
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 565
ccgccctcca gcctcaaaag c                                          21

<210> SEQ ID NO 566
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 566
gccctccagc ctcaaaagca ggaat                                      25

<210> SEQ ID NO 567
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 567
gccctccagc ctcaaaagca gga                                        23

<210> SEQ ID NO 568
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 568
gccctccagc ctcaaaagca g                                          21

```
<210> SEQ ID NO 569
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 569
gccctccagc ctcaaaagc                                              19

<210> SEQ ID NO 570
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 570
ccctccagcc tcaaaag                                                17

<210> SEQ ID NO 571
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 571
cctccagcct caaaa                                                  15

<210> SEQ ID NO 572
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 572
gccctccagt caaaagcagg a                                           21

<210> SEQ ID NO 573
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 573
gccctccagc aaaagcagg                                              19

<210> SEQ ID NO 574
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 574
ccgccctcca gtcaaaagca gga                                         23

<210> SEQ ID NO 575
<211> LENGTH: 21
<212> TYPE: DNA
<213> ORGANISM: Artificial Sequence
<220> FEATURE:
<223> OTHER INFORMATION: Synthetic Oligonucleotide
```

<400> SEQUENCE: 575
ccgccctcca gcaaaagcag g                                              21

<210> SEQ ID NO 576
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 576
ctccgccctc cag                                                       13

<210> SEQ ID NO 577
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 577
ccgccctcca g                                                         11

<210> SEQ ID NO 578
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 578 gccctccag                                                             9

<210> SEQ ID NO 579
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 579
cccgctccgc cctcc                                                     15

<210> SEQ ID NO 580
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 580
cgctccgccc tcc                                                       13

<210> SEQ ID NO 581
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 581
ctccgccctc c                                                         11

<210> SEQ ID NO 582
<211> LENGTH: 9

```
<212> TYPE: DNA
<213> ORGANISM: Artificial Sequence
<220> FEATURE:
<223> OTHER INFORMATION: Synthetic Oligonucleotide

<400> SEQUENCE: 582 ccgccctcc                                                                  9

<210> SEQ ID NO 583
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 583
gcctttgaga aagca                                                          15

<210> SEQ ID NO 584
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 584
gactgtgggg ccttt                                                          15

<210> SEQ ID NO 585
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 585
aggaagtgga ggact                                                          15

<210> SEQ ID NO 586
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 586
tgcattttca ctgaa                                                          15

<210> SEQ ID NO 587
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 587
cattttcact gaagc                                                          15

<210> SEQ ID NO 588
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 588
```

```
actgaagcat ttatt                                                     15

<210> SEQ ID NO 589
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 589
cacacaaatg tatgg                                                     15

<210> SEQ ID NO 590
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 590
ggattttatt gacaa                                                     15

<210> SEQ ID NO 591
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 591
aaaacaacaa agttt                                                     15

<210> SEQ ID NO 592
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 592
agtgccataa aaagt                                                     15

<210> SEQ ID NO 593
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 593
tcaaatataa aaatt                                                     15

<210> SEQ ID NO 594
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 594 ttcccccac ccacc                                                      15

<210> SEQ ID NO 595
<211> LENGTH: 15
<212> TYPE: DNA
<213> ORGANISM: Artificial Sequence
```

```
<220> FEATURE:
<223> OTHER INFORMATION: Synthetic Oligonucleotide

<400> SEQUENCE: 595
catttgcttc caatt                                                          15

<210> SEQ ID NO 596
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 596
gctcaaccct ttttc                                                          15

<210> SEQ ID NO 597
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 597
agacctacta ctctg                                                          15

<210> SEQ ID NO 598
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 598
ccctccaccg gaagt                                                          15

<210> SEQ ID NO 599
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 599
gcccgcgctc gccgt                                                          15

<210> SEQ ID NO 600
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 600 acgcccctg gcagc                                                           15

<210> SEQ ID NO 601
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 601
gctcagcccc tcggc                                                          15
```

```
<210> SEQ ID NO 602
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 602
agcagaggaa gatca                                                        15

<210> SEQ ID NO 603
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 603
cagaggaaga tcaaa                                                        15

<210> SEQ ID NO 604
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 604 cagattttg aaact                                                         15

<210> SEQ ID NO 605
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 605
cagactaatt ttttg                                                        15

<210> SEQ ID NO 606
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 606
tttttgcttt ttcat                                                        15

<210> SEQ ID NO 607
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 607
aattttttgc ttttt                                                        15

<210> SEQ ID NO 608
<211> LENGTH: 15
<212> TYPE: DNA
<213> ORGANISM: Artificial Sequence
<220> FEATURE:
<223> OTHER INFORMATION: Synthetic Oligonucleotide
```

<400> SEQUENCE: 608
atgtttggca atact                                                    15

<210> SEQ ID NO 609
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 609
ttggcaatac ttttt                                                    15

<210> SEQ ID NO 610
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 610
gctgccctgg ccccg                                                    15

<210> SEQ ID NO 611
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 611
cggacacacc cctcg                                                    15

<210> SEQ ID NO 612
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 612
acgggacgcg agtcc                                                    15

<210> SEQ ID NO 613
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 613
gtctggggag aaagc                                                    15

<210> SEQ ID NO 614
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 614
ccactcggtg ggtct                                                    15

<210> SEQ ID NO 615

```
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 615
tgatctgtta tcatc                                                    15

<210> SEQ ID NO 616
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 616
ctgttatcat ctgta                                                    15

<210> SEQ ID NO 617
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 617
gtgtataaag atttt                                                    15

<210> SEQ ID NO 618
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 618
caatttacat tttag                                                    15

<210> SEQ ID NO 619
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 619
tacattttag accat                                                    15

<210> SEQ ID NO 620
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 620
tgctataaga tgtaa                                                    15

<210> SEQ ID NO 621
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 621
```
aaggaagccg gcaag                                                      15

<210> SEQ ID NO 622
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 622
cgccacaact cattc                                                      15

<210> SEQ ID NO 623
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 623
atgggagcat tgtgg                                                      15

<210> SEQ ID NO 624
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 624
cgcccgccca gcccc                                                      15

<210> SEQ ID NO 625
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 625
cccctccccc gcccg                                                      15

<210> SEQ ID NO 626
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 626
cttccgctgc tgctg                                                      15

<210> SEQ ID NO 627
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 627
cttcttagta ccaac                                                      15

<210> SEQ ID NO 628
<211> LENGTH: 15
<212> TYPE: DNA

```
<213> ORGANISM: Artificial Sequence
<220> FEATURE:
<223> OTHER INFORMATION: Synthetic Oligonucleotide

<400> SEQUENCE: 628
tttagagcaa aatcg                                                    15

<210> SEQ ID NO 629
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 629
ggtagttaaa tgttt                                                    15

<210> SEQ ID NO 630
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 630
tacttaagaa agaga                                                    15

<210> SEQ ID NO 631
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 631
tatacttaag aaaga                                                    15

<210> SEQ ID NO 632
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 632
cgccgccgac gccgg                                                    15

<210> SEQ ID NO 633
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 633
ctctctccga gagga                                                    15

<210> SEQ ID NO 634
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 634
cgccccgccc tcttg                                                    15
```

```
<210> SEQ ID NO 635
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 635
ccgcgcgctg ctgca                                               15

<210> SEQ ID NO 636
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 636
cactttcaca gagag                                               15

<210> SEQ ID NO 637
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 637
ctttcacatg tattaa                                              16

<210> SEQ ID NO 638
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 638
atgtattaaa aaact                                               15

<210> SEQ ID NO 639
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 639 gacatttta tgtaa                                                15

<210> SEQ ID NO 640
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 640 cattttatg taaat                                                15

<210> SEQ ID NO 641
<211> LENGTH: 15
<212> TYPE: DNA
<213> ORGANISM: Artificial Sequence
<220> FEATURE:
```

<223> OTHER INFORMATION: Synthetic Oligonucleotide

<400> SEQUENCE: 641
aaatttataa ggcaa                                                           15

<210> SEQ ID NO 642
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 642
aggcaaactc tttat                                                           15

<210> SEQ ID NO 643
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 643
gtctctggaa caatt                                                           15

<210> SEQ ID NO 644
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 644
cagttcaaac acaga                                                           15

<210> SEQ ID NO 645
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 645
caaacacaga agaga                                                           15

<210> SEQ ID NO 646
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 646
aacacagaag agatt                                                           15

<210> SEQ ID NO 647
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 647
gggggagaag aaagg                                                           15

```
<210> SEQ ID NO 648
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 648
tcgttttttt ttctt                                                    15

<210> SEQ ID NO 649
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 649 ctttttttc ttttt                                                     15

<210> SEQ ID NO 650
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 650
cctatgctat ggtta                                                    15

<210> SEQ ID NO 651
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 651
agtttactga aagaa                                                    15

<210> SEQ ID NO 652
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 652
actgaaagaa aaaaa                                                    15

<210> SEQ ID NO 653
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 653
ccttattcat atttt                                                    15

<210> SEQ ID NO 654
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 654
cttccttatt catat                                                15

<210> SEQ ID NO 655
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 655
caatccttca atatt                                                15

<210> SEQ ID NO 656
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 656
ggcatttcat tttac                                                15

<210> SEQ ID NO 657
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 657
cattttacaa atatt                                                15

<210> SEQ ID NO 658
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 658
gaaatgaaat aagta                                                15

<210> SEQ ID NO 659
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 659
agatatgcaa gataa                                                15

<210> SEQ ID NO 660
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 660
gcgggcccag caggt                                                15

<210> SEQ ID NO 661
<211> LENGTH: 15
```

```
<212> TYPE: DNA
<213> ORGANISM: Artificial Sequence
<220> FEATURE:
<223> OTHER INFORMATION: Synthetic Oligonucleotide

<400> SEQUENCE: 661
cagtgagtgc cgagt                                                    15

<210> SEQ ID NO 662
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 662
gcccgggcag tgagt                                                    15

<210> SEQ ID NO 663
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 663
tgtccgggcg gcccg                                                    15

<210> SEQ ID NO 664
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 664
cgcgcgtgtg cgagt                                                    15

<210> SEQ ID NO 665
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 665
cttcagacag gctgc                                                    15

<210> SEQ ID NO 666
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 666
acctctgcac ttcag                                                    15

<210> SEQ ID NO 667
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 667
```
cggcgcgggt ccctt                                              15

<210> SEQ ID NO 668
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 668
tggtattcga attat                                              15

<210> SEQ ID NO 669
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 669
cggcctgccc tggta                                              15

<210> SEQ ID NO 670
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 670
tcagagatta tgaaa                                              15

<210> SEQ ID NO 671
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 671
tgttttcaga gatta                                              15

<210> SEQ ID NO 672
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 672
catgtagaaa tgctt                                              15

<210> SEQ ID NO 673
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 673
aaacatgtag aaatg                                              15

<210> SEQ ID NO 674
<211> LENGTH: 15
<212> TYPE: DNA
<213> ORGANISM: Artificial Sequence

```
<220> FEATURE:
<223> OTHER INFORMATION: Synthetic Oligonucleotide

<400> SEQUENCE: 674
ttgataccat ttatg                                                       15

<210> SEQ ID NO 675
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 675
gaactcaatt attat                                                       15

<210> SEQ ID NO 676
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 676
aaaacgactc cacaa                                                       15

<210> SEQ ID NO 677
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 677
ctccgaggaa aaacg                                                       15

<210> SEQ ID NO 678
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 678
gctccgagga aaaac                                                       15

<210> SEQ ID NO 679
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 679
ctcggcggga gaaag                                                       15

<210> SEQ ID NO 680
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 680
gaaccgaaat ttt                                                         13
```

```
<210> SEQ ID NO 681
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 681
gagaagggtg cagat                                                   15

<210> SEQ ID NO 682
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 682
ctctccagat gagaa                                                   15

<210> SEQ ID NO 683
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 683
caggggtccg ctctc                                                   15

<210> SEQ ID NO 684
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 684
tccgggcagc caggg                                                   15

<210> SEQ ID NO 685
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 685
ggggctcgcc tccgg                                                   15

<210> SEQ ID NO 686
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 686
cccccgggaa ggggc                                                   15

<210> SEQ ID NO 687
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 687
cccacccccc gggaa                                                      15

<210> SEQ ID NO 688
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 688
gcgttgccgc ccccac                                                     16

<210> SEQ ID NO 689
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 689
gctgggtcgc gcgtt                                                      15

<210> SEQ ID NO 690
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 690
gcgcaggacc gctgg                                                      15

<210> SEQ ID NO 691
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 691
aggagggagg gtggg                                                      15

<210> SEQ ID NO 692
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 692
cgctggaggc ggagg                                                      15

<210> SEQ ID NO 693
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 693
tggagccgag cgctg                                                      15

<210> SEQ ID NO 694
```

<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 694
ctgccccttt gttgg                                                    15

<210> SEQ ID NO 695
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 695
ctccccgctg cgggc                                                    15

<210> SEQ ID NO 696
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 696
cggctcctcc tcctc                                                    15

<210> SEQ ID NO 697
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 697
ggctcgctcc ttcgg                                                    15

<210> SEQ ID NO 698
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 698
tttgtgcgcg agaga                                                    15

<210> SEQ ID NO 699
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 699
acgactccac aactt                                                    15

<210> SEQ ID NO 700
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 700
gcccgcttcc ctgct                                                      15

<210> SEQ ID NO 701
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 701
cggccggctg ctgct                                                      15

<210> SEQ ID NO 702
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 702
gcgggagaaa gcccg                                                      15

<210> SEQ ID NO 703
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 703
cctcctcgcc cctcg                                                      15

<210> SEQ ID NO 704
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 704
agaggctcct cctcg                                                      15

<210> SEQ ID NO 705
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 705
tcggcttctg gagcc                                                      15

<210> SEQ ID NO 706
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 706
ccgtgattcc ccaat                                                      15

<210> SEQ ID NO 707
<211> LENGTH: 15
<212> TYPE: DNA

<213> ORGANISM: Artificial Sequence
<220> FEATURE:
<223> OTHER INFORMATION: Synthetic Oligonucleotide

<400> SEQUENCE: 707
aggggggcgc cgctc                                              15

<210> SEQ ID NO 708
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 708
aaatgaccca aaaga                                              15

<210> SEQ ID NO 709
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 709
gttttccgtt tgcag                                              15

<210> SEQ ID NO 710
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 710
ccaaacgcta cagag                                              15

<210> SEQ ID NO 711
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 711
caggcaccaa ctttg                                              15

<210> SEQ ID NO 712
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 712
cctggaaggg gcgcg                                              15

<210> SEQ ID NO 713
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 713
cagtcaaagc gcaaa                                              15

<210> SEQ ID NO 714
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 714
ccaaaaacaa aacag                                             15

<210> SEQ ID NO 715
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 715
ttccgccaaa aacaa                                             15

<210> SEQ ID NO 716
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 716
ggaggaggga gggtg                                             15

<210> SEQ ID NO 717
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 717
cgagcgctgg aggcg                                             15

<210> SEQ ID NO 718
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 718
cctgccccTT tgttg                                             15

<210> SEQ ID NO 719
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 719
ggcggctcct cctcc                                             15

<210> SEQ ID NO 720
<211> LENGTH: 15
<212> TYPE: DNA
<213> ORGANISM: Artificial Sequence
<220> FEATURE:

<223> OTHER INFORMATION: Synthetic Oligonucleotide

<400> SEQUENCE: 720
tagacacttc cagaa 15

<210> SEQ ID NO 721
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 721
ttccagaatt gtcct 15

<210> SEQ ID NO 722
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 722
cagaattgtc cttta 15

<210> SEQ ID NO 723
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 723
ctgctggaac tcggc 15

<210> SEQ ID NO 724
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 724
ggccaggctc agctg 15

<210> SEQ ID NO 725
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 725
gcagccagga gcctg 15

<210> SEQ ID NO 726
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 726
actcggccag gctca 15

```
<210> SEQ ID NO 727
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 727
gctggcctgc tggaa                                                    15

<210> SEQ ID NO 728
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 728
tttaaattgt atcgg                                                    15

<210> SEQ ID NO 729
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 729
attgtatcgg gcaaa                                                    15

<210> SEQ ID NO 730
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 730
gattaaaaca aaaga                                                    15

<210> SEQ ID NO 731
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 731
aaaacaaaag aaacc                                                    15

<210> SEQ ID NO 732
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 732
gggataaagg aaggg                                                    15

<210> SEQ ID NO 733
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 733
cactgggata aagga                                                    15

<210> SEQ ID NO 734
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 734
gagccgcccg ctttg                                                    15

<210> SEQ ID NO 735
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 735
tctgggcccc actg                                                     14

<210> SEQ ID NO 736
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 736
caaaaggtct tagct                                                    15

<210> SEQ ID NO 737
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 737
tagctattat tactg                                                    15

<210> SEQ ID NO 738
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 738
actgttgttg tttta                                                    15

<210> SEQ ID NO 739
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 739
accttagagg ttgta                                                    15

<210> SEQ ID NO 740
<211> LENGTH: 15
```

```
<212> TYPE: DNA
<213> ORGANISM: Artificial Sequence
<220> FEATURE:
<223> OTHER INFORMATION: Synthetic Oligonucleotide

<400> SEQUENCE: 740
tacctgaaat tgcag                                                    15

<210> SEQ ID NO 741
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 741
gtcagaaaag ctacc                                                    15

<210> SEQ ID NO 742
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 742
cacgcttggt gtgca                                                    15

<210> SEQ ID NO 743
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 743
ctgtgaatgt gtgaa                                                    15

<210> SEQ ID NO 744
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 744
aacaggaagc acctg                                                    15

<210> SEQ ID NO 745
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 745
cgctccgccc tccagttttt ttttaggagg caacacatt                          39

<210> SEQ ID NO 746
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 746
```

-continued

```
cgctccgccc tccagccttt tttttagga ggcaacacat t        41
```

<210> SEQ ID NO 747
<211> LENGTH: 15
<212> TYPE: DNA
<213> ORGANISM: Homo sapiens

<400> SEQUENCE: 747

```
ctgttataag ctttt        15
```

<210> SEQ ID NO 748
<211> LENGTH: 15
<212> TYPE: DNA
<213> ORGANISM: Homo sapiens

<400> SEQUENCE: 748

```
gttataagct ttttc        15
```

<210> SEQ ID NO 749
<211> LENGTH: 15
<212> TYPE: DNA
<213> ORGANISM: Homo sapiens

<400> SEQUENCE: 749

```
tatctgttat aagct        15
```

<210> SEQ ID NO 750
<211> LENGTH: 15
<212> TYPE: DNA
<213> ORGANISM: Homo sapiens

<400> SEQUENCE: 750

```
agtagatgtt tattt        15
```

<210> SEQ ID NO 751
<211> LENGTH: 15
<212> TYPE: DNA
<213> ORGANISM: Homo sapiens

<400> SEQUENCE: 751

```
taggcaaagg aatag        15
```

<210> SEQ ID NO 752
<211> LENGTH: 15
<212> TYPE: DNA
<213> ORGANISM: Homo sapiens

<400> SEQUENCE: 752

```
ggtaggcaaa ggaat        15
```

<210> SEQ ID NO 753
<211> LENGTH: 15
<212> TYPE: DNA
<213> ORGANISM: Homo sapiens

<400> SEQUENCE: 753

```
ggcaaaggaa tagtt        15
```

<210> SEQ ID NO 754
<211> LENGTH: 15
<212> TYPE: DNA
<213> ORGANISM: Homo sapiens

<400> SEQUENCE: 754
gaaatgacac ccagt                                                     15

<210> SEQ ID NO 755
<211> LENGTH: 15
<212> TYPE: DNA
<213> ORGANISM: Homo sapiens

<400> SEQUENCE: 755
aaatgacacc cagta                                                     15

<210> SEQ ID NO 756
<211> LENGTH: 15
<212> TYPE: DNA
<213> ORGANISM: Homo sapiens

<400> SEQUENCE: 756
ggcaatggaa tgaaa                                                     15

<210> SEQ ID NO 757
<211> LENGTH: 15
<212> TYPE: DNA
<213> ORGANISM: Homo sapiens

<400> SEQUENCE: 757
caatggaatg aaatg                                                     15

<210> SEQ ID NO 758
<211> LENGTH: 15
<212> TYPE: DNA
<213> ORGANISM: Homo sapiens

<400> SEQUENCE: 758
atggaatgaa atgac                                                     15

<210> SEQ ID NO 759
<211> LENGTH: 15
<212> TYPE: DNA
<213> ORGANISM: Homo sapiens

<400> SEQUENCE: 759
gtttcaagta cccgc                                                     15

<210> SEQ ID NO 760
<211> LENGTH: 15
<212> TYPE: DNA
<213> ORGANISM: Homo sapiens

<400> SEQUENCE: 760
gaccggagaa cgaaa                                                     15

<210> SEQ ID NO 761
<211> LENGTH: 15
<212> TYPE: DNA
<213> ORGANISM: Homo sapiens

<400> SEQUENCE: 761
ctttggaagg tgttt                                                     15

<210> SEQ ID NO 762
<211> LENGTH: 15
<212> TYPE: DNA
<213> ORGANISM: Homo sapiens

```
<400> SEQUENCE: 762
tttctttgga aggtg                                                    15

<210> SEQ ID NO 763
<211> LENGTH: 15
<212> TYPE: DNA
<213> ORGANISM: Homo sapiens

<400> SEQUENCE: 763
agttaatccc cgccg                                                    15

<210> SEQ ID NO 764
<211> LENGTH: 15
<212> TYPE: DNA
<213> ORGANISM: Homo sapiens

<400> SEQUENCE: 764
tcctgcaaaa tgtca                                                    15

<210> SEQ ID NO 765
<211> LENGTH: 15
<212> TYPE: DNA
<213> ORGANISM: Homo sapiens

<400> SEQUENCE: 765
ccccgcagtc tccac                                                    15

<210> SEQ ID NO 766
<211> LENGTH: 15
<212> TYPE: DNA
<213> ORGANISM: Homo sapiens

<400> SEQUENCE: 766
tctccaccct cctcc                                                    15

<210> SEQ ID NO 767
<211> LENGTH: 15
<212> TYPE: DNA
<213> ORGANISM: Homo sapiens

<400> SEQUENCE: 767
gagcgccggc gactg                                                    15

<210> SEQ ID NO 768
<211> LENGTH: 15
<212> TYPE: DNA
<213> ORGANISM: Homo sapiens

<400> SEQUENCE: 768
aggatgtgcg ccttc                                                    15

<210> SEQ ID NO 769
<211> LENGTH: 14
<212> TYPE: DNA
<213> ORGANISM: Homo sapiens

<400> SEQUENCE: 769
ggcgcagcga ggaa                                                     14

<210> SEQ ID NO 770
<211> LENGTH: 15
<212> TYPE: DNA
<213> ORGANISM: Homo sapiens
```

```
<400> SEQUENCE: 770
tttcactgac atctc                                                      15

<210> SEQ ID NO 771
<211> LENGTH: 15
<212> TYPE: DNA
<213> ORGANISM: Homo sapiens

<400> SEQUENCE: 771
ggtggtctga gcccc                                                      15

<210> SEQ ID NO 772
<211> LENGTH: 15
<212> TYPE: DNA
<213> ORGANISM: Homo sapiens

<400> SEQUENCE: 772
gggcctgcca gggga                                                      15

<210> SEQ ID NO 773
<211> LENGTH: 15
<212> TYPE: DNA
<213> ORGANISM: Homo sapiens

<400> SEQUENCE: 773
accgagtgac agtcg                                                      15

<210> SEQ ID NO 774
<211> LENGTH: 15
<212> TYPE: DNA
<213> ORGANISM: Homo sapiens

<400> SEQUENCE: 774
gtctgggacc gagtg                                                      15

<210> SEQ ID NO 775
<211> LENGTH: 15
<212> TYPE: DNA
<213> ORGANISM: Homo sapiens

<400> SEQUENCE: 775
tgggaccgag tgaca                                                      15

<210> SEQ ID NO 776
<211> LENGTH: 15
<212> TYPE: DNA
<213> ORGANISM: Homo sapiens

<400> SEQUENCE: 776
gcagaggtgt gttca                                                      15

<210> SEQ ID NO 777
<211> LENGTH: 15
<212> TYPE: DNA
<213> ORGANISM: Homo sapiens

<400> SEQUENCE: 777
cggcagaggt gtgtt                                                      15

<210> SEQ ID NO 778
<211> LENGTH: 15
<212> TYPE: DNA
```

```
<213> ORGANISM: Homo sapiens

<400> SEQUENCE: 778
gggcagacgg ggtca                                                    15

<210> SEQ ID NO 779
<211> LENGTH: 15
<212> TYPE: DNA
<213> ORGANISM: Homo sapiens

<400> SEQUENCE: 779
ctctggtttg gaaaa                                                    15

<210> SEQ ID NO 780
<211> LENGTH: 15
<212> TYPE: DNA
<213> ORGANISM: Homo sapiens

<400> SEQUENCE: 780
ctggtttgga aaaca                                                    15

<210> SEQ ID NO 781
<211> LENGTH: 15
<212> TYPE: DNA
<213> ORGANISM: Homo sapiens

<400> SEQUENCE: 781
gtttggaaaa caaaa                                                    15

<210> SEQ ID NO 782
<211> LENGTH: 15
<212> TYPE: DNA
<213> ORGANISM: Homo sapiens

<400> SEQUENCE: 782
ggaaaacaaa agaac                                                    15

<210> SEQ ID NO 783
<211> LENGTH: 15
<212> TYPE: DNA
<213> ORGANISM: Homo sapiens

<400> SEQUENCE: 783
gaaaacaaaa gaacc                                                    15

<210> SEQ ID NO 784
<211> LENGTH: 15
<212> TYPE: DNA
<213> ORGANISM: Homo sapiens

<400> SEQUENCE: 784
tttggaaaac aaaag                                                    15

<210> SEQ ID NO 785
<211> LENGTH: 15
<212> TYPE: DNA
<213> ORGANISM: Homo sapiens

<400> SEQUENCE: 785
tggaaaacaa agaa                                                     15

<210> SEQ ID NO 786
<211> LENGTH: 15
```

```
<212> TYPE: DNA
<213> ORGANISM: Homo sapiens

<400> SEQUENCE: 786 tctgggcag cagga                                                    15

<210> SEQ ID NO 787
<211> LENGTH: 15
<212> TYPE: DNA
<213> ORGANISM: Homo sapiens

<400> SEQUENCE: 787
atagaaagga acctt                                                   15

<210> SEQ ID NO 788
<211> LENGTH: 15
<212> TYPE: DNA
<213> ORGANISM: Homo sapiens

<400> SEQUENCE: 788
tagaaaggaa ccttg                                                   15

<210> SEQ ID NO 789
<211> LENGTH: 15
<212> TYPE: DNA
<213> ORGANISM: Homo sapiens

<400> SEQUENCE: 789
attaacaatc cttcc                                                   15

<210> SEQ ID NO 790
<211> LENGTH: 15
<212> TYPE: DNA
<213> ORGANISM: Homo sapiens

<400> SEQUENCE: 790
cttccctgct aaatg                                                   15

<210> SEQ ID NO 791
<211> LENGTH: 15
<212> TYPE: DNA
<213> ORGANISM: Homo sapiens

<400> SEQUENCE: 791
ccctgctaaa tgata                                                   15

<210> SEQ ID NO 792
<211> LENGTH: 15
<212> TYPE: DNA
<213> ORGANISM: Homo sapiens

<400> SEQUENCE: 792
tgatataaac ataga                                                   15

<210> SEQ ID NO 793
<211> LENGTH: 15
<212> TYPE: DNA
<213> ORGANISM: Homo sapiens

<400> SEQUENCE: 793
tccccgggac tgaac                                                   15

<210> SEQ ID NO 794
```

```
<211> LENGTH: 16
<212> TYPE: DNA
<213> ORGANISM: Homo sapiens

<400> SEQUENCE: 794
tacaacttct ttgaat                                                     16

<210> SEQ ID NO 795
<211> LENGTH: 15
<212> TYPE: DNA
<213> ORGANISM: Homo sapiens

<400> SEQUENCE: 795
tctatcactt ccccg                                                      15

<210> SEQ ID NO 796
<211> LENGTH: 15
<212> TYPE: DNA
<213> ORGANISM: Homo sapiens

<400> SEQUENCE: 796
tcctgggcac ccgta                                                      15

<210> SEQ ID NO 797
<211> LENGTH: 15
<212> TYPE: DNA
<213> ORGANISM: Homo sapiens

<400> SEQUENCE: 797
tttctgtaca catca                                                      15

<210> SEQ ID NO 798
<211> LENGTH: 15
<212> TYPE: DNA
<213> ORGANISM: Homo sapiens

<400> SEQUENCE: 798
acagccactg aaaat                                                      15

<210> SEQ ID NO 799
<211> LENGTH: 15
<212> TYPE: DNA
<213> ORGANISM: Homo sapiens

<400> SEQUENCE: 799
ttcacagcca ctgaa                                                      15

<210> SEQ ID NO 800
<211> LENGTH: 15
<212> TYPE: DNA
<213> ORGANISM: Homo sapiens

<400> SEQUENCE: 800
taaagaaatg agttt                                                      15

<210> SEQ ID NO 801
<211> LENGTH: 15
<212> TYPE: DNA
<213> ORGANISM: Homo sapiens

<400> SEQUENCE: 801
acatttaaag aaatg                                                      15
```

```
<210> SEQ ID NO 802
<211> LENGTH: 15
<212> TYPE: DNA
<213> ORGANISM: Homo sapiens

<400> SEQUENCE: 802
aagaaatgag tttgt                                                    15

<210> SEQ ID NO 803
<211> LENGTH: 15
<212> TYPE: DNA
<213> ORGANISM: Homo sapiens

<400> SEQUENCE: 803
tgccattatg tttgc                                                    15

<210> SEQ ID NO 804
<211> LENGTH: 15
<212> TYPE: DNA
<213> ORGANISM: Homo sapiens

<400> SEQUENCE: 804
tcctgttgcc attat                                                    15

<210> SEQ ID NO 805
<211> LENGTH: 15
<212> TYPE: DNA
<213> ORGANISM: Homo sapiens

<400> SEQUENCE: 805
gaaaatcctg ttgcc                                                    15

<210> SEQ ID NO 806
<211> LENGTH: 15
<212> TYPE: DNA
<213> ORGANISM: Homo sapiens

<400> SEQUENCE: 806
ctgttgccat tatgt                                                    15

<210> SEQ ID NO 807
<211> LENGTH: 15
<212> TYPE: DNA
<213> ORGANISM: Homo sapiens

<400> SEQUENCE: 807
tagaattgaa gtaac                                                    15

<210> SEQ ID NO 808
<211> LENGTH: 15
<212> TYPE: DNA
<213> ORGANISM: Homo sapiens

<400> SEQUENCE: 808
tgaagtaaca atcaa                                                    15

<210> SEQ ID NO 809
<211> LENGTH: 15
<212> TYPE: DNA
<213> ORGANISM: Homo sapiens

<400> SEQUENCE: 809
aagtaacaat caatt                                                    15
```

```
<210> SEQ ID NO 810
<211> LENGTH: 15
<212> TYPE: DNA
<213> ORGANISM: Homo sapiens

<400> SEQUENCE: 810
tcatcaagat ttctt                                                    15

<210> SEQ ID NO 811
<211> LENGTH: 15
<212> TYPE: DNA
<213> ORGANISM: Homo sapiens

<400> SEQUENCE: 811
tatctagccc aatat                                                    15

<210> SEQ ID NO 812
<211> LENGTH: 15
<212> TYPE: DNA
<213> ORGANISM: Homo sapiens

<400> SEQUENCE: 812
ttctatctag cccaa                                                    15

<210> SEQ ID NO 813
<211> LENGTH: 33
<212> TYPE: DNA
<213> ORGANISM: Homo sapiens

<400> SEQUENCE: 813
ctccgccctc cagtttttat tattttgctt ttt                                33

<210> SEQ ID NO 814
<211> LENGTH: 31
<212> TYPE: DNA
<213> ORGANISM: Homo sapiens

<400> SEQUENCE: 814
ccgccctcca gtttttatta ttttgctttt t                                  31

<210> SEQ ID NO 815
<211> LENGTH: 29
<212> TYPE: DNA
<213> ORGANISM: Homo sapiens

<400> SEQUENCE: 815
gccctccagt tttattatt ttgcttttt                                      29

<210> SEQ ID NO 816
<211> LENGTH: 33
<212> TYPE: DNA
<213> ORGANISM: Homo sapiens

<400> SEQUENCE: 816
cgctccgccc tccagttttt attatttgc ttt                                 33

<210> SEQ ID NO 817
<211> LENGTH: 31
<212> TYPE: DNA
<213> ORGANISM: Homo sapiens

<400> SEQUENCE: 817
cgctccgccc tccagttttt attatttgc t                                   31
```

<210> SEQ ID NO 818
<211> LENGTH: 29
<212> TYPE: DNA
<213> ORGANISM: Homo sapiens

<400> SEQUENCE: 818
cgctccgccc tccagttttt attattttg                                29

<210> SEQ ID NO 819
<211> LENGTH: 31
<212> TYPE: DNA
<213> ORGANISM: Homo sapiens

<400> SEQUENCE: 819
ctccgccctc cagttttat tattttgctt t                              31

<210> SEQ ID NO 820
<211> LENGTH: 27
<212> TYPE: DNA
<213> ORGANISM: Homo sapiens

<400> SEQUENCE: 820
ccgccctcca gtttttatta ttttgct                                  27

<210> SEQ ID NO 821
<211> LENGTH: 25
<212> TYPE: DNA
<213> ORGANISM: Homo sapiens

<400> SEQUENCE: 821
gccctccagt ttttattatt ttgct                                    25

<210> SEQ ID NO 822
<211> LENGTH: 23
<212> TYPE: DNA
<213> ORGANISM: Homo sapiens

<400> SEQUENCE: 822
ccctccagtt tttattattt tgc                                      23

<210> SEQ ID NO 823
<211> LENGTH: 21
<212> TYPE: DNA
<213> ORGANISM: Homo sapiens

<400> SEQUENCE: 823
cctccagttt ttattatttt g                                        21

<210> SEQ ID NO 824
<211> LENGTH: 29
<212> TYPE: DNA
<213> ORGANISM: Homo sapiens

<400> SEQUENCE: 824
gctccgccct ccagattatt ttgctttt                                 29

<210> SEQ ID NO 825
<211> LENGTH: 27
<212> TYPE: DNA
<213> ORGANISM: Homo sapiens

<400> SEQUENCE: 825

```
tccgccctcc agattatttt gctttt                                            27

<210> SEQ ID NO 826
<211> LENGTH: 25
<212> TYPE: DNA
<213> ORGANISM: Homo sapiens

<400> SEQUENCE: 826
cgccctccag attatttgc ttttt                                              25

<210> SEQ ID NO 827
<211> LENGTH: 23
<212> TYPE: DNA
<213> ORGANISM: Homo sapiens

<400> SEQUENCE: 827
ccctccagat tattttgctt ttt                                               23

<210> SEQ ID NO 828
<211> LENGTH: 27
<212> TYPE: DNA
<213> ORGANISM: Homo sapiens

<400> SEQUENCE: 828
gctccgccct ccagattatt ttgcttt                                           27

<210> SEQ ID NO 829
<211> LENGTH: 25
<212> TYPE: DNA
<213> ORGANISM: Homo sapiens

<400> SEQUENCE: 829
gctccgccct ccagattatt ttgct                                             25

<210> SEQ ID NO 830
<211> LENGTH: 23
<212> TYPE: DNA
<213> ORGANISM: Homo sapiens

<400> SEQUENCE: 830
gctccgccct ccagattatt ttg                                               23

<210> SEQ ID NO 831
<211> LENGTH: 25
<212> TYPE: DNA
<213> ORGANISM: Homo sapiens

<400> SEQUENCE: 831
tccgccctcc agattatttt gcttt                                             25

<210> SEQ ID NO 832
<211> LENGTH: 21
<212> TYPE: DNA
<213> ORGANISM: Homo sapiens

<400> SEQUENCE: 832
cgccctccag attatttgc t                                                  21

<210> SEQ ID NO 833
<211> LENGTH: 19
<212> TYPE: DNA
<213> ORGANISM: Homo sapiens

<400> SEQUENCE: 833
```

```
gccctccaga ttattttgc                                              19

<210> SEQ ID NO 834
<211> LENGTH: 17
<212> TYPE: DNA
<213> ORGANISM: Homo sapiens

<400> SEQUENCE: 834
ccctccagat tattttg                                                17

<210> SEQ ID NO 835
<211> LENGTH: 15
<212> TYPE: DNA
<213> ORGANISM: Homo sapiens

<400> SEQUENCE: 835
ctccagatta ttttg                                                  15

<210> SEQ ID NO 836
<211> LENGTH: 35
<212> TYPE: DNA
<213> ORGANISM: Homo sapiens

<400> SEQUENCE: 836
cgctccgccc tccagttttt attattttgc ttttt                            35

<210> SEQ ID NO 837
<211> LENGTH: 28
<212> TYPE: DNA
<213> ORGANISM: Mus musculus

<400> SEQUENCE: 837
agttcaagga tcagccattt tggaaagg                                    28

<210> SEQ ID NO 838
<211> LENGTH: 25
<212> TYPE: DNA
<213> ORGANISM: Mus musculus

<400> SEQUENCE: 838
tcaaggatca gccattttgg aaagg                                       25

<210> SEQ ID NO 839
<211> LENGTH: 23
<212> TYPE: DNA
<213> ORGANISM: Mus musculus

<400> SEQUENCE: 839
aaggatcagc cattttggaa agg                                         23

<210> SEQ ID NO 840
<211> LENGTH: 21
<212> TYPE: DNA
<213> ORGANISM: Mus musculus

<400> SEQUENCE: 840
ggatcagcca ttttggaaag g                                           21

<210> SEQ ID NO 841
<211> LENGTH: 25
<212> TYPE: DNA
<213> ORGANISM: Mus musculus
```

```
<400> SEQUENCE: 841
agttcaagga tcagccattt tggaa                                          25

<210> SEQ ID NO 842
<211> LENGTH: 23
<212> TYPE: DNA
<213> ORGANISM: Mus musculus

<400> SEQUENCE: 842
agttcaagga tcagccattt tgg                                            23

<210> SEQ ID NO 843
<211> LENGTH: 27
<212> TYPE: DNA
<213> ORGANISM: Mus musculus

<400> SEQUENCE: 843
gttcaaggat cagccatttt ggaaagg                                        27

<210> SEQ ID NO 844
<211> LENGTH: 23
<212> TYPE: DNA
<213> ORGANISM: Mus musculus

<400> SEQUENCE: 844
tcaaggatca gccattttgg aaa                                            23

<210> SEQ ID NO 845
<211> LENGTH: 21
<212> TYPE: DNA
<213> ORGANISM: Mus musculus

<400> SEQUENCE: 845
aaggatcagc cattttggaa a                                              21

<210> SEQ ID NO 846
<211> LENGTH: 19
<212> TYPE: DNA
<213> ORGANISM: Mus musculus

<400> SEQUENCE: 846
aggatcagcc attttggaa                                                 19

<210> SEQ ID NO 847
<211> LENGTH: 17
<212> TYPE: DNA
<213> ORGANISM: Mus musculus

<400> SEQUENCE: 847
ggatcagcca ttttgga                                                   17

<210> SEQ ID NO 848
<211> LENGTH: 28
<212> TYPE: DNA
<213> ORGANISM: Mus musculus

<400> SEQUENCE: 848
ctccgacagt ctgccatttt ggaaaggt                                       28

<210> SEQ ID NO 849
<211> LENGTH: 25
<212> TYPE: DNA
<213> ORGANISM: Mus musculus
```

```
<400> SEQUENCE: 849
cgacagtctg ccattttgga aaggt                                              25

<210> SEQ ID NO 850
<211> LENGTH: 23
<212> TYPE: DNA
<213> ORGANISM: Mus musculus

<400> SEQUENCE: 850
acagtctgcc attttggaaa ggt                                                23

<210> SEQ ID NO 851
<211> LENGTH: 25
<212> TYPE: DNA
<213> ORGANISM: Mus musculus

<400> SEQUENCE: 851
ctccgacagt ctgccatttt ggaaa                                              25

<210> SEQ ID NO 852
<211> LENGTH: 23
<212> TYPE: DNA
<213> ORGANISM: Mus musculus

<400> SEQUENCE: 852
ctccgacagt ctgccatttt gga                                                23

<210> SEQ ID NO 853
<211> LENGTH: 21
<212> TYPE: DNA
<213> ORGANISM: Mus musculus

<400> SEQUENCE: 853
ctccgacagt ctgccatttt g                                                  21

<210> SEQ ID NO 854
<211> LENGTH: 27
<212> TYPE: DNA
<213> ORGANISM: Mus musculus

<400> SEQUENCE: 854
ctccgacagt ctgccatttt ggaaagg                                            27

<210> SEQ ID NO 855
<211> LENGTH: 23
<212> TYPE: DNA
<213> ORGANISM: Mus musculus

<400> SEQUENCE: 855
ccgacagtct gccattttgg aaa                                                23

<210> SEQ ID NO 856
<211> LENGTH: 19
<212> TYPE: DNA
<213> ORGANISM: Mus musculus

<400> SEQUENCE: 856
gacagtctgc cattttgga                                                     19

<210> SEQ ID NO 857
<211> LENGTH: 17
<212> TYPE: DNA
```

```
<213> ORGANISM: Mus musculus

<400> SEQUENCE: 857
acagtctgcc attttgg                                              17

<210> SEQ ID NO 858
<211> LENGTH: 30
<212> TYPE: DNA
<213> ORGANISM: Mus musculus

<400> SEQUENCE: 858
cggagctctc cgacacattt tggaaaggtt                                30

<210> SEQ ID NO 859
<211> LENGTH: 29
<212> TYPE: DNA
<213> ORGANISM: Mus musculus

<400> SEQUENCE: 859
ggagctctcc gacacatttt ggaaaggtt                                 29

<210> SEQ ID NO 860
<211> LENGTH: 25
<212> TYPE: DNA
<213> ORGANISM: Mus musculus

<400> SEQUENCE: 860
agctctccga cacattttgg aaagg                                     25

<210> SEQ ID NO 861
<211> LENGTH: 21
<212> TYPE: DNA
<213> ORGANISM: Mus musculus

<400> SEQUENCE: 861
ctctccgaca cattttggaa a                                         21

<210> SEQ ID NO 862
<211> LENGTH: 19
<212> TYPE: DNA
<213> ORGANISM: Mus musculus

<400> SEQUENCE: 862
tctccgacac attttggaa                                            19

<210> SEQ ID NO 863
<211> LENGTH: 17
<212> TYPE: DNA
<213> ORGANISM: Mus musculus

<400> SEQUENCE: 863
ctccgacaca ttttgga                                              17

<210> SEQ ID NO 864
<211> LENGTH: 15
<212> TYPE: DNA
<213> ORGANISM: Mus musculus

<400> SEQUENCE: 864
tccgacacat tttgg                                                15

<210> SEQ ID NO 865
<211> LENGTH: 15
```

```
<212> TYPE: DNA
<213> ORGANISM: Homo sapiens

<400> SEQUENCE: 865
cgctccgccc tccag                                                    15

<210> SEQ ID NO 866
<211> LENGTH: 15
<212> TYPE: DNA
<213> ORGANISM: Homo sapiens

<400> SEQUENCE: 866
attattttgc tttttt                                                   15

<210> SEQ ID NO 867
<211> LENGTH: 29
<212> TYPE: RNA
<213> ORGANISM: Artificial Sequence
<220> FEATURE:
<223> OTHER INFORMATION: Synthetic Oligonucleotide

<400> SEQUENCE: 867
aaaaaaaaaa aaaaaaaaaa aaaaaaaaa                                     29

<210> SEQ ID NO 868
<211> LENGTH: 11
<212> TYPE: RNA
<213> ORGANISM: Artificial Sequence
<220> FEATURE:
<223> OTHER INFORMATION: Synthetic Oligonucleotide

<400> SEQUENCE: 868
aaaaaaaaaa a                                                        11
```

NANOPARTICLE FORMULATIONS FOR DELIVERY OF NUCLEIC ACID COMPLEXES

CROSS-REFERENCE TO RELATED APPLICATIONS

This application is a national stage filing under U.S.C. § 371 of PCT International Application No. PCT/US2016/058842, with an international filing date of Oct. 26, 2016, which claims the benefit under 35 U.S.C. § 119 (e) of U.S. Provisional Application No. U.S. 62/246,305, filed on Oct. 26, 2015, U.S. Provisional Application No. U.S. 62/246,290, filed on Oct. 26, 2015, U.S. Provisional Application No. U.S. 62/288,154, filed on Jan. 28, 2016, and U.S. Provisional Application No. U.S. 62/288,128, filed on Jan. 28, 2016, the contents of each of which are incorporated herein by reference in its entirety.

FIELD OF THE DISCLOSURE

The disclosure relates to particle formulations, e.g., nanoparticle formulations, as well as methods of using such formulations for delivering oligonucleotides and/or synthetic RNA.

BACKGROUND OF THE DISCLOSURE

A considerable portion of human diseases can be treated by selectively altering protein and/or RNA levels of disease-associated transcription units (noncoding RNAs, protein-coding RNAs or other regulatory coding or noncoding genomic regions). Methods for inhibiting the expression of genes are known in the art and include, for example, antisense, RNAi and miRNA mediated approaches. Such methods may involve blocking translation of mRNAs or causing degradation of target RNAs. However, limited approaches are available for increasing the expression of genes. Furthermore, there is a need for effective formulation and delivery of agents useful for increasing the expression of genes in a subject.

SUMMARY OF THE DISCLOSURE

Aspects of the disclosure described herein relate to formulations and methods for delivery of a stabilizing oligonucleotide that is useful for modulating nucleic acids. In some embodiments, formulations and methods provided herein are useful for protecting RNAs (e.g., RNA transcripts) from degradation (e.g., exonuclease mediated degradation). In some embodiments, the protected RNAs are present outside of cells. In some embodiments, the protected RNAs are present in cells. In some embodiments, formulations and methods are provided that are useful for posttranscriptionally altering protein and/or RNA levels in a targeted manner. In some embodiments, methods disclosed herein involve reducing or preventing degradation or processing of targeted RNAs thereby elevating steady state levels of the targeted RNAs, e.g., in cells. In some embodiments, methods disclosed herein may also or alternatively involve increasing translation or increasing transcription of targeted RNAs, thereby elevating levels of RNA and/or protein levels in a targeted manner. In some embodiments, formulations and methods provided herein are useful for delivering a stabilizing oligonucleotide to a cell or tissue of interest.

Aspects of the disclosure relate to a recognition that certain RNA degradation is mediated by exonucleases. In some embodiments, exonucleases may destroy RNA from its 3' end and/or 5' end. As used herein, the term "stabilizing oligonucleotide" refers to an oligonucleotide (oligo) that hybridizes with RNA at or near one or both ends. Without wishing to be bound by theory, in some embodiments, it is believed that one or both ends of RNA can be protected from exonuclease enzyme activity by contacting the RNA with such stabilizing oligonucleotides, thereby increasing stability and/or levels of the RNA. The ability to increase stability and/or levels of a RNA by targeting the RNA at or near one or both ends, as disclosed herein, is surprising in part because of the presence of endonucleases (e.g., in cells) capable of destroying the RNA through internal cleavage. Moreover, in some embodiments, it is surprising that a 5' targeting oligonucleotide is effective alone (e.g., not in combination with a 3' targeting oligonucleotide or in the context of a pseudocircularization oligonucleotide) at stabilizing RNAs or increasing RNA levels because in cells, for example, 3' end processing exonucleases may be dominant (e.g., compared with 5' end processing exonucleases). However, in some embodiments, 3' targeting oligonucleotides are used in combination with 5' targeting oligonucleotides, or alone, to stabilize a target RNA.

In some embodiments, where a targeted RNA is protein-coding, increases in steady state levels of the RNA result in concomitant increases in levels of the encoded protein. Thus, in some embodiments, stabilizing oligonucleotides (including 5'-targeting, 3'-targeting and pseudocircularization oligonucleotides) are provided herein that when delivered to cells increase protein levels of target RNAs. In some embodiments, not only are target RNA levels increased but the resulting translation products are also increased. In some embodiments, this result is surprising in part because of an understanding that for translation to occur ribosomal machinery requires access to certain regions of the RNA (e.g., the 5' cap region, start codon, etc.) to facilitate translation.

In some embodiments, where the targeted RNA is non-coding, increases in steady state levels of the non-coding RNA result in concomitant increases activity associated with the non-coding RNA. For example, in instances where the non-coding RNA is an miRNA, increases in steady state levels of the miRNA may result in increased degradation of mRNAs targeted by the miRNA.

In some embodiments, stabilizing oligonucleotides are provided with chemistries suitable for delivery, hybridization and stability within cells to target and stabilize RNA transcripts. Furthermore, in some embodiments, stabilizing oligonucleotide chemistries are provided that are useful for controlling the pharmacokinetics, biodistribution, bioavailability and/or efficacy of the oligonucleotides.

In some aspects of the disclosure, methods are provided for stabilizing a synthetic RNA (e.g., a synthetic RNA that is to be delivered to a cell). In some embodiments, the methods involve contacting a synthetic RNA with one or more stabilizing oligonucleotides that bind to a 5' region of the synthetic RNA and a 3' region of the synthetic RNA and that when bound to the synthetic RNA form a circularized product with the synthetic RNA. In some embodiments, the synthetic RNA is contacted with the one or more stabilizing oligonucleotides outside of a cell. Aspects of the disclosure relate to a formulation comprising: a single stranded synthetic nucleic acid, one or more stabilizing oligonucleotides complementary with the single stranded synthetic nucleic acid, and a particle. In some embodiments, the single stranded synthetic nucleic acid is a synthetic RNA.

In other aspects of the disclosure, methods are provided for stabilizing a nucleic acid in a cell (e.g., a messenger RNA present in a cell). In some embodiments, the methods involve contacting a messenger RNA in a cell with one or more stabilizing oligonucleotides that bind to a 5' region of the RNA and a 3' region of the messenger RNA and that when bound to the messenger RNA form a circularized product with the messenger RNA. Accordingly, aspects of the disclosure also relate to a formulation comprising: one or more stabilizing oligonucleotides, and a particle. In some embodiments, the particle is a nanoparticle. In some embodiments, the nanoparticle is a lipid nanoparticle.

In some embodiments, the particle is a nanoparticle. In some embodiments, the nanoparticle is a lipid nanoparticle.

In some embodiments, the lipid nanoparticle includes: (a) one or more cationic lipids, (b) one or more non-cationic lipids, (c) one or more conjugated lipids that inhibits aggregation of particles, or a combination thereof. In some embodiments, the lipid nanoparticle includes (a) one or more cationic lipids. In some embodiments, the lipid nanoparticle includes (a) one or more cationic lipid and (b) one or more non-cationic lipids. In some embodiments, the lipid nanoparticle includes (a) one or more cationic lipids, (b) one or more non-cationic lipids, and (c) one or more conjugated lipids that inhibit aggregation of particle.

In some embodiments, the lipid nanoparticle includes a cationic lipid selected from N,N-dioleyl-N,N-dimethylammonium chloride (DODAC), N,N-distearyl-N,N-dimethylammonium bromide (DDAB), N—(I-(2,3-dioleyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9, 12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino) ethyl)piperazin-1-yl)ethylazanediyl)didodecan-2-ol (Tech G1), 2,2-Dilinoleyl-4-dimethylaminoethyl-[1,3]-dioxolane, β-L-arginyl-2,3-L-diaminopropionic acid-N-palmityl-N-oleylamide trihydrochloride, N',N'-dioctadecyl-N-4,8-diaza-10-aminodecanoylglycine amide[71], 1,2-dilinoleyloxy-3-dimethylaminopropane, DLin-KC2-DMA, amino lipid 2,2-dilinoleyl-4-dimethylaminoethyl-[1,3]-dioxolane (DLin-KC2-DMA, 1), 1,2-distearloxy-/V,N-dimethylaminopropane (DSDMA), dilinoleylmethyl-4-dimethylaminobutyrate (DLin-MC3-DMA), DLin-D-DMA, C12-200, 98N12-5, (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimethylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1 S,2R)-2-octylcyclopropyl]henicosan-10-amine,N,N-dimeth-yl-1-[(1S,2S)-2-{[(1R,2R)-2-pentylcyclopropyl] methyl}cyclopropyl]nonadecan-10-amine,N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl] heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propa-n-2-amine, S—N,N-dimethyl-1-[(9Z,12Z)-octadeca-9,12-dien-1-yloxy]-3-(octy-loxy) propan-2-amine, 1-{2-[(9Z,12Z)-octadeca-9,12-dien-1-yloxy]-1-Roctyloxy)methyl]ethyl}pyrro-lidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azet-idine, (2S)-1-(hexyloxy)-N,N-dimethyl-3-[(9Z,12Z)-octadeca-9,12-dien-1-ylo-xy]propan-2-amine, (2S)-1-(heptyloxy)-N,N-dimethyl-3-[(9Z,12Z)-octadeca-9,12-dien-1-yloxy]pr-opan-2-amine, N,N-dimethyl-1-(nonyloxy)-3-[(9Z,12Z)-octadeca-9,12-dien-1-yloxy] propan-2-amine, N,N-dimethyl-1-[(9Z)-octadec-9-en-1-yloxy]-3-(octyloxy)propan-2-am-ine; (2S)—N,N-dimethyl-1-[(6Z,9Z,12Z)-octadeca-6,9,12-trien-1-yloxy]-3-(o-ctyloxy)propan-2-amine, (2 S)-1-[(11Z,14Z)-icosa-11,14-dien-1-yloxy]-N,N-dimethyl-3-(pentyloxy)propa-n-2-amine, (2S)-1-(hexyloxy)-3-[(11Z,14Z)-icosa-11,14-dien-1-yloxy]-N,N-di-methylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)pr-opan-2-amine, (2S)-1-[(13Z,16Z)- docosa-13,16-dien-1-yloxy]-3-(hexyloxy)-N,N-dimethylpro-pan-2-amine, (2S)-1-[(13Z)-docos-13-en-1-yloxy]-3-(hexyloxy)-N,N-dimethylpropan-2-amin-e, 1-[(13Z)-docos-13-en-1-yloxy]-N,N-dimethyl-3-(octyloxy) propan-2-amine, 1-[(9Z)-hexadec-9-en-1-yloxy]-N,N-dimethyl-3-(octyloxy)propan-2-amine, (2R)—N,N-dimethyl-H (1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-di-en-1-yloxy]propan-2-amine, N,N-dimethyl-1-(octyloxy)-3-({8-[(1S, 2S)-2-{[(1R,2R)-2-pentylcyclopropyl]-methyl}cyclopropyl]octyl}oxy)propan-2-amine, N,N-dimethyl-1-{[8-(2-oclylcyclopropyl)octyl]oxy}-3-(octyloxy)propan-2-am-ine and (11E,20Z,23Z)—N,N-dimethylnonacosa-11,20,2-trien-10-amine, 5-carboxyspermylglycine dioctaoleoylamide ("DOGS"), dipalmitoylphosphatidylethanolamine 5-carboxyspermyl-amide ("DPPES"), 1,2-dimyristyloxypropyl-3-dimethyl-hydroxy ethyl ammonium bromide (DMRIE), DMRIE-HP, Lipofectamine (DOSPA), 3b-(N—(N',N'-dimethylamino-ethane)-carbamoyl)cholesterol ("DC-Choi"), N-(1,2-dimyhstyloxyprop-3-yl)-N,N-dimethyl-N-hydroxyethyl ammonium bromide ("DMRIE"), 1,2-Dioleoyl-3-dimethylammonium-propane ("DODAP"), DMDMA cationic lipid-based transfection reagents TransIT-TKO, LIPOFECTIN, Lipofectamine, OLIGOFECTAMINE or DHARMAFECT, DSDMA, DODMA, DLinDMA, DLenDMA, gamma-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, y-DLen-C2K-DMA, DLin-M-C2-DMA (also known as MC2), DLin-M-C3-DMA (also known as MC3) and (DLin-MP-DMA)(also known as 1-B11), or a mixture thereof.

In some embodiments, the lipid nanoparticle includes a non-cationic lipid, wherein the non-cationic lipid is an anionic lipid. In some embodiments, the lipid nanoparticle includes a non-cationic lipid, wherein the non-cationic lipid is a neutral lipid.

In some embodiments, the lipid nanoparticle includes a non-cationic lipid selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids, or a mixture thereof.

In some embodiments, the anionic lipid is 1,2-dioleoyl-sn-glycero-3-phospho-(1'-rac-glycerol).

In some embodiments, the neutral lipid is 1,2-dioleoyl-sn-glycero-3-phosphatidylcholine.

In some embodiments, the lipid nanoparticle includes a conjugated lipid that inhibits aggregation of particles. In some embodiments, the conjugated lipid is a PEG lipid. In some embodiments, the PEG lipid is a PEG-diacylglycerol (DAG), a PEG-dialkyloxypropyl (DAA), a PEG-phospholipid, a PEG-ceramide (Cer), or a mixture thereof. In some embodiments, PLGA is conjugated to a lipid-terminating PEG forming PLGA-DSPE-PEG. In some embodiments, a PEG lipid is selected from PEG-c-DOMG and 1,2-Dimyristoyl-sn-glycerol, methoxypolyethylene Glycol (PEG-DMG), 1,2-Distearoyl-sn-glycerol, methoxypolyethylene Glycol (PEG-DSG), PEG-c-DOMG, 1,2-Distearoyl-sn-glycerol, methoxypolyethylene glycol (PEG-DSG) 1,2-Dipalmitoyl-sn-glycerol, methoxypolyethylene glycol (PEG-DPG), PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers (e.g., ATTA-lipid conjugates), and mixtures thereof. In some embodiments, the PEG is a PEG-dilauryloxypropyl (C12), a PEG-dimyristyloxypropyl (C14), a PEG-dipalmityloxypropyl (C16), a PEG-distearyloxypropyl (C18), PEG-c-DOMG, PEG-DMG, or a mixture thereof.

In some embodiments, the conjugated PEG lipid is coupled to the surface of the lipid nanoparticle. In some embodiments, the PEG lipid is coupled to the surface of the lipid nanoparticle by an oxime linkage. In some embodiments, the conjugated PEG lipid is susceptible to decomposition in an acidic environment.

In some embodiments, formulations are provided in which the lipid nanoparticle comprises more than one cationic lipid, more than one non-cationic lipid, more than one conjugated lipid, or a combination thereof.

In some embodiments, formulations are provided in which the one or more stabilizing oligonucleotides are substantially encapsulated within an aqueous interior of the lipid nanoparticle.

In some embodiments, the lipid nanoparticle is about 50 to 150 nm in diameter. In some embodiments, the lipid nanoparticle is about 20-50 nm in diameter. In some embodiments, the lipid nanoparticle is about 30 nm in diameter.

In some embodiments, formulations are provided in which the lipid to stabilizing oligonucleotide ratio (mass/mass ratio; w/w ratio) is from about 1:1 to about 50:1, from about 1:1 to about 25:1, from about 10:1 to about 14:1, from about 3:1 to about 15:1, from about 4:1 to about 10:1, from about 5:1 to about 9:1, or about 6:1 to about 9:1.

In some embodiments, formulations are provided in which the particle is a microsphere. In some embodiments, the microsphere comprises poly(lactic-co-glycolic acid) (PLGA). In some embodiments, the microsphere particle is about 4 and 20 m in diameter.

In some embodiments, formulations are provided in which the particle includes a polymer. In some embodiments, the polymer comprises a layer of a hydrogel or surgical sealant. In some embodiments, the polymer is PLGA, ethylene vinyl acetate, poloxamer, GELSITE®, or a combination thereof.

In some embodiments, formulations are provided which further include protamine or calcium phosphate. In some embodiments, formulations are provided which further include hyaluronic acid. In some embodiments, formulations are provided which further include polyglutamate.

In some embodiments, formulations are provided in which the particle comprises a lipoprotein or lipoprotein mimetic. In some embodiments, the lipoprotein is HDL, LDL, or a combination thereof.

In some embodiments, formulations are provided in which the particle comprises a lipidoid. In some embodiments, the lipidoid is penta[3-(1-laurylaminopropionyl)]-triethylenetetramine hydrochloride (TETA-5LAP; 98N12-5), C12-200, MD1, or a combination thereof.

In some embodiments, the stabilizing oligonucleotide is a modified oligonucleotide. In some embodiments, the modified oligonucleotide comprises a modified sugar moiety, a modified internucleoside linkage, or a modified nucleotide, or a combination thereof.

In some embodiments, the stabilizing oligonucleotide is a mixmer. In some embodiment, the stabilizing oligonucleotide is a morpholino.

In some embodiments, the synthetic RNA comprises a transcription start site.

In some embodiments, the one or more stabilizing oligonucleotides comprises an oligonucleotide of 8 to 50 nucleotides in length and comprising a region of complementarity that is complementary with at least 5 contiguous nucleotides of the synthetic RNA, wherein the nucleotide at the 3'-end of the region of complementarity is complementary with a nucleotide within 10 nucleotides of the transcription start site of the synthetic RNA, wherein the oligonucleotide comprises nucleotides linked by at least one modified internucleoside linkage or at least one bridged nucleotide.

In some embodiments, the one or more stabilizing oligonucleotides comprises an oligonucleotide comprising two regions of complementarity each of which is complementary with at least 5 contiguous nucleotides of the synthetic RNA, wherein the nucleotide at the 3'-end of the first region of complementary is complementary with a nucleotide within 100 nucleotides of the transcription start site of the synthetic RNA and wherein the second region of complementarity is complementary with a region of the synthetic RNA that ends within 300 nucleotides of the 3'-end of the RNA transcript.

In some embodiments, the one or more stabilizing oligonucleotides comprises an oligonucleotide comprising the general formula 5'-$X_1$—$X_2$-3', wherein $X_1$ comprises 5 to 20 nucleotides that have a region of complementarity that is complementary with at least 5 contiguous nucleotides of a synthetic RNA, wherein the nucleotide at the 3'-end of the region of complementarity of $X_1$ is complementary with the nucleotide at the transcription start site of the RNA transcript; and $X_2$ comprises 1 to 20 nucleotides.

In some embodiments, the synthetic RNA has a 7-methylguanosine cap at its 5'-end. In some embodiments, the synthetic RNA has a 7-methylguanosine cap, and the nucleotide at the 3'-end of the region of complementary of $X_1$ is complementary with the nucleotide of the synthetic RNA that is immediately internal to the 7-methylguanosine cap.

In some embodiments, at least the first nucleotide at the 5'-end of $X_2$ is a pyrimidine complementary with guanine. In some embodiments, the second nucleotide at the 5'-end of $X_2$ is a pyrimidine complementary with guanine. In some embodiments, $X_2$ comprises the formula 5'-$Y_1$-$Y_2$—$Y_3$-3', wherein $X_2$ forms a stem-loop structure having a loop region comprising the nucleotides of $Y_2$ and a stem region comprising at least two contiguous nucleotides of $Y_1$ hybridized with at least two contiguous nucleotides of $Y_3$. In some embodiments, $Y_1$, $Y_2$ and $Y_3$ independently comprise 1 to 10 nucleotides. In some embodiments, $Y_3$ comprises, at a position immediately following the 3'-end of the stem region, a pyrimidine complementary with guanine. In some embodiments, the pyrimidine complementary with guanine is cytosine.

In some embodiments, $X_2$ comprises a region of complementarity that is complementary with at least 5 contiguous nucleotides of the synthetic RNA that do not overlap the region of the synthetic RNA that is complementary with the region of complementarity of $X_1$. In some embodiments, the region of complementarity of $X_2$ is within 100 nucleotides of a polyadenylation junction of the synthetic RNA. In some embodiments, the region of complementarity of $X_2$ is complementary with the synthetic RNA immediately adjacent to or overlapping the polyadenylation junction of the synthetic RNA. In some embodiments, $X_2$ further comprises at least 2 consecutive pyrimidine nucleotides complementary with adenine nucleotides of the poly(A) tail of the synthetic RNA.

In some embodiments, the synthetic RNA is an mRNA, non-coding RNA, long non-coding RNA, miRNA, or snoRNA or any other suitable RNA.

In some embodiments, the synthetic RNA is an mRNA transcript, and wherein $X_2$ comprises a region of complementarity that is complementary with at least 5 contiguous nucleotides in the 3'-UTR of the transcript.

In some embodiments, formulations are provided in which the one or more stabilizing oligonucleotides comprises an oligonucleotide of 10 to 50 nucleotides in length having a first region complementary with at least 5 consecutive nucleotides of the 5'-UTR of a synthetic RNA, and a second region complementary with at least 5 consecutive nucleotides of the 3'-UTR, poly(A) tail, or overlapping the polyadenylation junction of the synthetic RNA. In some embodiments, the first of the at least 5 consecutive nucleotides of the 5'-UTR of the stabilizing oligonucleotide is within 10 nucleotides of the 5'-methylguanosine cap of the synthetic RNA. In some embodiments, the second region of the stabilizing oligonucleotide is complementary with at least 5 consecutive nucleotides overlapping the polyadenylation junction.

In some embodiments, the stabilizing oligonucleotide further comprises 2-20 nucleotides that link the 5' end of the first region with the 3' end of the second region. In some embodiments, the stabilizing oligonucleotide further comprises 2-20 nucleotides that link the 3' end of the first region with the 5' end of the second region. In some embodiments, the oligonucleotide is 10 to 50 nucleotide in length. In some embodiments, the oligonucleotide is 9 to 20 nucleotide in length.

In some embodiments, formulations are provided in which the one or more stabilizing oligonucleotides comprises an oligonucleotide comprising the general formula 5'-X1-X2-3', wherein X1 comprises 2 to 20 pyrimidine nucleotides that form base pairs with adenine; and X2 comprises a region of complementarity that is complementary with at least 3 contiguous nucleotides of a polyadenylated synthetic RNA, wherein the nucleotide at the 5'-end of the region of complementary of X2 is complementary with the nucleotide of the synthetic RNA that is immediately internal to the poly-adenylation junction of the synthetic RNA.

In some embodiments, formulations are provided in which the one or more stabilizing oligonucleotides comprises: a first oligonucleotide having 5 to 25 nucleotides linked through internucleoside linkages, and a second oligonucleotide having 5 to 25 nucleotides linked through internucleoside linkages, wherein the first oligonucleotide is complementary with at least 5 consecutive nucleotides within 100 nucleotides of the 5'-end of a synthetic RNA and wherein the second oligonucleotide is complementary with at least 5 consecutive nucleotides within 100 nucleotides of the 3'-end of a synthetic RNA.

In some embodiments, the first oligonucleotide and second oligonucleotide are joined by a linker that is not an oligonucleotide having a sequence complementary with the synthetic RNA. In some embodiments, the linker is an oligonucleotide. In some embodiments, the linker is a polypeptide.

In some embodiments, the synthetic RNA encodes a protein. In some embodiments, the synthetic RNA comprises one or more modified nucleotides.

In some embodiments, the formulation comprises a first and a second stabilizing oligonucleotide.

In some embodiments, the first stabilizing oligonucleotide comprises a region of complementarity to a 5' region of the synthetic RNA and the second stabilizing oligonucleotide comprises a region of complementarity to a 3' region of the synthetic RNA. In some embodiments, the first stabilizing oligonucleotide is covalently linked with the second stabilizing oligonucleotide. In some embodiments, the first stabilizing oligonucleotide and second stabilizing oligonucleotide are covalently linked through an internucleoside linkage. In some embodiments, the first stabilizing oligonucleotide and second stabilizing oligonucleotide are covalently linked through an oligonucleotide. In some embodiments, the first stabilizing oligonucleotide and second stabilizing oligonucleotide are covalently linked through a linker.

In some embodiments, the synthetic RNA is circularized. In some embodiments, the synthetic RNA has a 7-methylguanosine cap at its 5'-end.

In some embodiments, the first stabilizing oligonucleotide comprises a region of complementarity that is complementary with the synthetic RNA at a position within 10 nucleotides of the first nucleotide at the 5' end of the synthetic RNA.

In some embodiments, the synthetic RNA comprises a 5'-methylguanosine cap, and wherein the first stabilizing oligonucleotide comprises a region of complementarity that is complementary with the synthetic RNA at a position within 10 nucleotides of the nucleotide immediately internal to the 5'-methylguanosine cap.

In some embodiments, the second stabilizing oligonucleotide comprises a region of complementarity that is complementary with the synthetic RNA at a position within 250 nucleotides of the 3' end of the synthetic RNA.

In some embodiments, the synthetic RNA comprises a 3'-poly(A) tail, and wherein the second stabilizing oligonucleotide comprises a region of complementarity that is complementary with the synthetic RNA at a position within 100 nucleotides of the polyadenylation junction of the synthetic RNA.

In some embodiments, the region of complementarity of the second stabilizing oligonucleotide is immediately adjacent to or overlapping the polyadenylation junction of the synthetic RNA.

In some embodiments, the synthetic RNA is an RNA transcript. In some embodiments, the synthetic RNA is a functional RNA. In some embodiments, the synthetic RNA is up to 10 kb in length.

In some embodiments, the synthetic RNA comprises one or more modified nucleotides. In some embodiments, the one or more modified nucleotides are selected from the group consisting of: 2'-amino-2'-deoxynucleotide, 2'-azido-2'-deoxynucleotide, 2'-fluoro-2'-deoxynucleotide, 2'-O-methyl-nucleotide, 2' sugar super modifier, 2'-modified thermostability enhancer, 2'-fluoro-2'-deoxyadenosine-5'-triphosphate, 2'-fluoro-2'-deoxycytidine-5'-triphosphate, 2'-fluoro-2'-deoxyguanosine-5'-triphosphate, 2'-fluoro-2'-deoxyuridine-5'-triphosphate, 2'-O-methyladenosine-5'-triphosphate, 2'-O-methylcytidine-5'-triphosphate, 2'-O-methylguanosine-5'-triphosphate, 2'-O-methyluridine-5'-triphosphate, pseudouridine-5'-triphosphate, 2'-O-methylinosine-5'-triphosphate, 2'-amino-2'-deoxycytidine-5'-triphosphate, 2'-amino-2'-deoxyuridine-5'-triphosphate, 2'-azido-2'-deoxycytidine-5'-triphosphate, 2'-azido-2'-deoxyuridine-5'-triphosphate, 2'-O-methylpseudouridine-5'-triphosphate, 2'-O-methyl-5-methyluridine-5'-triphosphate, 2'-azido-2'-deoxyadenosine-5'-triphosphate, 2'-amino-2'-deoxyadenosine-5'-triphosphate, 2'-fluoro-thymidine-5'-triphosphate, 2'-azido-2'-deoxyguanosine-5'-triphosphate, 2'-amino-2'-deoxyguanosine-5'-triphosphate, and N4-methylcytidine-5'-triphosphate.

In some aspects of the disclosure, methods are provided for delivering a synthetic RNA to a cell, the method comprising delivering to a cell a formulation of the present disclosure. In some embodiments, the increase in the level of gene expression results from an increase in the level of a protein encoded by the synthetic RNA. In some embodiments, the increase in the level of protein encoded by the synthetic RNA is at least a 50% increase compared with an appropriate cell to which the formulation was not delivered. In some embodiments, the cell is in vitro. In some embodiments, the cell is in vivo.

In some embodiments, the one or more stabilizing oligonucleotides comprises an oligonucleotide comprising two regions of complementarity each of which is complementary with at least 5 contiguous nucleotides of an RNA transcript, wherein the nucleotide at the 3'-end of the first region of complementary is complementary with a nucleotide within 100 nucleotides of the transcription start site of the RNA transcript and wherein the second region of complementarity is complementary with a region of the RNA transcript that ends within 300 nucleotides of the 3'-end of the RNA transcript.

In some embodiments, the one or more stabilizing oligonucleotides comprises an oligonucleotide comprising the general formula 5'-$X_1$—$X_2$-3', wherein X1 comprises 5 to 20 nucleotides that have a region of complementarity that is complementary with at least 5 contiguous nucleotides of an RNA transcript, wherein the nucleotide at the 3'-end of the region of complementary of $X_1$ is complementary with the nucleotide at the transcription start site of the RNA transcript; and $X_2$ comprises 1 to 20 nucleotides.

In some embodiments, the RNA transcript has a 7-methylguanosine cap at its 5'-end. In some embodiments, the RNA transcript has a 7-methylguanosine cap, and the nucleotide at the 3'-end of the region of complementarity of $X_1$ is complementary with the nucleotide of the RNA transcript that is immediately internal to the 7-methylguanosine cap.

In some embodiments, at least the first nucleotide at the 5'-end of $X_2$ is a pyrimidine complementary with guanine. In some embodiments, the second nucleotide at the 5'-end of $X_2$ is a pyrimidine complementary with guanine. In some embodiments, $X_2$ comprises the formula 5'-$Y_1$-$Y_2$—$Y_3$-3', wherein $X_2$ forms a stem-loop structure having a loop region comprising the nucleotides of $Y_2$ and a stem region comprising at least two contiguous nucleotides of $Y_1$ hybridized with at least two contiguous nucleotides of $Y_3$. In some embodiments, $Y_1$, $Y_2$ and $Y_3$ independently comprise 1 to 10 nucleotides. In some embodiments, $Y_3$ comprises, at a position immediately following the 3'-end of the stem region, a pyrimidine complementary with guanine. In some embodiments, the pyrimidine complementary with guanine is cytosine.

In some embodiments, $X_2$ comprises a region of complementarity that is complementary with at least 5 contiguous nucleotides of the RNA transcript that do not overlap the region of the RNA transcript that is complementary with the region of complementarity of $X_1$. In some embodiments, the region of complementarity of $X_2$ is within 100 nucleotides of a polyadenylation junction of the RNA transcript. In some embodiments, the region of complementarity of $X_2$ is complementary with the RNA transcript immediately adjacent to or overlapping the polyadenylation junction of the RNA transcript. In some embodiments, $X_2$ further comprises at least 2 consecutive pyrimidine nucleotides complementary with adenine nucleotides of the poly(A) tail of the RNA transcript.

In some embodiments, the RNA transcript is an mRNA, non-coding RNA, long non-coding RNA, miRNA, or snoRNA or any other suitable RNA.

In some embodiments, the RNA transcript is an mRNA transcript, and wherein $X_2$ comprises a region of complementarity that is complementary with at least 5 contiguous nucleotides in the 3'-UTR of the transcript.

In some embodiments, formulations are provided in which the one or more stabilizing oligonucleotides comprises an oligonucleotide of 10 to 50 nucleotides in length having a first region complementary with at least 5 consecutive nucleotides of the 5'-UTR of an mRNA transcript, and a second region complementary with at least 5 consecutive nucleotides of the 3'-UTR, poly(A) tail, or overlapping the polyadenylation junction of the mRNA transcript. In some embodiments, the first of the at least 5 consecutive nucleotides of the 5'-UTR of the stabilizing oligonucleotide is within 10 nucleotides of the 5'-methylguanosine cap of the mRNA transcript. In some embodiments, the second region of the stabilizing oligonucleotide is complementary with at least 5 consecutive nucleotides overlapping the polyadenylation junction.

In some embodiments, the stabilizing oligonucleotide further comprises 2-20 nucleotides that link the 5' end of the first region with the 3' end of the second region. In some embodiments, the stabilizing oligonucleotide further comprises 2-20 nucleotides that link the 3' end of the first region with the 5' end of the second region. In some embodiments, the oligonucleotide is 10 to 50 nucleotide in length. In some embodiments, the oligonucleotide is 9 to 20 nucleotide in length.

In some embodiments, formulations are provided in which the one or more stabilizing oligonucleotides comprises an oligonucleotide comprising the general formula 5'-X1-X2-3', wherein X1 comprises 2 to 20 pyrimidine nucleotides that form base pairs with adenine; and X2 comprises a region of complementarity that is complementary with at least 3 contiguous nucleotides of a polyadenylated RNA transcript, wherein the nucleotide at the 5'-end of the region of complementarity of X2 is complementary with the nucleotide of the RNA transcript that is immediately internal to the poly-adenylation junction of the RNA transcript.

In some embodiments, formulations are provided in which the one or more stabilizing oligonucleotides comprises: a first oligonucleotide having 5 to 25 nucleotides linked through internucleoside linkages, and a second oligonucleotide having 5 to 25 nucleotides linked through internucleoside linkages, wherein the first oligonucleotide is complementary with at least 5 consecutive nucleotides within 100 nucleotides of the 5'-end of an RNA transcript and wherein the second oligonucleotide is complementary with at least 5 consecutive nucleotides within 100 nucleotides of the 3'-end of an RNA transcript.

In some embodiments, the first oligonucleotide and second oligonucleotide are joined by a linker that is not an oligonucleotide having a sequence complementary with the RNA transcript. In some embodiments, the linker is an oligonucleotide. In some embodiments, the linker is a polypeptide.

In some aspects of the disclosure, methods are provided for increasing gene expression in a cell, the method comprising delivering to a cell a formulation of the present disclosure. In some embodiments, the increase in the level of gene expression results from an increase in the level of a protein encoded by an mRNA that is stabilized by the one or more stabilizing oligonucleotides. In some embodiments, the increase in the level of protein encoded by an mRNA is at least a 50% increase compared with an appropriate cell to which the formulation was not delivered. In some embodiments, the cell is in vitro. In some embodiments, the cell is in vivo.

In some aspects of the disclosure, methods are provided for treating a condition or disease associated with decreased levels of an RNA transcript in a subject, the method comprising administering a formulation of the present disclosure to the subject. In some embodiments, the formulation is administered via topical, oral, or parenteral administration. In some embodiments, the parental administration is intravenous, subcutaneous, intraperitoneal, intramuscular, intrathecal, or intraventricular administration.

In some aspects of the disclosure, kits are provided, which include a container housing a formulation of the present disclosure.

BRIEF DESCRIPTION OF THE FIGURES

FIG. 1 is an illustration depicting exemplary oligo designs for targeting 3' RNA ends. The first example shows oligos complementary to the 3' end of RNA, before the polyA-tail. The second example shows oligos complementary to the 3' end of RNA with a 5' T-stretch to hybridize to a polyA tail.

FIG. 2 is an illustration depicting exemplary oligos for targeting 5' RNA ends. The first example shows oligos complementary to the 5' end of RNA. The second example shows oligos complementary to the 5' end of RNA, the oligo having 3' overhang residues to create a RNA-oligo duplex with a recessed end. Overhang can include a combination of nucleotides including, but not limited to, C to potentially interact with a 5' methylguanosine cap and stabilize the cap further.

FIG. 3A is an illustration depicting exemplary oligos for targeting 5' RNA ends and exemplary oligos for targeting 5' and 3' RNA ends. The example shows oligos with loops to stabilize a 5' RNA cap or oligos that bind to a 5' and 3' RNA end to create a pseudo-circularized RNA.

DETAILED DESCRIPTION OF CERTAIN EMBODIMENTS OF THE DISCLOSURE

Figure 3B:
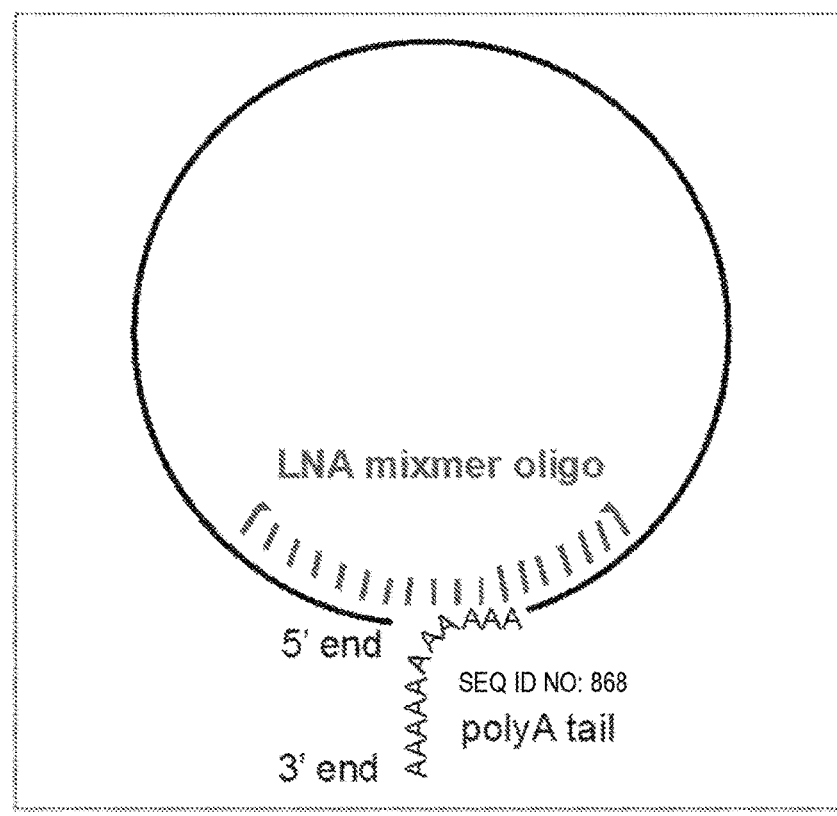
FIG. 3B is an illustration depicting exemplary oligo-mediated RNA pseudocircularization. The illustration shows an LNA mixmer oligo binding to the 5' and 3' regions of an exemplary RNA.

Formulations and methods disclosed herein are useful in a variety of different contexts in which it is desirable to protect RNAs from degradation, including protecting RNAs inside or outside of cells. In some embodiments, formulations and methods are provided that are useful for posttranscriptionally altering protein and/or RNA levels in cells in a targeted manner. For example, formulations and methods are provided that involve reducing or preventing degradation or processing of targeted RNAs thereby elevating steady state levels of the targeted RNAs. In some embodiments, the stability of an RNA is increased by protecting one or both ends (5' or 3' ends) of the RNA from exonuclease activity, thereby increasing stability of the RNA.

In some embodiments, methods of increasing gene expression are provided. As used herein the term, "gene expression" refers generally to the level or representation of a product of a gene in a cell, tissue or subject. It should be appreciated that a gene product may be an RNA transcript or a protein, for example. An RNA transcript may be protein coding. An RNA transcript may be non-protein coding, such as, for example, a long non-coding RNA, a long intergenic non-coding RNA, a non-coding RNA, an miRNA, a small nuclear RNA (snRNA), or other functional RNA. In some embodiments, formulations and methods for increasing gene expression may involve increasing stability of a RNA transcript, and thereby increasing levels of the RNA transcript in the cell. Formulations and methods for of increasing gene expression may alternatively or in addition involve increasing transcription or translation of RNAs. In some embodiments, other mechanisms of manipulating gene expression may be involved in methods disclosed herein.

In some embodiments, methods provided herein involve delivering to a cell one or more sequence specific oligonucleotides that hybridize with an RNA transcript at or near one or both ends, thereby protecting the RNA transcript from exonuclease mediated degradation. In embodiments where the targeted RNA transcript is protein-coding, increases in steady state levels of the RNA typically result in concomitant increases in levels of the encoded protein. In embodiments where the targeted RNA is non-coding, increases in steady state levels of the non-coding RNA typically result in concomitant increases in activity associated with the non-coding RNA.

In some embodiments, approaches disclosed herein based on regulating RNA levels and/or protein levels using oligonucleotides targeting RNA transcripts by mechanisms that increase RNA stability and/or translation efficiency may have several advantages over other types of oligos or compounds, such as oligonucleotides that alter transcription levels of target RNAs using cis or noncoding based mechanisms. For example, in some embodiments, lower concentrations of oligos may be used when targeting RNA transcripts in the cytoplasm as multiple copies of the target molecules exist. In contrast, in some embodiments, oligos that target transcriptional processes may need to saturate the cytoplasm and before entering nuclei and interacting with corresponding genomic regions, of which there are only one/two copies per cell, in many cases. In some embodiments, response times may be shorter for RNA transcript targeting because RNA copies need not to be synthesized transcriptionally. In some embodiments, a continuous dose response may be easier to achieve. In some embodiments, well defined RNA transcript sequences facilitate design of oligonucleotides that target such transcripts. In some embodiments, oligonucleotide design approaches provided herein, e.g., designs having sequence overhangs, loops, and other features facilitate high oligo specificity and sensitivity compared with other types of oligonucleotides, e.g., certain oligonucleotides that target transcriptional processes.

In some embodiments, methods provided herein involve use of oligonucleotides that stabilize a nucleic acid (e.g., an RNA) by hybridizing at a single stranded 5' and/or 3' region of the nucleic acid. In some embodiments, oligonucleotides that prevent or inhibit degradation of an nucleic acid by hybridizing with the nucleic acid may be referred to herein as "stabilizing oligonucleotides." In some examples, such oligonucleotides hybridize with an RNA and prevent or inhibit exonuclease mediated degradation of the RNA. Inhibition of exonuclease mediated degradation includes, but is not limited to, reducing the extent of degradation of a particular RNA by exonucleases. For example, an exonuclease that processes only single stranded RNA may cleave a portion of the RNA up to a region where an oligonucleotide is hybridized with the RNA because the exonuclease cannot effectively process (e.g., pass through) the duplex region. Thus, in some embodiments, using an oligonucleotide that targets a particular region of an RNA makes it possible to control the extent of degradation of the RNA by exonucleases up to that region. For example, use of an oligonucleotide that hybridizes at an end of an RNA may reduce or eliminate degradation by an exonuclease that processes only single stranded RNAs from that end. For example, use of an oligonucleotide that hybridizes at the 5' end of an RNA may reduce or eliminate degradation by an exonuclease that processes single stranded RNAs in a 5' to 3' direction. Similarly, use of an oligonucleotide that hybridizes at the 3' end of an RNA may reduce or eliminate degradation by an exonuclease that processes single stranded RNAs in a 3' to 5' direction. In some embodiments, lower concentrations of an oligo may be used when the oligo hybridizes at both the 5' and 3' regions of the RNA. In some embodiments, an oligo that hybridizes at both the 5' and 3' regions of the RNA protects the 5' and 3' regions of the RNA from degradation (e.g., by an exonuclease). In some embodiments, an oligo that hybridizes at both the 5' and 3' regions of the RNA creates a pseudo-circular RNA (e.g., a circularized RNA with a region of the poly A tail that protrudes from the circle, see FIG. 3B). In some embodiments, a pseudo-circular RNA is translated at a higher efficiency than a non-pseudo-circular RNA.

In some embodiments, an oligonucleotide may be used that comprises multiple regions of complementarity with an RNA, such that at one region the oligonucleotide hybridizes at or near the 5' end of the RNA and at another region it hybridizes at or near the 3' end of the RNA, thereby preventing or inhibiting degradation of the RNA by exonucleases at both ends. In some embodiments, when an oligonucleotide hybridizes both at or near the 5' end of an RNA and at or near the 3' end of the RNA a circularized complex results that is protected from exonuclease mediated degradation. In some embodiments, when an oligonucleotide hybridizes both at or near the 5' end of an mRNA and at or near the 3' end of the mRNA, the circularized complex that results is protected from exonuclease mediated degradation and the mRNA in the complex retains its ability to be translated into a protein.

As used herein the term, "synthetic RNA" refers to a RNA produced through an in vitro transcription reaction or through artificial (non-natural) chemical synthesis. In some embodiments, a synthetic RNA is an RNA transcript. In some embodiments, a synthetic RNA encodes a protein. In some embodiments, the synthetic RNA is a functional RNA (e.g., a lncRNA, miRNA, etc.). In some embodiments, a synthetic RNA comprises one or more modified nucleotides. In some embodiments, a synthetic RNA is up to 0.5 kilobases (kb), 1 kb, 1.5 kb, 2 kb, 2.5 kb, 3 kb, 4 kb, 5 kb, 6 kb, 7 kb, 8 kb, 9 kb, 10 kb, 15 kb, 20 kb, 25 kb, 30 kb or more in length. In some embodiments, a synthetic RNA is in a range of 0.1 kb to 1 kb, 0.5 kb to 2 kb, 0.5 kb to 10 kb, 1 kb to 5 kb, 2 kb to 5 kb, 1 kb to 10 kb, 3 kb to 10 kb, 5 kb to 15 kb, or 1 kb to 30 kb in length.

As used herein, the term "RNA transcript" refers to an RNA that has been transcribed from a nucleic acid by a polymerase enzyme. An RNA transcript may be produced inside or outside of cells. For example, an RNA transcript may be produced from a DNA template encoding the RNA transcript using an in vitro transcription reaction that utilizes recombination or purified polymerase enzymes. An RNA transcript may also be produced from a DNA template (e.g., chromosomal gene, an expression vector) in a cell by an RNA polymerase (e.g., RNA polymerase I, II, or III). In some embodiments, the RNA transcript is a protein coding mRNA. In some embodiments, the RNA transcript is a non-coding RNA (e.g., a tRNA, rRNA, snoRNA, miRNA, ncRNA, long-noncoding RNA, shRNA). In some embodiments, RNA transcript is up to 0.5 kilobases (kb), 1 kb, 1.5 kb, 2 kb, 2.5 kb, 3 kb, 4 kb, 5 kb, 6 kb, 7 kb, 8 kb, 9 kb, 10 kb, 15 kb, 20 kb, 25 kb, 30 kb or more in length. In some embodiments, a RNA transcript is in a range of 0.1 kb to 1 kb, 0.5 kb to 2 kb, 0.5 kb to 10 kb, 1 kb to 5 kb, 2 kb to 5 kb, 1 kb to 10 kb, 3 kb to 10 kb, 5 kb to 15 kb, or 1 kb to 30 kb in length.

In some embodiments, the RNA transcript is capped post-transcriptionally, e.g., with a 7'-methylguanosine cap. In some embodiments, the 7'-methylguanosine is added to the RNA transcript by a guanylyltransferase during transcription (e.g., before the RNA transcript is 20-50 nucleotides long.) In some embodiments, the 7'-methylguanosine is linked to the first transcribed nucleotide through a 5'-5' triphosphate bridge. In some embodiments, the nucleotide immediately internal to the cap is an adenosine that is N6 methylated. In some embodiments, the first and second nucleotides immediately internal to the cap of the RNA transcript are not 2'-O-methylated. In some embodiments, the first nucleotide immediately internal to the cap of the RNA transcript is 2'-O-methylated. In some embodiments, the second nucleotide immediately internal to the cap of the RNA transcript is 2'-O-methylated. In some embodiments, the first and second nucleotides immediately internal to the cap of the RNA transcript are 2'-O-methylated.

In some embodiments, the RNA transcript is a non-capped transcript (e.g., a transcript produced from a mitochondrial gene). In some embodiments, the RNA transcript is a nuclear RNA that was capped but that has been decapped. In some embodiments, decapping of an RNA is catalyzed by the decapping complex, which may be composes of Dcp1 and Dcp2, e.g., that may compete with eIF-4E to bind the cap. In some embodiments, the process of RNA decapping involves hydrolysis of the 5' cap structure on the RNA exposing a 5' monophosphate. In some embodiments, this 5' monophosphate is a substrate for the exonuclease XRN1. Accordingly, in some embodiments, an oligonucleotide that targets the 5' region of an RNA may be used to stabilize (or restore stability) to a decapped RNA, e.g., protecting it from degradation by an exonuclease such as XRN1.

In some embodiments, in vitro transcription (e.g., performed via a T7 RNA polymerase or other suitable polymerase) may be used to produce an RNA transcript. In some embodiments transcription may be carried out in the presence of anti-reverse cap analog (ARCA) (TriLink Cat. # N-7003). In some embodiments, transcription with ARCA results in insertion of a cap (e.g., a cap analog (mCAP)) on the RNA in a desirable orientation.

In some embodiments, transcription is performed in the presence of one or more modified nucleotides (e.g., pseudouridine, 5-methylcytosine, etc.), such that the modified nucleotides are incorporated into the RNA transcript. It should be appreciated that any suitable modified nucleotide may be used, including, but not limited to, modified nucleotides that reduced immune stimulation, enhance translation and increase nuclease stability. Non-limiting examples of modified nucleotides that may be used include: 2'-amino-2'-deoxynucleotide, 2'-azido-2'-deoxynucleotide, 2'-fluoro-2'-deoxynucleotide, 2'-O-methyl-nucleotide, 2' sugar super modifier, 2'-modified thermostability enhancer, 2'-fluoro-2'-deoxyadenosine-5'-triphosphate, 2'-fluoro-2'-deoxycytidine-5'-triphosphate, 2'-fluoro-2'-deoxyguanosine-5'-triphosphate, 2'-fluoro-2'-deoxyuridine-5'-triphosphate, 2'-O-methyladenosine-5'-triphosphate, 2'-O-methylcytidine-5'-triphosphate, 2'-O-methylguanosine-5'-triphosphate, 2'-O-methyluridine-5'-triphosphate, pseudouridine-5'-triphosphate, 2'-O-methylinosine-5'-triphosphate, 2'-amino-2'-deoxycytidine-5'-triphosphate, 2'-amino-2'-deoxyuridine-5'-triphosphate, 2'-azido-2'-deoxycytidine-5'-triphosphate, 2'-azido-2'-deoxyuridine-5'-triphosphate, 2'-O-methylpseudouridine-5'-triphosphate, 2'-O-methyl-5-methyluridine-5'-triphosphate, 2'-azido-2'-deoxyadenosine-5'-triphosphate, 2'-amino-2'-deoxyadenosine-5'-triphosphate, 2'-fluoro-thymidine-5'-triphosphate, 2'-azido-2'-deoxyguanosine-5'-triphosphate, 2'-amino-2'-deoxyguanosine-5'-triphosphate, and N4-methylcytidine-5'-triphosphate. In one embodiment, RNA degradation or processing can be reduced/prevented to elevate steady state RNA and, at least for protein-coding transcripts, protein levels. In some embodiments, a majority of degradation of RNA transcripts is done by exonucleases. In such embodiments, these enzymes start destroying RNA from either their 3' or 5' ends. By protecting the ends of the RNA transcripts from exonuclease enzyme activity, for instance, by hybridization of sequence-specific blocking oligonucleotides with proper chemistries for proper delivery, hybridization and stability within cells, RNA stability may be increase, along with protein levels for protein-coding transcripts.

In some embodiments, for the 5' end, oligonucleotides may be used that are fully/partly complementary to 10-20 nts of the RNA 5' end. In some embodiments, such oligonucleotides may have overhangs to form a hairpin (e.g., the 3' nucleotide of the oligonucleotide can be, but not limited to, a C to interact with the mRNA 5' cap's G nucleoside) to protect the RNA 5' cap. In some embodiments, all nucleotides of an oligonucleotide may be complementary to the 5' end of an RNA transcript, with or without few nucleotide overhangs to create a blunt or recessed 5'RNA-oligo duplex. In some embodiments, for the 3' end, oligonucleotides may be partly complementary to the last several nucleotides of the RNA 3' end, and optionally may have a poly(T)-stretch to protect the poly(A) tail from complete degradation (for transcripts with a poly(A)-tail). In some embodiments, similar strategies can be employed for other RNA species with different 5' and 3' sequence composition and structure (such as transcripts containing 3' poly(U) stretches or transcripts with alternate 5' structures). In some embodiments, oligonucleotides as described herein, including, for example, oligonucleotides with overhangs, may have higher specificity and sensitivity to their target RNA end regions compared to oligonucleotides designed to be perfectly complementary to RNA sequences, because the overhangs provide a destabilizing effect on mismatch regions and prefer binding in regions that are at the 5' or 3' ends of the RNAs. In some embodiments, oligonucleotides that protect the very 3' end of the poly(A) tail with a looping mechanism (e.g., TTTTTTTTTTGGTTTTCC, SEQ ID NO: 458). In some embodiments, this latter approach may nonspecifically target all protein-coding transcripts. However, in some embodiments, such oligonucleotides, may be useful in combination with other target-specific oligos.

In some embodiments, methods provided herein involve the use of an oligonucleotide that comprises a region of complementarity that is complementary with the RNA transcript at a position at or near the first transcribed nucleotide of the RNA transcript. In some embodiments, an oligonucleotide (e.g., an oligonucleotide that stabilizes an RNA transcript) comprises a region of complementarity that is complementary with the RNA transcript (e.g., with at least 5 contiguous nucleotides) at a position that begins within 100 nucleotides, within 50 nucleotides, within 30 nucleotides, within 20 nucleotides, within 10 nucleotides or within 5 nucleotides of the 5'-end of the transcript. In some embodiments, an oligonucleotide (e.g., an oligonucleotide that stabilizes an RNA transcript) comprises a region of complementarity that is complementary with the RNA transcript (e.g., with at least 5 contiguous nucleotides of the RNA transcript) at a position that begins at the 5'-end of the transcript. In some embodiments, an oligonucleotide (e.g., an oligonucleotide that stabilizes an RNA transcript) comprises a region of complementarity that is complementary with an RNA transcript at a position within a region of the 5' untranslated region (5' UTR) of the RNA transcript spanning from the transcript start site to 50, 100, 150, 200, 250, 500 or more nucleotides upstream from a translation start site (e.g., a start codon, AUG, arising in a Kozak sequence of the transcript).

In some embodiments, an RNA transcript is poly-adenylated. Polyadenylation refers to the post-transcriptional addition of a polyadenosine (poly(A)) tail to an RNA transcript. Both protein-coding and non-coding RNA transcripts may be polyadenylated. Poly(A) tails contain multiple adenosines linked together through internucleoside linkages. In some embodiments, a poly(A) tail may contain 10 to 50, 25 to 100, 50 to 200, 150 to 250 or more adenosines. In some embodiments, the process of polyadenlyation involves endonucleolytic cleavage of an RNA transcript at or near its 3'-end followed by one by one addition of multiple adenosines to the transcript by a polyadenylate polymerase, the first of which adenonsines is added to the transcript at the 3' cleavage site. Thus, often a polyadenylated RNA transcript comprises transcribed nucleotides (and possibly edited nucleotides) linked together through internucleoside linkages that are linked at the 3' end to a poly(A) tail. The location of the linkage between the transcribed nucleotides and poly(A) tail may be referred to herein as, a "polyadenylation junction." In some embodiments, endonucleolytic cleavage may occur at any one of several possible sites in an RNA transcript. In such embodiments, the sites may be determined by sequence motifs in the RNA transcript that are recognized by endonuclease machinery, thereby guiding the position of cleavage by the machinery. Thus, in some embodiments, polyadenylation can produce different RNA transcripts from a single gene, e.g., RNA transcripts have different polyadenylation junctions. In some embodiments, length of a poly(A) tail may determine susceptibility of the RNA transcript to enzymatic degradation by exonucleases with 3'-5' processing activity. In some embodiments, oligonucleotides that target an RNA transcript at or near its 3' end target a region overlapping a polyadenylation junction. In some embodiments, such oligonucleotides may have at least 3, 4, 5, 6, 7, 8, 9, 10, 11, 12 or more nucleotides that are complementary with the transcribed portion of the transcript (5' to the junction). In some embodiments, it is advantageous to have a limited number of nucleotides (e.g., T, U) complementary to the polyA side of the junction. In some embodiments, having a limited number of nucleotides complementary to the polyA side of the junction it is advantageous because it reduces toxicity associated with cross hybridization of the oligonucleotide to the polyadenylation region of non-target RNAs in cells. In some embodiments, the oligonucleotide has only 1, 2, 3, 4, 5, or 6 nucleotides complementary to the poly A region.

In some embodiments, methods provided herein involve the use of an oligonucleotide that hybridizes with a target RNA transcript at or near its 3' end and prevents or inhibits degradation of the RNA transcript by 3'-5' exonucleases. For example, in some embodiments, RNA stabilization methods provided herein involve the use of an oligonucleotide that comprises a region of complementarity that is complementary with the RNA transcript at a position within 100 nucleotides, within 50 nucleotides, within 30 nucleotides, within 20 nucleotides, within 10 nucleotides, within 5 nucleotides of the last transcribed nucleotide of the RNA transcript. In a case where the RNA transcript is a polyadenylated transcript, the last transcribed nucleotide of the RNA transcript is the first nucleotide upstream of the polyadenylation junction. In some embodiments, RNA stabilization methods provided herein involve the use of an oligonucleotide that comprises a region of complementarity that is complementary with the RNA transcript at a position immediately adjacent to or overlapping the polyadenylation junction of the RNA transcript. In some embodiments, RNA stabilization methods provided herein involve the use of an oligonucleotide that comprises a region of complementarity that is complementary with the RNA transcript within the poly(A) tail.

Particle Formulation, Delivery, and Dosing

Nucleic acids, e.g., stabilizing oligonucleotides and/or synthetic RNAs, described herein can be formulated with a particle for administration to a subject for treating a condition associated with decreased levels of expression of gene or instability or low stability of an RNA transcript that results in decreased levels of expression of a gene (e.g., decreased protein levels or decreased levels of functional RNAs, such as miRNAs, snoRNAs, lncRNAs, etc.). It should be understood that the formulations, compositions and methods can be practiced with any of the oligonucleotides and/or synthetic RNAs disclosed herein.

Any of the formulations, excipients, vehicles, etc. disclosed herein may be adapted or used to facilitate delivery of nucleic acids, e.g., stabilizing oligonucleotides and/or synthetic RNAs (e.g., linear or circularized synthetic RNAs), to a cell. Formulations, excipients, vehicles, etc. disclosed herein may be adapted or used to facilitate delivery of a nucleic acid to a cell in vitro or in vivo. Nucleic acids, e.g., stabilizing oligonucleotides and/or synthetic RNAs, may be formulated with a particle as described herein. For example, nucleic acids may be formulated with a nanoparticle, poly(lactic-co-glycolic acid) (PLGA) microsphere, lipidoid, lipoplex, liposome, polymer, carbohydrate (including simple sugars), cationic lipid, a fibrin gel, a fibrin hydrogel, a fibrin glue, a fibrin sealant, fibrinogen, thrombin, rapidly eliminated lipid nanoparticles (reLNPs) and combinations thereof. In some embodiments, a nucleic acid, e.g., stabilizing oligonucleotides and/or synthetic RNAs (e.g., linear or circularized synthetic RNAs), may be delivered to a cell gymnotically. In some embodiments, nucleic acids, e.g., stabilizing oligonucleotides and/or synthetic RNAs, may be conjugated with factors that facilitate delivery to cells. In some embodiments, a nucleic acid, e.g., stabilizing oligonucleotide and/or synthetic RNA, is conjugated with a carbohydrate, such as GalNac, or other targeting moiety.

In some aspects, a particle of the present disclosure is a nanoparticle, e.g., lipid nanoparticle. In some embodiments, a lipid nanoparticle may include one or more cationic lipids, one or more non-cationic lipids, one or more conjugated lipids that inhibits aggregation of particles, or a combination thereof. Such lipids can be used alone or in combination. In some embodiments, a lipid nanoparticle comprises more than one cationic lipid, more than one non-cationic lipid, more than one conjugated lipid, or a combination thereof. Exemplary components that may be present in the formulations and methods of the present disclosure are described below.

In some embodiments, a particle of the present disclosure includes a cationic lipid. As used herein, the term "cationic lipid" refers to a positively charged lipid. In some embodiments, cationic lipids can have certain features including a head group, one or more hydrophobic tails, and a linker between the head group and the one or more tails. The head group may include an amine. Under certain conditions, the amine nitrogen can be a site of positive charge. The cationic lipid for use in accordance with the present disclosure may be any appropriate cationic lipid for particle formulation, e.g., nanoparticle formulation, e.g., lipid nanoparticle formulation. For example, without limitation, the cationic lipid may be N,N-dioleyl-N,N-dimethylammonium chloride (DODAC), N,N-distearyl-N,N-dimethylammonium bromide (DDAB), N—(I-(2,3-dioleyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino) ethyl)piperazin-1-yl)ethylazanediyl)didodecan-2-ol (Tech G1), 2,2-Dilinoleyl-4-dimethylaminoethyl-[1,3]-dioxolane, β-L-arginyl-2,3-L-diaminopropionic acid-N-palmityl-N-oleylamide trihydrochloride, N',N'-dioctadecyl-N-4,8-diaza-10-aminodecanoylglycine amide[71], 1,2-dilinoleyloxy-3-dimethylaminopropane, DLin-KC2-DMA, amino lipid 2,2-dilinoleyl-4-dimethylaminoethyl-[1,3]-dioxolane (DLin-KC2-DMA, 1), 1,2-distearloxy-/V,N-dimethylaminopropane (DSDMA), dilinoleylmethyl-4-dimethylaminobutyrate (DLin-MC3-DMA), DLin-D-DMA, C12-200, 98N12-5, (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimethylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine,N,N-dimeth-yl-1-[(1S,2S)-2-{[(1R,2R)-2-pentylcyclopropyl] methyl}cyclopropyl]nonadecan-10-amine,N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1 S,2R)-2-octylcyclopropyl] heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propa-n-2-amine, S—N,N-dimethyl-1-[(9Z,12Z)-octadeca-9,12-dien-1-yloxy]-3-(octy-loxy) propan-2-amine, 1-{2-[(9Z,12Z)-octadeca-9,12-dien-1-yloxy]-1-Roctyloxy)methyl]ethyl}pyrro-lidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azet-idine, (2S)-1-(hexyloxy)-N,N-dimethyl-3-[(9Z,12Z)-octadeca-9,12-dien-ylo-xy]propan-2-amine, (2S)-1-(heptyloxy)-N,N-dimethyl-3-[(9Z,12Z)-octadeca-9,12-dien-1-yloxy]pr-opan-2-amine, N,N-dimethyl-1-(nonyloxy)-3-[(9Z,12Z)-octadeca-9,12-dien-1-yloxy] propan-2-amine, N,N-dimethyl-1-[(9Z)-octadec-9-en-1-yloxy]-3-(octyloxy)propan-2-am-ine; (2S)—N,N-dimethyl-1-[(6Z,9Z,12Z)-octadeca-6,9,12-trien-1-yloxy]-3-(o-ctyloxy)propan-2-amine, (2 S)-1-[(11Z,14Z)-icosa-11,14-dien-1-yloxy]-N,N-dimethyl-3-(pentyloxy)propa-n-2- amine, (2S)-1-(hexyloxy)-3-[(11Z,14Z)-icosa-11,14-dien-1-yloxy]-N,N-di-methylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)pr-opan-2-amine, (2S)-1-[(13Z,16Z)-docosa-13,16-dien-1-yloxy]-3-(hexyloxy)-N,N-dimethylpro-pan-2-amine, (2S)-1-[(13Z)-docos-13-en-1-yloxy]-3-(hexyloxy)-N,N-dimethylpropan-2-amin-e, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H (1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-di-en-1-yloxy] propan-2-amine, N,N-dimethyl-1-(octyloxy)-3-({8-[(1S, 2S)-2-{[(1R,2R)-2-pentylcyclopropyl]-methyl}cyclopropyl]octyl}oxy)propan-2-amine, N,N-dimethyl-1-{[8-(2-oclylcyclopropyl)octyl]oxy}-3-(octyloxy)propan-2-am-ine and (11E,20Z,23Z)—N,N-dimethylnonacosa-11,20,2-trien-10-amine, 5-carboxyspermylglycine dioctaoleoylamide ("DOGS"), dipalmitoylphosphatidylethanolamine 5-carboxyspermylamide ("DPPES"), 1,2-dimyristyloxypropyl-3-dimethyl-hydroxy ethyl ammonium bromide (DMRIE), DMRIE-HP, Lipofectamine (DOSPA), 3b-(N—(N',N'-dimethylamino-ethane)-carbamoyl)cholesterol ("DC-Choi"), N-(1,2-dimyhstyloxyprop-3-yl)-N,N-dimethyl-N-hydroxyethyl ammonium bromide ("DMRIE"), 1,2-Dioleoyl-3-dimethylammonium-propane ("DODAP"), DMDMA, cationic lipid-based transfection reagents TransIT-TKO, LIPOFECTIN, Lipofectamine, OLIGOFECTAMINE or DHARMAFECT, DSDMA, DODMA, DLinDMA, DLenDMA, gamma-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, y-DLen-C2K-DMA, DLin-M-C2-DMA (also known as MC2), DLin-M-C3-DMA (also known as MC3) and (DLin-MP-DMA)(also known as 1-B11) or a mixture thereof. In some embodiments, the cationic lipid may comprise from about 20 mol percent to about 50 mol percent or about 40 mol percent of the total lipid present in the particle.

The non-cationic lipid may be any appropriate non-cationic lipid for particle, e.g., nanoparticle, e.g., lipid nanoparticle, formulation. For example, the non-cationic lipid may be an anionic lipid or a neutral lipid. Anionic lipids suitable for use in particles of the present disclosure include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids. In some embodiments, the anionic lipid is 1,2-dioleoyl-sn-glycero-3-phospho-(1'-rac-glycerol).

A neutral lipid generally refers to a lipid which exists either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. In some embodiments, the neutral lipid component is a lipid having two acyl groups, (e.g., diacylphosphatidylcholine and diacylphosphatidylethanolamine). Lipids having a variety of acyl chain groups of varying chain length and degree of saturation are available or may be isolated or synthesized by well-known techniques. In some embodiments, lipids contain saturated fatty acids with carbon chain lengths in the range of $C_{10}$ to $C_{20}$. In some embodiments, lipids with mono or diunsaturated fatty acids with carbon chain lengths in the range of $C_{10}$ to $C_{20}$ may be used. Additionally, lipids having mixtures of saturated and unsaturated fatty acid chains can be used. For example, a neutral lipid for use in accordance with the present disclosure is DOPE, DSPC, POPC, DPPC or any related phosphatidylcholine. In some embodiments, a neutral lipid may be composed of sphingomyelin, dihydrosphingomyeline, or phospholipids with other head groups, such as serine and inositol. In some embodiments, the neutral lipid is 1,2-dioleoyl-sn-glycero-3-phosphatidylcholine.

In some embodiments, exemplary non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids or a mixture thereof. In some embodiments, the anionic lipid is 1,2-dioleoyl-sn-glycero-3-phospho-(1'-rac-glycerol). In some embodiments, the neutral lipid is 1,2-dioleoyl-sn-glycero-3-phosphatidylcholine.

Particles of the present disclosure may include a lipid that inhibits and/or reduces aggregation of particles during formation. Examples of lipids that reduce aggregation of particles during formation include polyethylene glycol (PEG)-modified lipids, monosialoganglioside Gm1, and polyamide oligomers ("PAO") such as (described in U.S. Pat. No. 6,320,017). Other compounds with uncharged, hydrophilic, steric-barrier moieties, which prevent aggregation during formulation, like PEG, Gm1 or ATTA, can also be coupled to lipids for use as in accordance with the disclosure. Exemplary ATTA-lipids are described, e.g., in U.S. Pat. No. 6,320,017, and exemplary PEG-lipid conjugates are described, e.g., in U.S. Pat. Nos. 5,820,873, 5,534,499 and 5,885,613.

In some embodiments, the conjugated lipid is a PEG lipid. In some embodiments, the PEG lipid is a PEG-diacylglycerol (DAG), a PEG-dialkyloxypropyl (DAA), a PEG-phospholipid, a PEG-ceramide (Cer), or a mixture thereof. As a non-limiting example, PLGA may be conjugated to a lipid-terminating PEG forming PLGA-DSPE-PEG, PEG lipid is selected from PEG-c-DOMG and 1,2-Dimyristoyl-sn-glycerol, methoxypolyethylene Glycol (PEG-DMG), 1,2-Distearoyl-sn-glycerol, methoxypolyethylene Glycol (PEG-DSG), PEG-c-DOMG, 1,2-Distearoyl-sn-glycerol, methoxypolyethylene glycol (PEG-DSG) 1,2-Dipalmitoyl-sn-glycerol, methoxypolyethylene glycol (PEG-DPG), PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers (e.g., ATTA-lipid conjugates), and mixtures thereof. In some embodiments, the PEG is a PEG-dilauryloxypropyl (C12), a PEG-dimyristyloxypropyl (C14), a PEG-dipalmityloxypropyl (C16), a PEG-distearyloxypropyl (C18), PEG-c-DOMG, PEG-DMG, or a mixture thereof.

In some embodiments, the conjugated lipid that prevents aggregation of particles may be from 0% to about 20%, e.g., about 1% to about 15%, e.g., about 2% of the total lipid present in the particle (by mole percent of lipids). In some embodiments, the nucleic acid-lipid particle further includes cholesterol at, e.g., about 10 mol percent to about 60 mol percent or about 48 mol percent of the total lipid present in the particle.

In some embodiments, the conjugated PEG lipid is coupled to the surface of the lipid nanoparticle. In some embodiments, the PEG lipid is coupled to the surface of the lipid nanoparticle by an oxime linkage. In some embodiments, the conjugated PEG lipid is susceptible to decomposition in an acidic environment.

In some embodiments, the lipid nanoparticles of the present disclosure have a mean diameter of about 50 nm to about 150 nm, e.g., about 60 nm to about 130 nm, about 70 nm to about 110 nm, about 60 nm to about 80 nm. In some embodiments, the lipid nanoparticles of the present disclosure have a mean diameter of about 20-50 nm. In some embodiments, the lipid nanoparticles of the present disclosure have a mean diameter of about 30 nm. In some embodiments, the particle size is at least 30 nm, at least 40 nm, at least 50 nm, at least 60 nm, at least 70 nm, at least 80 nm, at least 90 nm, at least 100 nm, at least 110 nm, or at least 120 nm. In some embodiments, the particle size range is about at least 50 nm to about at least 110 nm, about at least 60 nm to about at least 100 nm, or about at least 50 nm to about at least 80 nm.

In some embodiments, nucleic acids, e.g., stabilizing oligonucleotide and/or synthetic RNA, are encapsulated in the particle of the present disclosure. In some embodiments, encapsulated nucleic acids are resistant in aqueous solution to degradation with a nuclease. In some embodiments, the nucleic acid, e.g., stabilizing oligonucleotide and/or synthetic RNA, encapsulated in the particles is not significantly degraded after exposure to serum or a nuclease assay that would significantly degrade free nucleic acid. Nuclease degradation of nucleic acids may be determined by an Oligreen® assay (Invitrogen Corporation, Carlsbad, CA), which is an ultra-sensitive fluorescent nucleic acid stain for quantitating oligonucleotides and single-stranded DNA in solution. In some embodiments, nucleic acids, e.g., stabilizing oligonucleotide and/or synthetic RNA, are at least 50%, at least 60%, at least 70%, at least 80%, at least 90%, at least 95%, or at least 97% encapsulated in the particle.

In one embodiment, the lipid to drug ratio (mass/mass ratio; w/w ratio) (e.g., lipid to dsRNA ratio) will be in the range of from about 1:1 to about 50:1, from about 1:1 to about 25:1, from about 10:1 to about 14:1, from about 3:1 to about 15:1, from about 4:1 to about 10:1, from about 5:1 to about 9:1, or about 6:1 to about 9:1.

In some embodiments, a particle of the present disclosure comprises a polymer. In some embodiments, the polymer comprises a layer of a hydrogel or surgical sealant. In some embodiments, the polymer is PLGA, ethylene vinyl acetate, poloxamer, GELSITE®, or a combination thereof. In some embodiments, a particle of the present disclosure comprises a fibrin sealant.

In some embodiments, it is desirable to precondense the nucleic acid, e.g., stabilizing oligonucleotide and/or synthetic RNA, into the core of a particle described herein. In some embodiments, a heper cationic polymer, such as protamine is included in the formulation. In some embodiments, protamine interacts with nucleic acid to form a negatively charged compact core.

In some embodiments, calcium phosphate is included in a formulation described herein. In some embodiments, hyaluronic acid is included in a formulation described herein. In some embodiments, polyglutamate is included in a formulation described herein In some embodiments, a particle of the disclosure comprises a lipoprotein or lipoprotein mimetic, or fragment thereof. In some embodiments, the lipoprotein is HDL, LDL, or a combination thereof.

In some aspects, a particle in accordance with the present disclosure comprises a lipidoid. The synthesis of lipidoids has been extensively described and formulations containing these compounds are particularly suited for delivery of modified nucleic acid molecules or mmRNA (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties). Complexes, micelles, liposomes or particles can be prepared containing a lipidoid and therefore, can result in an effective delivery of the nucleic acids, e.g., stabilizing oligonucleotides and/or synthetic RNAs, of the present disclosure. In some embodiments, the lipidoid is penta[3-(1-laurylaminopropionyl)]-triethylenetetramine hydrochloride (TETA-5LAP; 98N12-5), C12-200, MD1, or a combination thereof. The lipidoid formulations can include particles comprising, e.g., 3 or 4 or more components in addition to stabilizing oligonucleotide and/or synthetic RNA. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

In some embodiments, a formulation comprises a rapidly eliminated lipid nanoparticle (reLNP). In some embodiments, a reLNPcomprises a reLNP lipid, a fusogenic lipid, cholesterol and a PEG lipid at a molar ratio of 50:10:38.5:1.5 (reLNP lipid:fusogenic lipid:cholesterol:PEG lipid). The fusogenic lipid may be DSPC and the PEG lipid may be PEG-c-DOMG. The reLNP lipid may be DLin-DMA with an internal or terminal ester or DLin-MC3-DMA with an internal or terminal ester. In some embodiments, the total lipid to modified mRNA weight ratio is between 10:1 and 30:1.

The formulations may conveniently be presented in unit dosage form and may be prepared by any methods well known in the art of pharmacy. The amount of active ingredient (e.g., an oligonucleotide or compound of the disclosure) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g. tumor regression.

Pharmaceutical formulations of this disclosure can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

A formulated nucleic acid, e.g., oligonucleotide and/or synthetic RNA, and particle composition can assume a variety of states. In some examples, the composition is at least partially crystalline, uniformly crystalline, and/or anhydrous (e.g., less than 80, 50, 30, 20, or 10% water). In another example, a nucleic acid, e.g., oligonucleotide and/or synthetic RNA, is in an aqueous phase, e.g., in a solution that includes water. The aqueous phase or the crystalline compositions can, e.g., be incorporated into a delivery vehicle, e.g., a liposome (particularly for the aqueous phase) or a particle (e.g., a microparticle as can be appropriate for a crystalline composition) as described herein. Generally, a nucleic acid, e.g., oligonucleotide and/or synthetic RNA, composition is formulated in a manner that is compatible with the intended method of administration.

In some embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A nucleic acid, e.g., oligonucleotide and/or synthetic RNA, preparation can be formulated or administered (together or separately) in combination with another agent, e.g., another therapeutic agent or an agent that stabilizes an oligonucleotide, e.g., a protein that complexes with oligonucleotide. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, an formulation comprising an oligonucleotide includes another oligonucleotide, e.g., a second oligonucleotide that modulates expression of a second gene or a second oligonucleotide that modulates expression of the first gene. Still other preparation can include at least 3,5, ten, twenty, fifty, or a hundred or more different oligonucleotide species. Such oligonucleotides can mediated gene expression with respect to a similar number of different genes. In one embodiment, an oligonucleotide preparation includes at least a second therapeutic agent (e.g., an agent other than an oligonucleotide).

Ligand Modified Particles

In some aspects, a particle of the present disclosure may be conjugated to a targeting ligand that targets the particle to a particular ligand binding molecule, e.g., a ligand binding molecule present in a particular tissue or on the surface of a particular cell. Any suitable ligand may be used, including protein, lipid, polynucleotide, polysaccharide, or other molecules. In some embodiments, without limitation, the ligand is an antibody or antigen binding fragment thereof, a small molecule, a drug, a chemical, an ion, an aptamer, an oligonucleotide, a single stranded oligonucleotide, DNA, RNA, a peptide, a protein, a neuropeptide, or a neurotransmitter.

In some embodiments, a targeting ligand may be conjugated to a particle directly, e.g., through a direct covalent linkage. However, in some embodiments, a targeting ligand may be conjugated to a particle indirectly, e.g., via another molecule, such as a linker or adaptor molecule. As used herein, the term "particle linker" refers to any linker that is conjugated to a particle. In some embodiments, a targeting ligand is conjugated to a particle (e.g., a lipid nanoparticle) via a particle linker. Any suitable particle linker may be used. In some embodiments, a particle linker is conjugated to a targeting ligand. In some embodiments, the particle linker is a hetero-bifunctional molecule, such as polyethylene glycol (PEG) (e.g., as described herein and/or in U.S. Pat. Nos. 5,820,873, 5,534,499 and/or 5,885,613, incorporated by reference herein, in their entireties). In some embodiments, the particle linker is a monosialoganglioside (Gm1/GM1/GM-1), a polyamide oligomer (e.g., PAO e.g., ATTA, e.g., N-(w-azido-octa-(14'-amino-3',6',9',12'-tetraoxatetradecanoyl))-1,2-distearoyl-sn-glycero-3-phosphoethanolamine (*ATTA*-DPSE)) (e.g., as described in U.S. Pat. Nos. 6,320,017 and/or 6,586,559, incorporated by reference herein, in their entireties). GM1 is a member of the ganglio series of gangliosides which contain one sialic acid residue. GM1 impacts neuronal plasticity and repair mechanisms and the release of neurotrophins in the brain. Polyamides are cell permeable, synthetic oligomers. In some embodiments, the particle is conjugated to a mixture of particle linkers. In some embodiments, the particle is conjugated to a targeting ligand. In some embodiments, the particle is conjugated to a mixture of targeting ligands. In some embodiments, the particle is conjugated to a mixture of particle linkers and targeting ligands.

In some embodiments the particle is a nanoparticle. In some embodiments, the nanoparticle is a polymeric nanoparticle, micelle, dendrimer, or liposome as described herein.

In some aspects, a nucleic acid complex (e.g., containing a stabilizing oligonucleotide and synthetic mRNA) or an oligonucleotide (e.g., stabilizing oligonucleotide) formulation disclosed herein can be targeted to a specific cell or tissue type of interest via a ligand conjugated to a particle or via a ligand conjugated to a particle linker, which is conjugated to the particle, wherein the ligand targets a receptor of the cell or tissue of interest. For example, in some embodiments, a ligand can be mannose, which can be conjugated directly to a particle or conjugated to a particle linker that is conjugated to the particle, and the mannose can bind to a mannose receptor on the surface of a macrophage or dendritic cell. In other embodiments, a ligand can be glutamate, which can be conjugated directly to a particle or conjugated to a particle linker that is conjugated to the particle, and the glutamate can bind to a glutamate receptor on the surface of a central nervous system (CNS) cell, e.g. neuron or glial cell, or dendrite of a postsynaptic cell.

In other embodiments, a ligand can be PD-L1 or PD-L2, which can be conjugated directly to a particle or conjugated to a particle linker that is conjugated to the particle, and the PD-L1 or PD-L2 ligand can bind to a PD-1 receptor on the surface of an antigen presenting cell (APC), e.g., a dendritic cell, or a T cell. However, other appropriate ligands may be used for targeting to a particular receptor.

In some embodiments, without limitation, the ligand is a ligand of a PD-1 receptor (e.g., PD-L1 or PD-L2), a CTLA4 receptor, a glutamate receptor, mannose receptor, natural killer group 2D (NKG2D) receptor, chemokine receptor (e.g., CCL19 or CCL21 ligands of CCR7 receptor, or CXCL9 or CXCL10 ligands of CXCR3 receptor), pattern recognition receptor (PRR), Toll-like receptor (TLR), killer activated receptor (KAR), killer inhibitor receptor (KIR), complement receptor, Fc receptor, B cell receptor, or T cell receptor, acetylcholine (ACh) receptor (e.g., nicotine acetylcholine receptor (nAChR) or muscarinic or metabotropic acetylcholine receptor (mAChR)), metabotropic receptor (e.g., G-protein coupled receptor or G-protein coupled receptor linked to a second messenger or second messenger system), ionotropic receptor (e.g., N-methyl D-aspartate (NMDA), amino methyl propionic acid (AMPA), Kainite), transferrin receptor, adenosine receptor (AR), 5-HT receptor (5-HT$_1$, 5-HT$_2$, or 5-HT$_3$), insulin receptor, γ-aminobutyric acid, 4-aminobutanoic acid (GABA) receptor, dopamine receptor (including D1-type and D2-type), or adrenergic receptor (α or β). In some embodiments, the ligand is glutamate, aspartate, mannose, N-acetylglucosamine, fucose, an NKG2D ligand (e.g. MICA or MICB), B7-H1 (PD-L1), B7-DC (PD-L2), CD80, CD86, delta-like ligand 4 (DLL4), transferrin, insulin, Apo-protein, IGF-1, leptin, NMDA, AMPA, GABA, bicuculline, picrotoxinin, dopamine, nicotine, muscarine, acetylcholine, adenosine, serotonin, phenylephrine, adenylate cyclase, or melatonin. In some embodiments, a ligand facilitates blood brain barrier transport (e.g., a transferrin ligand may be used to target a transferrin binding receptor in cells of the brain vasculature to facilitate blood brain barrier transport). In some embodiments, the ligand facilitates blood brain barrier transport via receptor-mediated transcytosis.

In some embodiments, without limitation, the ligand receptor is a PD-1 receptor, CTLA4 receptor, glutamate receptor, mannose receptor, natural killer group 2D (NKG2D) receptor, chemokine receptor, pattern recognition receptor (PRR), Toll-like receptor (TLR), killer activated receptor (KAR), killer inhibitor receptor (KIR), complement receptor, Fc receptor, B cell receptor, or T cell receptor, acetylcholine (ACh) receptor (e.g., nicotine acetylcholine receptor (nAChR) or muscarinic or metabotropic acetylcholine receptor (mAChR)), metabotropic receptor (e.g., G-protein coupled receptor or G-protein coupled receptor linked to a second messenger or second messenger system), ionotropic receptor (e.g., N-methyl D-aspartate (NMDA), amino methyl propionic acid (AMPA), Kainite), transferrin receptor, adenosine receptor (AR), a 5-HT receptor (5-HT$_1$, 5-HT$_2$, or 5-HT$_3$), insulin receptor, γ-aminobutyric acid, 4-aminobutanoic acid (GABA) receptor, dopamine receptor (including D1-type and D2-type), or adrenergic receptor (α or β).

In some embodiments the cell or tissue to be targeted is in vitro. In some embodiments the cell or tissue to be targeted is in vivo. In some embodiments, without limitation, the cell or tissue that has the ligand receptor is a cell or tissue of the immune system or central nervous system (CNS). In some embodiments, the tissue is a tissue of the central nervous system, muscle, or immune system. In some embodiments, the cell is an antigen presenting cell (APC), e.g., dendritic cell, macrophage, or B cell, a T cell, cytotoxic T cell, natural killer (NK) cell, T helper (T$_h$) cell, neuron, projection neuron, interneuron, glial cell, microglial cell, astrocyte, oligodendrocyte, ependymal cell, radial glial cell, or dendrite. In some embodiments, the cell is from a cell line that was derived from a normal, transformed or immortalized cell, e.g., a normal, transformed or immortalized immune cell or central nervous system cell.

Other cells may be targeted by using appropriate cell targeting ligands. For example, in some embodiments, cells to be targeted are stem cells, e.g., embryonic stem cells, mesenchymal stem cells, hematopoietic stem cells, cancer stem cells, stromal cells etc. In some embodiments, cells to be targeted are epithelial cells (e.g., corneal epithelial cells, mammary epithelial cells, etc.), fibroblasts, myoblasts (e.g., human skeletal myoblasts), keratinocytes, endothelial cells (e.g., vascular endothelial cells), neural cells, smooth muscle cells, marrow cells, bone cells (e.g., osteocytes, osteoblasts, osteoclasts) hematopoietic cells (e.g., monocytes, macrophages, megakaryocytes, etc.) or placental cells.

Oligonucleotides

Oligonucleotides provided herein are useful for stabilizing RNAs by inhibiting or preventing degradation of the RNAs (e.g., degradation mediated by exonucleases). Such oligonucleotides may be referred to as "stabilizing oligonucleotides." In some embodiments, oligonucleotides hybridize at a 5' and/or 3' region of the RNA resulting in duplex regions that stabilize the RNA by preventing degradation by exonucleotides having single strand processing activity.

In some embodiments, oligonucleotides are provided having a region complementary with at least 5 consecutive nucleotides of a 5' region of an RNA transcript. In some embodiments, oligonucleotides are provided having a region complementary with at least 5 consecutive nucleotides of a 3'-region of an RNA transcript. In some embodiments, oligonucleotides are provided having a first region complementary with at least 5 consecutive nucleotides of a 5' region of an RNA transcript, and a second region complementary with at least 5 consecutive nucleotides of a 3'-region of an RNA transcript.

In some embodiments, oligonucleotides are provided having a region complementary with at least 5 consecutive nucleotides of the 5'-UTR of an mRNA transcript. In some embodiments, oligonucleotides are provided having a region complementary with at least 5 consecutive nucleotides of the 3'-UTR, poly(A) tail, or overlapping the polyadenylation junction of the mRNA transcript. In some embodiments, oligonucleotides are provided having a first region complementary with at least 5 consecutive nucleotides of the 5'-UTR of an mRNA transcript, and a second region complementary with at least 5 consecutive nucleotides of the 3'-UTR, poly(A) tail, or overlapping the polyadenylation junction of the mRNA transcript.

In some embodiments, oligonucleotides are provided that have a region of complementarity that is complementary to an RNA transcript in proximity to the 5'-end of the RNA transcript. In such embodiments, the nucleotide at the 3'-end of the region of complementarity of the oligonucleotides may be complementary with the RNA transcript at a position that is within 10 nucleotides, within 20 nucleotides, within 30 nucleotides, within 40 nucleotides, within 50 nucleotides, or within 100 nucleotides, within 200 nucleotides, within 300 nucleotides, within 400 nucleotides or more of the transcription start site of the RNA transcript.

In some embodiments, oligonucleotides are provided that have a region of complementarity that is complementary to an RNA transcript in proximity to the 3'-end of the RNA transcript. In such embodiments, the nucleotide at the 3'-end and/or 5' end of the region of complementarity may be complementary with the RNA transcript at a position that is within 10 nucleotides, within 20 nucleotides, within 30 nucleotides, within 40 nucleotides, within 50 nucleotides, within 100 nucleotides, within 200 nucleotides, within 300 nucleotides, within 400 nucleotides or more of the 3'-end of the RNA transcript. In some embodiments, if the target RNA transcript is polyadenylated, the nucleotide at the 3'-end of the region of complementarity of the oligonucleotide may be complementary with the RNA transcript at a position that is within 10 nucleotides, within 20 nucleotides, within 30 nucleotides, within 40 nucleotides, within 50 nucleotides, within 100 nucleotides, within 200 nucleotides, within 300 nucleotides, within 400 nucleotides or more of polyadenylation junction. In some embodiments, an oligonucleotide that targets a 3' region of an RNA comprises a region of complementarity that is a stretch of pyrimidines (e.g., 4 to 10 or 5 to 15 thymine nucleotides) complementary with adenines.

In some embodiments, combinations of 5' targeting and 3' targeting oligonucleotides are contacted with a target RNA. In some embodiments, the 5' targeting and 3' targeting oligonucleotides a linked together via a linker (e.g., a stretch of nucleotides non-complementary with the target RNA). In some embodiments, the region of complementarity of the 5' targeting oligonucleotide is complementary to a region in the target RNA that is at least 2, 5, 10, 20, 50, 100, 500, 1000, 5000, 10000 nucleotides upstream from the region of the target RNA that is complementary to the region of complementarity of the 3' end targeting oligonucleotide.

In some embodiments, oligonucleotides are provided that have the general formula 5'-$X_1$—$X_2$-3', in which $X_1$ has a region of complementarity that is complementary with an RNA transcript (e.g., with at least 5 contiguous nucleotides of the RNA transcript). In some embodiments, the nucleotide at the 3'-end of the region of complementary of $X_1$ may be complementary with a nucleotide in proximity to the transcription start site of the RNA transcript. In some embodiments, the nucleotide at the 3'-end of the region of complementary of $X_1$ may be complementary with a nucleotide that is present within 1, 2, 3, 4, 5, 6, 7, 8, 9, or 10 nucleotides of the transcription start site of the RNA transcript. In some embodiments, the nucleotide at the 3'-end of the region of complementary of $X_1$ may be complementary with the nucleotide at the transcription start site of the RNA transcript.

In some embodiments, $X_1$ comprises 5 to 10 nucleotides, 5 to 15 nucleotides, 5 to 25 nucleotides, 10 to 25 nucleotides, 5 to 20 nucleotides, or 15 to 30 nucleotides. In some embodiments, $X_1$ comprises 5, 6, 7, 8, 9, 10, 11, 12, 13, 14, 15, 16, 17, 18, 19, 20, 25, 30 or more nucleotides. In some embodiments, the region of complementarity of $X_1$ may be complementary with at least 4, at least 5, at least 6, at least 7, at least 8, at least 9, or at least 10 contiguous nucleotides of the RNA transcript. In some embodiments, the region of complementarity of $X_1$ may be complementary with 4, 5, 6, 7, 8, 9, 10, 11, 12, 13, 14, 15, 16, 17, 18, 19, 20 or more contiguous nucleotides of the RNA transcript.

In some embodiments, $X_2$ is absent. In some embodiments, $X_2$ comprises 1 to 10, 1 to 20 nucleotides, 1 to 25 nucleotides, 5 to 20 nucleotides, 5 to 30 nucleotides, 5 to 40 nucleotides, or 5 to 50 nucleotides. In some embodiments, $X_2$ comprises 5, 6, 7, 8, 9, 10, 11, 12, 13, 14, 15, 16, 17, 18, 19, 20, 25, 30, 35, 40, 45, 50 or more nucleotides. In some embodiments, $X_2$ comprises a region of complementarity complementary with at least 4, at least 5, at least 6, at least 7, at least 8, at least 9, or at least 10 contiguous nucleotides of the RNA transcript. In some embodiments, $X_2$ comprises a region of complementarity complementary with 4, 5, 6, 7, 8, 9, 10, 11, 12, 13, 14, 15, 16, 17, 18, 19, 20 or more contiguous nucleotides of the RNA transcript.

In some embodiments, the RNA transcript has a 7-methylguanosine cap at its 5'-end. In some embodiments, the nucleotide at the 3'-end of the region of complementary of $X_1$ is complementary with the nucleotide of the RNA transcript that is immediately internal to the 7-methylguanosine cap or in proximity to the cap (e.g., with 10 nucleotides of the cap). In some embodiments, at least the first nucleotide at the 5'-end of $X_2$ is a pyrimidine complementary with guanine (e.g., a cytosine or analogue thereof). In some embodiments, the first and second nucleotides at the 5'-end of $X_2$ are pyrimidines complementary with guanine. Thus, in some embodiments, at least one nucleotide at the 5'-end of $X_2$ is a pyrimidine that may form stabilizing hydrogen bonds with the 7-methylguanosine of the cap.

In some embodiments, $X_2$ forms a stem-loop structure. In some embodiments, $X_2$ comprises the formula 5'-$Y_1$-$Y_2$—$Y_3$-3', in which $X_2$ forms a stem-loop structure having a loop region comprising the nucleotides of $Y_2$ and a stem region comprising at least two contiguous nucleotides of $Y_1$ hybridized with at least two contiguous nucleotides of $Y_3$. In some embodiments, the stem region comprises 1-6, 1-5, 2-5, 1-4, 2-4 or 2-3 nucleotides. In some embodiments, the stem region comprises LNA nucleotides. In some embodiments, the stem region comprises 1-6, 1-5, 2-5, 1-4, 2-4 or 2-3 LNA nucleotides. In some embodiments, $Y_1$ and $Y_3$ independently comprise 2 to 10 nucleotides, 2 to 20 nucleotides, 2 to 25 nucleotides, or 5 to 20 nucleotides. In some embodiments, $Y_1$ and $Y_3$ independently comprise 2, 3, 4, 5, 6, 7, 8, 9, 10, 11, 12, 13, 14, 15, 16, 17, 18, 19, 20, 25 or more nucleotides. In some embodiments, $Y_2$ comprises 3 to 10 nucleotides, 3 to 15 nucleotides, 3 to 25 nucleotides, or 5 to 20 nucleotides. In some embodiments, $Y_2$ comprises 3, 4, 5, 6, 7, 8, 9, 10, 11, 12, 13, 14, 15, 16, 17, 18, 19, 20, 25 or more nucleotides. In some embodiments, $Y_2$ comprises 2-8, 2-7, 2-6, 2-5, 3-8, 3-7, 3-6, 3-5 or 3-4 nucleotides. In some embodiments, $Y_2$ comprises at least one DNA nucleotide. In some embodiments, the nucleotides of $Y_2$ comprise at least one (e.g., 1, 2, 3, 4, 5, 6, 7, 8, 9, 10, 11, 12, 13, 14, 15, 16, 17, 18, 19, 20, 25 or more adenines). In some embodiments, $Y_3$ comprises 1-5, 1-4, 1-3 or 1-2 nucleotides following the 3' end of the stem region. In some embodiments, the nucleotides of $Y_3$ following the 3' end of the stem region are DNA nucleotides. In some embodiments, $Y_3$ comprises a pyrimidine complementary with guanine (e.g., cytosine or an analogue thereof). In some embodiments, $Y_3$ comprises one or more (e.g., two) pyrimidines complementary with guanine at a position following the 3'-end of the stem region (e.g., 1, 2, 3 or more nucleotide after the 3'-end of the stem region). Thus, in embodiments where the RNA transcript is capped, $Y_3$ may have a pyrimidine that forms stabilizing hydrogen bonds with the 7-methylguanosine of the cap.

In some embodiments, $X_1$ and $X_2$ are complementary with non-overlapping regions of the RNA transcript. In some embodiments, $X_1$ comprises a region complementary with a 5' region of the RNA transcript and $X_2$ comprises a region complementary with a 3' region of the RNA transcript. For example, if the RNA transcript is polyadenylated, $X_2$ may comprise a region of complementarity that is complementary with the RNA transcript at a region within 100 nucleotides, within 50 nucleotides, within 25 nucleotides or within 10 nucleotides of the polyadenylation junction of the RNA transcript. In some embodiments, $X_2$ comprises a region of complementarity that is complementary with the RNA transcript immediately adjacent to or overlapping the polyadenylation junction of the RNA transcript. In some embodiments, $X_2$ comprises at least 2 consecutive pyrimidine nucleotides (e.g., 5 to 15 pyrimidine nucleotides) complementary with adenine nucleotides of the poly(A) tail of the RNA transcript.

In some embodiments, oligonucleotides are provided that comprise the general formula 5'-$X_1$—$X_2$-3', in which $X_1$ comprises at least 2 nucleotides that form base pairs with adenine (e.g., thymidines or uridines or analogues thereof); and $X_2$ comprises a region of complementarity that is complementary with at least 3 contiguous nucleotides of a poly-adenylated RNA transcript, wherein the nucleotide at the 5'-end of the region of complementary of $X_2$ is complementary with the nucleotide of the RNA transcript that is immediately internal to the poly-adenylation junction of the RNA transcript. In such embodiments, $X_1$ may comprises 2 to 10, 2 to 20, 5 to 15 or 5 to 25 nucleotides and $X_2$ may independently comprises 2 to 10, 2 to 20, 5 to 15 or 5 to 25 nucleotides.

In some embodiments, compositions are provided that comprise a first oligonucleotide comprising at least 5 nucleotides (e.g., of 5 to 25 nucleotides) linked through internucleoside linkages, and a second oligonucleotide comprising at least 5 nucleotides (e.g., of 5 to 25 nucleotides) linked through internucleoside linkages, in which the first oligonucleotide is complementary with at least 5 consecutive nucleotides in proximity to the 5'-end of an RNA transcript and the second oligonucleotide is complementary with at least 5 consecutive nucleotides in proximity to the 3'-end of an RNA transcript. In some embodiments, the 5' end of the first oligonucleotide is linked with the 3' end of the second oligonucleotide. In some embodiments, the 3' end of the first oligonucleotide is linked with the 5' end of the second oligonucleotide. In some embodiments, the 5' end of the first oligonucleotide is linked with the 5' end of the second oligonucleotide. In some embodiments, the 3' end of the first oligonucleotide is linked with the 3' end of the second oligonucleotide.

In some embodiments, the first oligonucleotide and second oligonucleotide are joined by a linker. The term "linker" generally refers to a chemical moiety that is capable of covalently linking two or more oligonucleotides. In some embodiments, a linker is resistant to cleavage in certain biological contexts, such as in a mammalian cell extract, such as an endosomal extract. However, in some embodiments, at least one bond comprised or contained within the linker is capable of being cleaved (e.g., in a biological context, such as in a mammalian extract, such as an endosomal extract), such that at least two oligonucleotides are no longer covalently linked to one another after bond cleavage. In some embodiments, the linker is not an oligonucleotide having a sequence complementary with the RNA transcript. In some embodiments, the linker is an oligonucleotide (e.g., 2-8 thymines). In some embodiments, the linker is a polypeptide. Other appropriate linkers may also be used, including, for example, linkers disclosed in International Patent Application Publication WO 2013/040429 A1, published on Mar. 21, 2013, and entitled MULTIMERIC ANTISENSE OLIGONUCLEOTIDES, and in International Patent Application Publication WO 2014043544 A1, published on Mar. 20, 2014, and entitled MULTIMERIC ANTISENSE OLIGONUCLEOTIDES. The contents of these publications relating to linkers are incorporated herein by reference in their entireties.

An oligonucleotide may have a region of complementarity with a target RNA transcript (e.g., a mammalian mRNA transcript) that has less than a threshold level of complementarity with every sequence of nucleotides, of equivalent length, of an off-target RNA transcript. For example, an oligonucleotide may be designed to ensure that it does not have a sequence that targets RNA transcripts in a cell other than the target RNA transcript. The threshold level of sequence identity may be 50%, 60%, 70%, 80%, 85%, 90%, 95%, 99% or 100% sequence identity.

An oligonucleotide may be complementary to RNA transcripts encoded by homologues of a gene across different species (e.g., a mouse, rat, rabbit, goat, monkey, etc.) In some embodiments, oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease.

In some embodiments, the region of complementarity of an oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a target RNA. In some embodiments, the region of complementarity is complementary with at least 8 consecutive nucleotides of a target RNA.

Complementary, as the term is used in the art, refers to the capacity for precise pairing between two nucleotides. For example, if a nucleotide at a certain position of an oligonucleotide is capable of hydrogen bonding with a nucleotide at a corresponding position of a target RNA, then the nucleotide of the oligonucleotide and the nucleotide of the target RNA are complementary to each other at that position. The oligonucleotide and target RNA are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the oligonucleotide and target RNA. For example, if a base at one position of an oligonucleotide is capable of hydrogen bonding with a base at the corresponding position of a target RNA, then the bases are considered to be complementary to each other at that position. 100% complementarity is not required.

An oligonucleotide may be at least 80% complementary to (optionally one of at least 85%, 90%, 91%, 92%, 93%, 94%, 95%, 96%, 97%, 98%, 99% or 100% complementary to) the consecutive nucleotides of a target RNA. In some embodiments an oligonucleotide may contain 1, 2 or 3 base mismatches compared to the portion of the consecutive nucleotides of the target RNA. In some embodiments an oligonucleotide may have up to 3 mismatches over 15 bases, or up to 2 mismatches over 10 bases.

In some embodiments, a complementary nucleic acid sequence need not be 100% complementary to that of its target to be specifically hybridizable. In some embodiments, an oligonucleotide for purposes of the present disclosure is specifically hybridizable with a target RNA when hybridization of the oligonucleotide to the target RNA prevents or inhibits degradation of the target RNA, and when there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency.

In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80 or more nucleotides in length. In some embodiments, the oligonucleotide is 8 to 50, 10 to 30, 9 to 20, 15 to 30 or 8 to 80 nucleotides in length.

Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa.

In some embodiments, an oligonucleotide may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches. Contiguous runs of three or more Gs or Cs may not be preferable in some embodiments. Accordingly, in some embodiments, the oligonucleotide does not comprise a stretch of three or more guanosine nucleotides.

An oligonucleotide may have a sequence that is has greater than 30% G-C content, greater than 40% G-C content, greater than 50% G-C content, greater than 60% G-C content, greater than 70% G-C content, or greater than 80% G-C content. An oligonucleotide may have a sequence that has up to 100% G-C content, up to 95% G-C content, up to 90% G-C content, or up to 80% G-C content. In some embodiments, GC content of an oligonucleotide is preferably between about 30-60%.

It is to be understood that any oligonucleotide provided herein can be excluded.

In some embodiments, it has been found that oligonucleotides disclosed herein may increase stability of a target RNA by at least about 50% (e.g. 150% of normal or 1.5 fold), or by about 2 fold to about 5 fold. In some embodiments, stability (e.g., stability in a cell) may be increased by at least about 15 fold, 20 fold, 30 fold, 40 fold, 50 fold or 100 fold, or any range between any of the foregoing numbers. In some embodiments, increased mRNA stability has been shown to correlate to increased protein expression. Similarly, in some embodiments, increased stability of non-coding positively correlates with increased activity of the RNA.

It is understood that any reference to uses of oligonucleotides or other molecules throughout the description contemplates use of the oligonucleotides or other molecules in preparation of a pharmaceutical composition or medicament for use in the treatment of condition or a disease associated with decreased levels or activity of a RNA transcript. Thus, as one nonlimiting example, this aspect of the disclosure includes use of oligonucleotides or other molecules in the preparation of a medicament for use in the treatment of disease, wherein the treatment involves posttranscriptionally altering protein and/or RNA levels in a targeted manner.

Methods for identifying transcript start sites and polyadenylation junctions are known in the art and may be used in selecting oligonucleotides that specifically bind to these regions for stabilizing RNA transcripts. In some embodiments, 3' end oligonucleotides may be designed by identifying RNA 3' ends using quantitative end analysis of poly-A tails. In some embodiments, 5' end oligonucleotides may be designed by identifying 5' start sites using Cap analysis gene expression (CAGE). Appropriate methods are disclosed, for example, in Ozsolak et al. *Comprehensive Polyadenylation Site Maps in Yeast and Human Reveal Pervasive Alternative Polyadenylation*. Cell. Volume 143, Issue 6, 2010, Pages 1018-1029; Shiraki, T, et al., *Cap analysis gene expression for high-throughput analysis of transcriptional starting point and identification of promoter usage*. Proc Natl Acad Sci USA. 100 (26): 15776-81. 2003 Dec. 23; and Zhao, X, et al., (2011). Systematic Clustering of Transcription Start Site Landscapes. PLoS ONE (Public Library of Science) 6 (8): e23409, the contents of each of which are incorporated herein by reference. Other appropriate methods for identifying transcript start sites and polyadenylation junctions may also be used, including, for example, RNA-Paired-end tags (PET) (See, e.g., Ruan X, Ruan Y. Methods Mol Biol. 2012; 809:535-62); use of standard EST databases; RACE combined with microarray or sequencing, PAS-Seq (See, e.g., Peter J. Shepard, et al., RNA. 2011 April; 17(4): 761-772); and 3P-Seq (See, e.g., Calvin H. Jan, Nature. 2011 Jan. 6; 469(7328): 97-101; and others.

Exemplary oligonucleotides targeting the 5' and/or 3' ends of RNAs are provided in Example 2 and Tables 3-13.

Oligonucleotide Modifications

In some embodiments, oligonucleotides are provided with chemistries suitable for delivery, hybridization and stability within cells to target and stabilize RNA transcripts. Furthermore, in some embodiments, oligonucleotide chemistries are provided that are useful for controlling the pharmacokinetics, biodistribution, bioavailability and/or efficacy of the oligonucleotides. Accordingly, oligonucleotides described herein may be modified, e.g., comprise a modified sugar moiety, a modified internucleoside linkage, a modified nucleotide and/or combinations thereof. In addition, the oligonucleotides may exhibit one or more of the following properties: do not induce substantial cleavage or degradation of the target RNA; do not cause substantially complete cleavage or degradation of the target RNA; do not activate the RNAse H pathway; do not activate RISC; do not recruit any Argonaute family protein; are not cleaved by Dicer; do not mediate alternative splicing; are not immune stimulatory; are nuclease resistant; have improved cell uptake compared to unmodified oligonucleotides; are not toxic to cells or mammals; and may have improved endosomal exit.

Oligonucleotides that are designed to interact with RNA to modulate gene expression are a distinct subset of base sequences from those that are designed to bind a DNA target (e.g., are complementary to the underlying genomic DNA sequence from which the RNA is transcribed).

Any of the oligonucleotides disclosed herein may be linked to one or more other oligonucleotides disclosed herein by a linker, e.g., a cleavable linker.

Oligonucleotides of the disclosure can be stabilized against nucleolytic degradation such as by the incorporation of a modification, e.g., a nucleotide modification. For example, nucleic acid sequences of the disclosure include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," e.g., comprise nucleic acid analogues in which the ribose ring is "locked" by a methylene bridge connecting the 2'-O atom and the 4'-C atom.

Any of the modified chemistries or formats of oligonucleotides described herein can be combined with each other, and that one, two, three, four, five, or more different types of modifications can be included within the same molecule.

In some embodiments, the oligonucleotide may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States patent or patent application Publications: U.S. Pat. Nos. 7,399,845, 7,741,457, 8,022,193, 7,569,686, 7,335,765, 7,314,923, 7,335,765, and 7,816,333, US 20110009471, the entire contents of each of which are incorporated herein by reference for all purposes. The oligonucleotide may have one or more 2' O-methyl nucleotides. The oligonucleotide may consist entirely of 2' O-methyl nucleotides.

Often an oligonucleotide has one or more nucleotide analogues. For example, an oligonucleotide may have at least one nucleotide analogue that results in an increase in $T_m$ of the oligonucleotide in a range of 1° C., 2° C., 3° C., 4° C., or 5° C. compared with an oligonucleotide that does not have the at least one nucleotide analogue. An oligonucleotide may have a plurality of nucleotide analogues that results in a total increase in $T_m$ of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

The oligonucleotide may be of up to 50 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are nucleotide analogues. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are nucleotide analogues. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are nucleotide analogues. Optionally, the oligonucleotides may have every nucleotide except 1, 2, 3, 4, 5, 6, 7, 8, 9, or 10 nucleotides modified.

The oligonucleotide may consist entirely of bridged nucleotides (e.g., LNA nucleotides, cEt nucleotides, ENA nucleotides). The oligonucleotide may comprise alternating deoxyribonucleotides and 2'-fluoro-deoxyribonucleotides. The oligonucleotide may comprise alternating deoxyribonucleotides and 2'-O-methyl nucleotides. The oligonucleotide may comprise alternating deoxyribonucleotides and ENA nucleotide analogues. The oligonucleotide may comprise alternating deoxyribonucleotides and LNA nucleotides. The oligonucleotide may comprise alternating LNA nucleotides and 2'-O-methyl nucleotides. The oligonucleotide may have a 5' nucleotide that is a bridged nucleotide (e.g., a LNA nucleotide, cEt nucleotide, ENA nucleotide). The oligonucleotide may have a 5' nucleotide that is a deoxyribonucleotide.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide may have a 3' hydroxyl group. The 3' position of the oligonucleotide may have a 3' thiophosphate.

The oligonucleotide may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ligands of the asialoglycoprotein receptor (ASGPR), such as GalNac, or dynamic polyconjugates and variants thereof at its 5' or 3' end.

Preferably an oligonucleotide comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric oligonucleotides of the disclosure may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, an oligonucleotide comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (e.g., higher target binding affinity) than 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, oligonucleotides may have phosphorothioate backbones; heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula.

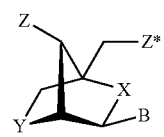

where X and Y are independently selected among the groups —O—,

—S—, —N(H)—, N(R)—, —CH$_2$— or —CH— (if part of a double bond),

—CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligonucleotides described herein comprises at least one LNA unit according any of the formulas

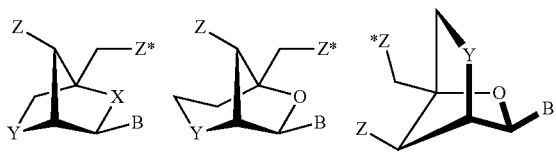

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

In some embodiments, the Locked Nucleic Acid (LNA) used in the oligonucleotides described herein comprises at least one Locked Nucleic Acid (LNA) unit according any of the formulas shown in Scheme 2 of PCT/DK2006/000512.

In some embodiments, the LNA used in the oligomer of the disclosure comprises internucleoside linkages selected from -0-P(O)$_2$—O—, —O—P(O,S)—O—, —O—P(S)$_2$—O—, —S—P(O)$_2$—O—, —S—P(O,S)—O—, —S—P(S)$_2$—O—, —0-P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —0-PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Other examples of LNA units are shown below:

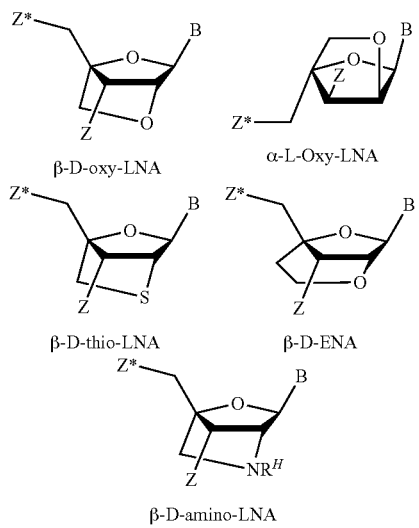

β-D-oxy-LNA
α-L-Oxy-LNA
β-D-thio-LNA
β-D-ENA
β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail herein.

One or more substituted sugar moieties can also be included, e.g., one of the following at the 2' position: OH, SH, SCH$_3$, F, OCN, OCH$_3$OCH$_3$, OCH$_3$O(CH$_2$)n CH$_3$, O(CH$_2$)n NH$_2$ or O(CH$_2$)n CH$_3$ where n is from 1 to about 10; C1 to C10 lower alkyl, alkoxyalkoxy, substituted lower alkyl, alkaryl or aralkyl; C1; Br; CN; CF$_3$; OCF$_3$; O-, S-, or N-alkyl; O—, S—, or N-alkenyl; SOCH$_3$; SO$_2$CH$_3$; ONO$_2$; NO$_2$; N$_3$; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)](Martin et al, Helv. Chim. Acta, 1995, 78, 486). Other preferred modifications include 2'-methoxy (2'-O—CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, e.g., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Oligonucleotides can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990, those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the disclosure. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the oligonucleotides are chemically linked to one or more moieties or conjugates that enhance the activity, cellular distribution, or cellular uptake of the oligonucleotide. For example, one or more oligonucleotides, of the same or different types, can be conjugated to each other; or oligonucleotides can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the disclosure include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this disclosure, include groups that improve uptake, distribution, metabolism or excretion of the compounds of the present disclosure. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025;

4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, oligonucleotide modification include modification of the 5' or 3' end of the oligonucleotide. In some embodiments, the 3' end of the oligonucleotide comprises a hydroxyl group or a thiophosphate. It should be appreciated that additional molecules (e.g. a biotin moiety or a fluorophor) can be conjugated to the 5' or 3' end of an oligonucleotide. In some embodiments, an oligonucleotide comprises a biotin moiety conjugated to the 5' nucleotide.

In some embodiments, an oligonucleotide comprises locked nucleic acids (LNA), ENA modified nucleotides, 2'-O-methyl nucleotides, or 2'-fluoro-deoxyribonucleotides. In some embodiments, an oligonucleotide comprises alternating deoxyribonucleotides and 2'-fluoro-deoxyribonucleotides. In some embodiments, an oligonucleotide comprises alternating deoxyribonucleotides and 2'-O-methyl nucleotides. In some embodiments, an oligonucleotide comprises alternating deoxyribonucleotides and ENA modified nucleotides. In some embodiments, an oligonucleotide comprises alternating deoxyribonucleotides and locked nucleic acid nucleotides. In some embodiments, an oligonucleotide comprises alternating locked nucleic acid nucleotides and 2'-O-methyl nucleotides.

In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, an oligonucleotide comprises phosphorothioate internucleotide linkages. In some embodiments, an oligonucleotide comprises phosphorothioate internucleotide linkages between at least two nucleotides. In some embodiments, an oligonucleotide comprises phosphorothioate internucleotide linkages between all nucleotides.

It should be appreciated that an oligonucleotide can have any combination of modifications as described herein.

The oligonucleotide may comprise a nucleotide sequence having one or more of the following modification patterns.
- (a) (X)Xxxxxx, (X)xXxxxx, (X)xxXxxx, (X)xxxXxx, (X)xxxxXx and (X)xxxxxX,
- (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX,
- (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)xXxXXx, (X)xXxxXX, (X)xxXxXX, (X)XxxXXx (X)XxxxXX, (X)xXxXXx, (X)xXxxXX, (X)xxXxXX, (X)xXxXxX and (X)XxXxXx,
- (d) (X)xxXXX, (X)xXxXXX, (X)xXXxXX, (X)xXXXxX, (X)xXXXXx, (X)XxxXXXX, (X)XxXxXX, (X)XxXXxX, (X)XxXXXx, (X)XXxxXX, (X)XXxXxX, (X)XXxXXx, (X)XXXxxX, (X)XXXxXx, (X)XXXXxx, and (X)XXXXxx,
- (e) (X)xXXXXX, (X)XxXXXX, (X)XXxXXX, (X)XXXxXX, (X)XXXXxX and (X)XXXXXx, and
- (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

Exemplary oligonucleotide modifications are also provided in Example 2 and Table 14.

RNA and RNA Transcripts

In some embodiments, an RNA transcript targeted by an oligonucleotide disclosed herein is an RNA transcript of a eukaryotic cell. In some embodiments, an RNA transcript targeted by an oligonucleotide disclosed herein is an RNA transcript of a cell of a vertebrate. In some embodiments, an RNA transcript targeted by an oligonucleotide disclosed herein is an RNA transcript of a cell of a mammal, e.g., a primate cell, mouse cell, rat cell, or human cell. In some embodiments, an RNA transcript targeted by an oligonucleotide disclosed herein is an RNA transcript of a cardiomyocyte. In some embodiments, an RNA transcript targeted by an oligonucleotide disclosed herein is an RNA transcribed in the nucleus of a cell. In some embodiments, an RNA transcript targeted by an oligonucleotide disclosed herein is an RNA transcribed in a mitochondrion of a cell. In some embodiments, an RNA transcript targeted by an oligonucleotide disclosed herein is an RNA transcript transcribed by a RNA polymerase II enzyme.

In some embodiments, an RNA transcript targeted by an oligonucleotide disclosed herein is an mRNA expressed from a gene, including, but not limited to, ABCA1, APOA1, ATP2A2, BDNF, FXN, HBA2, HBB, HBD, HBE1, HBG1, HBG2, SMN, UTRN, PTEN, MECP2, and FOXP3, ABCA4, ABCB11, ABCB4, ABCG5, ABCG8, ADIPOQ, ALB, APOE, BCL2L11, BRCA1, CD274, CEP290, CFTR, EPO, F7, F8, FLI1, FMR1, FNDC5, GCH1, GCK, GLP1R, GRN, HAMP, HPRT1, IDO1, IGF1, IL10, IL6, KCNMA1, KCNMB1, KCNMB2, KCNMB3, KCNMB4, KLF1, KLF4, LDLR, MSX2, MYBPC3, NANOG, NF1, NKX2-1, NKX2-1-AS 1, PAH, PTGS2, RB1, RPS 14, RPS 19, SCARB 1, SERPINF1, SIRT1, SIRT6, SMAD7, ST7, STAT3, TSIX, and XIST. RNA transcripts for these and other genes may be selected or identified experimentally, for example, using RNA sequencing (RNA-Seq) or other appropriate methods. RNA transcripts may also be selected based on information in public databases such as in UCSC, Ensembl and NCBI genome browsers and others. Non-limiting examples of RNA transcripts for certain genes are listed in Table 1.

TABLE 1

Non-limiting examples of RNA transcripts for certain genes

| GENE SYMBOL | MRNA | SPECIES | GENE NAME |
| --- | --- | --- | --- |
| ABCA1 | NM_013454 | Mus musculus | ATP-binding cassette, sub-family A (ABC1), member 1 |

TABLE 1-continued

Non-limiting examples of RNA transcripts for certain genes

| GENE SYMBOL | MRNA | SPECIES | GENE NAME |
| --- | --- | --- | --- |
| ABCA1 | NM_005502 | Homo sapiens | ATP-binding cassette, sub-family A (ABC1), member 1 |
| ABCA4 | NM_007378 | Mus musculus | ATP-binding cassette, sub-family A (ABC1), member 4 |
| ABCA4 | NM_000350 | Homo sapiens | ATP-binding cassette, sub-family A (ABC1), member 4 |
| ABCB11 | NM_003742 | Homo sapiens | ATP-binding cassette, sub-family B (MDR/TAP), member 11 |
| ABCB11 | NM_021022 | Mus musculus | ATP-binding cassette, sub-family B (MDR/TAP), member 11 |
| ABCB4 | NM_018850 | Homo sapiens | ATP-binding cassette, sub-family B (MDR/TAP), member 4 |
| ABCB4 | NM_000443 | Homo sapiens | ATP-binding cassette, sub-family B (MDR/TAP), member 4 |
| ABCB4 | NM_018849 | Homo sapiens | ATP-binding cassette, sub-family B (MDR/TAP), member 4 |
| ABCB4 | NM_008830 | Mus musculus | ATP-binding cassette, sub-family B (MDR/TAP), member 4 |
| ABCG5 | NM_022436 | Homo sapiens | ATP-binding cassette, sub-family G (WHITE), member 5 |
| ABCG5 | NM_031884 | Mus musculus | ATP-binding cassette, sub-family G (WHITE), member 5 |
| ABCG8 | NM_026180 | Mus musculus | ATP-binding cassette, sub-family G (WHITE), member 8 |
| ABCG8 | NM_022437 | Homo sapiens | ATP-binding cassette, sub-family G (WHITE), member 8 |
| ADIPOQ | NM_009605 | Mus musculus | adiponectin, C1Q and collagen domain containing |
| ADIPOQ | NM_004797 | Homo sapiens | adiponectin, C1Q and collagen domain containing |
| ALB | NM_000477 | Homo sapiens | albumin |
| ALB | NM_009654 | Mus musculus | albumin |
| APOA1 | NM_000039 | Homo sapiens | apolipoprotein A-I |
| APOA1 | NM_009692 | Mus musculus | apolipoprotein A-I |
| APOE | NM_009696 | Mus musculus | apolipoprotein E |
| APOE | XM_001724655 | Homo sapiens | hypothetical LOC100129500; apolipoprotein E |
| APOE | XM_001722911 | Homo sapiens | hypothetical LOC100129500; apolipoprotein E |
| APOE | XM_001724653 | Homo sapiens | hypothetical LOC100129500; apolipoprotein E |
| APOE | NM_000041 | Homo sapiens | hypothetical LOC100129500; apolipoprotein E |
| APOE | XM_001722946 | Homo sapiens | hypothetical LOC100129500; apolipoprotein E |
| ATP2A2 | NM_009722 | Mus musculus | ATPase, Ca++ transporting, cardiac muscle, slow twitch 2 |
| ATP2A2 | NM_001110140 | Mus musculus | ATPase, Ca++ transporting, cardiac muscle, slow twitch 2 |
| ATP2A2 | NM_001135765 | Homo sapiens | ATPase, Ca++ transporting, cardiac muscle, slow twitch 2 |
| ATP2A2 | NM_170665 | Homo sapiens | ATPase, Ca++ transporting, cardiac muscle, slow twitch 2 |
| ATP2A2 | NM_001681 | Homo sapiens | ATPase, Ca++ transporting, cardiac muscle, slow twitch 2 |
| BCL2L11 | NM_006538 | Homo sapiens | BCL2-like 11 (apoptosis facilitator) |
| BCL2L11 | NM_207002 | Homo sapiens | BCL2-like 11 (apoptosis facilitator) |
| BCL2L11 | NM_138621 | Homo sapiens | BCL2-like 11 (apoptosis facilitator) |
| BCL2L11 | NM_207680 | Mus musculus | BCL2-like 11 (apoptosis facilitator) |
| BCL2L11 | NM_207681 | Mus musculus | BCL2-like 11 (apoptosis facilitator) |
| BCL2L11 | NM_009754 | Mus musculus | BCL2-like 11 (apoptosis facilitator) |
| BDNF | NM_001143816 | Homo sapiens | brain-derived neurotrophic factor |

TABLE 1-continued

Non-limiting examples of RNA transcripts for certain genes

| GENE SYMBOL | MRNA | SPECIES | GENE NAME |
|---|---|---|---|
| BDNF | NM_001143815 | Homo sapiens | brain-derived neurotrophic factor |
| BDNF | NM_001143814 | Homo sapiens | brain-derived neurotrophic factor |
| BDNF | NM_001143813 | Homo sapiens | brain-derived neurotrophic factor |
| BDNF | NM_001143812 | Homo sapiens | brain-derived neurotrophic factor |
| BDNF | NM_001143806 | Homo sapiens | brain-derived neurotrophic factor |
| BDNF | NM_001143811 | Homo sapiens | brain-derived neurotrophic factor |
| BDNF | NM_001143805 | Homo sapiens | brain-derived neurotrophic factor |
| BDNF | NM_001143810 | Homo sapiens | brain-derived neurotrophic factor |
| BDNF | NM_001709 | Homo sapiens | brain-derived neurotrophic factor |
| BDNF | NM_170735 | Homo sapiens | brain-derived neurotrophic factor |
| BDNF | NM_170734 | Homo sapiens | brain-derived neurotrophic factor |
| BDNF | NM_170733 | Homo sapiens | brain-derived neurotrophic factor |
| BDNF | NM_170732 | Homo sapiens | brain-derived neurotrophic factor |
| BDNF | NM_170731 | Homo sapiens | brain-derived neurotrophic factor |
| BDNF | NM_001143809 | Homo sapiens | brain-derived neurotrophic factor |
| BDNF | NM_001143807 | Homo sapiens | brain-derived neurotrophic factor |
| BDNF | NM_001143808 | Homo sapiens | brain-derived neurotrophic factor |
| BDNF | NM_007540 | Mus musculus | brain derived neurotrophic factor |
| BDNF | NM_001048141 | Mus musculus | brain derived neurotrophic factor |
| BDNF | NM_001048142 | Mus musculus | brain derived neurotrophic factor |
| BDNF | NM_001048139 | Mus musculus | brain derived neurotrophic factor |
| BRCA1 | NM_009764 | Mus musculus | breast cancer 1 |
| BRCA1 | NM_007296 | Homo sapiens | breast cancer 1, early onset |
| BRCA1 | NM_007300 | Homo sapiens | breast cancer 1, early onset |
| BRCA1 | NM_007297 | Homo sapiens | breast cancer 1, early onset |
| BRCA1 | NM_007303 | Homo sapiens | breast cancer 1, early onset |
| BRCA1 | NM_007298 | Homo sapiens | breast cancer 1, early onset |
| BRCA1 | NM_007302 | Homo sapiens | breast cancer 1, early onset |
| BRCA1 | NM_007299 | Homo sapiens | breast cancer 1, early onset |
| BRCA1 | NM_007304 | Homo sapiens | breast cancer 1, early onset |
| BRCA1 | NM_007294 | Homo sapiens | breast cancer 1, early onset |
| BRCA1 | NM_007305 | Homo sapiens | breast cancer 1, early onset |
| BRCA1 | NM_007295 | Homo sapiens | breast cancer 1, early onset |
| CD274 | NM_014143 | Homo sapiens | CD274 molecule |
| CD274 | NM_021893 | Mus musculus | CD274 antigen |
| CEP290 | NM_025114 | Homo sapiens | centrosomal protein 290 kDa |
| CEP290 | NM_146009 | Mus musculus | centrosomal protein 290 |

TABLE 1-continued

Non-limiting examples of RNA transcripts for certain genes

| GENE SYMBOL | MRNA | SPECIES | GENE NAME |
|---|---|---|---|
| CFTR | NM_000492 | Homo sapiens | cystic fibrosis transmembrane conductance regulator (ATP-binding cassette sub-family C, member 7) |
| CFTR | NM_021050 | Mus musculus | cystic fibrosis transmembrane conductance regulator homolog |
| EPO | NM_000799 | Homo sapiens | erythropoietin |
| EPO | NM_007942 | Mus musculus | erythropoietin |
| F7 | NM_000131 | Homo sapiens | coagulation factor VII (serum prothrombin conversion accelerator) |
| F7 | NM_019616 | Homo sapiens | coagulation factor VII (serum prothrombin conversion accelerator) |
| F7 | NM_010172 | Mus musculus | coagulation factor VII |
| F8 | NM_019863 | Homo sapiens | coagulation factor VIII, procoagulant component |
| F8 | NM_000132 | Homo sapiens | coagulation factor VIII, procoagulant component |
| F8 | NM_001161373 | Mus musculus | coagulation factor VIII |
| F8 | NM_001161374 | Mus musculus | coagulation factor VIII |
| F8 | NM_007977 | Mus musculus | coagulation factor VIII |
| FLI1 | NM_002017 | Homo sapiens | Friend leukemia virus integration 1 |
| FLI1 | NM_001167681 | Homo sapiens | Friend leukemia virus integration 1 |
| FLI1 | NM_008026 | Mus musculus | Friend leukemia integration 1 |
| FMR1 | NM_008031 | Mus musculus | fragile X mental retardation syndrome 1 homolog |
| FMR1 | NM_002024 | Homo sapiens | fragile X mental retardation 1 |
| FNDC5 | NM_001171941 | Homo sapiens | fibronectin type III domain containing 5 |
| FNDC5 | NM_153756 | Homo sapiens | fibronectin type III domain containing 5 |
| FNDC5 | NM_001171940 | Homo sapiens | fibronectin type III domain containing 5 |
| FNDC5 | NM_027402 | Mus musculus | fibronectin type III domain containing 5 |
| FOXP3 | NM_054039 | Mus musculus | forkhead box P3 |
| FOXP3 | NM_001114377 | Homo sapiens | forkhead box P3 |
| FOXP3 | NM_014009 | Homo sapiens | forkhead box P3 |
| FXN | NM_001161706 | Homo sapiens | frataxin |
| FXN | NM_181425 | Homo sapiens | frataxin |
| FXN | NM_000144 | Homo sapiens | frataxin |
| FXN | NM_008044 | Mus musculus | frataxin |
| GCH1 | NM_008102 | Mus musculus | GTP cyclohydrolase 1 |
| GCH1 | NM_000161 | Homo sapiens | GTP cyclohydrolase 1 |
| GCH1 | NM_001024070 | Homo sapiens | GTP cyclohydrolase 1 |
| GCH1 | NM_001024071 | Homo sapiens | GTP cyclohydrolase 1 |
| GCH1 | NM_001024024 | Homo sapiens | GTP cyclohydrolase 1 |
| GCK | NM_010292 | Mus musculus | glucokinase |
| GCK | NM_000162 | Homo sapiens | glucokinase (hexokinase 4) |
| GCK | NM_033508 | Homo sapiens | glucokinase (hexokinase 4) |
| GCK | NM_033507 | Homo sapiens | glucokinase (hexokinase 4) |

TABLE 1-continued

Non-limiting examples of RNA transcripts for certain genes

| GENE SYMBOL | MRNA | SPECIES | GENE NAME |
| --- | --- | --- | --- |
| GLP1R | NM_021332 | *Mus musculus* | glucagon-like peptide 1 receptor; similar to glucagon-like peptide-1 receptor |
| GLP1R | XM_001471951 | *Mus musculus* | glucagon-like peptide 1 receptor; similar to glucagon-like peptide-1 receptor |
| GLP1R | NM_002062 | *Homo sapiens* | glucagon-like peptide 1 receptor |
| GRN | NM_002087 | *Homo sapiens* | granulin |
| GRN | NM_008175 | *Mus musculus* | granulin |
| HAMP | NM_021175 | *Homo sapiens* | hepcidin antimicrobial peptide |
| HAMP | NM_032541 | *Mus musculus* | hepcidin antimicrobial peptide |
| HBA2 | NM_000517 | *Homo sapiens* | hemoglobin, alpha 2; hemoglobin, alpha 1 |
| HBA2 | NM_000558 | *Homo sapiens* | hemoglobin, alpha 2; hemoglobin, alpha 1 |
| HBB | NM_000518 | *Homo sapiens* | hemoglobin, beta |
| HBB | XM_921413 | *Mus musculus* | hemoglobin beta chain complex |
| HBB | XM_903245 | *Mus musculus* | hemoglobin beta chain complex |
| HBB | XM_921395 | *Mus musculus* | hemoglobin beta chain complex |
| HBB | XM_903244 | *Mus musculus* | hemoglobin beta chain complex |
| HBB | XM_903246 | *Mus musculus* | hemoglobin beta chain complex |
| HBB | XM_909723 | *Mus musculus* | hemoglobin beta chain complex |
| HBB | XM_921422 | *Mus musculus* | hemoglobin beta chain complex |
| HBB | XM_489729 | *Mus musculus* | hemoglobin beta chain complex |
| HBB | XM_903242 | *Mus musculus* | hemoglobin beta chain complex |
| HBB | XM_903243 | *Mus musculus* | hemoglobin beta chain complex |
| HBB | XM_921400 | *Mus musculus* | hemoglobin beta chain complex |
| HBD | NM_000519 | *Homo sapiens* | hemoglobin, delta |
| HBE1 | NM_005330 | *Homo sapiens* | hemoglobin, epsilon 1 |
| HBG1 | NM_000559 | *Homo sapiens* | hemoglobin, gamma A |
| HBG2 | NM_000184 | *Homo sapiens* | hemoglobin, gamma G |
| HPRT1 | NM_000194 | *Homo sapiens* | hypoxanthine phosphoribosyltransferase 1 |
| IDO1 | NM_008324 | *Mus musculus* | indoleamine 2,3-dioxygenase 1 |
| IDO1 | NM_002164 | *Homo sapiens* | indoleamine 2,3-dioxygenase 1 |
| IGF1 | NM_001111284 | *Homo sapiens* | insulin-like growth factor 1 (somatomedin C) |
| IGF1 | NM_001111285 | *Homo sapiens* | insulin-like growth factor 1 (somatomedin C) |
| IGF1 | NM_001111283 | *Homo sapiens* | insulin-like growth factor 1 (somatomedin C) |
| IGF1 | NM_000618 | *Homo sapiens* | insulin-like growth factor 1 (somatomedin C) |
| IGF1 | NM_001111274 | *Mus musculus* | insulin-like growth factor 1 |
| IGF1 | NM_010512 | *Mus musculus* | insulin-like growth factor 1 |
| IGF1 | NM_184052 | *Mus musculus* | insulin-like growth factor 1 |
| IGF1 | NM_001111276 | *Mus musculus* | insulin-like growth factor 1 |
| IGF1 | NM_001111275 | *Mus musculus* | insulin-like growth factor 1 |

TABLE 1-continued

Non-limiting examples of RNA transcripts for certain genes

| GENE SYMBOL | MRNA | SPECIES | GENE NAME |
| --- | --- | --- | --- |
| IL10 | NM_000572 | *Homo sapiens* | interleukin 10 |
| IL10 | NM_010548 | *Mus musculus* | interleukin 10 |
| IL6 | NM_031168 | *Mus musculus* | interleukin 6 |
| IL6 | NM_000600 | *Homo sapiens* | interleukin 6 (interferon, beta 2) |
| KCNMA1 | NM_002247 | *Homo sapiens* | potassium large conductance calcium-activated channel, subfamily M, alpha member 1 |
| KCNMA1 | NM_001161352 | *Homo sapiens* | potassium large conductance calcium-activated channel, subfamily M, alpha member 1 |
| KCNMA1 | NM_001014797 | *Homo sapiens* | potassium large conductance calcium-activated channel, subfamily M, alpha member 1 |
| KCNMA1 | NM_001161353 | *Homo sapiens* | potassium large conductance calcium-activated channel, subfamily M, alpha member 1 |
| KCNMA1 | NM_010610 | *Mus musculus* | potassium large conductance calcium-activated channel, subfamily M, alpha member 1 |
| KCNMB1 | NM_031169 | *Mus musculus* | potassium large conductance calcium-activated channel, subfamily M, beta member 1 |
| KCNMB1 | NM_004137 | *Homo sapiens* | potassium large conductance calcium-activated channel, subfamily M, beta member 1 |
| KCNMB2 | NM_028231 | *Mus musculus* | potassium large conductance calcium-activated channel, subfamily M, beta member 2 |
| KCNMB2 | NM_005832 | *Homo sapiens* | potassium large conductance calcium-activated channel, subfamily M, beta member 2 |
| KCNMB2 | NM_181361 | *Homo sapiens* | potassium large conductance calcium-activated channel, subfamily M, beta member 2 |
| KCNMB3 | NM_171829 | *Homo sapiens* | potassium large conductance calcium-activated channel, subfamily M beta member 3 |
| KCNMB3 | NM_171828 | *Homo sapiens* | potassium large conductance calcium-activated channel, subfamily M beta member 3 |
| KCNMB3 | NM_001163677 | *Homo sapiens* | potassium large conductance calcium-activated channel, subfamily M beta member 3 |
| KCNMB3 | NM_014407 | *Homo sapiens* | potassium large conductance calcium-activated channel, subfamily M beta member 3 |
| KCNMB3 | NM_171830 | *Homo sapiens* | potassium large conductance calcium-activated channel, subfamily M beta member 3 |
| KCNMB3 | XM_001475546 | *Mus musculus* | potassium large conductance calcium-activated channel, subfamily M, beta member 3 |
| KCNMB3 | XM_912348 | *Mus musculus* | potassium large conductance calcium-activated channel, subfamily M, beta member 3 |
| KCNMB4 | NM_021452 | *Mus musculus* | potassium large conductance calcium-activated channel, subfamily M, beta member 4 |
| KCNMB4 | NM_014505 | *Homo sapiens* | potassium large conductance calcium-activated channel, subfamily M, beta member 4 |
| KLF1 | NM_010635 | *Mus musculus* | Kruppel-like factor 1 (erythroid) |
| KLF1 | NM_006563 | *Homo sapiens* | Kruppel-like factor 1 (erythroid) |
| KLF4 | NM_010637 | *Mus musculus* | Kruppel-like factor 4 (gut) |
| KLF4 | NM_004235 | *Homo sapiens* | Kruppel-like factor 4 (gut) |
| LAMA1 | NM_005559.3 | *Homo sapiens* | laminin, alpha 1 |
| LAMA1 | NM_008480.2 | *Mus musculus* | laminin, alpha 1 |
| LDLR | NM_000527 | *Homo sapiens* | low density lipoprotein receptor |

TABLE 1-continued

Non-limiting examples of RNA transcripts for certain genes

| GENE SYMBOL | MRNA | SPECIES | GENE NAME |
|---|---|---|---|
| LDLR | NM_010700 | Mus musculus | low density lipoprotein receptor |
| MBNL1 | NM_021038.3, NM_020007.3, NM_207293.1, NM_207294.1, NM_207295.1, NM_207296.1, NM_207297.1 | Homo sapiens | muscleblind-like splicing regulator 1 |
| MBNL1 | NM_001253708.1, NM_001253709.1, NM_001253710.1, NM_001253711.1, NM_001253713.1, NM_020007.3 | Mus musculus | muscleblind-like 1 (Drosophila) |
| MECP2 | NM_010788 | Mus musculus | methyl CpG binding protein 2 |
| MECP2 | NM_001081979 | Mus musculus | methyl CpG binding protein 2 |
| MECP2 | NM_001110792 | Homo sapiens | methyl CpG binding protein 2 (Rett syndrome) |
| MECP2 | NM_004992 | Homo sapiens | methyl CpG binding protein 2 (Rett syndrome) |
| MERTK | NM_006343.2 | Homo sapiens | MER proto-oncogene, tyrosine kinase |
| MERTK | NM_008587.1 | Mus musculus | c-mer proto-oncogene tyrosine kinase |
| MSX2 | NM_013601 | Mus musculus | similar to homeobox protein; homeobox, msh-like 2 |
| MSX2 | XM_001475886 | Mus musculus | similar to homeobox protein; homeobox, msh-like 2 |
| MSX2 | NM_002449 | Homo sapiens | msh homeobox 2 |
| MYBPC3 | NM_008653 | Mus musculus | myosin binding protein C, cardiac |
| MYBPC3 | NM_000256 | Homo sapiens | myosin binding protein C, cardiac |
| NANOG | NM_024865 | Homo sapiens | Nanog homeobox pseudogene 8; Nanog homeobox |
| NANOG | XM_001471588 | Mus musculus | similar to Nanog homeobox; Nanog homeobox |
| NANOG | NM_028016 | Mus musculus | similar to Nanog homeobox; Nanog homeobox |
| NANOG | NM_001080945 | Mus musculus | similar to Nanog homeobox; Nanog homeobox |
| NF1 | NM_000267 | Homo sapiens | neurofibromin 1 |
| NF1 | NM_001042492 | Homo sapiens | neurofibromin 1 |
| NF1 | NM_001128147 | Homo sapiens | neurofibromin 1 |
| NF1 | NM_010897 | Mus musculus | neurofibromatosis 1 |
| NKX2-1 | NM_001079668 | Homo sapiens | NK2 homeobox 1 |
| NKX2-1 | NM_003317 | Homo sapiens | NK2 homeobox 1 |
| NKX2-1 | XM_002344771 | Homo sapiens | NK2 homeobox 1 |
| NKX2-1 | NM_009385 | Mus musculus | NK2 homeobox 1 |
| NKX2-1 | NM_001146198 | Mus musculus | NK2 homeobox 1 |
| PAH | NM_008777 | Mus musculus | phenylalanine hydroxylase |
| PAH | NM_000277 | Homo sapiens | phenylalanine hydroxylase |
| PTEN | NM_000314 | Homo sapiens | phosphatase and tensin homolog; phosphatase and tensin homolog pseudogene 1 |
| PTEN | NM_177096 | Mus musculus | phosphatase and tensin homolog |
| PTEN | NM_008960 | Mus musculus | phosphatase and tensin homolog |

TABLE 1-continued

Non-limiting examples of RNA transcripts for certain genes

| GENE SYMBOL | MRNA | SPECIES | GENE NAME |
| --- | --- | --- | --- |
| PTGS2 | NM_011198 | *Mus musculus* | prostaglandin-endoperoxide synthase 2 |
| PTGS2 | NM_000963 | *Homo sapiens* | prostaglandin-endoperoxide synthase 2 (prostaglandin G/H synthase and cyclooxygenase) |
| RB1 | NM_009029 | *Mus musculus* | retinoblastoma 1 |
| RB1 | NM_000321 | *Homo sapiens* | retinoblastoma 1 |
| RPS14 | NM_020600 | *Mus musculus* | predicted gene 6204; ribosomal protein S14 |
| RPS14 | NM_001025071 | *Homo sapiens* | ribosomal protein S14 |
| RPS14 | NM_005617 | *Homo sapiens* | ribosomal protein S14 |
| RPS14 | NM_001025070 | *Homo sapiens* | ribosomal protein S14 |
| RPS19 | XM_204069 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_991053 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_905004 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_001005575 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | NM_023133 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_994263 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_001481027 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_913504 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_001479631 | *Mus musculus* | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_902221 | *Mus musculus* | predicted gene 4327; predicted gene 8683; similar to 40S ribosomal protein S19; predicted gene 4510; predicted gene 13143; predicted gene 9646; ribosomal protein S19; |

TABLE 1-continued

Non-limiting examples of RNA transcripts for certain genes

| GENE SYMBOL | MRNA | SPECIES | GENE NAME |
|---|---|---|---|
| RPS19 | XM_893968 | Mus musculus | predicted gene 9091; predicted gene 6636; predicted gene 14072 predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | NM_001022 | Homo sapiens | ribosomal protein S19 pseudogene 3; ribosomal protein S19 |
| SCARB1 | NM_016741 | Mus musculus | scavenger receptor class B, member 1 |
| SCARB1 | NM_001082959 | Homo sapiens | scavenger receptor class B, member 1 |
| SCARB1 | NM_005505 | Homo sapiens | scavenger receptor class B, member 1 |
| SERPINF1 | NM_011340 | Mus musculus | serine (or cysteine) peptidase inhibitor, clade F, member 1 |
| SERPINF1 | NM_002615 | Homo sapiens | serpin peptidase inhibitor, clade F (alpha-2 antiplasmin, pigment epithelium derived factor), member 1 |
| SIRT1 | NM_001159590 | Mus musculus | sirtuin 1 (silent mating type information regulation 2, homolog) 1 (S. cerevisiae) |
| SIRT1 | NM_019812 | Mus musculus | sirtuin 1 (silent mating type information regulation 2, homolog) 1 (S. cerevisiae) |
| SIRT1 | NM_001159589 | Mus musculus | sirtuin 1 (silent mating type information regulation 2, homolog) 1 (S. cerevisiae) |
| SIRT1 | NM_012238 | Homo sapiens | sirtuin (silent mating type information regulation 2 homolog) 1 (S. cerevisiae) |
| SIRT1 | NM_001142498 | Homo sapiens | sirtuin (silent mating type information regulation 2 homolog) 1 (S. cerevisiae) |
| SIRT6 | NM_016539 | Homo sapiens | sirtuin (silent mating type information regulation 2 homolog) 6 (S. cerevisiae) |
| SIRT6 | NM_001163430 | Mus musculus | sirtuin 6 (silent mating type information regulation 2, homolog) 6 (S. cerevisiae) |
| SIRT6 | NM_181586 | Mus musculus | sirtuin 6 (silent mating type information regulation 2, homolog) 6 (S. cerevisiae) |
| SMAD7 | NM_005904 | Homo sapiens | SMAD family member 7 |
| SMAD7 | NM_001042660 | Mus musculus | MAD homolog 7 (Drosophila) |
| SMN1 | NM_000344.3 | Homo sapiens | Survival Motor Neuron 1 |
| SMN1 | NM_022874.2 | Homo sapiens | Survival Motor Neuron 1 |
| SMN2 | NM_017411.3 NM_022875.2 NM_022876.2 NM_022877.2 | Homo sapiens | Survival Motor Neuron 2 |
| SSPN | NM_001135823.1, NM_005086.4 | Homo sapiens | sarcospan |
| SSPN | NM_010656.2 | Homo sapiens | sarcospan |
| ST7 | NM_021908 | Homo sapiens | suppression of tumorigenicity 7 |
| ST7 | NM_018412 | Homo sapiens | suppression of tumorigenicity 7 |
| STAT3 | NM_213660 | Mus musculus | similar to Stat3B; signal transducer and activator of transcription 3 |
| STAT3 | XM_001474017 | Mus musculus | similar to Stat3B; signal transducer and activator of transcription 3 |
| STAT3 | NM_213659 | Mus musculus | similar to Stat3B; signal transducer and activator of transcription 3 |
| STAT3 | NM_011486 | Mus musculus | similar to Stat3B; signal transducer and activator of transcription 3 |
| STAT3 | NM_213662 | Homo sapiens | signal transducer and activator of transcription 3 (acute-phase response factor) |
| STAT3 | NM_003150 | Homo sapiens | signal transducer and activator of transcription 3 (acute-phase response factor) |
| STAT3 | NM_139276 | Homo sapiens | signal transducer and activator of transcription 3 (acute-phase response factor) |
| UTRN | NM_007124 | Homo sapiens | utrophin |
| UTRN | NM_011682 | Mus musculus | utrophin |

TABLE 1-continued

Non-limiting examples of RNA transcripts for certain genes

| GENE SYMBOL | MRNA | SPECIES | GENE NAME |
| --- | --- | --- | --- |
| NFE2L2 | NM_001145412.2, NM_001145413.2, NM_006164.4 | Homo sapiens | nuclear factor, erythroid 2-like 2 |
| NFE2L2 | NM_010902.3 | Mus musculus | nuclear factor, erythroid 2-like 2 |
| ACTB | NM_001101.3 | Homo sapiens | actin, beta |
| ACTB | NM_007393.3 | Mus musculus | actin, beta |
| ANRIL | NR_003529.3, NR_047532.1, NR_047533.1, NR_047534.1, NR_047535.1, NR_047536.1, NR_047538.1, NR_047539.1, NR_047540.1, NR_047541.1, NR_047542.1, NR_047543.1 | Homo sapiens | CDKN2B antisense RNA 1 (also called CDKN2B) |
| HOTAIR | NR_003716.3, NR_047517.1, NR_047518.1 | Homo sapiens | HOX transcript antisense RNA |
| HOTAIR | NR_047528.1 | Mus musculus | HOX transcript antisense RNA |
| DINO | JX993265 | Homo sapiens | Damage Induced NOncoding |
| DINO | JX993266 | Mus musculus | Damage Induced NOncoding |
| HOTTIP | NR_037843.3 | Homo sapiens | HOXA distal transcript antisense RNA |
| HOTTIP | NR_110441.1, NR_110442.1 | Mus musculus | Hoxa distal transcript antisense RNA |
| NEST | NR_104124.1 | Homo sapiens | *Homo sapiens* IFNG antisense RNA 1 (IFNG-AS1), transcript variant 1, long non-coding RNA. |
| NEST | NR_104123.1 | Mus musculus | Theiler's murine encephalomyelitis virus persistence candidate gene 1 |

Synthetic RNAs

In some aspects of the disclosure, formulations and methods are provided for stabilizing a synthetic RNA (e.g., a synthetic RNA that is to be delivered to a cell). In some embodiments, the formulations and methods involve contacting a synthetic RNA with one or more stabilizing oligonucleotides that bind to a 5' region of the synthetic RNA and a 3' region of the synthetic RNA and that when bound to the synthetic RNA form a circularized product with the synthetic RNA. In some embodiments, the synthetic RNA is contacted with the one or more stabilizing oligonucleotides outside of a cell.

In some embodiments, synthetic RNAs are provided with chemistries suitable for delivery, hybridization and stability within cells which are targeted and stabilized by a stabilizing oligonucleotide, e.g., as described herein. Furthermore, in some embodiments, synthetic RNA chemistries are provided that are useful for controlling the pharmacokinetics, biodistribution, bioavailability and/or efficacy of the synthetic RNAs. Accordingly, synthetic RNAs described herein may be modified, e.g., comprise a modified sugar moiety, a modified internucleoside linkage, a modified nucleotide and/or combinations thereof. In addition, the synthetic RNAs may exhibit one or more of the following properties: do not induce substantial cleavage or degradation of the target RNA and/or stabilizing oligonucleotide; do not cause substantially complete cleavage or degradation of the target RNA and/or stabilizing oligonucleotide; do not activate the RNAse H pathway; do not activate RISC; do not recruit any Argonaute family protein; are not cleaved by Dicer; do not mediate alternative splicing; are not immune stimulatory; are nuclease resistant; have improved cell uptake compared to unmodified synthetic RNAs; are not toxic to cells or mammals; and may have improved endosomal exit.

Methods for Modulating Gene Expression

In one aspect, the disclosure relates to methods for modulating (e.g., increasing) stability of RNA transcripts in cells. The cells can be in vitro, ex vivo, or in vivo. The cells can be in a subject who has a disease resulting from reduced expression or activity of the RNA transcript or its corresponding protein product in the case of mRNAs. In some embodiments, methods for modulating stability of RNA transcripts in cells comprise delivering to the cell a formulation comprising a stabilizing oligonucleotide and a particle, e.g., nanoparticle. In some embodiments, delivery of a formulation comprising a stabilizing oligonucleotide and a particle as described herein to the cell results in an increase in stability of a target RNA that is at least 5%, 10%, 20%, 30%, 40%, 50%, 60%, 70%, 80%, 90%, 100%, 200% or more greater than a level of stability of the target RNA in a control cell. An appropriate control cell may be a cell to which a stabilizing oligonucleotide has not been delivered or to which a negative control has been delivered (e.g., a scrambled oligo, a carrier, etc.).

Another aspect of the disclosure provides methods of treating a disease or condition associated with low levels of a particular RNA in a subject. Accordingly, in some embodiments, methods are provided that comprise administering to a subject (e.g. a human) a formulation comprising a stabilizing oligonucleotide and a particle as described herein to increase mRNA stability in cells of the subject for purposes of increasing protein levels. In some embodiments, the increase in protein levels is at least 5%, 10%, 20%, 30%, 40%, 50%, 60%, 70%, 80%, 90%, 100%, 200%, or more, higher than the amount of a protein in the subject (e.g., in a cell or tissue of the subject) before administering or in a control subject which has not been administered the stabilizing oligonucleotide or that has been administered a negative control (e.g., a scrambled oligo, a carrier, etc.). In some embodiments, methods are provided that comprise administering to a subject (e.g. a human) a formulation comprising a stabilizing oligonucleotide and a particle as described herein to increase stability of non-coding RNAs in cells of the subject for purposes of increasing activity of those non-coding RNAs.

A subject can include a non-human mammal, e.g. mouse, rat, guinea pig, rabbit, cat, dog, goat, cow, or horse. In preferred embodiments, a subject is a human. Stabilizing oligonucleotides may be employed as therapeutic moieties in the treatment of disease states in animals, including humans. Stabilizing oligonucleotides can be useful therapeutic modalities that can be configured to be useful in treatment regimes for the treatment of cells, tissues and animals, especially humans.

For therapeutics, an animal, preferably a human, suspected of having a disease associated with low levels of an RNA or protein is treated by administering a formulation comprising a stabilizing oligonucleotide and a particle in accordance with this disclosure. For example, in one non-limiting embodiment, the methods comprise the step of administering to the animal in need of treatment, a therapeutically effective amount of an formulation as described herein. Table 2 listed examples of diseases or conditions that may be treated by targeting mRNA transcripts with stabilizing oligonucleotides. In some embodiments, cells used in the methods disclosed herein may, for example, be cells obtained from a subject having one or more of the conditions listed in Table 2, or from a subject that is a disease model of one or more of the conditions listed in Table 2.

TABLE 2

Examples of diseases or conditions treatable with oligonucleotides targeting associated mRNA.

| Gene | Disease or conditions |
|---|---|
| FXN | Friedreich's Ataxia |
| SMN | Spinal muscular atrophy (SMA) types I-IV, Amyotrophic Lateral Sclerosis (ALS) |
| UTRN | Muscular dystrophy (MD) (e.g., Duchenne's muscular dystrophy, Becker's muscular dystrophy, myotonic dystrophy) |
| HEMOGLOBIN | Anemia, microcytic anemia, sickle cell anemia and/or thalassemia (e.g., alpha-thalassemia, beta-thalaseemia, delta-thalessemia), beta-thalaseemia (e.g., thalassemia minor/intermedia/major) |
| ATP2A2 | Cardiac conditions (e.g., congenital heart disease, aortic aneurysms, aortic dissections, arrhythmia, cardiomyopathy, and congestive heart failure), Darier-White disease and Acrokeratosis verruciformi |
| APOA1/ ABCA1 | Dyslipidemia (e.g. Hyperlipidemia) and atherosclerosis (e.g. coronary artery disease (CAD) and myocardial infarction (MI)) |
| PTEN | Cancer, such as, leukemias, lymphomas, myelomas, carcinomas, metastatic carcinomas, sarcomas, adenomas, nervous system cancers and genito-urinary cancers. In some embodiments, the cancer is adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, |

TABLE 2-continued

Examples of diseases or conditions treatable with oligonucleotides targeting associated mRNA.

| Gene | Disease or conditions |
|---|---|
| | oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, or Wilms tumor |
| BDNF | Amyotrophic lateral sclerosis (ALS, also known as Lou Gehrig's disease), Alzheimer's Disease (AD), and Parkinson's Disease (PD), Neurodegeneration |
| MECP2 | Rett Syndrome, MECP2-related severe neonatal encephalopathy, Angelman syndrome, or PPM-X syndrome |
| FOXP3 | Diseases or disorders associated with aberrant immune cell (e.g., T cell) activation, e.g., autoimmune or inflammatory diseases or disorders. Examples of autoimmune diseases and disorders that may be treated according to the methods disclosed herein include, but are not limited to, Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, inflammatory bowel disease (e.g., Crohn's disease or Ulcerative colitis), Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, IPEX (Immunodysregulation, Polyendocrinopathy, and Enteropathy, X-linked) syndrome, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), systemic lupus erythematosus (SLE), chronic Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, |

TABLE 2-continued

Examples of diseases or conditions treatable with oligonucleotides targeting associated mRNA.

| Gene | Disease or conditions |
|------|----------------------|
|  | Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Undifferentiated connective tissue disease (UCTD), Uveitis, Vasculitis, Vesiculobullous dermatosis, Vitiligo, and Wegener's granulomatosis (also called Granulomatosis with Polyangiitis (GPA)). Further examples of autoimmune disease or disorder include inflammatory bowel disease (e.g., Crohn's disease or Ulcerative colitis), IPEX syndrome, Multiple sclerosis, Psoriasis, Rheumatoid arthritis, SLE or Type 1 diabetes. Examples of inflammatory diseases or disorders that may be treated according to the methods disclosed herein include, but are not limited to, Acne Vulgaris, Appendicitis, Arthritis, Asthma, Atherosclerosis, Allergies (Type 1 Hypersensitivity), Bursitis, Colitis, Chronic Prostatitis, Cystitis, Dermatitis, Glomerulonephritis, Inflammatory Bowel Disease, Inflammatory Myopathy (e.g., Polymyositis, Dermatomyositis, or Inclusion-body Myositis), Inflammatory Lung Disease, Interstitial Cystitis, Meningitis, Pelvic Inflammatory Disease, Phlebitis, Psoriasis, Reperfusion Injury, Rheumatoid Arthritis, Sarcoidosis, Tendonitis, Tonsilitis, Transplant Rejection, and Vasculitis. In some embodiments, the inflammatory disease or disorder is asthma. |

Route of Delivery

A formulation comprising a stabilizing oligonucleotide and a particle may be delivered to a subject by a variety of routes. Exemplary routes include: intravenous, intradermal, topical, rectal, parenteral, anal, intravaginal, intranasal, pulmonary, ocular. The term "therapeutically effective amount" is the amount of stabilizing oligonucleotide present in the composition that is needed to provide the desired level of gene expression (e.g., by stabilizing RNA transcripts) in the subject to be treated to give the anticipated physiological response. The term "physiologically effective amount" is that amount delivered to a subject to give the desired palliative or curative effect. The term "pharmaceutically acceptable carrier" means that the carrier can be administered to a subject with no significant adverse toxicological effects to the subject.

In some embodiments, formulations comprising stabilizing oligonucleotide molecules and particles of the disclosure can be incorporated into pharmaceutical compositions suitable for administration. In some embodiments, such formulations may include one or more species of stabilizing oligonucleotide and a particle, and a pharmaceutically acceptable carrier, e.g., to the extent such a carrier is compatible with desired oligonucleotide molecules and particles interactions. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The formulations of the present disclosure may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering a formulation in aerosol form. The vascular endothelial cells could be targeted by coating a balloon catheter with a formulation of the present disclosure and mechanically introducing the oligonucleotide.

Topical administration refers to the delivery to a subject by contacting the formulation directly to a surface of the subject. The most common form of topical delivery is to the skin, but a formulation disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a formulation disclosed herein via the transdermal route include hydration of the skin and the use of controlled release topical patches. The transdermal route provides a potentially effective means to deliver a formulation disclosed herein for systemic and/or local therapy. In addition, iontophoresis (transfer of ionic solutes through biological membranes under the influence of an electric field), phonophoresis or sonophoresis (use of ultrasound to enhance the absorption of various therapeutic agents across biological membranes, notably the skin and the cornea), and optimization of vehicle characteristics relative to dose position and retention at the site of administration may be useful methods for enhancing the transport of topically applied compositions across skin and mucosal sites.

Both the oral and nasal membranes offer advantages over other routes of administration. For example, formulations administered through these membranes may have a rapid onset of action, provide therapeutic plasma levels, avoid first pass effect of hepatic metabolism, and avoid exposure of the oligonucleotides to the hostile gastrointestinal (GI) environment. Additional advantages include easy access to the membrane sites so that the formulation can be applied, localized and removed easily.

In oral delivery, formulations can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A formulation may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Formulations for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a tumor).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Any of the formulations described herein can be administered to ocular tissue. For example, the formulations can be applied to the surface of the eye or nearby tissue, e.g., the inside of the eyelid. For ocular administration, ointments or droppable liquids may be delivered by ocular delivery systems known to the art such as applicators or eye droppers. Such formulations can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. A formulation can also be administered to the interior of the eye, and can be introduced by a needle or other delivery device which can introduce it to a selected area or structure.

Pulmonary delivery formulations can be delivered by inhalation by the patient of a dispersion so that the composition, preferably oligonucleotides, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A formulation may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 am in diameter preferably with a relatively uniform spheroidal shape distribution. More preferably the diameter is less than about 7.5 am and most preferably less than about 5.0 µm. Usually the particle size distribution is between about 0.1 µm and about 5 µm in diameter, particularly about 0.3 µm to about 5 µm.

The term "dry" means that the formulation has a moisture content below about 10% by weight (% w) water, usually below about 5% w and preferably less it than about 3% w. A dry composition can be such that the particles are readily dispersible in an inhalation device to form an aerosol.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar oligonucleotide formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to an oligonucleotide formulation, e.g., a device can release insulin.

In one embodiment, unit doses or measured doses of a formulation are dispensed by an implanted device. The device can include a sensor that monitors a parameter within a subject. For example, the device can include pump, e.g., and, optionally, associated electronics.

Tissue, e.g., cells or organs can be treated with a formulation, ex vivo and then administered or implanted in a subject. The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation. Introduction of treated tissue, whether autologous or transplant, can be combined with other therapies. In some implementations, oligonucleotide treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains a formulation comprising a stabilizing oligonucleotide and a particle. Exemplary devices include condoms, diaphragms, IUD (implantable uterine devices, sponges, vaginal sheaths, and birth control devices.

Dosage

In one aspect, the disclosure features a method of administering a formulation comprising a stabilizing oligonucleotide and a particle to a subject (e.g., a human subject). In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or disorder, e.g., a disease or disorder associated with low levels of an RNA or protein. The unit dose, for example, can be administered by injection (e.g., intravenous or intramuscular), an inhaled dose, or a topical application.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of a formulation comprising a stabilizing oligonucleotide and a particle. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the formulation may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some cases, a patient is treated with a formulation comprising a stabilizing oligonucleotide and a particle in conjunction with other therapeutic modalities.

Following successful treatment, it may be desirable to have the patient undergo maintenance therapy to prevent the recurrence of the disease state, wherein the formulation of the disclosure is administered in maintenance doses, ranging from 0.0001 mg to 100 mg per kg of body weight.

The concentration of an oligonucleotide formulation is an amount sufficient to be effective in treating or preventing a disorder or to regulate a physiological condition in humans. The concentration or amount of formulation administered will depend on the parameters determined for the agent and the method of administration, e.g. nasal, buccal, pulmonary. For example, nasal formulations may tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an oligonucleotide in a formulation can include a single treatment or, preferably, can include a series of treatments. It will also be appreciated that the effective dosage of an oligonucleotide in a formulation used for treatment may increase or decrease over the course of a particular treatment. For example, the subject can be monitored after administering a formulation comprising a stabilizing oligonucleotide and a particle. Based on information from the monitoring, an additional amount of a formulation comprising a stabilizing oligonucleotide and a particle can be administered.

Dosing is dependent on severity and responsiveness of the disease condition to be treated, with the course of treatment lasting from several days to several months, or until a cure is effected or a diminution of disease state is achieved. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models.

In one embodiment, the administration of a formulation comprising a stabilizing oligonucleotide and a particle is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The composition can be provided in measured doses or in a dispenser which delivers a metered dose. Selected modes of delivery are discussed in more detail below.

Kits

In certain aspects of the disclosure, kits are provided, comprising a container housing a formulation comprising a stabilizing oligonucleotide and a particle. In some embodiments, the formulation comprises a stabilizing oligonucleotide and a nanoparticle, e.g., lipid nanoparticle. In some embodiments, the formulation further comprises a synthetic RNA. In some embodiments, the individual components of the formulation may be provided in one container. Alternatively, it may be desirable to provide the components of the formulation separately in two or more containers, e.g., one container for stabilizing oligonucleotide, and at least another for the particle. In some embodiments, it is desirable to provide a further container for a synthetic RNA. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The present disclosure is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1. Oligonucleotide for Targeting 5' and 3' Ends of RNAs

Several exemplary oligonucleotide design schemes are provided herein for increasing mRNA stability. With regard to oligonucleotides targeting the 3' end of an RNA, at least two exemplary design schemes are provided. As a first scheme, an oligo nucleotide is designed to be complementary to the 3' end of an RNA, before the poly-A tail (FIG. 1). As a second scheme, an oligonucleotide is designed to be complementary to the 3' end of RNA with a 5' poly-T region that hybridizes to a poly-A tail (FIG. 1).

With regard to oligonucleotides targeting the 5' end of an RNA, at least three exemplary design schemes are provided. For scheme one, an oligonucleotide is designed to be complementary to the 5' end of RNA (FIG. 2). For scheme two, an oligonucleotide is designed to be complementary to the 5' end of RNA and has a 3' overhang to create a RNA-oligo duplex with a recessed end. In this example, the overhang is one or more C nucleotides, e.g., two Cs, which can potentially interact with a 5' methylguanosine cap and stabilize the cap further (FIG. 2). The overhang could also potentially be another type of nucleotide, and is not limited to C. For scheme 3, an oligonucleotide is designed to include a loop region to stabilize 5' RNA cap (FIG. 3A). FIG. 3A also shows an exemplary oligo for targeting 5' and 3' RNA ends. The example shows oligos that bind to a 5' and 3' RNA end to create a pseudo-circularized RNA (FIG. 3B).

An oligonucleotide designed as described in Example 1 may be used or evaluated for its ability to upregulate RNA by increasing mRNA stability using the methods outlined in Example 2.

Example 2: Oligos for Targeting the 5' and 3' End of Frataxin

Oligonucleotide Design

Oligonucleotides were designed to target the 5' and 3' ends of coding or non-coding mRNA. The 3' end oligonucleotides were designed by identifying putative mRNA 3' ends using quantitative end analysis of poly-A tails as described previously (see, e.g., Ozsolak et al. Comprehensive Polyadenylation Site Maps in Yeast and Human Reveal Pervasive Alternative Polyadenylation. Cell. Volume 143, Issue 6, 2010, Pages 1018-1029). The 5' end oligonucleotides were designed by identifying potential 5' start sites using Cap analysis gene expression (CAGE) as previously described (see, e.g., Cap analysis gene expression for high-throughput analysis of transcriptional starting point and identification of promoter usage. Proc Natl Acad Sci USA. 100 (26): 15776-81. 2003 Dec. 23 and Zhao, Xiaobei (2011). "Systematic Clustering of Transcription Start Site Landscapes". PLoS ONE (Public Library of Science) 6 (8): e23409).

The sequence and structure of each oligonucleotide is shown in Tables 3-13. Table 14 provides a description of the nucleotide analogs, modifications and intranucleotide linkages used for certain oligonucleotides tested and described in the Tables. Certain oligos in Table 3 and Table 4 have two oligo names the "Oligo Name" and the "Alternative Oligo Name", which are used interchangeably herein and are to be understood to refer to the same oligo.

TABLE 3

Oligonucleotides targeting 5' and 3' ends of FXN

| SEQ ID NO | Oligo Name | Alternative Oligo Name | Base Sequence | Targeting Region | Gene Name | Organism | Formatted Sequence |
|---|---|---|---|---|---|---|---|
| 1 | Oligo48 | FXN-371 | TGACCCAAGGGAGAC | 5'-End | FXN | human | dTs; InaGs; dAs; InaCs; dCs; InaCs; dAs; InaAs; dGs; InaGs; dGs; InaAs; dGs; InaAs; dC-Sup |
| 2 | Oligo49 | FXN-372 | TGGCCACTGGCCGCA | 5'-End | FXN | human | dTs; InaGs; dGs; InaCs; dCs; InaAs; dCs; InaTs; dGs; InaGs; dCs; InaCs; dGs; InaCs; dA-Sup |
| 3 | Oligo50 | FXN-373 | CGGCGACCCCTGGTG | 5'-End | FXN | human | dCs; InaGs; dGs; InaCs; dGs; InaAs; dCs; InaCs; dCs; InaCs; dTs; InaGs; dGs; InaTs; dG-Sup |
| 4 | Oligo51 | FXN-374 | CGCCCTCCAGCGCTG | 5'-End | FXN | human | dCs; InaGs; dCs; InaCs; dCs; InaTs; dCs; InaCs; dAs; InaGs; dCs; InaGs; dCs; InaTs; dG-Sup |
| 5 | Oligo52 | FXN-375 | CGCTCCGCCCTCCAG | 5'-End | FXN | human | dCs; InaGs; dCs; InaTs; dCs; InaCs; dGs; InaCs; dCs; InaCs; dTs; InaCs; dCs; InaAs; dG-Sup |
| 6 | Oligo53 | FXN-376 | TGACCCAAGGGAGACCC | 5'-End | FXN | human | dTs; InaGs; dAs; InaCs; dCs; InaCs; dAs; InaAs; dGs; InaGs; dGs; InaAs; dGs; InaAs; dCs; InaCs; dC-Sup |
| 7 | Oligo54 | FXN-377 | TGGCCACTGGCCGCACC | 5'-End | FXN | human | dTs; InaGs; dGs; InaCs; dCs; InaAs; dCs; InaTs; dGs; InaGs; dCs; InaCs; dGs; InaCs; dAs; InaCs; dC-Sup |
| 8 | Oligo55 | FXN-378 | CGGCGACCCCTGGTGCC | 5'-End | FXN | human | dCs; InaGs; dGs; InaCs; dGs; InaAs; dCs; InaCs; dCs; InaCs; dTs; InaGs; dGs; InaTs; dGs; InaCs; dC-Sup |
| 9 | Oligo56 | FXN-379 | CGCCCTCCAGCGCTGCC | 5'-End | FXN | human | dCs; InaGs; dCs; InaCs; dCs; InaTs; dCs; InaCs; dAs; InaGs; dCs; InaGs; dCs; InaTs; dGs; InaCs; dC-Sup |
| 10 | Oligo57 | FXN-380 | CGCTCCGCCCTCCAGCC | 5'-End | FXN | human | dCs; InaGs; dCs; InaTs; dCs; InaCs; dGs; InaCs; dCs; InaCs; dTs; InaCs; dCs; InaAs; dGs; InaCs; dC-Sup |
| 11 | Oligo58 | FXN-381 | TGACCCAAGGGAGACGGAAACCAC | 5'-End | FXN | human | dTs; InaGs; dAs; InaCs; dCs; InaCs; dAs; InaAs; dGs; InaGs; dGs; InaAs; dGs; InaAs; dCs; InaGs; dGs; dAs; dAs; dAs; dCs; InaCs; dAs; InaC-Sup |
| 12 | Oligo59 | FXN-382 | TGGCCACTGGCCGCAGGAAACCAC | 5'-End | FXN | human | dTs; InaGs; dGs; InaCs; dCs; InaAs; dCs; InaTs; dGs; InaGs; dCs; InaCs; dGs; InaCs; dAs; InaGs; dGs; dAs; dAs; dAs; dCs; InaCs; dAs; InaC-Sup |
| 13 | Oligo60 | FXN-383 | CGGCGACCCCTGGTGGGAAACCTC | 5'-End | FXN | human | dCs; InaGs; dGs; InaCs; dGs; InaAs; dCs; InaCs; dCs; InaCs; dTs; InaGs; dGs; InaTs; dGs; InaGs; dGs; dAs; dAs; dAs; dCs; InaCs; dTs; InaC-Sup |
| 14 | Oligo61 | FXN-384 | CGCCCTCCAGCGCTGGGAAACCTC | 5'-End | FXN | human | dCs; InaGs; dCs; InaCs; dCs; InaTs; dCs; InaCs; dAs; InaGs; dCs; InaGs; dCs; InaTs; dGs; InaGs; dGs; dAs; dAs; dAs; dCs; InaCs; dTs; InaC-Sup |
| 15 | Oligo62 | FXN-385 | CGCTCCGCCCTCCAGCCAAAGGTC | 5'-End | FXN | human | dCs; InaGs; dCs; InaTs; dCs; InaCs; dGs; InaCs; dCs; InaCs; dTs; InaCs; dCs; InaAs; dGs; InaCs; dCs; dAs; dAs; dAs; dGs; InaGs; dTs; InaC-Sup |

TABLE 3-continued

Oligonucleotides targeting 5' and 3' ends of FXN

| SEQ ID NO | Oligo Name | Alternative Oligo Name | Base Sequence | Targeting Region | Gene Name | Organism | Formatted Sequence |
|---|---|---|---|---|---|---|---|
| 16 | Oligo63 | FXN-386 | GGTTTTTAAGGCTTT | 3'-End | FXN | human | dGs; InaGs; dTs; InaTs; dTs; InaTs; dTs; InaAs; dAs; InaGs; dGs; InaCs; dTs; InaTs; dT-Sup |
| 17 | Oligo64 | FXN-387 | GGGGTCTTGGCCTGA | 3'-End | FXN | human | dGs; InaGs; dGs; dTs; InaCs; dTs; InaTs; dGs; InaGs; dCs; InaCs; dTs; InaGs; dA-Sup |
| 18 | Oligo65 | FXN-388 | CATAATGAAGCTGGG | 3'-End | FXN | human | dCs; InaAs; dTs; InaAs; dAs; InaTs; dGs; InaAs; dAs; InaGs; dCs; InaTs; dGs; InaGs; dG-Sup |
| 19 | Oligo66 | FXN-389 | AGGAGGCAACACATT | 3'-End | FXN | human | dAs; InaGs; dGs; InaAs; dGs; InaGs; dCs; InaAs; dAs; InaCs; dAs; InaCs; dAs; InaTs; dT-Sup |
| 20 | Oligo67 | FXN-390 | ATTATTTTGCTTTTT | 3'-End | FXN | human | dAs; InaTs; dTs; InaAs; dTs; InaTs; dTs; InaGs; dGs; InaCs; dTs; InaTs; dTs; InaTs; dT-Sup |
| 21 | Oligo68 | FXN-391 | CATTTTCCCTCCTGG | 3'-End | FXN | human | dCs; InaAs; dTs; InaTs; dTs; InaTs; dCs; InaCs; dCs; InaTs; dCs; InaCs; dTs; InaGs; dG-Sup |
| 22 | Oligo69 | FXN-392 | GTAGGCTACCCTTTA | 3'-End | FXN | human | dGs; InaTs; dAs; InaGs; dGs; InaCs; dTs; InaAs; dCs; InaCs; dCs; InaTs; dTs; InaTs; dA-Sup |
| 23 | Oligo70 | FXN-393 | GAGGCTTGTTGCTTT | 3'-End | FXN | human | dGs; InaAs; dGs; InaGs; dCs; InaTs; dTs; InaGs; dTs; InaTs; dGs; InaCs; dTs; InaTs; dT-Sup |
| 24 | Oligo71 | FXN-394 | CATGTATGATGTTAT | 3'-End | FXN | human | dCs; InaAs; dTs; InaGs; dTs; InaAs; dTs; InaGs; dAs; InaTs; dGs; InaTs; dTs; InaAs; dT-Sup |
| 25 | Oligo72 | FXN-395 | TTTTTGGTTTTTAAGGCTTT | 3'-End | FXN | human | dTs; InaTs; dTs; InaTs; dTs; InaGs; dGs; InaTs; dTs; InaTs; dTs; InaTs; dAs; InaAs; dGs; InaGs; dCs; InaTs; dTs; InaT-Sup |
| 26 | Oligo73 | FXN-396 | TTTTTGGGGTCTTGGCCTGA | 3'-End | FXN | human | dTs; InaTs; dTs; InaTs; dTs; InaGs; dGs; InaGs; dGs; InaTs; dCs; InaTs; dTs; InaGs; dGs; InaCs; dCs; InaTs; dGs; InaA-Sup |
| 27 | Oligo74 | FXN-397 | TTTTTCATAATGAAGCTGGG | 3'-End | FXN | human | dTs; InaTs; dTs; InaTs; dTs; InaCs; dAs; InaTs; dAs; InaAs; dTs; InaGs; dAs; InaAs; dGs; InaCs; dTs; InaGs; dGs; InaG-Sup |
| 28 | Oligo75 | FXN-398 | TTTTTAGGAGGCAACACATT | 3'-End | FXN | human | dTs; InaTs; dTs; InaTs; dTs; InaAs; dGs; InaGs; dAs; InaGs; dGs; InaCs; dAs; InaAs; dCs; InaAs; dCs; InaAs; dTs; InaT-Sup |
| 29 | Oligo76 | FXN-399 | TTTTTATTATTTTGCTTTTT | 3'-End | FXN | human | dTs; InaTs; dTs; InaTs; dTs; InaAs; dTs; InaTs; dAs; InaTs; dTs; InaTs; dTs; InaGs; dCs; InaTs; dTs; InaTs; dT-Sup |
| 30 | Oligo77 | FXN-400 | TTTTTCATTTTCCCTCCTGG | 3'-End | FXN | human | dTs; InaTs; dTs; InaTs; dTs; InaCs; dAs; InaTs; dTs; InaTs; dTs; InaCs; dCs; InaCs; dTs; InaCs; dCs; InaTs; dGs; InaG-Sup |
| 31 | Oligo78 | FXN-401 | TTTTTGTAGGCTACCCTTTA | 3'-End | FXN | human | dTs; InaTs; dTs; InaTs; dTs; InaGs; dTs; InaAs; dGs; InaGs; dCs; InaTs; dAs; InaCs; dCs; InaCs; dTs; InaTs; dTs; InaA-Sup |

TABLE 3-continued

Oligonucleotides targeting 5' and 3' ends of FXN

| SEQ ID NO | Oligo Name | Alternative Oligo Name | Base Sequence | Targeting Region | Gene Name | Organism | Formatted Sequence |
|---|---|---|---|---|---|---|---|
| 32 | Oligo79 | FXN-402 | TTTTTGAGGCTTGTTGCTTT | 3'-End | FXN | human | dTs; InaTs; dTs; InaTs; dTs; InaGs; dAs; InaGs; dGs; InaCs; dTs; InaTs; dGs; InaTs; dTs; InaGs; dCs; InaTs; dTs; InaT-Sup |
| 33 | Oligo80 | FXN-403 | TTTTTCATGTATGATGTTAT | 3'-End | FXN | human | dTs; InaTs; dTs; InaTs; dTs; InaCs; dAs; InaTs; dGs; InaTs; dAs; InaTs; dGs; InaAs; dTs; InaGs; dTs; InaTs; dAs; InaT-Sup |

TABLE 4

Other oligonucleotides targeting FXN

| SEQ ID NO | Oligo Name | Alternative Oligo Name | Base Sequence | Targeting Region | Gene Name | Organism | Formatted Sequence |
|---|---|---|---|---|---|---|---|
| 34 | Oligo1 | FXN-324 | CGGCGCCCGAGAGTCCACAT | Internal | FXN | human | dCs; InaGs; dGs; InaCs; dGs; InaCs; dCs; InaCs; dGs; InaAs; dGs; InaAs; dGs; InaTs; dCs; InaCs; dAs; InaCs; dAs; InaT-Sup |
| 35 | Oligo2 | FXN-325 | CCAGGAGGCCGGCTACTGCG | Internal | FXN | human | dCs; InaCs; dAs; InaGs; dGs; InaAs; dGs; InaGs; dCs; InaCs; dGs; InaGs; dCs; InaTs; dAs; InaCs; dTs; InaGs; dCs; InaG-Sup |
| 36 | Oligo3 | FXN-326 | CTGGGCTGGGCTGGGTGACG | Internal | FXN | human | dCs; InaTs; dGs; InaGs; dGs; InaCs; dTs; InaGs; dGs; InaGs; dCs; InaTs; dGs; dGs; InaTs; dGs; InaAs; dCs; InaG-Sup |
| 37 | Oligo4 | FXN-327 | ACCCGGGTGAGGGTCTGGGC | Internal | FXN | human | dAs; InaCs; dCs; InaCs; dGs; InaGs; dGs; InaTs; dGs; InaAs; dGs; InaGs; dGs; InaTs; dCs; InaTs; dGs; InaGs; dGs; InaC-Sup |
| 38 | Oligo5 | FXN-328 | CCAACTCTGCCGGCCGCGGG | Internal | FXN | human | dCs; InaCs; dAs; InaAs; dCs; InaTs; dCs; InaTs; dGs; InaCs; dCs; InaGs; dGs; InaCs; dCs; InaGs; dCs; InaGs; dGs; InaG-Sup |
| 39 | Oligo6 | FXN-329 | ACGGCGGCCGCAGAGTGGGG | Internal | FXN | human | dAs; InaCs; dGs; InaGs; dCs; InaGs; dGs; InaCs; dCs; InaGs; dCs; InaAs; dGs; InaAs; dGs; InaTs; dGs; InaGs; dGs; InaG-Sup |
| 40 | Oligo7 | FXN-330 | TCGATGTCGGTGCGCAGGCC | Internal | FXN | human | dTs; InaCs; dGs; InaAs; dTs; InaGs; dTs; InaCs; dGs; InaGs; dTs; InaGs; dCs; InaGs; dCs; InaAs; dGs; InaGs; dCs; InaC-Sup |
| 41 | Oligo8 | FXN-331 | GGCGGGGCGTGCAGGTCGCA | Internal | FXN | human | dGs; InaGs; dCs; InaGs; dGs; InaGs; dGs; InaCs; dGs; InaTs; dGs; |

TABLE 4-continued

Other oligonucleotides targeting FXN

| SEQ ID NO | Oligo Name | Alternative Oligo Name | Base Sequence | Targeting Region | Gene Name | Organism | Formatted Sequence |
|---|---|---|---|---|---|---|---|
| | | | | | | | InaCs; dAs; InaGs; dGs; InaTs; dCs; InaGs; dCs; InaA-Sup |
| 42 | Oligo9 | FXN-332 | ACGTTGGTTCGAACTTGCGC | Internal | FXN | human | dAs; InaCs; dGs; InaTs; dTs; InaGs; dGs; InaTs; dTs; InaCs; dGs; InaAs; dAs; InaCs; dTs; InaTs; dGs; InaCs; dGs; InaC-Sup |
| 43 | Oligo10 | FXN-333 | TTCCAAATCTGGTTGAGGCC | Internal | FXN | human | dTs; InaTs; dCs; InaCs; dAs; InaAs; dAs; InaTs; dCs; InaTs; dGs; InaGs; dTs; InaTs; dGs; InaAs; dGs; InaGs; dCs; InaC-Sup |
| 44 | Oligo11 | FXN-334 | AGACACTCTGCTTTTTGACA | Internal | FXN | human | dAs; InaGs; dAs; InaCs; dAs; InaCs; dTs; InaCs; dTs; InaGs; dCs; InaTs; dTs; InaTs; dTs; InaTs; dGs; InaAs; dCs; InaA-Sup |
| 45 | Oligo12 | FXN-335 | TTTCCTCAAATTCATCAAAT | Internal | FXN | human | dTs; InaTs; dTs; InaCs; dCs; InaTs; dCs; InaAs; dAs; InaAs; dTs; InaTs; dCs; InaAs; dTs; InaCs; dAs; InaAs; dAs; InaT-Sup |
| 46 | Oligo13 | FXN-336 | GGGTGGCCCAAAGTTCCAGA | Internal | FXN | human | dGs; InaGs; dGs; InaTs; dGs; InaGs; dCs; InaCs; dCs; InaAs; dAs; InaAs; dGs; InaAs; dGs; InaAs; dGs; InaCs; dCs; InaA-Sup |
| 47 | Oligo14 | FXN-337 | TGGTCTCATCTAGAGAGCCT | Internal | FXN | human | dTs; InaGs; dGs; InaTs; dCs; InaTs; dCs; InaAs; dTs; InaCs; dTs; InaAs; dGs; InaAs; dGs; InaAs; dGs; InaCs; dCs; InaT-Sup |
| 48 | Oligo15 | FXN-338 | CTCTGCTAGTCTTTCATAGG | Internal | FXN | human | dCs; InaTs; dCs; InaTs; dGs; InaCs; dTs; InaAs; dGs; InaTs; dCs; InaTs; dTs; InaTs; dCs; InaAs; dTs; InaAs; dGs; InaG-Sup |
| 49 | Oligo16 | FXN-339 | GCTAAAGAGTCCAGCGTTTC | Internal | FXN | human | dGs; InaCs; dTs; InaAs; dAs; InaAs; dGs; InaAs; dGs; InaTs; dCs; InaCs; dAs; InaGs; dCs; InaGs; dTs; InaTs; dTs; InaC-Sup |
| 50 | Oligo17 | FXN-340 | GCAAGGTCTTCAAAAAACTCT | Internal | FXN | human | dGs; InaCs; dAs; InaAs; dGs; InaGs; dTs; InaCs; dTs; InaTs; dCs; InaAs; dAs; InaAs; dAs; InaAs; dAs; InaCs; dTs; InaCs; dT-Sup |
| 51 | Oligo18 | FXN-341 | CTCAAACGTGTATGGCTTGTCT | Internal | FXN | human | dCs; InaTs; dCs; InaAs; dAs; InaAs; dCs; InaGs; dTs; InaGs; dTs; InaAs; dTs; InaGs; dGs; InaCs; dTs; InaTs; dGs; InaTs; dCs; InaT-Sup |

TABLE 4-continued

Other oligonucleotides targeting FXN

| SEQ ID NO | Oligo Name | Alternative Oligo Name | Base Sequence | Targeting Region | Gene Name | Organism | Formatted Sequence |
|---|---|---|---|---|---|---|---|
| 52 | Oligo19 | FXN-342 | CCCAAAG GAGACAT CATAGTC | Internal | FXN | human | dCs; InaCs; dCs; InaAs; dAs; InaAs; dGs; InaGs; dAs; InaGs; dAs; InaCs; dAs; InaTs; dCs; InaAs; dTs; InaAs; dGs; InaTs; dC-Sup |
| 53 | Oligo20 | FXN-343 | CAGTTTG ACAGTTA AGACACC ACT | Internal | FXN | human | dCs; InaAs; dGs; InaTs; dTs; InaTs; dGs; InaAs; dCs; InaAs; dGs; InaTs; dTs; InaAs; dAs; InaGs; dAs; InaCs; dAs; InaCs; dCs; InaAs; dCs; InaT-Sup |
| 54 | Oligo21 | FXN-344 | ATAGGTT CCTAGAT CTCCACC | Internal | FXN | human | dAs; InaTs; dAs; InaGs; dGs; InaTs; dTs; InaCs; dCs; InaTs; dAs; InaGs; dAs; InaTs; dCs; InaTs; dCs; InaCs; dAs; InaCs; dC-Sup |
| 55 | Oligo22 | FXN-345 | GGCGTCT GCTTGTT GATCAC | Internal | FXN | human | dGs; InaGs; dCs; InaGs; dTs; InaCs; dTs; InaGs; dCs; InaTs; dTs; InaGs; dTs; InaTs; dGs; InaAs; dTs; InaCs; dAs; InaC-Sup |
| 56 | Oligo23 | FXN-346 | AAGATAG CCAGATTT GCTTGTTT | Internal | FXN | human | dAs; InaAs; dGs; InaAs; dTs; InaAs; dGs; InaCs; dCs; InaAs; dGs; InaAs; dTs; InaTs; dTs; InaGs; dCs; InaTs; dTs; InaGs; dTs; InaTs; dT-Sup |
| 57 | Oligo24 | FXN-347 | GGTCCAC TACATACC TGGATGG AG | Internal | FXN | human | dGs; InaGs; dTs; InaCs; dCs; InaAs; dCs; InaTs; dAs; InaCs; dAs; InaTs; dAs; InaCs; dCs; InaTs; dGs; InaGs; dAs; InaTs; dGs; InaGs; dAs; InaG-Sup |
| 58 | Oligo25 | FXN-348 | CCCAGTC CAGTCAT AACGCTT | Internal | FXN | human | dCs; InaCs; dCs; InaAs; dGs; InaTs; dCs; InaCs; dAs; InaGs; dTs; InaCs; dAs; InaTs; dAs; InaAs; dCs; InaGs; dCs; InaTs; dT-Sup |
| 59 | Oligo26 | FXN-349 | CGTGGGA GTACACC CAGTTTTT | Internal | FXN | human | dCs; InaGs; dTs; InaGs; dGs; InaGs; dAs; InaGs; dTs; InaAs; dCs; InaAs; dCs; InaCs; dCs; InaAs; dGs; InaTs; dTs; InaTs; dTs; InaT-Sup |
| 60 | Oligo27 | FXN-350 | CATGGAG GGACACG CCGT | Internal | FXN | human | dCs; InaAs; dTs; InaGs; dGs; InaAs; dGs; InaGs; dGs; InaAs; dCs; InaAs; dCs; InaGs; dCs; InaCs; dGs; InaT-Sup |
| 61 | Oligo28 | FXN-351 | GTGAGCT CTGCGGC CAGCAGC T | Internal | FXN | human | dGs; InaTs; dGs; InaAs; dGs; InaCs; dTs; InaCs; dTs; InaGs; dCs; InaGs; dGs; InaCs; dCs; InaAs; dGs; InaCs; dAs; InaGs; dCs; InaT-Sup |

TABLE 4-continued

Other oligonucleotides targeting FXN

| SEQ ID NO | Oligo Name | Alternative Oligo Name | Base Sequence | Targeting Region | Gene Name | Organism | Formatted Sequence |
|---|---|---|---|---|---|---|---|
| 62 | Oligo29 | FXN-352 | AGTTTGGTTTTTAAGCTTTA | Internal | FXN | human | dAs; InaGs; dTs; InaTs; dTs; InaGs; dGs; InaTs; dTs; InaTs; dTs; InaTs; dAs; InaAs; dGs; InaGs; dCs; InaTs; dTs; InaTs; dA-Sup |
| 63 | Oligo30 | FXN-353 | TAGGCCAAGGAAGACAAGTCC | Internal | FXN | human | dTs; InaAs; dGs; InaGs; dCs; InaCs; dAs; InaAs; dGs; InaGs; dAs; InaAs; dGs; InaAs; dCs; InaAs; dAs; InaGs; dTs; InaCs; dC-Sup |
| 64 | Oligo31 | FXN-354 | TCAAGCATCTTTTCCGGAA | Internal | FXN | human | dTs; InaCs; dAs; InaAs; dGs; InaCs; dAs; InaTs; dCs; InaTs; dTs; InaTs; dTs; InaCs; dCs; naGs; dGs; InaAs; dA-Sup |
| 65 | Oligo32 | FXN-355 | TCCTTAAAACGGGGCTGGGCA | Internal | FXN | human | dTs; InaCs; dCs; InaTs; dTs; InaAs; dAs; InaAs; dAs; InaCs; dGs; InaGs; dGs; InaGs; dCs; InaTs; dGs; InaGs; dGs; InaCs; dA-Sup |
| 66 | Oligo33 | FXN-356 | TTGGCCTGATAGCTTTTAATG | Internal | FXN | human | dTs; InaTs; dGs; InaGs; dCs; InaCs; dTs; InaGs; dAs; InaTs; dAs; InaGs; dCs; InaTs; dTs; InaTs; dTs; InaAs; dAs; InaTs; dG-Sup |
| 67 | Oligo34 | FXN-357 | CCTCAGCTGCATAATGAAGCTGGGGTC | Internal | FXN | human | dCs; InaCs; dTs; InaCs; dAs; InaGs; dCs; InaTs; dGs; InaCs; dAs; InaTs; dAs; InaAs; dTs; InaGs; dAs; InaAs; dGs; InaCs; dTs; InaGs; dGs; InaGs; dGs; InaTs; dC-Sup |
| 68 | Oligo35 | FXN-358 | AACAACAACAACAACAAAAAACAGA | Internal | FXN | human | dAs; InaAs; dCs; InaAs; dAs; InaCs; dAs; InaAs; dCs; InaAs; dAs; InaCs; dAs; InaAs; dAs; InaAs; dAs; InaAs; dAs; InaAs; dAs; InaCs; dAs; InaGs; dA-Sup |
| 69 | Oligo36 | FXN-359 | CCTCAAAAGCAGGAATAAAAAAAATA | Internal | FXN | human | dCs; InaCs; dTs; InaCs; dAs; InaAs; dAs; InaAs; dGs; InaCs; dAs; InaGs; dGs; InaAs; dAs; InaTs; dAs; InaAs; dAs; InaAs; dAs; InaAs; dTs; InaA-Sup |
| 70 | Oligo37 | FXN-360 | GCTGTGACACATAGCCCAACTGT | Internal | FXN | human | dGs; InaCs; dTs; InaGs; dTs; InaGs; dAs; InaCs; dAs; InaCs; dAs; InaTs; dAs; InaCs; dCs; InaAs; dAs; InaCs; dTs; InaGs; dT-Sup |
| 71 | Oligo38 | FXN-361 | GGAGGCAACACATTCTTTCTACAGA | Internal | FXN | human | dGs; InaGs; dAs; InaGs; dGs; InaCs; dAs; InaAs; dCs; InaAs; dCs; InaAs; dTs; InaTs; dCs; InaTs; dTs; InaTs; dCs; |

TABLE 4-continued

Other oligonucleotides targeting FXN

| SEQ ID NO | Oligo Name | Alternative Oligo Name | Base Sequence | Targeting Region | Gene Name | Organism | Formatted Sequence |
|---|---|---|---|---|---|---|---|
| | | | | | | | InaTs; dAs; InaCs; dAs; InaGs; dA-Sup |
| 72 | Oligo39 | FXN-362 | CTATTAAT ATTACTG | Intron | FXN | human | dCs; InaTs; dAs; InaTs; dTs; InaAs; dAs; InaTs; dAs; InaTs; dTs; InaAs; dCs; InaTs; dG-Sup |
| 73 | Oligo40 | FXN-363 | CATTATGT GTATGTA T | Intron | FXN | human | dCs; InaAs; dTs; InaTs; dAs; InaTs; dGs; InaTs; dGs; InaTs; dAs; InaTs; dGs; InaTs; dAs; InaT-Sup |
| 74 | Oligo41 | FXN-364 | TTTATCTA TGTTATT | Intron | FXN | human | dTs; InaTs; dTs; InaAs; dTs; InaCs; dTs; InaAs; dTs; InaGs; dTs; InaTs; dAs; InaTs; dT-Sup |
| 75 | Oligo42 | FXN-365 | CTAATTTG AAGTTCT | Intron | FXN | human | dCs; InaTs; dAs; InaAs; dTs; InaTs; dTs; InaGs; dAs; InaAs; dGs; InaTs; dTs; InaCs; dT-Sup |
| 76 | Oligo43 | FXN-366 | TTCGAACT TGCGCGG | Exon Spanning | FXN | human | dTs; InaTs; dCs; InaGs; dAs; InaAs; dCs; InaTs; dTs; InaGs; dCs; InaGs; dCs; InaGs; dG-Sup |
| 77 | Oligo44 | FXN-367 | TAGAGAG CCTGGGT | Exon Spanning | FXN | human | dTs; InaAs; dGs; InaAs; dGs; InaAs; dGs; InaCs; dCs; InaTs; dGs; InaGs; dGs; InaT-Sup |
| 78 | Oligo45 | FXN-368 | ACACCAC TCCCAAA G | Exon Spanning | FXN | human | dAs; InaCs; dAs; InaCs; dCs; InaAs; dCs; InaTs; dCs; InaCs; dCs; InaAs; dAs; InaAs; dG-Sup |
| 79 | Oligo46 | FXN-369 | AGGTCCA CTACATAC | Exon Spanning | FXN | human | dAs; InaGs; dGs; InaTs; dCs; InaCs; dAs; InaCs; dTs; InaAs; dCs; InaAs; dTs; InaAs; dC-Sup |
| 80 | Oligo47 | FXN-370 | CGTTAAC CTGGATG G | Exon Spanning | FXN | human | dCs; InaGs; dTs; InaTs; dAs; InaAs; dCs; InaCs; dTs; InaGs; dGs; InaAs; dTs; InaGs; dG-Sup |
| 81 | Oligo81 | FXN-404 | AAAGCCT TAAAAAC C | Antisense | FXN | human | dAs; InaAs; dAs; InaGs; dCs; InaCs; dTs; InaTs; dAs; InaAs; dAs; InaAs; dAs; InaCs; dC-Sup |
| 82 | Oligo82 | FXN-405 | TCAGGCC AAGACCC C | Antisense | FXN | human | dTs; InaCs; dAs; InaGs; dGs; InaCs; dCs; InaAs; dAs; InaGs; dAs; InaCs; dCs; InaCs; dC-Sup |
| 83 | Oligo83 | FXN-406 | CCCAGCTT CATTATG | Antisense | FXN | human | dCs; InaCs; dCs; InaAs; dGs; InaCs; dTs; InaTs; dCs; InaAs; dTs; InaTs; dAs; InaTs; dG-Sup |

TABLE 4-continued

Other oligonucleotides targeting FXN

| SEQ ID NO | Oligo Name | Alternative Oligo Name | Base Sequence | Targeting Region | Gene Name | Organism | Formatted Sequence |
|---|---|---|---|---|---|---|---|
| 84 | Oligo84 | FXN-407 | AATGTGTTGCCTCCT | Antisense | FXN | human | dAs; InaGs; dTs; InaGs; dTs; InaGs; dTs; InaTs; dGs; InaCs; dCs; InaTs; dCs; InaCs; dT-Sup |
| 85 | Oligo85 | FXN-408 | AAAAAGCAAAATAAT | Antisense | FXN | human | dAs; InaAs; dAs; InaAs; dAs; InaGs; dCs; InaAs; dAs; InaAs; dAs; InaTs; dAs; InaAs; dT-Sup |
| 86 | Oligo86 | FXN-409 | CCAGGAGGGAAAATG | Antisense | FXN | human | dCs; InaCs; dAs; InaGs; dGs; InaAs; dGs; InaGs; dGs; InaAs; dAs; InaAs; dAs; InaTs; dG-Sup |
| 87 | Oligo87 | FXN-410 | TAAAGGGTAGCCTAC | Antisense | FXN | human | dTs; InaAs; dAs; InaAs; dGs; InaGs; dGs; InaTs; dAs; InaGs; dCs; InaCs; dTs; InaAs; dC-Sup |
| 88 | Oligo88 | FXN-411 | AAAGCAACAAGCCTC | Antisense | FXN | human | dAs; InaAs; dAs; InaGs; dCs; InaAs; dAs; InaCs; dAs; InaAs; dGs; InaCs; dCs; InaTs; dC-Sup |
| 89 | Oligo89 | FXN-412 | ATAACATCATACATG | Antisense | FXN | human | dAs; InaTs; dAs; InaAs; dCs; InaAs; dTs; InaCs; dAs; InaTs; dAs; InaCs; dAs; InaTs; dG-Sup |
| 90 | Oligo90 | FXN-413 | GATACTATCTTCCTC | Antisense | FXN | human | dGs; InaAs; dTs; InaAs; dCs; InaTs; dAs; InaTs; dCs; InaTs; dTs; InaCs; dCs; InaTs; dC-Sup |
| 91 | Oligo91 | FXN-414 | ATGGGGGACGGGGCA | Antisense | FXN | human | dAs; InaTs; dGs; InaGs; dGs; InaGs; dGs; InaAs; dCs; InaGs; dGs; InaGs; dGs; InaCs; dA-Sup |
| 92 | Oligo92 | FXN-415 | GGTTGAGACTGGGTG | Antisense | FXN | human | dGs; InaGs; dTs; InaTs; dGs; InaAs; dGs; InaAs; dCs; InaTs; dGs; InaGs; dGs; InaTs; dG-Sup |
| 93 | Oligo93 | FXN-416 | AGACTGAAGAGGTGC | Antisense | FXN | human | dAs; InaGs; dAs; InaCs; dTs; InaGs; dAs; InaAs; dGs; InaAs; dGs; InaGs; dTs; dC-Sup |
| 94 | Oligo94 | FXN-417 | CGGGACGGCTGTGTT | Antisense | FXN | human | dCs; InaGs; dGs; InaGs; dAs; InaCs; dGs; InaGs; dCs; InaTs; dGs; InaTs; dGs; InaTs; dT-Sup |
| 95 | Oligo95 | FXN-418 | TCTGTGTGGGCAGCA | Antisense | FXN | human | dTs; InaCs; dTs; InaGs; dTs; InaGs; dTs; InaGs; dGs; InaGs; dCs; InaAs; InaCs; dA-Sup |
| 96 | Oligo96 | FXN-419 | AAAGCCTTAAAAAC | Antisense | FXN | human | InaAs; InaAs; InaAs; dGs; dCs; dCs; dTs; dTs; |

TABLE 4-continued

Other oligonucleotides targeting FXN

| SEQ ID NO | Oligo Name | Alternative Oligo Name | Base Sequence | Targeting Region | Gene Name | Organism | Formatted Sequence |
|---|---|---|---|---|---|---|---|
| | | | C | | | | dAs; dAs; dAs; dAs; InaAs; InaCs; InaC-Sup |
| 97 | Oligo97 | FXN-420 | TCAGGCCAAGACCCC | Antisense | FXN | human | InaTs; InaCs; InaAs; dGs; dGs; dCs; dCs; dAs; dAs; dAs; dAs; dCs; InaCs; InaCs; InaC-Sup |
| 98 | Oligo98 | FXN-421 | CCCAGCTTCATTATG | Antisense | FXN | human | InaCs; InaCs; InaCs; dAs; dGs; dCs; dTs; dTs; dCs; dAs; dTs; dTs; InaAs; InaTs; InaG-Sup |
| 99 | Oligo99 | FXN-422 | AATGTGTTGCCTCCT | Antisense | FXN | human | InaAs; InaAs; InaTs; dGs; dTs; dGs; dTs; dTs; dGs; dCs; dCs; dTs; InaCs; InaCs; InaT-Sup |
| 100 | Oligo100 | FXN-423 | AAAAAGCAAAATAAT | Antisense | FXN | human | InaAs; InaAs; InaAs; dAs; dAs; dGs; dCs; dAs; dAs; dAs; dAs; dTs; InaAs; InaAs; InaT-Sup |
| 101 | Oligo101 | FXN-424 | CCAGGAGGGAAAATG | Antisense | FXN | human | InaCs; InaCs; InaAs; dGs; dGs; dAs; dGs; dGs; dGs; dAs; dAs; dAs; InaAs; InaTs; InaG-Sup |
| 102 | Oligo102 | FXN-425 | TAAAGGGTAGCCTAC | Antisense | FXN | human | InaTs; InaAs; InaAs; dAs; dGs; dGs; dGs; dTs; dAs; dGs; dCs; dCs; InaTs; InaAs; InaC-Sup |
| 103 | Oligo103 | FXN-426 | AAAGCAACAAGCCTC | Antisense | FXN | human | InaAs; InaAs; InaAs; dGs; dCs; dAs; dAs; dCs; dAs; dAs; dGs; dCs; InaCs; InaTs; InaC-Sup |
| 104 | Oligo104 | FXN-427 | ATAACATCATACATG | Antisense | FXN | human | InaAs; InaTs; InaAs; dAs; dCs; dAs; dTs; dCs; dAs; dTs; dAs; dCs; InaAs; InaTs; InaG-Sup |
| 105 | Oligo105 | FXN-428 | GATACTATCTTCCTC | Antisense | FXN | human | InaGs; InaAs; InaTs; dAs; dCs; dTs; dAs; dTs; dCs; dTs; dTs; dCs; InaCs; InaTs; InaC-Sup |
| 106 | Oligo106 | FXN-429 | ATGGGGGACGGGGCA | Antisense | FXN | human | InaAs; InaTs; InaGs; dGs; dGs; dGs; dGs; dAs; dCs; dGs; dGs; dGs; InaGs; InaCs; InaA-Sup |
| 107 | Oligo107 | FXN-430 | GGTTGAGACTGGGTG | Antisense | FXN | human | InaGs; InaGs; InaTs; dTs; dGs; dAs; dGs; dAs; dCs; dTs; dGs; dGs; InaGs; InaTs; InaG-Sup |
| 108 | Oligo108 | FXN-431 | AGACTGAAGAGGTGC | Antisense | FXN | human | InaAs; InaGs; InaAs; dCs; dTs; dGs; dAs; dAs; dGs; dAs; dGs; dGs; InaTs; InaGs; InaC-Sup |
| 109 | Oligo109 | FXN-432 | CGGGACGGCTGTGT | Antisense | FXN | human | InaCs; InaGs; InaGs; dGs; dAs; dCs; dGs; dGs; |

TABLE 4-continued

Other oligonucleotides targeting FXN

| SEQ ID NO | Oligo Name | Alternative Oligo Name | Base Sequence | Targeting Region | Gene Name | Organism | Formatted Sequence |
|---|---|---|---|---|---|---|---|
| | | | T | | | | dCs; dTs; dGs; dTs; InaGs; InaTs; InaT-Sup |
| 110 | Oligo110 | FXN-433 | TCTGTGTGGGCAGCA | Antisense | FXN | human | InaTs; InaCs; InaTs; dGs; dTs; dGs; dTs; dGs; dGs; dGs; dCs; dAs; InaGs; InaCs; InaA-Sup |
| 111 | Oligo111 | FXN-115 | GAAGAAGAAGAAGAA | Antisense | FXN | human | InaGs; InaAs; InaAs; dGs; dAs; dAs; dGs; dAs; dAs; dGs; dAs; dAs; InaGs; InaAs; InaA-Sup |
| 112 | Oligo112 | FXN-117 | TTCTTCTTCTTCTTC | Antisense | FXN | human | InaTs; InaTs; InaCs; dTs; dTs; dCs; dTs; dTs; dCs; dTs; dTs; dCs; InaTs; InaTs; InaC-Sup |

TABLE 5

Other targeting FXN

| SEQ ID NO | Oligo Name | Base Sequence | Gene Name | Organism | Formatted Sequence |
|---|---|---|---|---|---|
| 113 | 324 | CGGCGCCCGAGAGTCCACAT | FXN | human | dCs; InaGs; dGs; InaCs; dGs; InaCs; dCs; InaCs; dGs; InaAs; dGs; InaAs; dGs; InaTs; dCs; InaCs; dAs; InaCs; dAs; InaT-Sup |
| 114 | 329 | ACGGCGGCCGCAGAGTGGGG | FXN | human | dAs; InaCs; dGs; InaGs; dCs; InaGs; dGs; InaCs; dCs; InaGs; dCs; InaAs; dGs; InaAs; dGs; InaTs; dGs; InaGs; dGs; InaG-Sup |
| 115 | 359 | CCTCAAAAGCAGGAATAAAAAAATA | FXN | human | dCs; InaCs; dTs; InaCs; dAs; InaAs; dAs; InaAs; dGs; InaCs; dAs; InaGs; dGs; InaAs; dAs; InaTs; dAs; InaAs; dAs; InaAs; dAs; InaAs; dAs; InaAs; dAs; dTs; InaA-Sup |
| 116 | 414 | ATGGGGACGGGGCA | FXN | human | dAs; InaTs; dGs; InaGs; dGs; InaGs; dGs; InaAs; dCs; InaGs; dGs; InaGs; dGs; InaCs; dA-Sup |
| 117 | 415 | GGTTGAGACTGGGTG | FXN | human | dGs; InaGs; dTs; InaTs; dGs; InaAs; dGs; InaAs; dCs; InaTs; dGs; InaGs; dGs; InaTs; dG-Sup |
| 118 | 429 | ATGGGGACGGGGCA | FXN | human | dAs; InaTs; dGs; InaGs; dGs; InaGs; dGs; InaAs; dCs; InaGs; dGs; InaGs; dGs; InaCs; dA-Sup |

Several additional oligonucleotides were designed to target the 5' end of an RNA, the 3' end of an RNA, or target both the 5' end and 3' end of an RNA ("bridging oligos"). These oligos are shown in Table 6.

TABLE 6

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 119 | FXN-437 m02 | TGACCCAAGGGAGACTT TTTGGTTTTTAAGGCTTT | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dGs; InaGs; dTs; InaTs; dTs; InaTs; dTs; InaAs; dAs; InaGs; dGs; InaCs; dTs; InaTs; dT-Sup |
| 120 | FXN-438 m02 | TGGCCACTGGCCGCATT TTTGGTTTTTAAGGCTTT | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dGs; InaGs; dTs; InaTs; dTs; InaTs; dTs; InaAs; dAs; InaGs; dGs; InaCs; dTs; InaTs; dT-Sup |
| 121 | FXN-439 m02 | CGGCGACCCCTGGTGTT TTTGGTTTTTAAGGCTTT | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dGs; InaGs; dTs; InaTs; dTs; InaTs; dTs; InaAs; dAs; InaGs; dGs; InaCs; dTs; InaTs; dT-Sup |
| 122 | FXN-440 m02 | CGCCCTCCAGCGCTGTT TTTGGTTTTTAAGGCTTT | FXN | 5' and 3' | human | dCs; InaGs; dCs; InaCs; dCs; InaTs; dCs; dAs; InaGs; dCs; InaGs; dCs; InaTs; dGs; InaTs; dTs; InaTs; dTs; InaTs; dGs; InaGs; dTs; InaTs; dTs; InaTs; dTs; InaAs; dAs; InaGs; dGs; InaCs; dTs; InaTs; dT-Sup |
| 123 | FXN-441 m02 | CGCTCCGCCCTCCAGTTT TTGGTTTTTAAGGCTTT | FXN | 5' and 3' | human | dCs; InaGs; dCs; InaTs; dCs; InaCs; dGs; dCs; InaCs; dTs; InaCs; dCs; InaAs; dGs; InaTs; dTs; InaTs; dTs; InaTs; dGs; InaGs; dTs; InaTs; dTs; InaTs; dTs; InaAs; dAs; InaGs; dGs; InaCs; dTs; InaTs; dT-Sup |
| 124 | FXN-442 m02 | TGACCCAAGGGAGACTT TTTGGGGTCTTGGCCTG A | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dGs; InaGs; dGs; InaGs; dTs; InaCs; dTs; InaTs; dGs; InaGs; dCs; InaCs; dTs; InaGs; dA-Sup |
| 125 | FXN-443 m02 | TGGCCACTGGCCGCATT TTTGGGGTCTTGGCCTG A | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dGs; InaGs; dGs; InaGs; dTs; InaCs; dTs; InaTs; dGs; InaGs; dCs; InaCs; dTs; InaGs; dA-Sup |
| 126 | FXN-444 m02 | CGGCGACCCCTGGTGTT TTTGGGGTCTTGGCCTG A | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dGs; InaGs; dGs; InaGs; dTs; InaCs; dTs; InaTs; dGs; InaGs; dCs; InaCs; dTs; InaGs; dA-Sup |
| 127 | FXN-445 m02 | CGCCCTCCAGCGCTGTT TTTGGGGTCTTGGCCTG A | FXN | 5' and 3' | human | dCs; InaGs; dCs; InaCs; dCs; InaTs; dCs; InaCs; dAs; InaGs; dCs; InaGs; dCs; InaTs; dGs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaTs; dTs; InaTs; dTs; InaTs; ; dGs; InaGs; dGs; InaGs; dTs; InaCs; dTs; InaTs; dGs; InaGs; dCs; InaCs; dTs; InaGs; dA-Sup |
| 128 | FXN-446 m02 | CGCTCCGCCCTCCAGTTT TTGGGGTCTTGGCCTGA | FXN | 5' and 3' | human | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; dGs; InaGs; dGs; InaGs; dTs; InaCs; dTs; InaTs; dGs; InaGs; dCs; InaCs; dTs; InaGs; dA-Sup |
| 129 | FXN-447 m02 | TGACCCAAGGGAGACTT TTTCATAATGAAGCTGG G | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dCs; InaAs; dTs; InaAs; dAs; InaTs; dGs; InaAs; dAs; InaGs; dCs; InaTs; dGs; InaGs; dG-Sup |
| 130 | FXN-448 m02 | TGGCCACTGGCCGCATT TTTCATAATGAAGCTGG G | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dCs; InaAs; dTs; InaAs; dAs; InaTs; dGs; InaAs; dAs; InaGs; dCs; InaTs; dGs; InaGs; dG-Sup |
| 131 | FXN-449 m02 | CGGCGACCCCTGGTGTT TTTCATAATGAAGCTGG G | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dCs; InaAs; dTs; InaAs; dAs; InaTs; dGs; InaAs; dAs; InaGs; dCs; InaTs; dGs; InaGs; dG-Sup |
| 132 | FXN-450 m02 | CGCCCTCCAGCGCTGTT TTTCATAATGAAGCTGG G | FXN | 5' and 3' | human | dCs; InaGs; dCs; InaCs; dCs; InaTs; dCs; InaCs; dAs; InaGs; dCs; InaGs; dCs; InaTs; dGs; InaTs; dTs; InaTs; dTs; InaTs; dCs; InaAs; dTs; InaAs; dAs; InaTs; dGs; InaAs; dAs; InaGs; dCs; InaTs; dGs; InaGs; dG-Sup |
| 133 | FXN-451 m02 | CGCTCCGCCCTCCAGTTT TTCATAATGAAGCTGGG | FXN | 5' and 3' | human | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; dCs; InaAs; dTs; InaAs; dAs; InaTs; dGs; InaAs; dAs; InaGs; dCs; InaTs; dGs; InaGs; dG-Sup |
| 134 | FXN-452 m02 | TGACCCAAGGGAGACTT TTTAGGAGGCAACACAT T | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dAs; InaGs; dGs; InaAs; dGs; InaGs; dCs; InaAs; dAs; InaCs; dAs; InaCs; dAs; InaTs; dT-Sup |
| 135 | FXN-453 m02 | TGGCCACTGGCCGCATT TTTAGGAGGCAACACAT T | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dAs; InaGs; dGs; InaAs; dGs; InaGs; dCs; InaAs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dAs; InaCs; dAs; InaCs; dAs; InaTs; dT-Sup |
| 136 | FXN-454 m02 | CGGCGACCCCTGGTGTT TTTAGGAGGCAACACAT T | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dAs; InaGs; dGs; InaAs; dGs; InaGs; dCs; InaAs; dAs; InaCs; dAs; InaCs; dAs; InaTs; dT-Sup |
| 137 | FXN-455 m02 | CGCCCTCCAGCGCTGTT TTTAGGAGGCAACACAT T | FXN | 5' and 3' | human | dCs; InaGs; dCs; InaCs; dCs; InaTs; dCs; InaCs; dAs; InaGs; dCs; InaGs; dCs; InaTs; dGs; InaTs; dTs; InaTs; dTs; InaTs; dAs; InaGs; dGs; InaAs; dGs; InaGs; dCs; InaAs; dAs; InaCs; dAs; InaCs; dAs; InaTs; dT-Sup |
| 138 | FXN-456 m02 | CGCTCCGCCCTCCAGTTT TTAGGAGGCAACACATT | FXN | 5' and 3' | human | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; dAs; InaGs; dGs; InaAs; dGs; InaGs; dCs; InaAs; dAs; InaCs; dAs; InaCs; dAs; InaTs; dT-Sup |
| 139 | FXN-457 m02 | TGACCCAAGGGAGACTT TTTATTATTTTGCTTTTT | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dAs; InaTs; dTs; InaAs; dTs; InaTs; dTs; InaTs; dGs; InaCs; dTs; InaTs; dTs; InaTs; dT-Sup |
| 140 | FXN-458 m02 | TGGCCACTGGCCGCATT TTTATTATTTTGCTTTTT | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dAs; InaTs; dTs; InaAs; dTs; InaTs; dTs; InaTs; dGs; InaCs; dTs; InaTs; dTs; InaTs; dT-Sup |
| 141 | FXN-459 m02 | CGGCGACCCCTGGTGTT TTTATTATTTTGCTTTTT | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dAs; InaTs; dTs; InaAs; dTs; InaTs; dTs; InaTs; dGs; InaCs; dTs; InaTs; dTs; InaTs; dT-Sup |
| 142 | FXN-460 m02 | CGCCCTCCAGCGCTGTT TTTATTATTTTGCTTTTT | FXN | 5' and 3' | human | dCs; InaGs; dCs; InaCs; dCs; InaTs; dCs; InaCs; dAs; InaGs; dCs; InaGs; dCs; InaTs; dGs; InaTs; dTs; InaTs; dTs; InaTs; dAs; InaTs; dTs; InaAs; dTs; InaTs; dTs; InaTs; dGs; InaCs; dTs; InaTs; dTs; InaTs; dT-Sup |
| 143 | FXN-461 m02 | CGCTCCGCCCTCCAGTTT TTATTATTTTGCTTTTT | FXN | 5' and 3' | human | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; dAs; InaTs; dTs; InaAs; dTs; InaTs; dTs; InaTs; dGs; InaCs; dTs; InaTs; dTs; InaTs; dT-Sup |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 144 | FXN-462 m02 | TGACCCAAGGGAGACTT TTTCATTTTCCCTCCTGG | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dCs; InaAs; dTs; InaTs; dTs; InaTs; dCs; InaCs; dCs; InaTs; dCs; InaCs; dTs; InaGs; dG-Sup |
| 145 | FXN-463 m02 | TGGCCACTGGCCGCATT TTTCATTTTCCCTCCTGG | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dCs; InaAs; dTs; InaTs; dTs; InaTs; dCs; InaCs; dCs; InaTs; dCs; InaCs; dTs; InaGs; dG-Sup |
| 146 | FXN-464 m02 | CGGCGACCCCTGGTGTT TTTCATTTTCCCTCCTGG | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dCs; InaAs; dTs; InaTs; dTs; InaTs; dCs; InaCs; dCs; InaTs; dCs; InaCs; dTs; InaGs; dG-Sup |
| 147 | FXN-465 m02 | CGCCCTCCAGCGCTGTT TTTCATTTTCCCTCCTGG | FXN | 5' and 3' | human | dCs; InaGs; dCs; InaCs; dCs; InaTs; dCs; InaCs; dAs; InaGs; dCs; InaGs; dCs; InaTs; dGs; InaTs; dTs; InaTs; dTs; InaTs; dCs; InaAs; dTs; InaTs; dTs; InaTs; dCs; InaCs; dCs; InaTs; dCs; InaCs; dTs; InaGs; dG-Sup |
| 148 | FXN-466 m02 | CGCTCCGCCCTCCAGTTT TTCATTTTCCCTCCTGG | FXN | 5' and 3' | human | dCs; InaGs; dCs; InaTs; dCs; InaCs; dGs; dCs; InaCs; dTs; InaCs; dCs; InaAs; dGs; InaTs; dTs; InaTs; dTs; InaTs; dCs; InaAs; dTs; InaTs; dTs; InaTs; dCs; InaCs; dCs; InaTs; dCs; InaCs; dTs; InaGs; dG-Sup |
| 149 | FXN-467 m02 | TGACCCAAGGGAGACTT TTTGTAGGCTACCCTTTA | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dGs; InaTs; dAs; InaGs; dGs; InaCs; dTs; InaAs; dCs; InaCs; dCs; InaTs; dTs; InaTs; dA-Sup |
| 150 | FXN-468 m02 | TGGCCACTGGCCGCATT TTTGTAGGCTACCCTTTA | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dGs; InaTs; dAs; InaGs; dGs; InaCs; dTs; InaAs; dCs; InaCs; dCs; InaTs; dTs; InaTs; dA-Sup |
| 151 | FXN-469 m02 | CGGCGACCCCTGGTGTT TTTGTAGGCTACCCTTTA | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dGs; InaTs; dAs; InaGs; dGs; InaCs; dTs; InaAs; dCs; InaCs; dCs; InaTs; dTs; InaTs; s; dA-Sup |
| 152 | FXN-470 m02 | CGCCCTCCAGCGCTGTT TTTGTAGGCTACCCTTTA | FXN | 5' and 3' | human | dCs; InaGs; dCs; InaCs; dCs; InaTs; dCs; InaCs; dAs; InaGs; dCs; InaGs; dCs; InaTs; dG |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaTs; dTs; InaTs; dTs; InaTs; dGs; InaTs; dAs; InaGs; dGs; InaCs; dTs; InaAs; dCs; InaCs; dCs; InaTs; dTs; InaTs; dA-Sup |
| 153 | FXN-471 m02 | CGCTCCGCCCTCCAGTTT TTGTAGGCTACCCTTTA | FXN | 5' and 3' | human | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; dGs; InaTs; dAs; InaGs; dGs; InaCs; dTs; InaAs; dCs; InaCs; dCs; InaTs; dTs; InaTs; dA-Sup |
| 154 | FXN-472 m02 | TGACCCAAGGGAGACTT TTTGAGGCTTGTTGCTTT | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dGs; InaAs; dGs; InaGs; dCs; InaTs; dTs; InaGs; dTs; InaTs; dGs; InaCs; dTs; InaTs; dT-Sup |
| 155 | FXN-473 m02 | TGGCCACTGGCCGCATT TTTGAGGCTTGTTGCTTT | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dGs; InaAs; dGs; InaGs; dCs; InaTs; dTs; InaGs; dTs; InaTs; dGs; InaCs; dTs; InaTs; dT-Sup |
| 156 | FXN-474 m02 | CGGCGACCCCTGGTGTT TTTGAGGCTTGTTGCTTT | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dGs; InaAs; dGs; InaGs; dCs; InaTs; dTs; InaGs; dTs; InaTs; dGs; InaCs; dTs; InaTs; dT-Sup |
| 157 | FXN-475 m02 | CGCCCTCCAGCGCTGTT TTTGAGGCTTGTTGCTTT | FXN | 5' and 3' | human | dCs; InaGs; dCs; InaCs; dCs; InaTs; dCs; InaCs; dAs; InaGs; dCs; InaGs; dCs; InaTs; dGs; InaTs; dTs; InaTs; dTs; InaTs; dGs; InaAs; dGs; InaGs; dCs; InaTs; dTs; InaGs; dTs; InaTs; dGs; InaCs; dTs; InaTs; dT-Sup |
| 158 | FXN-476 m02 | CGCTCCGCCCTCCAGTTT TTGAGGCTTGTTGCTTT | FXN | 5' and 3' | human | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; ; dGs; InaAs; dGs; InaGs; dCs; InaTs; dTs; InaGs; dTs; InaTs; dGs; InaCs; dTs; InaTs; dT-Sup |
| 159 | FXN-477 m02 | TGACCCAAGGGAGACTT TTTCATGTATGATGTTAT | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dCs; InaAs; dTs; InaGs; dTs; InaAs; dTs; InaGs; dAs; InaTs; dGs; InaTs; dTs; InaAs; dT-Sup |
| 160 | FXN-478 m02 | TGGCCACTGGCCGCATT TTTCATGTATGATGTTAT | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dCs; InaAs; dTs; InaGs; dTs; InaAs; dTs; InaGs; dAs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaTs; dGs; InaTs; dTs; InaAs; dT-Sup |
| 161 | FXN-479 m02 | CGGCGACCCCTGGTGTT TTTCATGTATGATGTTAT | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dCs; InaAs; dTs; InaGs; dTs; InaAs; dTs; InaGs; dAs; InaTs; dGs; InaTs; dTs; InaAs; dT-Sup |
| 162 | FXN-480 m02 | CGCCCTCCAGCGCTGTT TTTCATGTATGATGTTAT | FXN | 5' and 3' | human | dCs; InaGs; dCs; InaCs; dCs; InaTs; dCs; InaCs; dAs; InaGs; dCs; InaGs; dCs; InaTs; dGs; InaTs; dTs; InaTs; dTs; InaTs; dCs; InaAs; dTs; InaGs; dTs; InaAs; dTs; InaGs; dAs; InaTs; dGs; InaTs; dTs; InaAs; dT-Sup |
| 163 | FXN-481 m02 | CGCTCCGCCCTCCAGTTT TTCATGTATGATGTTAT | FXN | 5' and 3' | human | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; dCs; InaAs; dTs; InaGs; dTs; InaAs; dTs; InaGs; dAs; InaTs; dGs; InaTs; dTs; InaAs; dT-Sup |
| 164 | FXN-482 m02 | CGCCCTCCAGTTTTTGGT TTTTAAG | FXN | 5' and 3' | human | dCs; InaGs; dCs; InaCs; dCs; InaTs; dCs; InaCs; dAs; InaGs; dTs; InaTs; dTs; InaTs; dTs; naGs; dGs; InaTs; dTs; InaTs; dTs; InaTs; dAs; InaAs; dG-Sup |
| 165 | FXN-483 m02 | CGCCCTCCAGTTTTTGG GGTCTTGG | FXN | 5' and 3' | human | dCs; InaGs; dCs; InaCs; dCs; InaTs; dCs; InaCs; dAs; InaGs; dTs; InaTs; dTs; InaTs; dTs; InaGs; dGs; InaGs; dGs; InaTs; dCs; InaTs; dTs; InaGs; dG-Sup |
| 166 | FXN-484 m02 | CGCCCTCCAGTTTTTCAT AATGAAG | FXN | 5' and 3' | human | dCs; InaGs; dCs; InaCs; dCs; InaTs; dCs; InaCs; dAs; InaGs; dTs; InaTs; dTs; InaTs; dTs; InaCs; dAs; InaTs; dAs; InaAs; dTs; InaGs; dAs; InaAs; dG-Sup |
| 167 | FXN-485 m02 | CGCCCTCCAGTTTTTAG GAGGCAAC | FXN | 5' and 3' | human | dCs; InaGs; dCs; InaCs; dCs; InaTs; dCs; InaCs; dAs; InaGs; dTs; InaTs; dTs; InaTs; dTs; InaAs; dGs; InaGs; dAs; InaGs; dGs; InaCs; dAs; InaAs; dC-Sup |
| 168 | FXN-486 m02 | CGCCCTCCAGTTTTTATT ATTTTGC | FXN | 5' and 3' | human | dCs; InaGs; dCs; InaCs; dCs; InaTs; dCs; InaCs; dAs; InaGs; dTs; InaTs; dTs; InaTs; dTs; InaAs; dTs; InaTs; dAs; InaTs; dTs; InaTs; dTs; InaGs; dC-Sup |
| 169 | FXN-487 m02 | CGCCCTCCAGTTTTTCAT TTTCCCT | FXN | 5' and 3' | human | dCs; InaGs; dCs; InaCs; dCs; InaTs; dCs; InaCs; dAs; InaGs; dTs; InaTs; dTs; InaTs; dTs; InaCs; dAs; InaTs; dTs; InaTs; dTs; InaCs; dCs; InaCs; dT-Sup |
| 170 | FXN-488 m02 | CGCCCTCCAGTTTTTGTA GGCTACC | FXN | 5' and 3' | human | dCs; InaGs; dCs; InaCs; dCs; InaTs; dCs; InaCs; dAs; InaGs; dTs; InaTs; dTs; InaTs; dTs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaGs; dTs; InaAs; dGs; InaGs; dCs; InaTs; dAs; InaCs; dC-Sup |
| 171 | FXN-489 m02 | CGCCCTCCAGTTTTTGA GGCTTGTT | FXN | 5' and 3' | human | dCs; InaGs; dCs; InaCs; dCs; InaTs; dCs; InaCs; dAs; InaGs; dTs; InaTs; dTs; InaTs; dTs; InaGs; dAs; InaGs; dGs; InaCs; dTs; InaTs; dGs; InaTs; dT-Sup |
| 172 | FXN-490 m02 | CGCCCTCCAGTTTTTCAT GTATGAT | FXN | 5' and 3' | human | dCs; InaGs; dCs; InaCs; dCs; InaTs; dCs; InaCs; dAs; InaGs; dTs; InaTs; dTs; InaTs; dTs; InaCs; dAs; InaTs; dGs; InaTs; dAs; InaTs; dGs; InaAs; dT-Sup |
| 173 | FXN-491 m02 | TGACCCAAGGGAGACTT TTTTTTTTT | FXN | 5' and 3' | human | dTs; InaGs; dAs; InaCs; dCs; InaCs; dAs; InaAs; dGs; InaGs; dGs; InaAs; dGs; InaAs; dCs; InaTs; dTs; InaTs; dTs; InaTs; dTs; InaTs; dTs; InaTs; dTs; InaTs; dT-Sup |
| 174 | FXN-492 m02 | TGGCCACTGGCCGCATT TTTTTTTTT | FXN | 5' and 3' | human | dTs; InaGs; dGs; InaCs; dCs; InaAs; dCs; InaTs; dGs; InaGs; dCs; InaCs; dGs; InaCs; dAs; InaTs; dTs; InaTs; dTs; InaTs; dTs; InaTs; dTs; InaTs; dTs; InaTs; dT-Sup |
| 175 | FXN-493 m02 | CGGCGACCCCTGGTGTT TTTTTTTTT | FXN | 5' and 3' | human | dCs; InaGs; dGs; InaCs; dGs; InaAs; dCs; InaCs; dCs; InaCs; dTs; InaGs; dGs; InaTs; dGs; InaTs; dTs; InaTs; dTs; InaTs; dTs; InaTs; dTs; InaTs; dTs; InaTs; dT-Sup |
| 176 | FXN-494 m02 | CGCCCTCCAGCGCTGTT TTTTTTTTT | FXN | 5' and 3' | human | dCs; InaGs; dCs; InaCs; dCs; InaTs; dCs; InaCs; dAs; InaGs; dCs; InaGs; dCs; InaTs; dGs; InaTs; dTs; InaTs; dTs; InaTs; dTs; InaTs; dTs; InaTs; dTs; InaTs; dT-Sup |
| 177 | FXN-495 m02 | CGCTCCGCCCTCCAGTTT TTTTTTTT | FXN | 5' and 3' | human | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; dTs; InaTs; dTs; InaTs; dTs; InaTs; dT-Sup |
| 178 | FXN-496 m02 | AAAATAAACAACAAC | FXN | UTR | human | dAs; InaAs; dAs; InaAs; dTs; InaAs; dAs; InaAs; dCs; InaAs; dAs; InaCs; dAs; InaAs; dC-Sup |
| 179 | FXN-497 m02 | AGGAATAAAAAAATA | FXN | UTR | human | dAs; InaGs; dGs; InaAs; dAs; InaTs; dAs; InaAs; dAs; InaAs; dAs; InaAs; dAs; InaAs; dTs; InaA-Sup |
| 180 | FXN-498 m02 | TCAAAAGCAGGAATA | FXN | UTR | human | dTs; InaCs; dAs; InaAs; dAs; InaAs; dGs; InaCs; dAs; InaGs; dGs; InaAs; dAs; InaTs; dA-Sup |
| 181 | FXN-499 m02 | ACTGTCCTCAAAAGC | FXN | UTR | human | dAs; InaCs; dTs; InaGs; dTs; InaCs; dCs; InaTs; dCs; InaAs; dAs; InaAs; dAs; InaGs; dC-Sup |
| 182 | FXN-500 m02 | AGCCCAACTGTCCTC | FXN | UTR | human | dAs; InaGs; dCs; InaCs; dCs; InaAs; dAs; InaCs; dTs; InaGs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dTs; InaCs; dCs; InaTs; dC-Sup |
| 183 | FXN-501 m02 | TGACACATAGCCCAA | FXN | UTR | human | dTs; InaGs; dAs; InaCs; dAs; InaCs; dAs; InaTs; dAs; InaGs; dCs; InaCs; dCs; InaAs; dA-Sup |
| 184 | FXN-502 m02 | GAGCTGTGACACATA | FXN | UTR | human | dGs; InaAs; dGs; InaCs; dTs; InaGs; dTs; InaGs; dAs; InaCs; dAs; InaCs; dAs; InaTs; dA-Sup |
| 185 | FXN-503 m02 | TCTGGGCCTGGGCTG | FXN | UTR/internal | human | dTs; InaCs; dTs; InaGs; dGs; InaGs; dCs; InaCs; dTs; InaGs; dGs; InaGs; dCs; InaTs; dG-Sup |
| 186 | FXN-504 m02 | GGTGAGGGTCTGGGC | FXN | UTR/internal | human | dGs; InaGs; dTs; InaGs; dAs; InaGs; dGs; InaGs; dTs; InaCs; dTs; InaGs; dGs; InaGs; dC-Sup |
| 187 | FXN-505 m02 | GGGACCCGGGTGAGG | FXN | UTR/internal | human | dGs; InaGs; dGs; InaAs; dCs; InaCs; dCs; InaGs; dGs; InaGs; dTs; InaGs; dAs; InaGs; dG-Sup |
| 188 | FXN-506 m02 | CCGGCCGCGGGACCC | FXN | UTR/internal | human | dCs; InaCs; dGs; InaGs; dCs; InaCs; dGs; InaCs; dGs; InaGs; dGs; InaAs; dCs; InaCs; dC-Sup |
| 189 | FXN-507 m02 | CAACTCTGCCGGCCG | FXN | UTR/internal | human | dCs; InaAs; dAs; InaCs; dTs; InaCs; dTs; InaGs; dCs; InaCs; dGs; InaGs; dCs; InaCs; dG-Sup |
| 190 | FXN-508 m02 | AGTGGGGCCAACTCT | FXN | UTR/internal | human | dAs; InaGs; dTs; InaGs; dGs; InaGs; dGs; InaCs; dCs; InaAs; dAs; InaCs; dTs; InaCs; dT-Sup |
| 191 | FXN-509 m02 | GGCCGCAGAGTGGGG | FXN | UTR/internal | human | dGs; InaGs; dCs; InaCs; dGs; InaCs; dAs; InaGs; dAs; InaGs; dTs; InaGs; dGs; InaGs; dG-Sup |
| 192 | FXN-510 m02 | GCCACGGCGGCCGCA | FXN | UTR/internal | human | dGs; InaCs; dCs; InaAs; dCs; InaGs; dGs; InaCs; dGs; InaGs; dCs; InaCs; dGs; InaCs; dA-Sup |
| 193 | FXN-511 m02 | GTGCGCAGGCCACGG | FXN | UTR/internal | human | dGs; InaTs; dGs; InaCs; dGs; InaCs; dAs; InaGs; dGs; InaCs; dCs; InaAs; dCs; InaGs; dG-Sup |
| 194 | FXN-512 m02 | GGGGGACGGGGCAGG | FXN | intron | human | dGs; InaGs; dGs; InaGs; dGs; InaAs; dCs; InaGs; dGs; InaGs; dGs; InaCs; dAs; InaGs; dG-Sup |
| 195 | FXN-513 m02 | GGGACGGGGCAGGTT | FXN | intron | human | dGs; InaGs; dGs; InaAs; dCs; InaGs; dGs; InaGs; dGs; InaCs; dAs; InaGs; dGs; InaTs; dT-Sup |
| 196 | FXN-514 m02 | GACGGGGCAGGTTGA | FXN | intron | human | dGs; InaAs; dCs; InaGs; dGs; InaGs; dGs; InaCs; dAs; InaGs; dGs; InaTs; dTs; InaGs; dA-Sup |
| 197 | FXN-515 m02 | CGGGGCAGGTTGAGA | FXN | intron | human | dCs; InaGs; dGs; InaGs; dGs; InaCs; dAs; InaGs; dGs; InaTs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dTs; InaGs; dAs; InaGs; dA-Sup |
| 198 | FXN-516 m02 | GGGCAGGTTGAGACT | FXN | intron | human | dGs; InaGs; dGs; InaCs; dAs; InaGs; dGs; InaTs; dTs; InaGs; dAs; InaGs; dAs; InaCs; dT-Sup |
| 199 | FXN-517 m02 | GCAGGTTGAGACTGG | FXN | intron | human | dGs; InaCs; dAs; InaGs; dGs; InaTs; dTs; InaGs; dAs; InaGs; dAs; InaCs; dTs; InaGs; dG-Sup |
| 200 | FXN-518 m02 | AGGTTGAGACTGGGT | FXN | intron | human | dAs; InaGs; dGs; InaTs; dTs; InaGs; dAs; InaGs; dAs; InaCs; dTs; In aGs; dGs; InaGs; dT-Sup |
| 201 | FXN-519 m02 | GGAAAAATTCCAGGA | FXN | Antisense/ UTR | human | dGs; InaGs; dAs; InaAs; dAs; InaAs; dAs; InaTs; dTs; InaCs; dCs; InaAs; dGs; InaGs; dA-Sup |
| 202 | FXN-520 m02 | AATTCCAGGAGGGAA | FXN | Antisense/ UTR | human | dAs; InaAs; dTs; InaTs; dCs; InaCs; dAs; InaGs; dGs; InaAs; dGs; InaGs; dGs; InaAs; dA-Sup |
| 203 | FXN-521 m02 | GAGGGAAAATGAATT | FXN | Antisense/ UTR | human | dGs; InaAs; dGs; InaGs; dGs; InaAs; dAs; InaAs; dAs; InaTs; dGs; InaAs; dAs; InaTs; dT-Sup |
| 204 | FXN-522 m02 | GAAAATGAATTGTCTTC | FXN | Antisense/ UTR | human | dGs; InaAs; dAs; InaAs; dAs; InaTs; dGs; InaAs; dAs; InaTs; dTs; InaGs; dTs; InaCs; dTs; InaTs; dC-Sup |
| 205 | FXN-512 m08 | GGGGGACGGGGCAGG | FXN | intron | human | InaGs; InaGs; InaGs; dGs; dGs; dAs; dCs; dGs; dGs; dGs; dGs; dCs; InaAs; InaGs; InaG-Sup |
| 206 | FXN-513 m08 | GGGACGGGGCAGGTT | FXN | intron | human | InaGs; InaGs; InaGs; dAs; dCs; dGs; dGs; dGs; dGs; dCs; dAs; dGs; InaGs; InaTs; InaT-Sup |
| 207 | FXN-514 m08 | GACGGGGCAGGTTGA | FXN | intron | human | InaGs; InaAs; InaCs; dGs; dGs; dGs; dCs; dAs; dGs; dGs; dTs; InaTs; InaGs; InaA-Sup |
| 208 | FXN-515 m08 | CGGGGCAGGTTGAGA | FXN | intron | human | InaCs; InaGs; InaGs; dGs; dGs; dCs; dAs; dGs; dTs; dTs; dGs; InaAs; InaGs; InaA-Sup |
| 209 | FXN-516 m08 | GGGCAGGTTGAGACT | FXN | intron | human | InaGs; InaGs; InaGs; dCs; dAs; dGs; dGs; dTs; dTs; dGs; dAs; dGs; InaAs; InaCs; InaT-Sup |
| 210 | FXN-517 m08 | GCAGGTTGAGACTGG | FXN | intron | human | InaGs; InaCs; InaAs; dGs; dGs; dTs; dTs; dGs; dAs; dGs; dAs; dCs; InaTs; InaGs; InaG-Sup |
| 211 | FXN-518 m08 | AGGTTGAGACTGGGT | FXN | intron | human | InaAs; InaGs; InaGs; dTs; dTs; dGs; dAs; dGs; dAs; dCs; dTs; InaGs; InaGs; InaT-Sup |
| 212 | FXN-519 m08 | GGAAAAATTCCAGGA | FXN | Antisense/ UTR | human | InaGs; InaGs; InaAs; dAs; dAs; dAs; dAs; dTs; dTs; dCs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dCs; dAs; InaGs; InaGs; InaA-Sup |
| 213 | FXN-520 m08 | AATTCCAGGAGGGAA | FXN | Antisense/UTR | human | InaAs; InaAs; InaTs; dTs; dCs; dCs; dAs; dGs; dGs; dAs; dGs; dGs; InaGs; InaAs; InaA-Sup |
| 214 | FXN-521 m08 | GAGGGAAAATGAATT | FXN | Antisense/UTR | human | InaGs; InaAs; InaGs; dGs; dGs; dAs; dAs; dAs; dAs; dTs; dGs; dAs; InaAs; InaTs; InaT-Sup |
| 215 | FXN-522 m08 | GAAAATGAATTGTCTTC | FXN | Antisense/UTR | human | InaGs; InaAs; InaAs; dAs; dAs; dTs; dGs; dAs; dAs; dTs; dTs; dGs; dTs; dCs; InaTs; InaTs; InaC-Sup |
| 216 | EPO-37 m02 | GGTGGTTTCAGTTCT | EPO | 3' | human | dGs; InaGs; dTs; InaGs; dGs; InaTs; dTs; InaTs; dCs; InaAs; dGs; InaTs; dTs; InaCs; dT-Sup |
| 217 | EPO-38 m02 | TTTTTGGTGGTTTCAGTTCT | EPO | 3' | human | dTs; InaTs; dTs; InaTs; dTs; InaGs; dGs; InaTs; dGs; InaGs; dTs; InaTs; dTs; InaCs; dAs; InaGs; dTs; InaTs; dCs; InaT-Sup |
| 218 | EPO-39 m02 | AGCGTGCTATCTGGG | EPO | 5' | human | dAs; InaGs; dCs; InaGs; dTs; InaGs; dCs; InaTs; dAs; InaTs; dCs; InaTs; dGs; InaGs; dG-Sup |
| 219 | EPO-40 m02 | TGGCCCAGGGACTCT | EPO | 5' | human | dTs; InaGs; dGs; InaCs; dCs; InaCs; dAs; InaGs; dGs; InaGs; dAs; InaCs; dTs; InaCs; dT-Sup |
| 220 | EPO-41 m02 | TCTGCGGCTCTGGC | EPO | 5' | human | dTs; InaCs; dTs; InaGs; dCs; InaGs; dGs; InaCs; dTs; InaCs; dTs; InaGs; dGs; InaC-Sup |
| 221 | EPO-42 m02 | CGGTCCGGCTCTGGG | EPO | 5' | human | dCs; InaGs; dGs; InaTs; dCs; InaCs; dGs; InaGs; dCs; InaTs; dCs; InaTs; dGs; InaGs; dG-Sup |
| 222 | EPO-43 m02 | TCATCCCGGGAAGCT | EPO | 5' | human | dTs; InaCs; dAs; InaTs; dCs; InaCs; dCs; InaGs; dGs; InaGs; dAs; InaAs; dGs; InaCs; dT-Sup |
| 223 | EPO-44 m02 | CCCCAAGTCCCCGCT | EPO | 5' | human | dCs; InaCs; dCs; InaCs; dAs; InaAs; dGs; InaTs; dCs; InaCs; s; dCs; InaCs; dGs; InaCs; dT-Sup |
| 224 | EPO-45 m02 | CCAACCATGCAAGCA | EPO | 5' | human | dCs; InaCs; dAs; InaAs; dCs; InaCs; dAs; InaTs; dGs; InaCs; dAs; InaAs; dGs; InaCs; dA-Sup |
| 225 | EPO-46 m02 | TGGCCCAGGGACTCTTC | EPO | 5' | human | dTs; InaGs; dGs; InaCs; dCs; InaCs; dAs; InaGs; dGs; InaGs; dAs; InaCs; dTs; InaCs; dTs; InaTs; dC-Sup |
| 226 | EPO-47 m02 | CGGTCCGGCTCTGGGTTC | EPO | 5' | human | dCs; InaGs; dGs; InaTs; dCs; InaCs; dGs; InaGs; dCs; InaTs; dCs; InaTs; dGs; InaGs; dGs; InaTs; dTs; InaC-Sup |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 227 | EPO-48 m02 | CCAACCATGCAAGCACC | EPO | 5' | human | dCs; InaCs; dAs; InaAs; dCs; InaCs; dAs; InaTs; dGs; InaCs; dAs; InaAs; dGs; InaCs; dAs; InaCs; dC-Sup |
| 228 | EPO-49 m02 | TGGCCCAGGGACTCTCACAAAGTGAC | EPO | 5' | human | dTs; InaGs; dGs; InaCs; dCs; InaCs; dAs; InaGs; dGs; InaGs; Gs; dAs; InaCs; dTs; InaCs; dTs; InaCs; dAs; dCs; dAs; dAs; dAs; dGs; dTs; InaGs; dAs; InaC-Sup |
| 229 | EPO-50 m02 | CGGTCCGGCTCTGGGAAGAAACTTTC | EPO | 5' | human | dCs; InaGs; dGs; InaTs; dCs; InaCs; dGs; InaGs; dCs; InaTs; dCs; InaTs; dGs; InaGs; dGs; InaAs; dAs; dGs; dAs; dAs; dAs; dCs; dTs; InaTs; dTs; InaC-Sup |
| 230 | EPO-51 m02 | CCAACCATGCAAGCACTCAAAGAGTC | EPO | 5' | human | dCs; InaCs; dAs; InaAs; dCs; InaCs; dAs; InaTs; dGs; InaCs; dAs; InaAs; dGs; InaCs; dAs; InaCs; dTs; dCs; dAs; dAs; dAs; dGs; dAs; InaGs; dTs; InaC-Sup |
| 231 | EPO-52 m02 | TGGCCCAGGGACTCTTTTTGGTGGTTTCAGTTCT | EPO | 5' and 3' | human | dTs; InaGs; dGs; InaCs; dCs; InaCs; dAs; InaGs; dGs; InaGs; dAs; InaCs; dTs; InaCs; dTs; InaTs; dTs; InaTs; dTs; InaGs; dGs; InaTs; dGs; InaGs; dTs; InaTs; dTs; InaCs; dAs; InaGs; dTs; dCs; InaT-Sup |
| 232 | EPO-53 m02 | CGGTCCGGCTCTGGGTTTTTGGTGGTTTCAGTTCT | EPO | 5' and 3' | human | dCs; InaGs; dGs; InaTs; dCs; InaCs; dGs; InaGs; dCs; InaTs; dCs; InaTs; dGs; InaGs; dGs; InaTs; dTs; InaTs; dTs; InaTs; dGs; InaGs; dTs; InaGs; dGs; InaTs; dTs; InaTs; dCs; InaAs; dGs; InaTs; dTs; InaCs; dT-Sup |
| 233 | EPO-54 m02 | CCAACCATGCAAGCATTTTTGGTGGTTTCAGTTCT | EPO | 5' and 3' | human | dCs; InaCs; dAs; InaAs; dCs; InaCs; dAs; InaTs; dGs; InaCs; dAs; InaAs; dGs; InaCs; dAs; InaTs; dTs; InaTs; dTs; InaTs; dGs; InaGs; dTs; InaGs; dGs; InaTs; dTs; InaTs; dCs; InaAs; dGs; InaTs; dTs; InaCs; dT-Sup |
| 234 | EPO-55 m02 | CAGGGACTCTTTTTGGTGGTTTCA | EPO | 5' and 3' | human | dCs; InaAs; dGs; InaGs; dGs; InaAs; dCs; InaTs; dCs; InaTs; dTs; InaTs; dTs; InaTs; dGs; InaGs; dTs; InaGs; dGs; InaTs; dTs; InaCs; dA-Sup |
| 235 | EPO-56 m02 | CGGCTCTGGGTTTTTGGTGGTTTCA | EPO | 5' and 3' | human | dCs; InaGs; dGs; InaCs; dTs; InaCs; dTs; InaGs; dGs; dTs; InaTs; dTs; InaTs; dTs; InaGs; dGs; InaTs; dGs; InaGs; dTs; InaTs; dTs; InaCs; dA-Sup |
| 236 | EPO-57 m02 | CATGCAAGCATTTTTGGTGGTTTCA | EPO | 5' and 3' | human | dCs; InaAs; dTs; InaGs; dCs; InaAs; dAs; InaGs; dCs; InaAs; dTs; InaTs; dTs; InaTs; dTs; InaGs; dGs; InaTs; dGs; InaGs; dTs; InaTs; dTs; InaCs; dA-Sup |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 237 | EPO-58 m02 | TGGCCCAGGGACTCGGT GGTTTCAGTTCT | EPO | 5' and 3' | human | dTs; InaGs; dGs; InaCs; dCs; InaCs; dAs; InaGs; dGs; InaGs; dAs; InaCs; dTs; InaCs; dGs; InaGs; dTs; InaGs; dGs; InaTs; dTs; InaTs; dCs; InaAs; dGs; InaTs; dTs; InaCs; dT-Sup |
| 238 | EPO-59 m02 | CGGTCCGGCTCTGGTGG TGGTTTCAGTTCT | EPO | 5' and 3' | human | dCs; InaGs; dGs; InaTs; dCs; InaCs; dGs; InaGs; dCs; InaTs; dCs; InaTs; dGs; InaGs; dTs; InaGs; dGs; InaTs; dGs; InaGs; dTs; InaTs; dTs; InaCs; dAs; InaGs; dTs; InaTs; dCs; InaT-Sup |
| 239 | EPO-60 m02 | CCAACCATGCAAGCAGG TGGTTTCAGTTCT | EPO | 5' and 3' | human | dCs; InaCs; dAs; InaAs; dCs; InaCs; dAs; InaTs; dGs; InaCs; dAs; InaAs; dGs; InaCs; dAs; InaGs; dGs; InaTs; dGs; InaGs; dTs; InaTs; dTs; InaCs; dAs; InaGs; dTs; InaTs; dCs; InaT-Sup |
| 240 | KLF4-31 m02 | TTTTTAGATAAAATATTA TA | KLF4 | 3' | human | dTs; InaTs; dTs; InaTs; dTs; InaAs; dGs; InaAs; dTs; InaAs; dAs; InaAs; dAs; InaTs; dAs; InaTs; dTs; InaAs; dTs; InaA-Sup |
| 241 | KLF4-32 m02 | TTTTTATTCAGATAAAAT A | KLF4 | 3' | human | dTs; InaTs; dTs; InaTs; dTs; InaAs; dTs; InaTs; dCs; InaAs; dGs; InaAs; dTs; InaAs; dAs; InaAs; dAs; InaTs; dA-Sup |
| 242 | KLF4-33 m02 | TTTTTGGTTTATTTAAAA CT | KLF4 | 3' | human | dTs; InaTs; dTs; InaTs; dTs; InaGs; dGs; InaTs; dTs; InaTs; dAs; InaTs; dTs; InaTs; dAs; InaAs; dAs; InaAs; dCs; InaT-Sup |
| 243 | KLF4-34 m02 | TTTTTAAATTTATATTAC AT | KLF4 | 3' | human | dTs; InaTs; dTs; InaTs; dTs; InaAs; dAs; InaAs; dTs; InaTs; dTs; InaAs; dTs; InaAs; dTs; InaTs; dAs; InaCs; dAs; InaT-Sup |
| 244 | KLF4-35 m02 | TTTTTCTTAAATTTATAT TA | KLF4 | 3' | human | dTs; InaTs; dTs; InaTs; dTs; InaCs; dTs; InaTs; dAs; InaAs; dAs; InaTs; dTs; InaTs; dAs; InaTs; dAs; InaTs; dTs; InaA-Sup |
| 245 | KLF4-36 m02 | TTTTTCACAAAATGTTCA TT | KLF4 | 3' | human | dTs; InaTs; dTs; InaTs; dTs; InaCs; dAs; InaCs; dAs; InaAs; dAs; InaAs; dTs; InaGs; dTs; InaTs; dCs; InaAs; dTs; InaT-Sup |
| 246 | KLF4-37 m02 | CCTCCGCCTTCTCCC | KLF4 | 5' | human | dCs; InaCs; dTs; InaCs; dCs; InaGs; dCs; InaCs; dTs; InaTs; dCs; InaTs; dCs; InaCs; dC-Sup |
| 247 | KLF4-38 m02 | TCTGGTCGGGAAACT | KLF4 | 5' | human | dTs; InaCs; dTs; InaGs; dGs; InaTs; dCs; InaGs; dGs; InaGs; dAs; InaAs; dAs; InaCs; dT-Sup |
| 248 | KLF4-39 m02 | GCTACAGCCTTTTCC | KLF4 | 5' | human | dGs; InaCs; dTs; InaAs; dCs; InaAs; dGs; InaCs; dCs; InaTs; dTs; InaTs; dTs; InaCs; dC-Sup |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 249 | KLF4-40 m02 | CCTCCGCCTTCTCCCC | KLF4 | 5' | human | dCs; InaCs; dTs; InaCs; dCs; InaGs; dCs; InaCs; dTs; InaTs; dCs; InaTs; dCs; InaCs; dCs; InaC-Sup |
| 250 | KLF4-41 m02 | TCTGGTCGGGAAACTCC | KLF4 | 5' | human | dTs; InaCs; dTs; InaGs; dGs; InaTs; dCs; InaGs; dGs; InaGs; dAs; InaAs; dAs; InaCs; dTs; InaCs; dC-Sup |
| 251 | KLF4-42 m02 | GCTACAGCCTTTTCCC | KLF4 | 5' | human | dGs; InaCs; dTs; InaAs; dCs; InaAs; dGs; InaCs; dCs; InaTs; dTs; InaTs; dTs; InaCs; dCs; InaC-Sup |
| 252 | KLF4-43 m02 | CCTCCGCCTTCTCCCTCT TTGATC | KLF4 | 5' | human | dCs; InaCs; dTs; InaCs; dCs; InaGs; dCs; InaCs; dTs; InaTs; dCs; InaTs; dCs; InaCs; dCs; InaTs; dCs; dTs; dTs; dTs; dGs; InaAs; dTs; InaC-Sup |
| 253 | KLF4-44 m02 | TCTGGTCGGGAAACTCA ATTATTGTC | KLF4 | 5' | human | dTs; InaCs; dTs; InaGs; dGs; InaTs; dCs; InaGs; dGs; InaGs; dAs; InaAs; dAs; InaCs; dTs; InaCs; dAs; dAs; dTs; dTs; dAs; dTs; dTs; InaGs; dTs; InaC-Sup |
| 254 | KLF4-45 m02 | GCTACAGCCTTTTCCACT TTGTTC | KLF4 | 5' | human | dGs; InaCs; dTs; InaAs; dCs; InaAs; dGs; InaCs; dCs; InaTs; dTs; InaTs; dTs; InaCs; dCs; InaAs; dCs; dTs; dTs; dTs; dGs; InaTs; dTs; InaC-Sup |
| 255 | KLF4-46 m02 | CCTCCGCCTTCTCCCTTT TTAGATAAAATATTATA | KLF4 | 5' and 3' | human | dCs; InaCs; dTs; InaCs; dCs; InaGs; dCs; InaCs; dTs; InaTs; dCs; InaTs; dCs; InaCs; dCs; InaTs; dTs; InaTs; dTs; InaTs; dAs; InaGs; dAs; InaTs; dAs; InaAs; dAs; InaAs; dTs; InaAs; dTs; InaTs; dAs; InaTs; dA-Sup |
| 256 | KLF4-47 m02 | TCTGGTCGGGAAACTTT TTAGATAAAATATTATA | KLF4 | 5' and 3' | human | dTs; InaCs; dTs; InaGs; dGs; InaTs; dCs; InaGs; dGs; InaGs; dAs; InaAs; dAs; InaCs; dTs; InaTs; dTs; InaTs; dTs; InaAs; dGs; InaAs; dTs; InaAs; dAs; InaAs; dAs; InaTs; dAs; InaTs; dTs; InaAs; dTs; InaA-Sup |
| 257 | KLF4-48 m02 | GCTACAGCCTTTTCCTTT TTAGATAAAATATTATA | KLF4 | 5' and 3' | human | dGs; InaCs; dTs; InaAs; dCs; InaAs; dGs; InaCs; dCs; InaTs; dTs; InaTs; dTs; InaCs; dCs; InaTs; dTs; InaTs; dTs; InaTs; dAs; InaGs; dAs; InaTs; dAs; InaAs; dAs; InaAs; dTs; InaAs; dTs; InaTs; dAs; InaTs; dA-Sup |
| 258 | KLF4-49 m02 | CCTCCGCCTTCTCCCTTT TTGGTTTATTTAAAACT | KLF4 | 5' and 3' | human | dCs; InaCs; dTs; InaCs; dCs; InaGs; dCs; InaCs; dTs; InaTs; dCs; InaTs; dCs; InaCs; dCs; InaTs; dTs; InaTs; dTs; InaTs; dGs; InaGs; dTs; InaTs; dTs; InaAs; dTs; InaTs; dTs; InaAs; dAs; InaAs; dAs; InaCs; dT-Sup |
| 259 | KLF4-50 m02 | TCTGGTCGGGAAACTTT TTGGTTTATTTAAAACT | KLF4 | 5' and 3' | human | dTs; InaCs; dTs; InaGs; dGs; InaTs; dCs; InaGs; dGs; InaGs; dAs; InaAs; dAs; InaCs; dTs; InaTs; dTs; InaTs; dTs; InaGs; dGs; InaTs; dTs; InaTs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dAs; InaTs; dTs; InaTs; dAs; InaAs; dAs; InaAs; dCs; InaT-Sup |
| 260 | KLF4-51 m02 | GCTACAGCCTTTTCCTTT TTGGTTTATTTAAAACT | KLF4 | 5' and 3' | human | dGs; InaCs; dTs; InaAs; dCs; InaAs; dGs; InaCs; dCs; InaTs; dTs; InaTs; dTs; InaCs; dCs; InaTs; dTs; InaTs; dTs; InaTs; dGs; InaGs; dTs; InaTs; dTs; InaAs; dTs; InaTs; dTs; InaAs; dAs; InaAs; dAs; InaCs; dT-Sup |
| 261 | KLF4-52 m02 | CCTCCGCCTTCTCCCTTT TTAAATTTATATTACAT | KLF4 | 5' and 3' | human | dCs; InaCs; dTs; InaCs; dCs; InaGs; dCs; InaCs; dTs; InaTs; dCs; InaTs; dCs; InaCs; dCs; InaTs; dTs; InaTs; dTs; InaTs; dAs; InaAs; dAs; InaTs; dTs; InaTs; dAs; InaTs; dAs; InaTs; dTs; InaAs; dCs; InaAs; dT |
| 262 | KLF4-53 m02 | TCTGGTCGGGAAACTTT TTAAATTTATATTACAT | KLF4 | 5' and 3' | human | dTs; InaCs; dTs; InaGs; dGs; InaTs; dCs; InaGs; dGs; InaGs; dAs; InaAs; dAs; InaCs; dTs; InaTs; dTs; InaTs; dTs; InaAs; dAs; InaAs; dTs; InaTs; dTs; InaAs; dTs; InaAs; dTs; InaTs; dAs; InaCs; dAs; InaT-Sup |
| 263 | KLF4-54 m02 | GCTACAGCCTTTTCCTTT TTAAATTTATATTACAT | KLF4 | 5' and 3' | human | dGs; InaCs; dTs; InaAs; dCs; InaAs; dGs; InaCs; dCs; InaTs; dTs; InaTs; dTs; InaCs; dCs; InaTs; dTs; InaTs; dTs; InaTs; dAs; InaAs; dAs; InaTs; dTs; InaTs; dAs; InaTs; dAs; InaTs; dAs; InaTs; dTs; InaAs; dCs; InaAs; dT-Sup |
| 264 | KLF4-55 m02 | GCCTTCTCCCTTTTTAGA TAAAATA | KLF4 | 5' and 3' | human | dGs; InaCs; dCs; InaTs; dTs; InaCs; dTs; InaCs; dCs; InaCs; dTs; InaTs; dTs; InaTs; dTs; InaAs; dGs; InaAs; dTs; InaAs; dAs; InaAs; dAs; InaTs; dA-Sup |
| 265 | KLF4-56 m02 | TCGGGAAACTTTTTAGA TAAAATA | KLF4 | 5' and 3' | human | dTs; InaCs; dGs; InaGs; dGs; InaAs; dAs; InaAs; dCs; InaTs; dTs; InaTs; dTs; InaTs; dAs; InaGs; dAs; InaTs; dAs; InaAs; dAs; InaTs; dA-InaA-Sup |
| 266 | KLF4-57 m02 | AGCCTTTTCCTTTTTAGA TAAAATA | KLF4 | 5' and 3' | human | dAs; InaGs; dCs; InaCs; dTs; InaTs; dTs; InaTs; dCs; InaCs; dTs; InaTs; dTs; InaTs; dTs; InaAs; dGs; InaAs; dTs; InaAs; dAs; InaAs; dAs; InaTs; dA-Sup |
| 267 | KLF4-58 m02 | GCCTTCTCCCTTTTTGGT TTATTTA | KLF4 | 5' and 3' | human | dGs; InaCs; dCs; InaTs; dTs; InaCs; dTs; InaCs; dCs; InaCs; dTs; InaTs; dTs; InaTs; dTs; InaGs; dGs; InaTs; dTs; InaTs; dAs; InaTs; dTs; InaTs; dA-Sup |
| 268 | KLF4-59 m02 | TCGGGAAACTTTTTGGT TTATTTA | KLF4 | 5' and 3' | human | dTs; InaCs; dGs; InaGs; dGs; InaAs; dAs; InaAs; dCs; InaTs; dTs; InaTs; dTs; InaTs; dGs; InaGs; dTs; InaTs; dTs; InaAs; dTs; InaTs; dTs; InaA-Sup |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 269 | KLF4-60 m02 | AGCCTTTTCCTTTTGGT TTATTTA | KLF4 | 5' and 3' | human | dAs; InaGs; dCs; InaCs; dTs; InaTs; dTs; InaTs; dCs; InaCs; dTs; InaTs; dTs; InaTs; dTs; InaTs; dTs; InaGs; dGs; InaTs; dTs; InaGs; dAs; InaTs; dTs; InaTs; dA-Sup |
| 270 | KLF4-61 m02 | GCCTTCTCCCTTTTTAAA TTTATAT | KLF4 | 5' and 3' | human | dGs; InaCs; dCs; InaTs; dTs; InaCs; dTs; InaCs; dCs; InaCs; dTs; InaTs; dTs; InaTs; dTs; InaAs; dAs; InaAs; dTs; InaTs; dTs; InaTs; dTs; InaAs; dT-Sup |
| 271 | KLF4-62 m02 | TCGGGAAACTTTTTAAA TTTATAT | KLF4 | 5' and 3' | human | dTs; InaCs; dGs; InaGs; dGs; InaAs; dAs; InaAs; dCs; InaTs; dTs; InaTs; dTs; InaTs; dAs; InaAs; dAs; InaTs; dTs; InaTs; dAs; InaTs; dAs; InaT-Sup |
| 272 | KLF4-63 m02 | AGCCTTTTCCTTTTTAAA TTTATAT | KLF4 | 5' and 3' | human | dAs; InaGs; dCs; InaCs; dTs; InaTs; dTs; InaTs; dCs; InaCs; dTs; InaTs; dTs; InaTs; dTs; InaAs; dAs; InaAs; dTs; InaTs; dTs; InaAs; dTs; InaAs; dT-Sup |
| 273 | ACTB-01 m02 | AGGTGTGCACTTTTA | ACTB | 3' | human | dAs; InaGs; dGs; InaTs; dGs; InaTs; dGs; InaCs; dAs; InaCs; dTs; InaTs; dTs; InaTs; dA-Sup |
| 274 | ACTB-02 m02 | TCATTTTTAAGGTGT | ACTB | 3' | human | dTs; InaCs; dAs; InaTs; dTs; InaTs; dTs; InaTs; dAs; InaAs; dGs; InaGs; dTs; InaGs; dT-Sup |
| 275 | ACTB-03 m02 | TTTTTAGGTGTGCACTTT TA | ACTB | 3' | human | dTs; InaTs; dTs; InaTs; dTs; InaAs; dGs; InaGs; dTs; InaGs; dTs; InaGs; dCs; InaAs; dCs; InaTs; dTs; InaTs; dTs; InaA-Sup |
| 276 | ACTB-04 m02 | TTTTTCATTTTTAAGGTG T | ACTB | 3' | human | dTs; InaTs; dTs; InaTs; dTs; InaCs; dAs; InaTs; dTs; InaTs; dTs; InaTs; dAs; InaAs; dGs; InaGs; dTs; InaGs; dT-Sup |
| 277 | ACTB-05 m02 | CGCGGTCTCGGCGGT | ACTB | 5' | human | dCs; InaGs; dCs; InaGs; dGs; InaTs; dCs; InaTs; dCs; InaGs; dGs; InaCs; dGs; InaGs; dT-Sup |
| 278 | ACTB-06 m02 | ATCATCCATGGTGAG | ACTB | 5' | human | dAs; InaTs; dCs; InaAs; dTs; InaCs; dCs; InaAs; dTs; InaGs; dGs; InaTs; dGs; InaAs; dG-Sup |
| 279 | ACTB-07 m02 | CGCGGTCTCGGCGGTTT TTAGGTGTGCACTTTTA | ACTB | 5' and 3' | human | dCs; InaGs; dCs; InaGs; InaTs; dCs; InaTs; dCs; InaGs; dGs; InaCs; dGs; InaGs; dTs; InaTs; dTs; InaTs; dTs; InaAs; dGs; InaGs; dTs; InaGs; dTs; InaGs; dCs; InaAs; dCs; InaTs; dTs; InaTs; dTs; InaA-Sup |
| 280 | ACTB-08 m02 | ATCATCCATGGTGAGTT TTAGGTGTGCACTTTTA | ACTB | 5' and 3' | human | dAs; InaTs; dCs; InaAs; dTs; InaCs; dCs; InaAs; dTs; InaGs; dGs; InaTs; dGs; InaAs; dGs; InaTs; dTs; InaTs; dTs; InaTs; dAs; InaGs; dGs; InaTs; dGs; InaTs; dGs; InaCs; dAs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaCs; dTs; InaTs; dTs; InaTs; dA-Sup |
| 281 | ACTB-09 m02 | CGCGGTCTCGGCGGTTT TTCATTTTTAAGGTGT | ACTB | 5' and 3' | human | dCs; InaGs; dCs; InaGs; dGs; InaTs; dCs; InaTs; dCs; InaGs; dGs; InaCs; dGs; InaGs; dTs; InaTs; dTs; InaTs; dTs; InaCs; dAs; InaTs; dTs; InaTs; dTs; InaTs; dAs; InaAs; dGs; InaGs; dTs; InaGs; dT-Sup |
| 282 | ACTB-10 m02 | ATCATCCATGGTGAGTT TTTCATTTTTAAGGTGT | ACTB | 5' and 3' | human | dAs; InaTs; dCs; InaAs; dTs; InaCs; dCs; InaAs; dTs; InaGs; dGs; InaTs; dGs; InaAs; dGs; InaTs; dTs; InaTs; dTs; InaTs; dCs; InaAs; dTs; InaTs; dTs; InaTs; dTs; InaAs; dAs; InaGs; dGs; InaTs; dGs; InaT-Sup |
| 283 | ACTB-11 m02 | TCTCGGCGGTTTTTAGG TGTGCAC | ACTB | 5' and 3' | human | dTs; InaCs; dTs; InaCs; dGs; InaGs; dCs; InaGs; dGs; InaTs; dTs; InaTs; dTs; InaTs; dAs; InaGs; dGs; InaTs; dGs; InaTs; dGs; InaCs; dAs; InaC-Sup |
| 284 | ACTB-12 m02 | CCATGGTGAGTTTTTAG GTGTGCAC | ACTB | 5' and 3' | human | dCs; InaCs; dAs; InaTs; dGs; InaGs; dTs; InaGs; dAs; InaGs; dTs; InaTs; dTs; InaTs; dTs; InaAs; dGs; InaGs; dTs; InaGs; dTs; InaGs; dCs; InaAs; dC-Sup |
| 285 | ACTB-13 m02 | TCTCGGCGGTTTTTCATT TTTAA | ACTB | 5' and 3' | human | dTs; InaCs; dTs; InaCs; dGs; InaGs; dCs; InaGs; dGs; InaTs; dTs; InaTs; dTs; InaTs; dCs; InaAs; dTs; InaTs; dTs; InaTs; dTs; InaAs; dA-Sup |
| 286 | ACTB-14 m02 | CCATGGTGAGTTTTTCA TTTTTAA | ACTB | 5' and 3' | human | dCs; InaCs; dAs; InaTs; dGs; InaGs; dTs; InaGs; dAs; InaGs; dTs; InaTs; dTs; InaTs; dTs; InaCs; dAs; InaTs; dTs; InaTs; dTs; InaTs; dAs; InaA-Sup |
| 287 | ACTB-15 m02 | CGCGGTCTCGGCGGTA GGTGTGCACTTTTA | ACTB | 5' and 3' | human | dCs; InaGs; dCs; InaGs; dGs; InaTs; dCs; InaTs; dCs; InaGs; dGs; InaCs; dGs; InaGs; dTs; InaAs; dGs; InaGs; dTs; InaGs; dTs; InaGs; dCs; InaAs; dCs; InaTs; dTs; InaTs; dTs; InaA-Sup |
| 288 | ACTB-16 m02 | ATCATCCATGGTGAGAG GTGTGCACTTTTA | ACTB | 5' and 3' | human | dAs; InaTs; dCs; InaAs; dTs; InaCs; dCs; InaAs; dTs; InaGs; dGs; InaTs; dGs; InaAs; dGs; InaAs; dGs; InaTs; dGs; InaTs; dGs; InaCs; dAs; InaCs; dTs; InaTs; dTs; InaTs; dTs; InaA-Sup |
| 289 | ACTB-17 m02 | CGCGGTCTCGGCGGTTC ATTTTTAAGGTGT | ACTB | 5' and 3' | human | dCs; InaGs; dCs; InaGs; dGs; InaTs; dCs; InaTs; dCs; InaGs; dGs; InaCs; dGs; InaGs; dTs; InaTs; dCs; InaAs; dTs; InaTs; dTs; InaTs; dTs; InaAs; dAs; InaGs; dGs; InaTs; dGs; InaT-Sup |
| 290 | ACTB-18 m02 | ATCATCCATGGTGAGTC ATTTTTAAGGTGT | ACTB | 5' and 3' | human | dAs; InaTs; dCs; InaAs; dTs; InaCs; dCs; InaAs; dTs; InaGs; dGs; InaTs; dGs; InaAs; dGs; InaTs; dCs; InaAs; dTs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaTs; dTs; InaTs; dTs; InaAs; dAs; InaGs; dGs; InaTs; dGs; InaT-Sup |
| 291 | UTRN-192 m02 | TGGAGCCGAGCGCTG | UTRN | 5' | human | dTs; InaGs; dGs; InaAs; dGs; InaCs; dCs; InaGs; dAs; InaGs; dCs; InaGs; dCs; InaTs; dG-Sup |
| 292 | UTRN-193 m02 | GGGCCTGCCCCTTTG | UTRN | 5' | human | dGs; InaGs; dGs; InaCs; dCs; InaTs; dGs; InaCs; dCs; InaCs; dCs; InaTs; dTs; InaTs; dG-Sup |
| 293 | UTRN-194 m02 | CCCCAAGTCACCTGA | UTRN | 5' | human | dCs; InaCs; dCs; InaCs; dAs; InaAs; dGs; InaTs; dCs; InaAs; dCs; InaCs; dTs; InaGs; dA-Sup |
| 294 | UTRN-195 m02 | GACATCAATACCTAA | UTRN | 5' | human | dGs; InaAs; dCs; InaAs; dTs; InaCs; dAs; InaAs; dTs; InaAs; dCs; InaCs; dTs; InaAs; dA-Sup |
| 295 | UTRN-196 m02 | AAACTTTACCAAGTC | UTRN | 5' | human | dAs; InaAs; dAs; InaCs; dTs; InaTs; dTs; InaAs; dCs; InaCs; dAs; InaAs; dGs; InaTs; dC-Sup |
| 296 | UTRN-197 m02 | TGGAGCCGAGCGCTGC | UTRN | 5' | human | dTs; InaGs; dGs; InaAs; dGs; InaCs; dCs; InaGs; dAs; InaGs; dCs; InaGs; dCs; InaTs; dGs; InaCs; dC-Sup |
| 297 | UTRN-198 m02 | GGGCCTGCCCCTTTGCC | UTRN | 5' | human | dGs; InaGs; dGs; InaCs; dCs; InaTs; dGs; InaCs; dCs; InaCs; dCs; InaTs; dTs; InaTs; dGs; InaCs; dC-Sup |
| 298 | UTRN-199 m02 | CCCCAAGTCACCTGACC | UTRN | 5' | human | dCs; InaCs; dCs; InaCs; dAs; InaAs; dGs; InaTs; dCs; InaAs; dCs; InaCs; dTs; InaGs; dAs; InaCs; dC-Sup |
| 299 | UTRN-200 m02 | GACATCAATACCTAACC | UTRN | 5' | human | dGs; InaAs; dCs; InaAs; dTs; InaCs; dAs; InaAs; dTs; InaAs; dCs; InaCs; dTs; InaAs; dAs; InaCs; dC-Sup |
| 300 | UTRN-201 m02 | AAACTTTACCAAGTCCC | UTRN | 5' | human | dAs; InaAs; dAs; InaCs; dTs; InaTs; dTs; InaAs; dCs; InaCs; dAs; InaAs; dGs; InaTs; dCs; InaCs; dC-Sup |
| 301 | UTRN-202 m1000 | TGGAGCCGAGCGCTGG GAAACCAC | UTRN | 5' | human | dTs; InaGs; dGs; InaAs; dGs; InaCs; dCs; InaGs; dAs; InaGs; dCs; InaGs; dCs; InaTs; dGs; InaGs; dGs; dAs; dAs; dAs; dCs; InaCs; dAs; InaC-Sup |
| 302 | UTRN-203 m1000 | GGGCCTGCCCCTTTGGG AAACCAC | UTRN | 5' | human | dGs; InaGs; dGs; InaCs; dCs; InaTs; dGs; InaCs; dCs; InaCs; dCs; InaTs; dTs; InaTs; dGs; InaGs; dGs; dAs; dAs; dAs; dCs; InaCs; dAs; InaC-Sup |
| 303 | UTRN-204 m1000 | CCCCAAGTCACCTGAGG AAACCAC | UTRN | 5' | human | dCs; InaCs; dCs; InaCs; dAs; InaAs; dGs; InaTs; dCs; InaAs; dCs; InaCs; dTs; InaGs; dAs; InaGs; dGs; dAs; dAs; dAs; dCs; InaCs; dAs; InaC-Sup |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 304 | UTRN-205 m1000 | GACATCAATACCTAAGG AAACCAC | UTRN | 5' | human | dGs; InaAs; dCs; InaAs; dTs; InaCs; dAs; InaAs; dTs; InaAs; dCs; InaCs; dTs; dAs; dAs; InaGs; dGs; dAs; dAs; dAs; dCs; InaCs; dAs; InaC-Sup |
| 305 | UTRN-206 m1000 | AAACTTTACCAAGTCGG AAACCAC | UTRN | 5' | human | dAs; InaAs; dAs; InaAs; dTs; InaTs; dTs; InaAs; dCs; InaCs; dAs; InaAs; dGs; InaTs; dCs; InaGs; dGs; dAs; dAs; dAs; dCs; InaCs; dAs; InaC-Sup |
| 306 | UTRN-207 m02 | ACTGCAATATATTTC | UTRN | 3' | human | dAs; InaCs; dTs; InaGs; dCs; InaAs; dAs; InaTs; dAs; InaTs; dAs; InaTs; dTs; InaTs; dC-Sup |
| 307 | UTRN-208 m02 | GTGTTAAAATTACTT | UTRN | 3' | human | dGs; InaTs; dGs; InaTs; dTs; InaAs; dAs; InaAs; dAs; InaTs; dTs; InaAs; dCs; InaTs; dT-Sup |
| 308 | UTRN-209 m02 | TTTTTACTGCAATATATT TC | UTRN | 3' | human | dTs; InaTs; dTs; InaTs; dTs; InaAs; dCs; InaTs; dGs; InaCs; dAs; InaAs; dTs; InaAs; dTs; InaAs; dTs; InaTs; dTs; InaC-Sup |
| 309 | UTRN-210 m02 | TTTTTGTGTTAAAATTAC TT | UTRN | 3' | human | dTs; InaTs; dTs; InaTs; dTs; InaGs; dTs; InaGs; dTs; InaTs; dAs; InaAs; dAs; InaAs; dTs; InaTs; dAs; InaCs; dTs; InaT-Sup |
| 310 | UTRN-211 m02 | CCGAGCGCTGTTTTTAC TGCAATAT | UTRN | 5' and 3' | human | dCs; InaCs; dGs; InaAs; dGs; InaCs; dGs; InaCs; dTs; InaGs; dTs; InaTs; dTs; InaTs; dTs; InaAs; dCs; InaTs; dGs; InaCs; dAs; InaAs; dTs; InaAs; dT-Sup |
| 311 | UTRN-212 m02 | TGCCCCTTTGTTTTTACT GCAATAT | UTRN | 5' and 3' | human | dTs; InaGs; dCs; InaCs; dCs; InaCs; dTs; InaTs; dTs; InaGs; dTs; InaTs; dTs; InaTs; dTs; InaAs; dCs; InaTs; dGs; InaCs; dAs; InaAs; dTs; InaAs; dT-Sup |
| 312 | UTRN-213 m02 | AGTCACCTGATTTTTACT GCAATAT | UTRN | 5' and 3' | human | dAs; InaGs; dTs; InaCs; dAs; InaCs; dCs; InaTs; dGs; InaAs; dTs; InaTs; dTs; InaTs; dTs; InaAs; dCs; InaTs; dGs; InaCs; dAs; InaAs; dTs; InaAs; dT-Sup |
| 313 | UTRN-214 m02 | CAATACCTAATTTTTACT GCAATAT | UTRN | 5' and 3' | human | dCs; InaAs; dAs; InaTs; dAs; InaCs; dCs; InaTs; dAs; InaAs; dTs; InaTs; dTs; InaTs; dTs; InaAs; dCs; InaTs; dGs; InaCs; dAs; InaAs; dTs; InaAs; dT-Sup |
| 314 | UTRN-215 m02 | TTACCAAGTCTTTTTACT GCAATAT | UTRN | 5' and 3' | human | dTs; InaTs; dAs; InaCs; dCs; InaAs; dAs; InaGs; dTs; InaCs; dTs; InaTs; dTs; InaTs; dTs; InaAs; dCs; InaTs; dGs; InaCs; dAs; InaAs; dTs; InaAs; dT-Sup |
| 315 | UTRN-216 m02 | CCGAGCGCTGTTTTTGT GTTAAAAT | UTRN | 5' and 3' | human | dCs; InaCs; dGs; InaAs; dGs; InaCs; dGs; InaCs; dTs; InaGs; dTs; InaTs; dTs; InaTs; dTs; InaGs; dTs; InaGs; dTs; InaTs; dAs; InaAs; dAs; InaAs; dT-Sup |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 316 | UTRN-217 m02 | TGCCCCTTTGTTTTTGTG TTAAAAT | UTRN | 5' and 3' | human | dTs; InaGs; dCs; InaCs; dCs; InaCs; dTs; InaTs; dTs; InaGs; dTs; InaTs; dTs; InaTs; dTs; InaGs; dTs; InaGs; dTs; InaTs; dAs; InaAs; dAs; InaAs; dT-Sup |
| 317 | UTRN-218 m02 | AGTCACCTGATTTTTGT GTTAAAAT | UTRN | 5' and 3' | human | dAs; InaGs; dTs; InaCs; dAs; InaCs; dCs; InaTs; dGs; InaAs; dTs; InaTs; dTs; InaTs; dTs; InaGs; dTs; InaGs; dTs; InaTs; dAs; InaAs; dAs; InaAs; dT-Sup |
| 318 | UTRN-219 m02 | CAATACCTAATTTTTGTG TTAAAAT | UTRN | 5' and 3' | human | dCs; InaAs; dAs; InaTs; dAs; InaCs; dCs; InaTs; dAs; InaAs; dTs; InaTs; dTs; InaTs; dTs; InaGs; dTs; InaGs; dTs; InaTs; dAs; InaAs; dAs; InaAs; dT-Sup |
| 319 | UTRN-220 m02 | TTACCAAGTCTTTTGTG TTAAAAT | UTRN | 5' and 3' | human | dTs; InaTs; dAs; InaCs; dCs; InaAs; dAs; InaGs; dTs; InaCs; dTs; InaTs; dTs; InaTs; dTs; InaGs; dTs; InaGs; dTs; InaTs; dAs; InaAs; dAs; InaAs; dT-Sup |
| 320 | HBF-XXX m02 | TGTCTGTAGCTCCAG | HBF | 5' | human | dTs; InaGs; dTs; InaCs; dTs; InaG; dTs; InaA; dGs; InaC; dTs; InaC; dCs; InaA; dGs-Sup |
| 321 | HBF-XXX m02 | TAGCTCCAGTGAGGC | HBF | 5' | human | dTs; InaAs; dGs; InaCs; dTs; InaCs; dCs; InaAs; dGs; InaTs; dGs; InaAs; dGs; InaGs; dC-Sup |
| 322 | HBF-XXX m02 | TTTCTTCTCCCACCA | HBF | 5' | human | dTs; InaTs; dTs; InaCs; dTs; InaTs; dCs; InaTs; dCs; InaCs; dCs; InaAs; dCs; InaCs; dA-Sup |
| 323 | HBF-XXX m02 | TGTCTGTAGCTCCAGC C | HBF | 5' | human | dTs; InaGs; dTs; InaCs; dTs; InaG; dTs; InaA; dGs; InaC; dTs; InaC; dCs; InaA; dGs; InaCs; dC-Sup |
| 324 | HBF-XXX m02 | TAGCTCCAGTGAGGC CC | HBF | 5' | human | dTs; InaAs; dGs; InaCs; dTs; InaCs; dCs; InaAs; dGs; InaTs; dGs; InaAs; dGs; InaGs; dC; InaCs; dC-Sup |
| 325 | HBF-XXX m02 | TTTCTTCTCCCACCAC C | HBF | 5' | human | dTs; InaTs; dTs; InaCs; dTs; InaTs; dCs; InaTs; dCs; InaCs; dCs; InaAs; dCs; InaCs; dA; InaCs; dC-Sup |
| 326 | HBF-XXX m03 | TGTCTGTAGCTCCAG GGAAACCAC | HBF | 5' | human | dTs; InaGs; dTs; InaCs; dTs; InaG; dTs; InaA; dGs; InaC; dTs; InaC; dCs; InaA; dGs; InaGs; dGs; dAs; dAs; dAs; dCs; InaCs; dAs; InaC-Sup |
| 327 | HBF-XXX m04 | TAGCTCCAGTGAGGC GGAAACCAC | HBF | 5' | human | dTs; InaAs; dGs; InaCs; dTs; InaCs; dCs; InaAs; dGs; InaTs; dGs; InaAs; dGs; InaGs; dC; InaGs; dGs; dAs; dAs; dAs; dCs; InaCs; dAs; InaC-Sup |
| 328 | HBF-XXX m05 | TTTCTTCTCCCACCAG GAAACCAC | HBF | 5' | human | dTs; InaTs; dTs; InaCs; dTs; InaTs; dCs; InaTs; dCs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaCs; dCs; InaAs; dCs; InaCs; dA; InaGs; dGs; dAs; dAs; dAs; dCs; InaCs; dAs; InaC-Sup |
| 329 | HBF-XXX m06 | TTTTTGTGTGATCTCT TAGC | HBF | 3' | human | dTs; InaTs; dT; InaTs; dTs; InaGs; dATs; InaGs; dTs; InaGs; dAs; InaTs; dCs; InaTs; dCs; InaTs; dTs; InaAs; dGs; InaC-Sup |
| 330 | HBF-XXX m07 | TTTTTGTGATCTCTTA GCAG | HBF | 3' | human | dTs; InaTs; dT; InaTs; dTs; InaGs; dTs; InaGs; dAs; InaTs; dCs; InaTs; dCs; InaTs; dTs; InaAs; dGs; InaCs; dAs; InaG-Sup |
| 331 | HBF-XXX m08 | TTTTTTGATCTCTTAG CAGA | HBF | 3' | human | dTs; InaTs; dT; InaTs; dTs; InaTs; dGs; InaAs; dTs; InaCs; dTs; InaCs; dTs; InaTs; dAs; InaGs; dCs; InaAs; dGs; InaA-Sup |
| 332 | SMN-XXX m02 | ATTTCTCTCAATCCT | SMN | 5' | human | dAs; InaTs; dT; InaTs; dCs; InaT; dCs; InaT; dCs; InaA; dAs; InaT; dCs; InaC; dTs-Sup |
| 333 | SMN-XXX m03 | GGCGTGTATATTTTT | SMN | 5' | human | dGs; InaGs; dCs; InaGs; dTs; InaGs; dTs; InaAs; dTs; InaAs; dTs; InaTs; dTs; InaTs; dT-Sup |
| 334 | SMN-XXX m04 | GGTTATCGCCCTCCC | SMN | 5' | human | dGs; InaGs; dTs; InaTs; dAs; InaTs; dCs; InaGs; dCs; InaCs; dCs; InaTs; dCs; InaCs; dC-Sup |
| 335 | SMN-XXX m05 | ACGACTTCCGCCGCC | SMN | 5' | human | dAs; InaCs; dGs; InaAs; dCs; InaTs; dTs; InaCs; dCs; InaGs; dCs; InaCs; dGs; InaCs; dC-Sup |
| 336 | SMN-XXX m06 | ATTTCTCTCAATCCTC C | SMN | 5' | human | dAs; InaTs; dT; InaTs; dCs; InaT; dCs; InaT; dCs; InaA; dAs; InaT; dCs; InaC; dTs; InaCs; dC-Sup |
| 337 | SMN-XXX m07 | GGCGTGTATATTTTTC C | SMN | 5' | human | dGs; InaGs; dCs; InaGs; dTs; InaGs; dTs; InaAs; dTs; InaAs; dTs; InaTs; dTs; InaTs; dT; InaCs; dC-Sup |
| 338 | SMN-XXX m08 | GGTTATCGCCCTCCCC C | SMN | 5' | human | dGs; InaGs; dTs; InaTs; dAs; InaTs; dCs; InaGs; dCs; InaCs; dCs; InaTs; dCs; InaCs; dC; InaCs; dC-Sup |
| 339 | SMN-XXX m09 | ACGACTTCCGCCGCCC C | SMN | 5' | human | dAs; InaCs; dGs; InaAs; dCs; InaTs; dTs; InaCs; dCs; InaGs; dCs; InaCs; dGs; InaCs; dC; InaCs; dC-Sup |
| 340 | SMN-XXX m10 | ATTTCTCTCAATCCTG GAAACCAC | SMN | 5' | human | dAs; InaTs; dT; InaTs; dCs; InaT; dCs; InaT; dCs; InaA; dAs; InaT; dCs; InaC; dTs; InaGs; dGs; dAs; dAs; dAs; dCs; InaCs; dAs; InaC-Sup |
| 341 | SMN-XXX m11 | GGCGTGTATATTTTTG GAAACCAC | SMN | 5' | human | dGs; InaGs; dCs; InaGs; dTs; InaGs; dTs; InaAs; dTs; InaTs; dT; InaTs; dTs; InaTs; dT; InaGs; dGs; dAs; |

TABLE 6-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dAs; dAs; dCs; InaCs; dAs; InaC-Sup |
| 342 | SMN-XXX m12 | GGTTATCGCCCTCCCG GAAACCAC | SMN | 5' | human | dGs; InaGs; dTs; InaTs; dAs; InaTs; dCs; InaGs; dCs; InaCs; dCs; InaTs; dCs; InaCs; dC; InaGs; dGs; dAs; dAs; dAs; dCs; InaCs; dAs; InaC-Sup |
| 343 | SMN-XXX m13 | ACGACTTCCGCCGCC GGAAACCAC | SMN | 5' | human | dAs; InaCs; dGs; InaAs; dCs; InaTs; dTs; InaCs; dCs; InaGs; dCs; InaCs; dGs; InaCs; dC; InaGs; dGs; dAs; dAs; dAs; dCs; InaCs; dAs; InaC-Sup |
| 344 | SMN-XXX m14 | TTTTTTAATTTTTTTT AAA | SMN | 3' | human | dTs; InaTs; dTs; InaTs; dTs; InaTs; dAs; InaAs; dTs; InaTs; dTs; InaTs; dTs; InaTs; dTs; InaTs; dTs; dAs; InaA-Sup |
| 345 | SMN-XXX m15 | TTTTTATATGCAAAAA AGAA | SMN | 3' | human | dTs; InaTs; dTs; InaTs; dTs; InaAs; dTs; InaAs; dTs; InaGs; dCs; InaAs; dAs; InaAs; dAs; InaAs; dAs; InaGs; dAs; InaA-Sup |
| 346 | SMN-XXX m16 | TTTTTCAAAATATGGG CCAA | SMN | 3' | human | dTs; InaTs; dTs; InaTs; dTs; InaCs; dAs; InaAs; dAs; InaAs; dTs; InaAs; dTs; InaGs; dGs; InaGs; dCs; InaCs; dAs; InaA-Sup |

Table 7 provides exemplary oligonucleotides for targeting the 5' and 3' ends of noncoding RNAs HOTAIR and ANRIL.

TABLE 7

Oligos targeting non-coding RNAs

| SEQ ID NO | Oligo Name | Base Sequence | Gene Name | Target Region (5' or 3' End) | Organism | Formatted Sequence |
|---|---|---|---|---|---|---|
| 347 | HOTAIR-1 | TTCACCACATGTAAA | HOTAIR | 3' | Human | dTs; InaTs; dCs; InaAs; dCs; InaCs; dAs; InaCs; dAs; InaTs; dGs; InaTs; dAs; InaAs; dA-Sup |
| 348 | HOTAIR-2 | TTTTTTCACCACATGTAA A | HOTAIR | 3' | Human | dTs; InaTs; dTs; InaTs; dTs; InaTs; dCs; InaAs; dCs; InaCs; dAs; InaCs; dAs; InaTs; dGs; InaTs; dAs; InaAs; dA-Sup |
| 349 | HOTAIR-3 | AAATCAGGGCAGAATG T | HOTAIR | 5' | Human | dAs; InaAs; dAs; InaTs; dCs; InaAs; dGs; InaGs; dGs; InaCs; dAs; InaGs; dAs; InaAs; dTs; InaGs; dT-Sup |
| 350 | HOTAIR-4 | AAATCAGGGCAGAATG TCC | HOTAIR | 5' | Human | dAs; InaAs; dAs; InaTs; dCs; InaAs; dGs; InaGs; dGs; InaCs; dAs; InaGs; dAs; InaAs; dTs; InaGs; |

TABLE 7-continued

Oligos targeting non-coding RNAs

| SEQ ID NO | Oligo Name | Base Sequence | Gene Name | Target Region (5' or 3' End) | Organism | Formatted Sequence |
|---|---|---|---|---|---|---|
| | | | | | | dTs; InaCs; dC-Sup |
| 351 | HOTAIR-5 | AAATCAGGGCAGAATGTCCAAAGGTC | HOTAIR | 5' | Human | dAs; InaAs; dAs; InaTs; dCs; InaAs; dGs; InaGs; dGs; InaCs; dAs; InaGs; dAs; InaAs; dTs; InaGs; dTs; InaCs; dCs; InaAs; dAs; InaAs; dGs; InaGs; dTs; dC-Sup |
| 352 | HOTAIR-6 | AAATCAGGGCAGAATGTTTTTTTCACCACATGTAAA | HOTAIR | 5' and 3' | Human | dAs; InaAs; dAs; InaTs; dCs; InaAs; dGs; InaGs; dGs; InaCs; dAs; InaGs; dAs; InaAs; dTs; InaGs; dTs; InaTs; dTs; InaTs; dTs; InaTs; dTs; InaCs; dAs; InaCs; dCs; InaAs; dCs; InaAs; dTs; InaGs; dTs; InaAs; dAs; dA-Sup |
| 353 | ANRIL-1 | TTATTGTCTGAGCCC | ANRIL | 3' | Human | dTs; InaTs; dAs; InaTs; dTs; InaGs; dTs; InaCs; dTs; InaGs; dAs; InaGs; dCs; InaCs; dC-Sup |
| 354 | ANRIL-2 | TTTTTATTGTCTGAGCCC | ANRIL | 3' | Human | dTs; InaTs; dTs; InaTs; dTs; InaAs; dTs; InaTs; dGs; InaTs; dCs; InaTs; dGs; InaAs; dGs; InaCs; dCs; dC-Sup |
| 355 | ANRIL-3 | TCAGGTGACGGATGT | ANRIL | 5' | Human | dTs; InaCs; dAs; InaGs; dGs; InaTs; dGs; InaAs; dCs; InaGs; dGs; InaAs; dTs; InaGs; dT-Sup |
| 356 | ANRIL-4 | TCAGGTGACGGATGTCC | ANRIL | 5' | Human | dTs; InaCs; dAs; InaGs; dGs; InaTs; dGs; InaAs; dCs; InaGs; dGs; InaAs; dTs; InaGs; dTs; InaCs; dC-Sup |
| 357 | ANRIL-5 | TCAGGTGACGGATGTCCAAAGGTC | ANRIL | 5' | Human | dTs; InaCs; dAs; InaGs; dGs; InaTs; dGs; InaAs; dCs; InaGs; dGs; InaAs; dTs; InaGs; dTs; InaCs; dCs; InaAs; dAs; InaAs; dGs; InaGs; dTs; dC-Sup |
| 358 | ANRIL-6 | TCAGGTGACGGATGTTTTTTATTGTCTGAGCCC | ANRIL | 5' and 3' | Human | dTs; InaCs; dAs; InaGs; dGs; InaTs; dGs; InaAs; dCs; InaGs; dGs; InaAs; dTs; InaGs; dTs; InaTs; dTs; InaTs; dTs; InaTs; dAs; InaTs; dTs; InaGs; dTs; InaCs; dTs; InaGs; dAs; InaGs; dCs; InaCs; dC-Sup |

Table 8 provides further exemplary RNA stability oligos for multiple human and mouse genes.

TABLE 8

| SEQ ID NO | Oligo Name | Base Sequence | Gene Name | Target Region | Organism | Formatted Sequence |
|---|---|---|---|---|---|---|
| 359 | FOXP3-61 m02 | TGTGGGGAGCTCGGC | FOXP3 | 3' | human | dTs; InaGs; dTs; InaGs; dGs; InaGs; dGs; InaAs; dGs; InaCs; dTs; InaCs; dGs; InaGs; dC-Sup |
| 360 | FOXP3-62 m02 | GGGGAGCTCGGCTGC | FOXP3 | 3' | human | dGs; InaGs; dGs; InaGs; dAs; InaGs; dCs; InaTs; dCs; InaGs; dGs; InaCs; dTs; InaGs; dC-Sup |
| 361 | FOXP3-63 m02 | TTTTTGTGGGGAGCTCGGC | FOXP3 | 3' | human | dTs; InaTs; dTs; InaTs; dTs; InaGs; dTs; InaGs; dGs; InaGs; dGs; InaAs; dGs; InaCs; dTs; InaCs; dGs; InaGs; dC-Sup |
| 362 | FOXP3-64 m02 | TTTTGGGGAGCTCGGCTGC | FOXP3 | 3' | human | dTs; InaTs; dTs; InaTs; dGs; InaGs; dGs; InaGs; dAs; InaGs; dCs; InaTs; dCs; InaGs; dGs; InaCs; dTs; InaGs; dC-Sup |
| 363 | FOXP3-65 m02 | TTGTCCAAGGGCAGG | FOXP3 | 5' | human | dTs; InaTs; dGs; InaTs; dCs; InaCs; dAs; InaAs; dGs; InaGs; dGs; InaCs; dAs; InaGs; dG-Sup |
| 364 | FOXP3-66 m02 | TCGATGAGTGTGTGC | FOXP3 | 5' | human | dTs; InaCs; dGs; InaAs; dTs; InaGs; dAs; InaGs; dTs; InaGs; dTs; InaGs; dTs; InaGs; dC-Sup |
| 365 | FOXP3-67 m02 | AGAAGAAAACCACG | FOXP3 | 5' | human | dAs; InaGs; dAs; InaAs; dGs; InaAs; dAs; InaAs; dAs; InaAs; dCs; InaCs; dAs; InaCs; dG-Sup |
| 366 | FOXP3-68 m02 | AATATGATTTCTTCC | FOXP3 | 5' | human | dAs; InaAs; dTs; InaAs; dTs; InaGs; dAs; InaTs; dTs; InaTs; dCs; InaTs; dTs; InaCs; dC-Sup |
| 367 | FOXP3-69 m02 | GAGATGGGGACATG | FOXP3 | 5' | human | dGs; InaAs; dGs; InaAs; dTs; InaGs; dGs; InaGs; dGs; InaGs; dAs; InaCs; dAs; InaTs; dG-Sup |
| 368 | PTEN-101 m02 | TTCAGTTTATTCAAG | PTEN | 3' | human | dTs; InaTs; dCs; InaAs; dGs; InaTs; dTs; InaTs; dAs; InaTs; dTs; InaCs; dAs; InaAs; dG-Sup |
| 369 | PTEN-102 m02 | CTGTCTCCACTTTTT | PTEN | 3' | human | dCs; InaTs; dGs; InaTs; dCs; InaTs; dCs; InaCs; dAs; InaCs; dTs; InaTs; dTs; InaTs; dT-Sup |
| 370 | PTEN-103 m02 | TGGAATAAACGGG | PTEN | 3' | human | dTs; InaGs; dGs; InaAs; dAs; InaTs; dAs; InaAs; dAs; InaAs; |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dCs; InaGs; dGs; InaG-Sup |
| 371 | PTEN-104 m02 | ACAATTGAGAAAACA | PTEN | 3' | human | dAs; InaCs; dAs; InaAs; dTs; InaTs; dGs; InaAs; dGs; InaAs; dAs; InaAs; dAs; InaCs; dA-Sup |
| 372 | PTEN-105 m02 | CAGTTTTAAGTGGAG | PTEN | 3' | human | dCs; InaAs; dGs; InaTs; dTs; InaTs; dTs; InaAs; dAs; InaGs; dTs; InaGs; dGs; InaAs; dG-Sup |
| 373 | PTEN-106 m02 | TGACAAGAATGAGAC | PTEN | 3' | human | dTs; InaGs; dAs; InaCs; dAs; InaAs; dGs; InaAs; dAs; InaTs; dGs; InaAs; dGs; InaAs; dC-Sup |
| 374 | PTEN-107 m02 | CCGGGCGAGGGGAGG | PTEN | 5' | human | dCs; InaCs; dGs; InaGs; dGs; InaCs; dGs; InaAs; dGs; InaGs; dGs; InaGs; dAs; InaGs; dG-Sup |
| 375 | PTEN-108 m02 | CCGCCGGCCTGCCCG | PTEN | 5' | human | dCs; InaCs; dGs; InaCs; dCs; InaGs; dGs; InaCs; dCs; InaTs; dGs; InaCs; dCs; InaCs; dG-Sup |
| 376 | PTEN-109 m02 | CGAGCGCGTATCCTG | PTEN | 5' | human | dCs; InaGs; dAs; InaGs; dCs; InaGs; dCs; InaGs; dTs; InaAs; dTs; InaCs; dCs; InaTs; dG-Sup |
| 377 | PTEN-110 m02 | CTGCTTCTCCTCAGC | PTEN | 5' | human | dCs; InaTs; dGs; InaCs; dTs; InaTs; dCs; InaTs; dCs; InaCs; dTs; InaCs; dAs; InaGs; dC-Sup |
| 378 | PTEN-111 m02 | TTTTCAGTTTATTCAAG | PTEN | 3' | human | dTs; InaTs; dTs; InaTs; dCs; InaAs; dGs; InaTs; dTs; InaTs; dAs; InaTs; dTs; InaCs; dAs; InaAs; dG-Sup |
| 379 | PTEN-112 m02 | TTTTCTGTCTCCACTTTTT | PTEN | 3' | human | dTs; InaTs; dTs; InaTs; dCs; InaTs; dGs; InaTs; dCs; InaTs; dCs; InaCs; dAs; InaCs; dTs; InaTs; dTs; InaTs; dT-Sup |
| 380 | PTEN-113 m02 | TTTTTGGAATAAAACGGG | PTEN | 3' | human | dTs; InaTs; dTs; InaTs; dTs; InaGs; dGs; InaAs; dAs; InaTs; dAs; InaAs; dAs; InaAs; dCs; InaGs; dGs; InaG-Sup |
| 381 | PTEN-114 m02 | TTTTACAATTGAGAAAACA | PTEN | 3' | human | dTs; InaTs; dTs; InaTs; dAs; InaCs; dAs; InaAs; dTs; InaTs; dGs; InaAs; dGs; InaAs; dAs; InaAs; dAs; InaCs; dA-Sup |
| 382 | PTEN-115 m02 | TTTTCAGTTTTAAGTGGAG | PTEN | 3' | human | dTs; InaTs; dTs; InaTs; dCs; InaAs; dGs; InaTs; dTs; InaTs; dTs; |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaAs; dAs; InaGs; dTs; InaGs; dGs; InaAs; dG-Sup |
| 383 | PTEN-116 m02 | TTTTTGACAAGAATGAGAC | PTEN | 3' | human | dTs; InaTs; dTs; InaTs; dTs; InaGs; dAs; InaCs; dAs; InaAs; dGs; InaAs; dAs; InaTs; dGs; InaAs; dGs; InaAs; dC-Sup |
| 384 | NFE2L2-01 m02 | AACAGTCATAATAAT | NFE2L2 | 3' | human | dAs; InaAs; dCs; InaAs; dGs; InaTs; dCs; InaAs; dTs; InaAs; dAs; InaTs; dAs; InaAs; dT-Sup |
| 385 | NFE2L2-02 m02 | TAATTTAACAGTCAT | NFE2L2 | 3' | human | dTs; InaAs; dAs; InaTs; dTs; InaTs; dAs; InaAs; dCs; InaAs; dGs; InaTs; dCs; InaAs; dT-Sup |
| 386 | NFE2L2-03 m02 | GCACGCTATAAAGCA | NFE2L2 | 5' | human | dGs; InaCs; dAs; InaCs; dGs; InaCs; dTs; InaAs; dTs; InaAs; dAs; InaAs; dGs; InaCs; dA-Sup |
| 387 | NFE2L2-04 m02 | CCCGGGGCTGGGCTT | NFE2L2 | 5' | human | dCs; InaCs; dCs; InaGs; dGs; InaGs; dGs; InaCs; dTs; InaGs; dGs; InaGs; dCs; InaTs; dT-Sup |
| 388 | NFE2L2-05 m02 | CCCCGCTCCGCCTCC | NFE2L2 | 5' | human | dCs; InaCs; dCs; InaCs; dGs; InaCs; dTs; InaCs; dCs; InaGs; dCs; InaCs; dTs; InaCs; dC-Sup |
| 389 | NFE2L2-06 m02 | GCGCCTCCCTGATTT | NFE2L2 | 5' | human | dGs; InaCs; dGs; InaCs; dCs; InaTs; dCs; InaCs; dCs; InaTs; sdG; InaAs; dTs; InaTs; dT-Sup |
| 390 | NFE2L2-07 m02 | TCGCCGCGGTGGCTG | NFE2L2 | 5' | human | dTs; InaCs; dGs; InaCs; dCs; InaGs; dCs; InaGs; dGs; InaTs; dGs; InaGs; dCs; InaTs; dG-Sup |
| 391 | NFE2L2-08 m02 | CAGCGAATGGTCGCG | NFE2L2 | 5' | human | dCs; InaAs; dGs; InaCs; dGs; InaAs; dAs; InaTs; dGs; InaGs; dTs; InaCs; dGs; InaCs; dG-Sup |
| 392 | NFE2L2-09 m02 | TTTTTAACAGTCATAATAAT | NFE2L2 | 3' | human | dTs; InaTs; dTs; InaTs; dTs; InaAs; dAs; InaCs; dAs; InaGs; dTs; InaCs; dAs; InaTs; dAs; InaAs; dTs; InaAs; dAs; InaT-Sup |
| 393 | NFE2L2-10 m02 | TTTTTAATTTAACAGTCAT | NFE2L2 | 3' | human | dTs; InaTs; dTs; InaTs; dTs; InaAs; dAs; InaTs; dTs; InaTs; dAs; InaAs; dCs; InaAs; dGs; InaTs; dCs; InaAs; dT-Sup |
| 394 | ATP2A2-56 m02 | GCGGCGGCTGCTCTA | ATP2A2 | 5' | human | dGs; InaCs; dGs; InaGs; dCs; InaGs; dGs; |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaCs; dTs; InaGs; dCs; InaTs; dCs; InaTs; dA-Sup |
| 395 | ATP2A2-34 m02 | TTATCGGCCGCTGCC | ATP2A2 | 5' | human | dTs; InaTs; dAs; InaTs; dCs; InaGs; dGs; InaCs; dCs; InaGs; dCs; InaTs; dGs; InaCs; dC-Sup |
| 396 | ATP2A2-57 m02 | GCGTCGGGGACGGCT | ATP2A2 | 5' | human | dGs; InaCs; dGs; InaTs; dCs; InaGs; dGs; InaGs; dGs; InaAs; dCs; InaGs; dGs; InaCs; dT-Sup |
| 397 | ATP2A2-58 m02 | GCGGAGGAAACTGCG | ATP2A2 | 5' | human | dGs; InaCs; dGs; InaGs; dAs; InaGs; dGs; InaAs; dAs; InaAs; dCs; InaTs; dGs; InaCs; dG-Sup |
| 398 | ATP2A2-59 m02 | GCCGCACGCCCGACA | ATP2A2 | 5' | human | dGs; InaCs; dCs; InaGs; dCs; InaAs; dCs; InaGs; dCs; InaCs; dCs; InaGs; dAs; InaCs; dA-Sup |
| 399 | ATP2A2-60 m02 | CCTGACCCACCCTCC | ATP2A2 | 5' | human | dCs; InaCs; dTs; InaGs; dAs; InaCs; dCs; InaCs; dAs; InaCs; dCs; InaCs; dTs; InaCs; dC-Sup |
| 400 | ATP2A2-61 m02 | AGGGCAGGCCGCGGC | ATP2A2 | 5' | human | dAs; InaGs; dGs; InaGs; dCs; InaAs; dGs; InaGs; dCs; InaCs; dGs; InaCs; dGs; InaGs; dC-Sup |
| 401 | ATP2A2-62 m02 | CTGAATCACCCCGCG | ATP2A2 | 5' | human | dCs; InaTs; dGs; InaAs; dAs; InaTs; dCs; InaAs; dCs; InaCs; dCs; InaCs; dGs; InaCs; dG-Sup |
| 402 | ATP2A2-63 m02 | GGCCCCGAGCTCCGC | ATP2A2 | 5' | human | dGs; InaGs; dCs; InaCs; dCs; InaCs; dGs; InaAs; dGs; InaCs; dTs; InaCs; dCs; InaGs; dC-Sup |
| 403 | ATP2A2-64 m02 | GCGGCTGCTCTAATA | ATP2A2 | 5' | human | dGs; InaCs; dGs; InaGs; dCs; InaTs; dGs; InaCs; dTs; InaCs; dTs; InaAs; dAs; InaTs; dA-Sup |
| 404 | ATP2A2-65 m02 | CGCCGCGGCATGTGG | ATP2A2 | 5' | human | dCs; InaGs; dCs; InaCs; dGs; InaCs; dGs; InaGs; dCs; InaAs; dTs; InaGs; dTs; InaGs; dG-Sup |
| 405 | ATP2A2-66 m02 | CCCTCCTCCTCTTGC | ATP2A2 | 5' | human | dCs; InaCs; dCs; InaTs; dCs; InaCs; dTs; InaCs; dCs; InaTs; dCs; InaTs; dTs; InaGs; dC-Sup |
| 406 | ATP2A2-67 m02 | GGCCGCGGGCTCGTG | ATP2A2 | 5' | human | dGs; InaCs; dCs; InaCs; dGs; InaCs; dGs; InaGs; dGs; InaCs; dTs; InaCs; dGs; InaTs; dG-Sup |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 407 | ATP2A2-68 m02 | GTTATTTTTCTCTGT | ATP2A2 | 3' | human | dGs; InaTs; dTs; InaAs; dTs; InaTs; dTs; InaTs; dTs; InaCs; dTs; InaCs; dTs; InaGs; dT-Sup |
| 408 | ATP2A2-69 m02 | ATTTAAAATGTTTTA | ATP2A2 | 3' | human | dAs; InaTs; dTs; InaTs; dAs; InaAs; dAs; InaAs; dTs; InaGs; dTs; InaTs; dTs; InaTs; dA-Sup |
| 409 | ATP2A2-70 m02 | TCTCTGTCCATTTAA | ATP2A2 | 3' | human | dTs; InaCs; dTs; InaCs; dTs; InaGs; dTs; InaCs; dCs; InaAs; dTs; InaTs; dTs; InaAs; dA-Sup |
| 410 | ATP2A2-71 m02 | TCATTTGGTCATGTG | ATP2A2 | 3' | human | dTs; InaCs; dAs; InaTs; dTs; InaTs; dGs; InaGs; dTs; InaCs; dAs; InaTs; dGs; InaTs; dG-Sup |
| 411 | ATP2A2-72 m02 | TAGTTCTCTGTACAT | ATP2A2 | 3' | human | dTs; InaAs; dGs; InaTs; dTs; InaCs; dTs; InaCs; dTs; InaGs; dTs; InaAs; dCs; InaAs; dT-Sup |
| 412 | ATP2A2-73 m02 | TCTGCTGGCTCAACT | ATP2A2 | 3' | human | dTs; InaCs; dTs; InaGs; dCs; InaTs; dGs; InaGs; dCs; InaTs; dCs; InaAs; dAs; InaCs; dT-Sup |
| 413 | ATP2A2-74 m02 | ATCATAGAATAGATT | ATP2A2 | 3' | human | dAs; InaTs; dCs; InaAs; dTs; InaAs; dGs; InaAs; dAs; InaTs; dAs; InaGs; dAs; InaTs; dT-Sup |
| 414 | ATP2A2-75 m02 | TTATCATAGAATAGA | ATP2A2 | 3' | human | dTs; InaTs; dAs; InaTs; dCs; InaAs; dTs; InaAs; dGs; InaAs; dAs; InaTs; dAs; InaGs; dA-Sup |
| 415 | ATP2A2-76 m02 | AATTGACATTTAGCA | ATP2A2 | 3' | human | dAs; InaAs; dTs; InaTs; dGs; InaAs; dCs; InaAs; dTs; InaTs; dTs; InaAs; dGs; InaCs; dA-Sup |
| 416 | ATP2A2-77 m02 | GACATTTAGCATTTT | ATP2A2 | 3' | human | dGs; InaAs; dCs; InaAs; dTs; InaTs; dTs; InaAs; dGs; InaCs; dAs; InaTs; dTs; InaTs; dT-Sup |
| 417 | ATP2A2-78 m02 | TTAACCATTCAACAC | ATP2A2 | 3' | human | dTs; InaTs; dAs; InaAs; dCs; InaCs; dAs; InaTs; dTs; InaCs; dAs; InaAs; dCs; InaAs; dC-Sup |
| 418 | mKLF4-01 m02 | CTTGGCCGGGGAACT | KLF4 | 5' | mouse | dCs; InaTs; dTs; InaGs; dGs; InaCs; dCs; InaGs; dGs; InaGs; dGs; InaAs; dAs; InaCs; dT-Sup |
| 419 | mKLF4-02 m02 | GCCGGGGAACTGCCG | KLF4 | 5' | mouse | dGs; InaCs; dCs; InaGs; dGs; InaGs; dGs; |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaAs; dAs; InaCs; dTs; InaGs; dCs; InaCs; dG-Sup |
| 420 | mKLF4-03 m02 | CGCCCGGAGCCGCGC | KLF4 | 5' | mouse | dCs; InaGs; dCs; InaCs; dCs; InaGs; dGs; InaAs; dGs; InaCs; dCs; InaGs; dCs; InaGs; dC-Sup |
| 421 | mKLF4-04 m02 | CTTGGCCGGGGAACTCC | KLF4 | 5' | mouse | dCs; InaTs; dTs; InaGs; dGs; InaCs; dCs; InaGs; dGs; InaGs; dGs; InaAs; dAs; InaCs; dTs; InaCs; dC-Sup |
| 422 | mKLF4-05 m02 | GCCGGGGAACTGCCGC | KLF4 | 5' | mouse | dGs; InaCs; dCs; InaGs; dGs; InaGs; dGs; InaAs; dAs; InaCs; dTs; InaGs; dCs; InaCs; dGs; InaC-Sup |
| 423 | mKLF4-06 m02 | CGCCCGGAGCCGCGCC | KLF4 | 5' | mouse | dCs; InaGs; dCs; InaCs; dCs; InaGs; dGs; InaAs; dGs; InaCs; dCs; InaGs; dCs; InaGs; dCs; InaC-Sup |
| 424 | mKLF4-07 m02 | CTTGGCCGGGGAACTATAAAATTC | KLF4 | 5' and 3' | mouse | dCs; InaTs; dTs; InaGs; dGs; InaCs; dCs; InaGs; dGs; InaGs; dGs; InaAs; dAs; InaCs; dTs; InaAs; dTs; dAs; dAs; dAs; InaTs; dTs; InaC-Sup |
| 425 | mKLF4-08 m02 | CTTGGCCGGGGAACTTTTTGTCGTTCAGATAAAA | KLF4 | 5' and 3' | mouse | dCs; InaTs; dTs; InaGs; dGs; InaCs; dCs; InaGs; dGs; InaGs; dGs; InaAs; dAs; InaCs; dTs; InaTs; dTs; InaTs; dTs; InaGs; dTs; InaCs; dGs; InaTs; dTs; InaCs; dAs; InaGs; dAs; InaTs; dAs; InaAs; dAs; InaA-Sup |
| 426 | mKLF4-09 m02 | CTTGGCCGGGGAACTTTTTCAGATAAATATT | KLF4 | 5' and 3' | mouse | dCs; InaTs; dTs; InaGs; dGs; InaCs; dCs; InaGs; dGs; InaGs; dGs; InaAs; dAs; InaCs; dTs; InaTs; dTs; InaTs; dTs; InaCs; dAs; InaGs; dAs; InaTs; dAs; InaAs; dAs; InaAs; dTs; InaAs; dTs; InaT-Sup |
| 427 | mKLF4-10 m02 | CTTGGCCGGGGAACTGTCGTTCAGATAAAA | KLF4 | 5' and 3' | mouse | dCs; InaTs; dTs; InaGs; dGs; InaCs; dCs; InaGs; dGs; InaGs; dGs; InaAs; dAs; InaCs; dTs; InaGs; dTs; InaCs; dGs; InaTs; dTs; InaCs; dAs; InaGs; dAs; InaTs; dAs; InaAs; dAs; InaA-Sup |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 428 | mKLF4-11 m02 | CTTGGCCGGGGAAC TTTCAGATAAAATAT T | KLF4 | 5' and 3' | mouse | dCs; InaTs; dTs; InaGs; dGs; InaCs; dCs; InaGs; dGs; InaGs; dGs; InaAs; dAs; InaCs; dTs; InaTs; dTs; InaCs; dAs; InaGs; dAs; InaTs; dAs; InaAs; dAs; InaAs; dTs; InaAs; dTs; InaT-Sup |
| 429 | mKLF4-12 m02 | CCGGGGAACTTTTTG TCGTTCAGA | KLF4 | 5' and 3' | mouse | dCs; InaCs; dGs; InaGs; dGs; InaGs; dAs; InaAs; dCs; InaTs; dTs; InaTs; dTs; InaTs; dGs; InaTs; dCs; InaGs; dTs; InaTs; dCs; InaAs; dGs; InaA-Sup |
| 430 | mKLF4-13 m02 | CGGGGAACTTTTTCA GATAAA | KLF4 | 5' and 3' | mouse | dCs; InaGs; dGs; InaGs; dGs; InaAs; dAs; InaCs; dTs; InaTs; dTs; InaTs; dTs; InaCs; dAs; InaGs; dAs; InaTs; dAs; InaAs; dA-Sup |
| 431 | mKLF4-14 m02 | CGGGGAACTGTCGTT CAGA | KLF4 | 5' and 3' | mouse | dCs; InaGs; dGs; InaGs; dGs; InaAs; dAs; InaCs; dTs; InaGs; dTs; InaCs; dGs; InaTs; dTs; InaCs; dAs; InaGs; dA-Sup |
| 432 | mKLF4-15 m02 | CCGGGGAACTTTCAG ATAAA | KLF4 | 5' and 3' | mouse | dCs; InaCs; dGs; InaGs; dGs; InaGs; dAs; InaAs; dCs; InaTs; dTs; InaTs; dCs; InaAs; dGs; InaAs; dTs; InaAs; dAs; InaA-Sup |
| 433 | mKLF4-16 m02 | GTCGTTCAGATAAAA | KLF4 | 3' | mouse | dGs; InaTs; dCs; InaGs; dTs; InaTs; dCs; InaAs; dGs; InaAs; dTs; InaAs; dAs; InaAs; dA-Sup |
| 434 | mKLF4-17 m02 | TTCAGATAAAATATT | KLF4 | 3' | mouse | dTs; InaTs; dCs; InaAs; dGs; InaAs; dTs; InaAs; dAs; InaAs; dAs; InaTs; dAs; InaTs; dT-Sup |
| 435 | mKLF4-18 m02 | TTTTTGTCGTTCAGAT AAAA | KLF4 | 3' | mouse | dTs; InaTs; dTs; InaTs; dTs; InaGs; dTs; InaCs; dGs; InaTs; dTs; InaCs; dAs; InaGs; dAs; InaTs; dAs; InaAs; dAs; InaA-Sup |
| 436 | mKLF4-19 m02 | TTTTTCAGATAAAAT ATT | KLF4 | 3' | mouse | dTs; InaTs; dTs; InaTs; dTs; InaCs; dAs; InaGs; dAs; InaTs; dAs; InaAs; dAs; InaAs; dTs; InaAs; dTs; InaT-Sup |
| 437 | mFXN-01 m02 | CTCCGCGGCCGCTCC | FXN | 5' | mouse | dCs; InaTs; dCs; InaCs; dGs; InaCs; dGs; InaGs; dCs; InaCs; |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dGs; InaCs; dTs; InaCs; dC-Sup |
| 438 | mFXN-02 m02 | GCCCACATGCTACTC | FXN | 5' | mouse | dGs; InaCs; dCs; InaCs; dAs; InaCs; dAs; InaTs; dGs; InaCs; dTs; InaAs; dCs; InaTs; dC-Sup |
| 439 | mFXN-03 m02 | TCCGAACGCCCACAT | FXN | 5' | mouse | dTs; InaCs; dCs; InaGs; dAs; InaAs; dCs; InaGs; dCs; InaCs; dCs; InaAs; dCs; InaAs; dT-Sup |
| 440 | mFXN-04 m02 | CGAGGACTCGGTGGT | FXN | 5' | mouse | dCs; InaCs; dAs; InaGs; dGs; InaAs; dCs; InaTs; dCs; InaGs; dGs; InaTs; dGs; InaGs; dT-Sup |
| 441 | mFXN-05 m02 | CCAGCTCCGCGGCCG | FXN | 5' | mouse | dCs; InaCs; dAs; InaGs; dCs; InaTs; dCs; InaCs; dGs; InaCs; dGs; InaGs; dCs; InaCs; dG-Sup |
| 442 | mFXN-06 m02 | CTCCGCGGCCGCTCCC | FXN | 5' | mouse | dCs; InaTs; dCs; InaCs; dGs; InaCs; dGs; InaGs; dCs; InaCs; dGs; InaCs; dTs; InaCs; dCs; InaC-Sup |
| 443 | mFXN-07 m02 | GCCCACATGCTACTCC | FXN | 5' | mouse | dGs; InaCs; dCs; InaCs; dAs; InaCs; dAs; InaTs; dGs; InaCs; dTs; InaAs; dCs; InaTs; dCs; InaC-Sup |
| 444 | mFXN-08 m02 | CTCCGCGGCCGCTCCTCAAAGATC | FXN | 5' | mouse | dCs; InaTs; dCs; InaCs; dGs; InaCs; dGs; InaGs; dCs; InaCs; dGs; InaCs; dTs; InaCs; dCs; InaTs; dCs; dAs; dAs; dAs; dGs; InaAs; dTs; InaC-Sup |
| 445 | mFXN-09 m02 | GCCCACATGCTACTCCCAAAGGTC | FXN | 5' | mouse | dGs; InaCs; dCs; InaCs; dAs; InaCs; dAs; InaTs; dGs; InaCs; dTs; InaAs; dCs; InaTs; dCs; InaCs; dCs; dAs; dAs; dAs; dGs; InaGs; dTs; InaC-Sup |
| 446 | mFXN-10 m02 | CTCCGCGGCCGCTCCTTTTTGGGAGGGAACACACT | FXN | 5' and 3' | mouse | dCs; InaTs; dCs; InaCs; dGs; InaCs; dGs; InaGs; dCs; InaCs; dGs; InaCs; dTs; InaCs; dCs; InaTs; dTs; InaTs; dTs; InaGs; dGs; InaAs; dGs; InaGs; dGs; InaAs; dAs; InaCs; dAs; InaCs; dT-Sup |
| 447 | mFXN-11 m02 | GCCCACATGCTACTCTTTTTGGGAGGGAACACACT | FXN | 5' and 3' | mouse | dGs; InaCs; dCs; InaCs; dAs; InaCs; dAs; InaTs; dGs; |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaCs; dTs; InaAs; dCs; InaTs; dCs; InaTs; dTs; InaTs; dTs; InaTs; dGs; InaGs; dGs; InaAs; dGs; InaGs; dGs; InaAs; dAs; InaCs; dAs; InaCs; dAs; InaCs; dT-Sup |
| 448 | mFXN-12 m02 | CTCCGCGGCCGCTCCGGGAGGGAACACACT | FXN | 5' and 3' | mouse | dCs; InaTs; dCs; InaCs; dGs; InaCs; dGs; InaGs; dCs; InaCs; dGs; InaCs; dTs; InaCs; dCs; InaGs; dGs; InaGs; dAs; InaGs; dGs; InaGs; dAs; InaAs; dCs; InaAs; dCs; InaAs; dCs; InaT-Sup |
| 449 | mFXN-13 m02 | GCCCACATGCTACTCGGGAGGGAACACACT | FXN | 5' and 3' | mouse | dGs; InaCs; dCs; InaCs; dAs; InaCs; dAs; InaTs; dGs; InaCs; dTs; InaAs; dCs; InaTs; dCs; InaGs; dGs; InaGs; dAs; InaGs; dGs; InaGs; dAs; InaAs; dCs; InaAs; dCs; InaAs; dCs; InaT-Sup |
| 450 | mFXN-14 m02 | CGGCCGCTCCGGGAGGGAAC | FXN | 5' and 3' | mouse | dCs; InaGs; dGs; InaCs; dCs; InaGs; dCs; InaTs; dCs; InaCs; dGs; InaGs; dGs; InaAs; dGs; InaGs; dGs; InaAs; dAs; InaC-Sup |
| 451 | mFXN-15 m02 | CATGCTACTCGGGAGGGAAC | FXN | 5' and 3' | mouse | dCs; InaAs; dTs; InaGs; dCs; InaTs; dAs; InaCs; dTs; InaCs; dGs; InaGs; dGs; InaAs; dGs; InaGs; dGs; InaAs; dAs; InaC-Sup |
| 452 | mFXN-16 m02 | GGGAGGGAACACACT | FXN | 3' | mouse | dGs; InaGs; dGs; InaAs; dGs; InaGs; dGs; InaAs; dAs; InaCs; dAs; InaCs; dAs; InaCs; dT-Sup |
| 453 | mFXN-17 m02 | GGGGTCTTCACCTGA | FXN | 3' | mouse | dGs; InaGs; dGs; InaGs; dTs; InaCs; dTs; InaTs; dCs; InaAs; dCs; InaCs; dTs; InaGs; dA-Sup |
| 454 | mFXN-18 m02 | GGCTGTTATATCATG | FXN | 3' | mouse | dGs; InaGs; dCs; InaTs; dGs; InaTs; dTs; InaAs; dTs; InaAs; dTs; InaCs; dAs; InaTs; dG-Sup |
| 455 | mFXN-19 m02 | GGCATTTTAAGATGG | FXN | 3' | mouse | dGs; InaGs; dCs; InaAs; dTs; InaTs; dTs; InaTs; dAs; InaAs; InaAs; dTs; InaGs; dG-Sup |
| 456 | mFXN-20 m02 | TTTTTGGGAGGGAACACACT | FXN | 3' | mouse | dTs; InaTs; dTs; InaTs; dTs; InaGs; dGs; InaGs; dAs; InaGs; dGs; InaGs; Ads; InaAs; dCs; InaCs; dAs; InaCs; dCs; InaT-Sup |

TABLE 8-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 457 | mFXN-21 m02 | TTTTTGGCTGTTATATCATG | FXN | 3' | mouse | dTs; InaTs; dTs; InaTs; dTs; InaGs; dGs; InaCs; dTs; InaGs; dTs; InaTs; dAs; InaTs; dAs; InaTs; dCs; InaAs; dTs; InaG-Sup |

Table 9 provides further exemplary RNA 5' and 3' end targeting oligos for multiple human and mouse genes.

TABLE 9

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 459 | FXN-654 m02 | TGTCTCATTTGGAGA | FXN | 3' | human | dTs; InaGs; dTs; InaCs; dTs; InaCs; dAs; InaTs; dTs; InaTs; dGs; InaGs; dAs; InaGs; dA-Sup |
| 460 | FXN-655 m02 | ATAATGAAGCTGGG | FXN | 3' | human | dAs; InaTs; dAs; InaAs; dTs; InaGs; dAs; InaAs; dGs; InaCs; dTs; InaGs; dGs; InaG-Sup |
| 461 | FXN-656 m02 | TTTTCCCTCCTGGAA | FXN | 3' | human | dTs; InaTs; dTs; InaTs; dCs; InaCs; dCs; InaTs; dCs; InaCs; dTs; InaGs; dGs; InaAs; dA-Sup |
| 462 | FXN-657 m02 | TGCATAATGAAGCTG | FXN | 3' | human | dTs; InaGs; dCs; InaAs; dTs; InaAs; dAs; InaTs; dGs; InaAs; dAs; InaGs; dCs; InaTs; dG-Sup |
| 463 | FXN-658 m02 | AAATCCTTCAAAGAA | FXN | 3' | human | dAs; InaAs; dAs; InaTs; dCs; InaCs; dTs; InaTs; dCs; InaAs; dAs; InaAs; dGs; InaAs; dA-Sup |
| 464 | FXN-659 m02 | TTGGAAGATTTTTTG | FXN | 3' | human | dTs; InaTs; dGs; InaGs; dAs; InaAs; dGs; InaAs; dTs; InaTs; dTs; InaTs; dTs; InaTs; dG-Sup |
| 465 | FXN-660 m02 | GCATTCTTGTAGCAG | FXN | 3' | human | dGs; InaCs; dAs; InaTs; dTs; InaCs; dTs; InaTs; dGs; InaTs; dAs; InaGs; dCs; InaAs; dG-Sup |
| 466 | FXN-557 m02 | ACAACAAAAACAGA | FXN | 3' | human | dAs; InaCs; dAs; InaAs; dCs; InaAs; dAs; InaAs; dAs; InaAs; dAs; InaCs; dAs; InaGs; dA-Sup |
| 467 | FXN-662 m02 | TGAAGCTGGGGTCTT | FXN | 3' | human | dTs; InaGs; dAs; InaAs; dGs; InaCs; dTs; InaGs; dGs; InaGs; dGs; InaTs; dCs; InaTs; dT-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 468 | FXN-663 m02 | CCTGAAAACATTTGT | FXN | 3' | human | dCs; InaCs; dTs; InaGs; dAs; InaAs; dAs; InaAs; dCs; InaAs; dTs; InaTs; dTs; InaGs; dT-Sup |
| 469 | FXN-664 m02 | TTCATTTTCCCTCCT | FXN | 3' | human | dTs; InaTs; dCs; InaAs; dTs; InaTs; dTs; InaTs; dCs; InaCs; dCs; InaTs; dCs; InaCs; dT-Sup |
| 470 | FXN-665 m02 | TTATTATTATTATAT | FXN | 3' | human | dTs; InaTs; dAs; InaTs; dTs; InaAs; dTs; InaTs; dAs; InaTs; dTs; InaAs; dTs; InaAs; dT-Sup |
| 471 | FXN-666 m02 | TAACTTTGCATGAAT | FXN | 3' | human | dTs; InaAs; dAs; InaCs; dTs; InaTs; dTs; InaGs; dCs; InaAs; dTs; InaGs; dAs; InaAs; dT-Sup |
| 472 | FXN-667 m02 | ATACAAACATGTATG | FXN | 3' | human | dAs; InaTs; dAs; InaCs; dAs; InaAs; dAs; InaCs; dAs; InaTs; dGs; InaTs; dAs; InaTs; dG-Sup |
| 473 | FXN-668 m02 | ATTGTAAACCTATAA | FXN | 3' | human | dAs; InaTs; dTs; InaGs; dTs; InaAs; dAs; InaAs; dCs; InaCs; dTs; InaAs; dTs; InaAs; dA-Sup |
| 474 | FXN-669 m02 | TGGAGTTGGGGTTAT | FXN | 3' | human | dTs; InaGs; dGs; InaAs; dGs; InaTs; dTs; InaGs; dGs; InaGs; dGs; InaTs; dTs; InaAs; dT-Sup |
| 475 | FXN-670 m02 | GTTGGGGTTATTTAG | FXN | 3' | human | dGs; InaTs; dTs; InaGs; dGs; InaGs; dGs; InaTs; dTs; InaAs; dTs; InaTs; dTs; InaAs; dG-Sup |
| 476 | FXN-671 m02 | CTCCGCCCTCCAG | FXN | 5' | human | dCs; InaTs; dCs; InaCs; dGs; InaCs; dCs; InaCs; dTs; InaCs; dCs; InaAs; dG-Sup |
| 477 | FXN-672 m02 | CCGCCCTCCAG | FXN | 5' | human | dCs; InaCs; dGs; InaCs; dCs; InaCs; dTs; InaCs; dCs; InaAs; dG-Sup |
| 478 | FXN-673 m02 | GCCCTCCAG | FXN | 5' | human | dGs; InaCs; dCs; InaCs; dTs; InaCs; dCs; InaAs; dG-Sup |
| 479 | FXN-674 m02 | CCCGCTCCGCCCTCC | FXN | 5' | human | dCs; InaCs; dCs; InaGs; dCs; InaTs; dCs; InaCs; dGs; InaCs; dCs; InaCs; dTs; InaCs; dC-Sup |
| 480 | FXN-675 m02 | CGCTCCGCCCTCC | FXN | 5' | human | dCs; InaGs; dCs; InaTs; dCs; InaCs; dGs; InaCs; dCs; InaCs; dTs; InaCs; dC-Sup |
| 481 | FXN-676 m02 | CTCCGCCCTCC | FXN | 5' | human | dCs; InaTs; dCs; InaCs; dGs; InaCs; dCs; InaCs; dTs; InaCs; dC-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 482 | FXN-677 m02 | CCGCCCTCC | FXN | 5' | human | dCs; InaCs; dGs; InaCs; dCs; InaCs; dTs; InaCs; dC-Sup |
| 483 | FXN-678 m02 | GCCACTGGCCGCA | FXN | 5' | human | dGs; InaCs; dCs; InaAs; dCs; InaTs; dGs; InaGs; dCs; InaCs; dGs; InaCs; dA-Sup |
| 484 | FXN-679 m02 | CACTGGCCGCA | FXN | 5' | human | dCs; InaAs; dCs; InaTs; dGs; InaGs; dCs; InaCs; dGs; InaCs; dA-Sup |
| 485 | FXN-680 m02 | GCGACCCCTGGTG | FXN | 5' | human | dGs; InaCs; dGs; InaAs; dCs; InaCs; dCs; InaCs; dTs; InaGs; dGs; InaTs; dG-Sup |
| 486 | FXN-681 m02 | GACCCCTGGTG | FXN | 5' | human | dGs; InaAs; dCs; InaCs; dCs; InaCs; dTs; InaGs; dGs; InaTs; dG-Sup |
| 487 | FXN-682 m02 | CTGGCCGCAGGCA | FXN | 5' | human | dCs; InaTs; dGs; InaGs; dCs; InaCs; dGs; InaCs; dAs; InaGs; dGs; InaCs; dA-Sup |
| 488 | FXN-683 m02 | GGCCACTGGCCGC | FXN | 5' | human | dGs; InaGs; dCs; InaCs; dAs; InaCs; dTs; InaGs; dGs; InaCs; dCs; InaGs; dC-Sup |
| 489 | FXN-684 m02 | CTGGTGGCCACTG | FXN | 5' | human | dCs; InaTs; dGs; InaGs; dTs; InaGs; dGs; InaCs; dCs; InaAs; dCs; InaTs; dG-Sup |
| 490 | FXN-685 m02 | GACCCCTGGTGGC | FXN | 5' | human | dGs; InaAs; dCs; InaCs; dCs; InaCs; dTs; InaGs; dGs; InaTs; dGs; InaGs; dC-Sup |
| 491 | FXN-686 m02 | GCGGCGACCCCTG | FXN | 5' | human | dGs; InaCs; dGs; InaGs; dCs; InaGs; dAs; InaCs; dCs; InaCs; dCs; InaTs; dG-Sup |
| 492 | FXN-687 m02 | GTGCTGCGGCGAC | FXN | 5' | human | dGs; InaTs; dGs; InaCs; dTs; InaGs; dCs; InaGs; dGs; InaCs; dGs; InaAs; dC-Sup |
| 493 | FXN-688 m02 | GCTGGGTGCTGCG | FXN | 5' | human | dGs; InaCs; dTs; InaGs; dGs; InaGs; dTs; InaGs; dCs; InaTs; dGs; InaCs; dG-Sup |
| 494 | FXN-689 m02 | CCAGCGCTGGGTG | FXN | 5' | human | dCs; InaCs; dAs; InaGs; dCs; InaGs; dCs; InaTs; dGs; InaGs; dGs; InaTs; dG-Sup |
| 495 | FXN-690 m02 | GCCCTCCAGCGCT | FXN | 5' | human | dGs; InaCs; dCs; InaCs; dTs; InaCs; dCs; InaAs; dGs; InaCs; dGs; InaCs; dT-Sup |
| 496 | FXN-691 m02 | CGCCCGCTCCGCC | FXN | 5' | human | dCs; InaGs; dCs; InaCs; dCs; InaGs; dCs; InaTs; dCs; InaCs; dGs; InaCs; dC-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 497 | FXN-460 m1000 | CGCCCTCCAGCGCTGTT TTTATTATTTTGCTTTTT | FXN | 5' and 3' | human | dCs; InaGs; dCs; InaCs; dCs; InaTs; dCs; InaCs; dAs; InaGs; dCs; InaGs; dCs; InaTs; dGs; dT; dT; dT; dT; dT; dAs; InaTs; dTs; InaAs; dTs; InaTs; dTs; InaTs; dGs; InaCs; dTs; InaTs; dTs; InaTs; dT-Sup |
| 498 | FXN-461 m1000 | CGCTCCGCCCTCCAGTTT TTATTATTTTGCTTTTT | FXN | 5' and 3' | human | dCs; InaGs; dCs; InaTs; dCs; InaCs; dGs; InaCs; dCs; InaCs; dTs; InaCs; dCs; InaAs; dGs; dT; dT; dT; dT; dT; dAs; InaTs; dTs; InaAs; dTs; InaTs; dTs; InaTs; dGs; InaCs; dTs; InaTs; dTs; InaTs; dT-Sup |
| 499 | FXN-523 m01 | CAAGTCCAGTTTGGTTT | FXN | 3' | human | InaCs; omeAs; InaAs; omeGs; InaTs; omeCs; InaCs; omeAs; InaGs; omeUs; InaTs; omeUs; InaGs; omeGs; InaTs; omeUs; InaT-Sup |
| 500 | FXN-524 m01 | GAATAGGCCAAGGAAGA | FXN | 3' | human | InaGs; omeAs; InaAs; omeUs; InaAs; omeGs; InaGs; omeCs; InaCs; omeAs; InaAs; omeGs; InaGs; omeAs; InaAs; omeGs; InaA-Sup |
| 501 | FXN-525 m01 | ATCAAGCATCTTTTCCG | FXN | 3' | human | InaAs; omeUs; InaCs; omeAs; InaAs; omeGs; InaCs; omeAs; InaTs; omeCs; InaTs; omeUs; InaTs; omeUs; InaCs; omeCs; InaG-Sup |
| 502 | FXN-526 m01 | TTAAAACGGGGCTGGGC | FXN | 3' | human | InaTs; omeUs; InaAs; omeAs; InaAs; omeAs; InaCs; omeGs; InaGs; deaGs; InaGs; omeCs; InaTs; omeGs; InaGs; omeGs; InaC-Sup |
| 503 | FXN-527 m01 | GATAGCTTTTAATGTCC | FXN | 3' | human | InaGs; omeAs; InaTs; omeAs; InaGs; omeCs; InaTs; omeUs; InaTs; omeUs; InaAs; omeAs; InaTs; omeGs; InaTs; omeCs; InaC-Sup |
| 504 | FXN-528 m01 | AGCTGGGGTCTTGGCCT | FXN | 3' | human | InaAs; omeGs; InaCs; omeUs; InaGs; deaGs; InaGs; omeGs; InaTs; omeCs; InaTs; omeUs; InaGs; omeGs; InaCs; omeCs; InaT-Sup |
| 505 | FXN-529 m01 | CCTCAGCTGCATAATGA | FXN | 3' | human | InaCs; omeCs; InaTs; omeCs; InaAs; omeGs; InaCs; omeUs; InaGs; omeCs; InaAs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | omeUs; InaAs; omeAs; InaTs; omeGs; InaA-Sup |
| 506 | FXN-530 m01 | CAACAACAAAAAACAGA | FXN | 3' | human | InaCs; omeAs; InaAs; omeCs; InaAs; omeAs; InaCs; omeAs; InaAs; omeAs; InaAs; omeAs; InaAs; omeCs; InaAs; omeGs; InaA-Sup |
| 507 | FXN-531 m01 | AAAAAATAAACAACAA | FXN | 3' | human | InaAs; omeAs; InaAs; omeAs; InaAs; omeAs; InaAs; omeUs; InaAs; omeAs; InaAs; omeCs; InaAs; omeAs; InaCs; omeAs; InaA-Sup |
| 508 | FXN-532 m01 | CCTCAAAAGCAGGAATA | FXN | 3' | human | InaCs; omeCs; InaTs; omeCs; InaAs; omeAs; InaAs; omeAs; InaGs; omeCs; InaAs; omeGs; InaGs; omeAs; InaAs; omeUs; InaA-Sup |
| 509 | FXN-533 m01 | ACACATAGCCCAACTGT | FXN | 3' | human | InaAs; omeCs; InaAs; omeCs; InaAs; omeUs; InaAs; omeGs; InaCs; omeCs; InaCs; omeAs; InaAs; omeCs; InaTs; omeGs; InaT-Sup |
| 510 | FXN-534 m01 | CTTTCTACAGAGCTGTG | FXN | 3' | human | InaCs; omeUs; InaTs; omeUs; InaCs; omeUs; InaAs; omeCs; InaAs; omeGs; InaAs; omeGs; InaCs; omeUs; InaGs; omeUs; InaG-Sup |
| 511 | FXN-535 m01 | GTAGGAGGCAACACATT | FXN | 3' | human | InaGs; omeUs; InaAs; omeGs; InaGs; omeAs; InaGs; omeGs; InaCs; omeAs; InaAs; omeCs; InaAs; omeCs; InaAs; omeUs; InaT-Sup |
| 512 | FXN-536 m01 | CAGAACTTGGGGCAAG | FXN | 3' | human | InaCs; omeAs; InaGs; omeAs; InaAs; omeCs; InaTs; omeUs; InaGs; deaGs; InaGs; deaGs; InaGs; omeCs; InaAs; omeAs; InaG-Sup |
| 513 | FXN-537 m01 | CCATAGAAATTAAAAAT | FXN | 3' | human | InaCs; omeCs; InaAs; omeUs; InaAs; omeGs; InaAs; omeAs; InaAs; omeUs; InaTs; omeAs; InaAs; omeAs; InaAs; omeAs; InaT-Sup |
| 514 | FXN-538 m01 | ACAATCCAAAAAATCTT | FXN | 3' | human | InaAs; omeCs; InaAs; omeAs; InaTs; omeCs; InaCs; omeAs; InaAs; omeAs; InaAs; omeAs; InaAs; omeUs; InaCs; omeUs; InaT-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 515 | FXN-539 m01 | GTGAGGGAGGAAATCCG | FXN | 3' | human | InaGs; omeUs; InaGs; omeAs; InaGs; omeGs; InaGs; omeAs; InaGs; omeGs; InaAs; omeAs; InaAs; omeUs; InaCs; omeCs; InaG-Sup |
| 516 | FXN-540 m01 | AAGATAAGGGGTATCAT | FXN | 3' | human | InaAs; omeAs; InaGs; omeAs; InaTs; omeAs; InaAs; omeGs; InaGs; omeGs; InaGs; omeUs; InaAs; omeUs; InaCs; omeAs; InaT-Sup |
| 517 | FXN-541 m01 | GGCATAAGACATTATAA | FXN | 3' | human | InaGs; omeGs; InaCs; omeAs; InaTs; omeAs; InaAs; omeGs; InaAs; omeCs; InaAs; omeUs; InaTs; omeAs; InaTs; omeAs; InaA-Sup |
| 518 | FXN-542 m01 | TGTTATATTCAGGTATA | FXN | 3' | human | InaTs; omeGs; InaTs; omeUs; InaAs; omeUs; InaAs; omeUs; InaTs; omeCs; InaAs; omeGs; InaGs; omeUs; InaAs; omeUs; InaA-Sup |
| 519 | FXN-543 m01 | TTTGCTTTTTAAAGGT | FXN | 3' | human | InaTs; omeUs; InaTs; omeGs; InaCs; omeUs; InaTs; omeUs; InaTs; omeUs; InaTs; omeAs; InaAs; omeAs; InaGs; omeGs; InaT-Sup |
| 520 | FXN-544 m01 | TTTTTCCTTCTTATTAT | FXN | 3' | human | InaTs; omeUs; InaTs; omeUs; InaTs; omeCs; InaCs; omeUs; InaTs; omeCs; InaTs; omeUs; InaAs; omeUs; InaTs; omeAs; InaT-Sup |
| 521 | FXN-545 m01 | CATTTTCCCTCCTGGAA | FXN | 3' | human | InaCs; omeAs; InaTs; omeUs; InaTs; omeUs; InaCs; omeCs; InaCs; omeUs; InaCs; omeCs; InaTs; omeGs; InaGs; omeAs; InaA-Sup |
| 522 | FXN-546 m01 | GAAGAGTGAAGACAATT | FXN | 3' | human | InaGs; omeAs; InaAs; omeGs; InaAs; omeGs; InaTs; omeGs; InaAs; omeAs; InaGs; omeAs; InaCs; omeAs; InaAs; omeUs; InaT-Sup |
| 523 | FXN-547 m01 | TAAATCCTTCAAAGAAT | FXN | 3' | human | InaTs; omeAs; InaAs; omeAs; InaTs; omeCs; InaCs; omeUs; InaTs; omeCs; InaAs; omeAs; InaAs; omeGs; InaAs; omeAs; InaT-Sup |
| 524 | FXN-548 m01 | TCATGTACTTCTTGCAG | FXN | 3' | human | InaTs; omeCs; InaAs; omeUs; InaGs; omeUs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaAs; omeCs; InaTs; omeUs; InaCs; omeUs; InaTs; omeGs; InaCs; omeAs; InaG-Sup |
| 525 | FXN-549 m01 | GGTTGACCAGCTGCTCT | FXN | 3' | human | InaGs; omeGs; InaTs; omeUs; InaCs; omeAs; InaCs; omeCs; InaAs; omeGs; InaCs; omeUs; InaGs; omeCs; InaTs; omeCs; InaT-Sup |
| 526 | FXN-550 m01 | AGATAGAACAGTGAGCA | FXN | 3' | human | InaAs; omeGs; InaAs; omeUs; InaGs; omeGs; InaAs; omeAs; InaCs; omeAs; InaGs; omeUs; InaGs; omeAs; InaGs; omeCs; InaA-Sup |
| 527 | FXN-551 m01 | TAATGTGTCTCATTTGG | FXN | 3' | human | InaTs; omeAs; InaAs; omeUs; InaGs; omeUs; InaGs; omeUs; InaCs; omeUs; InaCs; omeAs; InaTs; omeUs; InaTs; omeGs; InaG-Sup |
| 528 | FXN-552 m01 | ATTTGTAGGCTACCCTT | FXN | 3' | human | InaAs; omeUs; InaTs; omeUs; InaGs; omeUs; InaAs; omeGs; InaGs; omeCs; InaTs; omeAs; InaCs; omeCs; InaCs; omeUs; InaT-Sup |
| 529 | FXN-553 m01 | GAAAGAAGCCTGAAAAC | FXN | 3' | human | InaGs; omeAs; InaAs; omeAs; InaGs; omeAs; InaAs; omeGs; InaCs; omeCs; InaTs; omeGs; InaAs; omeAs; InaAs; omeAs; InaC-Sup |
| 530 | FXN-554 m01 | AGAAGTGCTTACACTTT | FXN | 3' | human | InaAs; omeGs; InaAs; omeAs; InaGs; omeUs; InaGs; omeCs; InaTs; omeUs; InaAs; omeCs; InaAs; omeCs; InaTs; omeUs; InaT-Sup |
| 531 | FXN-555 m01 | TCAATGCTAAAGAGCTC | FXN | 3' | human | InaTs; omeCs; InaAs; omeAs; InaTs; omeGs; InaCs; omeUs; InaAs; omeAs; InaAs; omeGs; InaAs; omeGs; InaCs; omeUs; InaC-Sup |
| 532 | Apoa1_mus-01 m12 | AGTCTGGGTGTCC | Apoa1 | 5' | mouse | InaAs; dGs; InaTs; dCs; InaTs; dGs; InaGs; dGs; InaTs; dGs; InaTs; dCs; InaC-Sup |
| 533 | Apoa1_mus-02 m12 | CCGACAGTCTGGG | Apoa1 | 5' | mouse | InaCs; dCs; InaGs; dAs; InaCs; dAs; InaGs; dTs; InaCs; dTs; InaGs; dGs; InaG-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 534 | Apoa1_mus-03 m12 | CTCCGACAGTCTG | Apoa1 | 5' | mouse | InaCs; dTs; InaCs; dCs; InaGs; dAs; InaCs; dAs; InaGs; dTs; InaCs; dTs; InaG-Sup |
| 535 | Apoa1_mus-04 m12 | GACAGTCTGGGTG | Apoa1 | 5' | mouse | InaGs; dAs; InaCs; dAs; InaGs; dTs; InaCs; dTs; InaGs; dGs; InaGs; dTs; InaG-Sup |
| 536 | Apoa1_mus-05 m12 | CAGTCTGGGTG | Apoa1 | 5' | mouse | InaCs; dAs; InaGs; dTs; InaCs; dTs; InaGs; dGs; InaGs; dTs; InaG-Sup |
| 537 | Apoa1_mus-06 m12 | CTCAGCCTGGCCCTG | Apoa1 | 5' | mouse | InaCs; dTs; InaCs; dAs; InaGs; dCs; InaCs; dTs; InaGs; dGs; InaCs; dCs; InaCs; dTs; InaG-Sup |
| 538 | Apoa1_mus-07 m12 | AGTTCAAGGATCAGC | Apoa1 | 5' | mouse | InaAs; dGs; InaTs; dTs; InaCs; dAs; InaAs; dGs; InaGs; dAs; InaTs; dCs; InaAs; dGs; InaC-Sup |
| 539 | Apoa1_mus-08 m12 | GCTCTCCGACAGTCT | Apoa1 | 5' | mouse | InaGs; dCs; InaTs; dCs; InaTs; dCs; InaCs; dGs; InaAs; dCs; InaAs; dGs; InaTs; dCs; InaT-Sup |
| 540 | Apoa1_mus-09 m12 | TCTCCGACAGTCT | Apoa1 | 5' | mouse | InaTs; dCs; InaTs; dCs; InaCs; dGs; InaAs; dCs; InaAs; dGs; InaTs; dCs; InaT-Sup |
| 541 | Apoa1_mus-10 m12 | TCCGACAGTCT | Apoa1 | 5' | mouse | InaTs; dCs; InaCs; dGs; InaAs; dCs; InaAs; dGs; InaTs; dCs; InaT-Sup |
| 542 | Apoa1_mus-11 m12 | CGGAGCTCTCCGACA | Apoa1 | 5' | mouse | InaCs; dGs; InaGs; dAs; InaGs; dCs; InaTs; dCs; InaTs; dCs; InaCs; dGs; InaAs; dCs; InaA-Sup |
| 543 | Apoa1_mus-12 m12 | GAGCTCTCCGACA | Apoa1 | 5' | mouse | InaGs; dAs; InaGs; dCs; InaTs; dCs; InaTs; dCs; InaCs; dGs; InaAs; dCs; InaA-Sup |
| 544 | Apoa1_mus-13 m12 | GCTCTCCGACA | Apoa1 | 5' | mouse | InaGs; dCs; InaTs; dCs; InaTs; dCs; InaCs; dGs; InaAs; dCs; InaA-Sup |
| 545 | Apoa1_mus-14 m12 | CTATTCCATTTTGGA | Apoa1 | 3' | mouse | InaCs; dTs; InaAs; dTs; InaTs; dCs; InaCs; dAs; InaTs; dTs; InaTs; dTs; InaGs; dGs; InaA-Sup |
| 546 | Apoa1_mus-15 m12 | CTATTCCATTTTG | Apoa1 | 3' | mouse | InaCs; dTs; InaAs; dTs; InaTs; dCs; InaCs; dAs; InaTs; dTs; InaTs; dTs; InaG-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 547 | Apoa1_mus-16 m12 | ATTCCATTTTGGAAA | Apoa1 | 3' | mouse | InaAs; dTs; InaTs; dCs; InaCs; dAs; InaTs; dTs; InaTs; dTs; InaGs; dGs; InaAs; dAs; InaA-Sup |
| 548 | Apoa1_mus-17 m12 | CCATTTTGGAAAGGT | Apoa1 | 3' | mouse | InaCs; dCs; InaAs; dTs; InaTs; dTs; InaTs; dGs; InaGs; dAs; InaAs; dAs; InaGs; dGs; InaT-Sup |
| 549 | Apoa1_mus-18 m12 | CCATTTTGGAAAG | Apoa1 | 3' | mouse | InaCs; dCs; InaAs; dTs; InaTs; dTs; InaTs; dGs; InaGs; dAs; InaAs; dAs; InaG-Sup |
| 550 | Apoa1_mus-19 m12 | CATTTTGGAAAGGTT | Apoa1 | 3' | mouse | InaCs; dAs; InaTs; dTs; InaTs; dTs; InaGs; dGs; InaAs; dAs; InaAs; dGs; InaGs; dTs; InaT-Sup |
| 551 | Apoa1_mus-20 m12 | CATTTTGGAAAGG | Apoa1 | 3' | mouse | InaCs; dAs; InaTs; dTs; InaTs; dTs; InaGs; dGs; InaAs; dAs; InaAs; dGs; InaG-Sup |
| 552 | Apoa1_mus-21 m12 | GGAAAGGTTTATTGT | Apoa1 | 3' | mouse | InaGs; dGs; InaAs; dAs; InaAs; dGs; InaGs; dTs; InaTs; dTs; InaAs; dTs; InaTs; dGs; InaT-Sup |
| 553 | Apoa1_mus-22 m22 | TCCGACAGTCTCCATTTTGGAA | Apoa1 | 5' and 3' | mouse | InaTs; dCs; dCs; InaGs; dAs; dCs; InaAs; dGs; dTs; InaCs; dTs; dCs; InaCs; dAs; dTs; InaTs; dTs; dTs; InaGs; dGs; dAs; InaA-Sup |
| 554 | Apoa1_mus-23 m22 | GCTCTCCGACACCATTTTGGAA | Apoa1 | 5' and 3' | mouse | InaGs; dCs; dTs; InaCs; dTs; dCs; InaCs; dGs; dAs; InaCs; dAs; dCs; InaCs; dAs; dTs; InaTs; dTs; dTs; InaGs; dGs; dAs; InaA-Sup |
| 555 | Apoa1_mus-24 m22 | TCCGACAGTCTCATTTTGGAAA | Apoa1 | 5' and 3' | mouse | InaTs; dCs; dCs; InaGs; dAs; dCs; InaAs; dGs; dTs; InaCs; dTs; dCs; InaAs; dTs; dTs; InaTs; dTs; dGs; InaGs; dAs; dAs; InaA-Sup |
| 556 | Apoa1_mus-25 m22 | GCTCTCCGACACATTTTGGAAA | Apoa1 | 5' and 3' | mouse | InaGs; dCs; dTs; InaCs; dTs; dCs; InaCs; dGs; dAs; InaCs; dAs; dCs; InaAs; dTs; dTs; InaTs; dTs; dGs; InaGs; dAs; dAs; InaA-Sup |
| 557 | FXN-761 m01 | CCTCAAAAGCAGGAA | FXN | 3' | human | InaCs; omeCs; InaTs; omeCs; InaAs; omeAs; InaAs; omeAs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaGs; omeCs; InaAs; omeGs; InaGs; omeAs; InaA-Sup |
| 558 | FXN-762 m01 | CCTCAAAAGCAGG | FXN | 3' | human | InaCs; omeCs; InaTs; omeCs; InaAs; omeAs; InaAs; omeAs; InaGs; omeCs; InaAs; omeGs; InaG-Sup |
| 559 | FXN-763 m01 | CCTCAAAAGCA | FXN | 3' | human | InaCs; omeCs; InaTs; omeCs; InaAs; omeAs; InaAs; omeAs; InaGs; omeCs; InaA-Sup |
| 560 | FXN-764 m01 | TCAAAAGCAGGAA | FXN | 3' | human | InaTs; omeCs; InaAs; omeAs; InaAs; omeAs; InaGs; omeCs; InaAs; omeGs; InaGs; omeAs; InaA-Sup |
| 561 | FXN-765 m01 | CAAAAGCAGGA | FXN | 3' | human | InaCs; omeAs; InaAs; omeAs; InaAs; omeGs; InaCs; omeAs; InaGs; omeGs; InaA-Sup |
| 562 | FXN-766 m01 | CCGCCCTCCAGCCTCA AAAGCAGGAAT | FXN | 5' and 3' | human | InaCs; omeCs; InaGs; omeCs; InaCs; omeCs; InaTs; omeCs; InaCs; omeAs; InaGs; omeCs; InaCs; omeTs; InaCs; omeAs; InaAs; omeAs; InaAs; omeGs; InaCs; omeAs; InaGs; omeGs; InaAs; omeAs; InaT-Sup |
| 563 | FXN-767 m01 | CCGCCCTCCAGCCTCA AAAGCAGGA | FXN | 5' and 3' | human | InaCs; omeCs; InaGs; omeCs; InaCs; omeCs; InaTs; omeCs; InaCs; omeAs; InaGs; omeCs; InaCs; omeTs; InaCs; omeAs; InaAs; omeAs; InaAs; omeGs; InaCs; omeAs; InaGs; omeGs; InaA-Sup |
| 564 | FXN-768 m01 | CCGCCCTCCAGCCTCA AAAGCAG | FXN | 5' and 3' | human | InaCs; omeCs; InaGs; omeCs; InaCs; omeCs; InaTs; omeCs; InaCs; omeAs; InaGs; omeCs; InaCs; omeTs; InaCs; omeAs; InaAs; omeAs; InaAs; omeGs; InaCs; omeAs; InaG-Sup |
| 565 | FXN-769 m01 | CCGCCCTCCAGCCTCA AAAGC | FXN | 5' and 3' | human | InaCs; omeCs; InaGs; omeCs; InaCs; omeCs; InaTs; omeCs; InaCs; omeAs; InaGs; omeCs; InaCs; omeTs; InaCs; omeAs; InaAs; omeAs; InaAs; omeGs; InaC-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 566 | FXN-770 m01 | GCCCTCCAGCCTCAAA AGCAGGAAT | FXN | 5' and 3' | human | InaGs; omeCs; InaCs; omeCs; InaTs; omeCs; InaCs; omeAs; InaGs; omeCs; InaCs; omeTs; InaCs; omeAs; InaAs; omeAs; InaAs; omeGs; InaCs; omeAs; InaGs; omeGs; InaAs; omeAs; InaT-Sup |
| 567 | FXN-771 m01 | GCCCTCCAGCCTCAAA AGCAGGA | FXN | 5' and 3' | human | InaGs; omeCs; InaCs; omeCs; InaTs; omeCs; InaCs; omeAs; InaGs; omeCs; InaCs; omeTs; InaCs; omeAs; InaAs; omeAs; InaAs; omeGs; InaCs; omeAs; InaGs; omeGs; InaA-Sup |
| 568 | FXN-772 m01 | GCCCTCCAGCCTCAAA AGCAG | FXN | 5' and 3' | human | InaGs; omeCs; InaCs; omeCs; InaTs; omeCs; InaCs; omeAs; InaGs; omeCs; InaCs; omeTs; InaCs; omeAs; InaAs; omeAs; InaAs; omeGs; InaCs; omeAs; InaG-Sup |
| 569 | FXN-773 m01 | GCCCTCCAGCCTCAAA AGC | FXN | 5' and 3' | human | InaGs; omeCs; InaCs; omeCs; InaTs; omeCs; InaCs; omeAs; InaGs; omeCs; InaCs; omeTs; InaCs; omeAs; InaAs; omeAs; InaAs; omeGs; InaC-Sup |
| 570 | FXN-774 m01 | CCCTCCAGCCTCAAAA G | FXN | 5' and 3' | human | InaCs; omeCs; InaCs; omeTs; InaCs; omeCs; InaAs; omeGs; InaCs; omeCs; InaTs; omeCs; InaAs; omeAs; InaAs; omeAs; InaG-Sup |
| 571 | FXN-776 m01 | CCTCCAGCCTCAAAA | FXN | 5' and 3' | human | InaCs; omeCs; InaTs; omeCs; InaCs; omeAs; InaGs; omeCs; InaCs; omeTs; InaCs; omeAs; InaAs; omeAs; InaA-Sup |
| 572 | FXN-777 m01 | GCCCTCCAGTCAAAA GCAGGA | FXN | 5' and 3' | human | InaGs; omeCs; InaCs; omeCs; InaTs; omeCs; InaCs; omeAs; InaGs; omeTs; InaCs; omeAs; InaAs; omeAs; InaAs; omeGs; InaCs; omeAs; InaGs; omeGs; InaA-Sup |
| 573 | FXN-778 m01 | GCCCTCCAGCAAAAG CAGG | FXN | 5' and 3' | human | InaGs; omeCs; InaCs; omeCs; InaTs; omeCs; InaCs; omeAs; InaGs; omeCs; InaAs; omeAs; InaAs; omeAs; InaGs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | omeCs; InaAs; omeGs; InaG-Sup |
| 574 | FXN-779 m01 | CCGCCCTCCAGTCAAAAGCAGGA | FXN | 5' and 3' | human | InaCs; omeCs; InaGs; omeCs; InaCs; omeCs; InaTs; omeCs; InaCs; omeAs; InaGs; omeTs; InaCs; omeAs; InaAs; omeAs; InaAs; omeGs; InaCs; omeAs; InaGs; omeGs; InaA-Sup |
| 575 | FXN-780 m01 | CCGCCCTCCAGCAAAAGCAGG | FXN | 5' and 3' | human | InaCs; omeCs; InaGs; omeCs; InaCs; omeCs; InaTs; omeCs; InaCs; omeAs; InaGs; omeCs; InaAs; omeAs; InaAs; omeAs; InaGs; omeCs; InaAs; omeGs; InaG-Sup |
| 576 | FXN-671 m01 | CTCCGCCCTCCAG | FXN | 5' | human | InaCs; omeTs; InaCs; omeCs; InaGs; omeCs; InaCs; omeCs; InaTs; omeCs; InaCs; omeAs; InaG-Sup |
| 577 | FXN-672 m01 | CCGCCCTCCAG | FXN | 5' | human | InaCs; omeCs; InaGs; omeCs; InaCs; omeCs; InaTs; omeCs; InaCs; omeAs; InaG-Sup |
| 578 | FXN-673 m01 | GCCCTCCAG | FXN | 5' | human | InaGs; omeCs; InaCs; omeCs; InaTs; omeCs; InaCs; omeAs; InaG-Sup |
| 579 | FXN-674 m01 | CCCGCTCCGCCCTCC | FXN | 5' | human | InaCs; omeCs; InaCs; omeGs; InaCs; omeTs; InaCs; omeCs; InaGs; omeCs; InaCs; omeCs; InaTs; omeCs; InaC-Sup |
| 580 | FXN-675 m01 | CGCTCCGCCCTCC | FXN | 5' | human | InaCs; omeGs; InaCs; omeTs; InaCs; omeCs; InaGs; omeCs; InaCs; omeCs; InaTs; omeCs; InaC-Sup |
| 581 | FXN-676 m01 | CTCCGCCCTCC | FXN | 5' | human | InaCs; omeTs; InaCs; omeCs; InaGs; omeCs; InaCs; omeCs; InaTs; omeCs; InaC-Sup |
| 582 | FXN-677 m01 | CCGCCCTCC | FXN | 5' | human | InaCs; omeCs; InaGs; omeCs; InaCs; omeCs; InaTs; omeCs; InaC-Sup |
| 583 | CD247-90 m02 | GCCTTTGAGAAAGCA | CD247 | 5' | human | dGs; InaCs; dCs; InaTs; dTs; InaTs; dGs; InaAs; dGs; InaAs; dAs; InaAs; dGs; InaCs; dA-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 584 | CD247-91 m02 | GACTGTGGGGCCTTT | CD247 | 5' | human | dGs; InaAs; dCs; InaTs; dGs; InaTs; dGs; InaGs; dGs; InaGs; dCs; InaCs; dTs; InaTs; dT-Sup |
| 585 | CD247-92 m02 | AGGAAGTGGAGGACT | CD247 | 5' | human | dAs; InaGs; dGs; InaAs; dAs; InaGs; dTs; InaGs; dGs; InaAs; dGs; InaGs; dAs; InaCs; dT-Sup |
| 586 | CD247-93 m02 | TGCATTTTCACTGAA | CD247 | 3' | human | dTs; InaGs; dCs; InaAs; dTs; InaTs; dTs; InaTs; dCs; InaAs; dCs; InaTs; dGs; InaAs; dA-Sup |
| 587 | CD247-94 m02 | CATTTTCACTGAAGC | CD247 | 3' | human | dCs; InaAs; dTs; InaTs; dTs; InaTs; dCs; InaAs; dCs; InaTs; dGs; InaAs; dAs; InaGs; dC-Sup |
| 588 | CD247-95 m02 | ACTGAAGCATTTATT | CD247 | 3' | human | dAs; InaCs; dTs; InaGs; dAs; InaAs; dGs; InaCs; dAs; InaTs; dTs; InaTs; dAs; InaTs; dT-Sup |
| 589 | CFTR-84 m02 | CACACAAATGTATGG | CFTR | 3' | human | dCs; InaAs; dCs; InaAs; dCs; InaAs; dAs; InaAs; dTs; InaGs; dTs; InaAs; dTs; InaGs; dG-Sup |
| 590 | CFTR-85 m02 | GGATTTTATTGACAA | CFTR | 3' | human | dGs; InaGs; dAs; InaTs; dTs; InaTs; dTs; InaAs; dTs; InaTs; dGs; InaAs; dCs; InaAs; dA-Sup |
| 591 | CFTR-86 m02 | AAAACAACAAAGTTT | CFTR | 3' | human | dAs; InaAs; dAs; InaAs; dCs; InaAs; dAs; InaCs; dAs; InaAs; dAs; InaGs; dTs; InaTs; dT-Sup |
| 592 | CFTR-87 m02 | AGTGCCATAAAAAGT | CFTR | 3' | human | dAs; InaGs; dTs; InaGs; dCs; InaCs; dAs; InaTs; dAs; InaAs; dAs; InaAs; dAs; InaGs; dT-Sup |
| 593 | CFTR-88 m02 | TCAAATATAAAAATT | CFTR | 3' | human | dTs; InaCs; dAs; InaAs; dAs; InaTs; dAs; InaTs; dAs; InaAs; dAs; InaAs; dAs; InaTs; dT-Sup |
| 594 | CFTR-89 m02 | TTCCCCCCACCCACC | CFTR | 3' | human | dTs; InaTs; dCs; InaCs; dCs; InaCs; dCs; InaCs; dAs; InaCs; dCs; InaCs; dAs; InaCs; dC-Sup |
| 595 | CFTR-90 m02 | CATTTGCTTCCAATT | CFTR | 5' | human | dCs; InaAs; dTs; InaTs; dTs; InaGs; dCs; InaTs; dTs; InaCs; dCs; InaAs; dAs; InaTs; dT-Sup |
| 596 | CFTR-91 m02 | GCTCAACCCTTTTTC | CFTR | 5' | human | dGs; InaCs; dTs; InaCs; dAs; InaAs; dCs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaCs; dCs; InaTs; dTs; InaTs; dTs; InaTs; dC-Sup |
| 597 | CFTR-92 m02 | AGACCTACTACTCTG | CFTR | 5' | human | dAs; InaGs; dAs; InaCs; dCs; InaTs; dAs; InaCs; dTs; InaAs; dCs; InaTs; dCs; InaTs; dG-Sup |
| 598 | FMR1-58 m02 | CCCTCCACCGGAAGT | FMR1 | 5' | human | dCs; InaCs; dCs; InaTs; dCs; InaCs; dAs; InaCs; dCs; InaGs; dGs; InaAs; dAs; InaGs; dT-Sup |
| 599 | FMR1-59 m02 | GCCCGCGCTCGCCGT | FMR1 | 5' | human | dGs; InaCs; dCs; InaCs; dGs; InaCs; dGs; InaCs; dTs; InaCs; dGs; InaCs; dCs; InaGs; dT-Sup |
| 600 | FMR1-60 m02 | ACGCCCCTGGCAGC | FMR1 | 5' | human | dAs; InaCs; dGs; InaCs; dCs; InaCs; dCs; InaCs; dTs; InaGs; dGs; InaCs; dAs; InaGs; dC-Sup |
| 601 | FMR1-61 m02 | GCTCAGCCCCTCGGC | FMR1 | 5' | human | dGs; InaCs; dTs; InaCs; dAs; InaGs; dCs; InaCs; dCs; InaCs; dTs; InaCs; dGs; InaGs; dC-Sup |
| 602 | FMR1-62 m02 | AGCAGAGGAAGATCA | FMR1 | 3' | human | dAs; InaGs; dCs; InaAs; dGs; InaAs; dGs; InaGs; dAs; InaAs; dGs; InaAs; dTs; InaCs; dA-Sup |
| 603 | FMR1-63 m02 | CAGAGGAAGATCAAA | FMR1 | 3' | human | dCs; InaAs; dGs; InaAs; dGs; InaGs; dAs; InaAs; dGs; InaAs; dTs; InaCs; dAs; InaAs; dA-Sup |
| 604 | FMR1-64 m02 | CAGATTTTTGAAACT | FMR1 | 3' | human | dCs; InaAs; dGs; InaAs; dTs; InaTs; dTs; InaTs; dTs; InaGs; dAs; InaAs; dAs; InaCs; dT-Sup |
| 605 | FMR1-65 m02 | CAGACTAATTTTTG | FMR1 | 3' | human | dCs; InaAs; dGs; InaAs; dCs; InaTs; dAs; InaAs; dTs; InaTs; dTs; InaTs; dTs; InaTs; dG-Sup |
| 606 | FMR1-66 m02 | TTTTTGCTTTTTCAT | FMR1 | 3' | human | dTs; InaTs; dTs; InaTs; dTs; InaGs; dCs; InaTs; dTs; InaTs; dTs; InaTs; dCs; InaAs; dT-Sup |
| 607 | FMR1-67 m02 | AATTTTTGCTTTTT | FMR1 | 3' | human | dAs; InaAs; dTs; InaTs; dTs; InaTs; dTs; InaTs; dGs; InaCs; dTs; InaTs; dTs; InaTs; dT-Sup |
| 608 | FMR1-68 m02 | ATGTTTGGCAATACT | FMR1 | 3' | human | dAs; InaTs; dGs; InaTs; dTs; InaTs; dGs; InaGs; dCs; InaAs; dAs; InaTs; dAs; InaCs; dT-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 609 | FMR1-69 m02 | TTGGCAATACTTTTT | FMR1 | 3' | human | dTs; InaTs; dGs; InaGs; dCs; InaAs; dAs; InaTs; dAs; InaCs; dTs; InaTs; dTs; InaTs; dT-Sup |
| 610 | LAMA1-105 m02 | GCTGCCCTGGCCCCG | LAMA1 | 5' | human | dGs; InaCs; dTs; InaGs; dCs; InaCs; dCs; InaTs; dGs; InaGs; dCs; InaCs; dCs; InaCs; dG-Sup |
| 611 | LAMA1-106 m02 | CGGACACACCCCTCG | LAMA1 | 5' | human | dCs; InaGs; dGs; InaAs; dCs; InaAs; dCs; InaAs; dCs; InaCs; dCs; InaCs; dTs; InaCs; dG-Sup |
| 612 | LAMA1-107 m02 | ACGGGACGCGAGTCC | LAMA1 | 5' | human | dAs; InaCs; dGs; InaGs; dGs; InaAs; dCs; InaGs; dCs; InaGs; dAs; InaGs; dTs; InaCs; dC-Sup |
| 613 | LAMA1-108 m02 | GTCTGGGGAGAAAGC | LAMA1 | 5' | human | dGs; InaTs; dCs; InaTs; dGs; InaGs; dGs; InaGs; dAs; InaGs; dAs; InaAs; dAs; InaGs; dC-Sup |
| 614 | LAMA1-109 m02 | CCACTCGGTGGGTCT | LAMA1 | 5' | human | dCs; InaCs; dAs; InaCs; dTs; InaCs; dGs; InaGs; dTs; InaGs; dGs; InaGs; dTs; InaCs; dT-Sup |
| 615 | LAMA1-110 m02 | TGATCTGTTATCATC | LAMA1 | 5' | human | dTs; InaGs; dAs; InaTs; dCs; InaTs; dGs; InaTs; dTs; InaAs; dTs; InaCs; dAs; InaTs; dC-Sup |
| 616 | LAMA1-111 m02 | CTGTTATCATCTGTA | LAMA1 | 3' | human | dCs; InaTs; dGs; InaTs; dTs; InaAs; dTs; nIaCs; dAs; InaTs; dCs; InaTs; dGs; InaTs; dA-Sup |
| 617 | LAMA1-112 m02 | GTGTATAAAGATTTT | LAMA1 | 3' | human | dGs; InaTs; dGs; InaTs; dAs; InaTs; dAs; InaAs; dAs; InaGs; dAs; InaTs; dTs; InaTs; dT-Sup |
| 618 | LAMA1-113 m02 | CAATTTACATTTTAG | LAMA1 | 3' | human | dCs; InaAs; dAs; InaTs; dTs; InaTs; dAs; InaCs; dAs; InaTs; dTs; InaTs; dTs; InaAs; dG-Sup |
| 619 | LAMA1-114 m02 | TACATTTTAGACCAT | LAMA1 | 3' | human | dTs; InaAs; dCs; InaAs; dTs; InaTs; dTs; InaTs; dAs; InaGs; dAs; InaCs; dCs; InaAs; dT-Sup |
| 620 | MBNL1-73 m02 | TGCTATAAGATGTAA | MBNL1 | 5' | human | dTs; InaGs; dCs; InaTs; dAs; InaTs; dAs; InaAs; dGs; InaAs; dTs; InaGs; dTs; InaAs; dA-Sup |
| 621 | MBNL1-74 m02 | AAGGAAGCCGGCAAG | MBNL1 | 5' | human | dAs; InaAs; dGs; InaGs; dAs; InaAs; dGs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaCs; dCs; InaGs; dGs; InaCs; dAs; InaAs; dG-Sup |
| 622 | MBNL1-75 m02 | CGCCACAACTCATTC | MBNL1 | 5' | human | dCs; InaGs; dCs; InaCs; dAs; InaCs; dAs; InaAs; dCs; InaTs; dCs; InaAs; dTs; InaTs; dC-Sup |
| 623 | MBNL1-76 m02 | ATGGGAGCATTGTGG | MBNL1 | 5' | human | dAs; InaTs; dGs; InaGs; dGs; InaGs; dGs; InaCs; dAs; InaTs; dTs; InaGs; dTs; InaGs; dG-Sup |
| 624 | MBNL1-77 m02 | CGCCCGCCCAGCCCC | MBNL1 | 5' | human | dCs; InaGs; dCs; InaCs; dCs; InaGs; dCs; InaCs; dCs; InaAs; dGs; InaCs; dCs; InaCs; dC-Sup |
| 625 | MBNL1-78 m02 | CCCCTCCCCCGCCCG | MBNL1 | 5' | human | dCs; InaCs; dCs; InaCs; dTs; InaCs; dCs; InaCs; dCs; InaCs; dGs; InaCs; dCs; InaCs; dG-Sup |
| 626 | MBNL1-79 m02 | CTTCCGCTGCTGCTG | MBNL1 | 5' | human | dCs; InaTs; dTs; InaCs; dCs; InaGs; dCs; InaTs; dGs; InaCs; dTs; InaGs; dCs; InaTs; dG-Sup |
| 627 | MBNL1-80 m02 | CTTCTTAGTACCAAC | MBNL1 | 5' | human | dCs; InaTs; dTs; InaCs; dTs; InaTs; dAs; InaGs; dTs; InaAs; dCs; InaCs; dAs; InaAs; dC-Sup |
| 628 | MBNL1-81 m02 | TTTAGAGCAAAATCG | MBNL1 | 5' | human | dTs; InaTs; dTs; InaAs; dGs; InaAs; dGs; InaCs; dAs; InaAs; dAs; InaAs; dTs; InaCs; dG-Sup |
| 629 | MBNL1-82 m02 | GGTAGTTAAATGTTT | MBNL1 | 5' | human | dGs; InaGs; dTs; InaAs; dGs; InaTs; dTs; InaAs; dAs; InaAs; dTs; InaGs; dTs; InaTs; dT-Sup |
| 630 | MBNL1-83 m02 | TACTTAAGAAAGAGA | MBNL1 | 3' | human | dTs; InaAs; dCs; InaTs; dTs; InaAs; dAs; InaGs; dAs; InaAs; dAs; InaGs; dAs; InaGs; dA-Sup |
| 631 | MBNL1-84 m02 | TATACTTAAGAAAGA | MBNL1 | 3' | human | dTs; InaAs; dTs; InaAs; dCs; InaTs; dTs; InaAs; dAs; InaGs; dAs; InaAs; dAs; InaGs; dA-Sup |
| 632 | MECP2-61 m02 | CGCCGCCGACGCCGG | MECP2 | 5' | human | dCs; InaGs; dCs; InaCs; dGs; InaCs; dCs; InaGs; dAs; InaCs; dGs; InaCs; dCs; InaGs; dG-Sup |
| 633 | MECP2-62 m02 | CTCTCTCCGAGAGGA | MECP2 | 5' | human | dCs; InaTs; dCs; InaTs; dCs; InaTs; dCs; InaCs; dGs; InaAs; dGs; InaAs; dGs; InaGs; dA-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 634 | MECP2-63 m02 | CGCCCCGCCCTCTTG | MECP2 | 5' | human | dCs; InaGs; dCs; InaCs; dCs; InaCs; dGs; InaCs; dCs; InaCs; dTs; InaCs; dTs; InaTs; dG-Sup |
| 635 | MECP2-64 m02 | CCGCGCGCTGCTGCA | MECP2 | 5' | human | dCs; InaCs; dGs; InaCs; dGs; InaCs; dGs; InaCs; dTs; InaGs; dCs; InaTs; dGs; InaCs; dA-Sup |
| 636 | MECP2-65 m02 | CACTTTCACAGAGAG | MECP2 | 3' | human | dCs; InaAs; dCs; InaTs; dTs; InaTs; dCs; InaAs; dCs; InaAs; dGs; InaAs; dGs; InaAs; dG-Sup |
| 637 | MECP2-66 m02 | CTTTCACATGTATTAA | MECP2 | 3' | human | dCs; InaTs; dTs; InaTs; dCs; InaAs; dCs; InaAs; dTs; InaGs; dTs; InaAs; dTs; InaTs; dAs; dA-Sup |
| 638 | MECP2-67 m02 | ATGTATTAAAAAACT | MECP2 | 3' | human | dAs; InaTs; dGs; InaTs; dAs; InaTs; dTs; InaAs; dAs; InaAs; dAs; InaAs; dAs; InaCs; dT-Sup |
| 639 | MECP2-68 m02 | GACATTTTTATGTAA | MECP2 | 3' | human | dGs; InaAs; dCs; InaAs; dTs; InaTs; dTs; InaTs; dTs; InaAs; dTs; InaGs; dTs; InaAs; dA-Sup |
| 640 | MECP2-69 m02 | CATTTTTATGTAAAT | MECP2 | 3' | human | dCs; InaAs; dTs; InaTs; dTs; InaTs; dTs; InaAs; dTs; InaGs; dTs; InaAs; dAs; InaAs; dT-Sup |
| 641 | MECP2-70 m02 | AAATTTATAAGGCAA | MECP2 | 3' | human | dAs; InaAs; dAs; InaTs; dTs; InaTs; dAs; InaTs; dAs; InaAs; dGs; InaGs; dCs; InaAs; dA-Sup |
| 642 | MECP2-71 m02 | AGGCAAACTCTTTAT | MECP2 | 3' | human | dAs; InaGs; dGs; InaCs; dAs; InaAs; dAs; InaCs; dTs; InaCs; dTs; InaTs; dTs; InaAs; dT-Sup |
| 643 | MECP2-72 m02 | GTCTCTGGAACAATT | MECP2 | 3' | human | dGs; InaTs; dCs; InaTs; dCs; InaTs; dGs; InaGs; dAs; InaAs; dCs; InaAs; dAs; InaTs; dT-Sup |
| 644 | MECP2-73 m02 | CAGTTCAAACACAGA | MECP2 | 3' | human | dCs; InaAs; dGs; InaTs; dTs; InaCs; dAs; InaAs; dAs; InaCs; dAs; InaCs; dAs; InaGs; dA-Sup |
| 645 | MECP2-74 m02 | CAAACACAGAAGAGA | MECP2 | 3' | human | dCs; InaAs; dAs; InaAs; dCs; InaAs; dCs; InaAs; dGs; InaAs; dAs; InaGs; dAs; InaGs; dA-Sup |
| 646 | MECP2-75 m02 | AACACAGAAGAGATT | MECP2 | 3' | human | dAs; InaAs; dCs; InaAs; dCs; InaAs; dGs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaAs; dAs; InaGs; dAs; InaGs; dAs; InaTs; dT-Sup |
| 647 | MECP2-76 m02 | GGGGGAGAAGAAAGG | MECP2 | 3' | human | dGs; InaGs; dGs; InaGs; dGs; InaAs; dGs; InaAs; dAs; InaGs; dAs; InaAs; dAs; InaGs; dG-Sup |
| 648 | MECP2-77 m02 | TCGTTTTTTTTCTT | MECP2 | 3' | human | dTs; InaCs; dGs; InaTs; dTs; InaTs; dTs; InaTs; dTs; InaTs; dTs; InaTs; dCs; InaTs; dT-Sup |
| 649 | MECP2-78 m02 | CTTTTTTTCTTTTT | MECP2 | 3' | human | dCs; InaTs; dTs; InaTs; dTs; InaTs; dTs; InaTs; dTs; InaCs; dTs; InaTs; dTs; InaTs; dT-Sup |
| 650 | MECP2-79 m02 | CCTATGCTATGGTTA | MECP2 | 3' | human | dCs; InaCs; dTs; InaAs; dTs; InaGs; dCs; InaTs; dAs; InaTs; dGs; InaGs; dTs; InaTs; dA-Sup |
| 651 | MECP2-80 m02 | AGTTTACTGAAAGAA | MECP2 | 3' | human | dAs; InaGs; dTs; InaTs; dTs; InaAs; dCs; InaTs; dGs; InaAs; dAs; InaAs; dGs; InaAs; dA-Sup |
| 652 | MECP2-81 m02 | ACTGAAAGAAAAAAA | MECP2 | 3' | human | dAs; InaCs; dTs; InaGs; dAs; InaAs; dAs; InaGs; dAs; InaAs; dAs; InaAs; dAs; InaAs; dA-Sup |
| 653 | MERTK-66 m02 | CCTTATTCATATTTT | MERTK | 3' | human | dCs; InaCs; dTs; InaTs; dAs; InaTs; dTs; InaCs; dAs; InaTs; dAs; InaTs; dTs; InaTs; dT-Sup |
| 654 | MERTK-67 m02 | CTTCCTTATTCATAT | MERTK | 3' | human | dCs; InaTs; dTs; InaCs; dCs; InaTs; dTs; InaAs; dTs; InaTs; dCs; InaAs; dTs; InaAs; dT-Sup |
| 655 | MERTK-68 m02 | CAATCCTTCAATATT | MERTK | 3' | human | dCs; InaAs; dAs; InaTs; dCs; InaCs; dTs; InaTs; dCs; InaAs; dAs; InaTs; dAs; InaTs; dT-Sup |
| 656 | MERTK-69 m02 | GGCATTTCATTTTAC | MERTK | 3' | human | dGs; InaGs; dCs; InaAs; dTs; InaTs; dTs; InaCs; dAs; InaTs; dTs; InaTs; dTs; InaAs; dC-Sup |
| 657 | MERTK-70 m02 | CATTTTACAAATATT | MERTK | 3' | human | dCs; InaAs; dTs; InaTs; dTs; InaTs; dAs; InaCs; dAs; InaAs; dAs; InaTs; dAs; InaTs; dT-Sup |
| 658 | MERTK-71 m02 | GAAATGAAATAAGTA | MERTK | 3' | human | dGs; InaAs; dAs; InaAs; dTs; InaGs; dAs; InaAs; dAs; InaTs; dAs; InaAs; dGs; InaTs; dA-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 659 | MERTK-72 m02 | AGATATGCAAGATAA | MERTK | 3' | human | dAs; InaGs; dAs; InaTs; dAs; InaTs; dGs; InaCs; dAs; InaAs; dGs; InaAs; dTs; InaAs; dA-Sup |
| 660 | MERTK-73 m02 | GCGGGCCCAGCAGGT | MERTK | 5' | human | dGs; InaCs; dGs; InaGs; dGs; InaCs; dCs; InaCs; dAs; InaGs; dCs; InaAs; dGs; InaGs; dT-Sup |
| 661 | MERTK-74 m02 | CAGTGAGTGCCGAGT | MERTK | 5' | human | dCs; InaAs; dGs; InaTs; dGs; InaAs; dGs; InaTs; dGs; InaCs; dCs; InaGs; dAs; InaGs; dT-Sup |
| 662 | MERTK-75 m02 | GCCCGGGCAGTGAGT | MERTK | 5' | human | dGs; InaCs; dCs; InaCs; dGs; InaGs; dGs; InaCs; dAs; InaGs; dTs; InaGs; dAs; InaGs; dT-Sup |
| 663 | MERTK-76 m02 | TGTCCGGGCGGCCCG | MERTK | 5' | human | dTs; InaGs; dTs; InaCs; dCs; InaGs; dGs; InaGs; dCs; InaGs; dGs; InaCs; dCs; InaCs; dG-Sup |
| 664 | SSPN-47 m02 | CGCGCGTGTGCGAGT | SSPN | 5' | human | dCs; InaGs; dCs; InaGs; dCs; InaGs; dTs; InaGs; dTs; InaGs; dCs; InaGs; dAs; InaGs; dT-Sup |
| 665 | SSPN-48 m02 | CTTCAGACAGGCTGC | SSPN | 5' | human | dCs; InaTs; dTs; InaCs; dAs; InaGs; dAs; InaCs; dAs; InaGs; dGs; InaCs; dTs; InaGs; dC-Sup |
| 666 | SSPN-49 m02 | ACCTCTGCACTTCAG | SSPN | 5' | human | dAs; InaCs; dCs; InaTs; dCs; InaTs; dGs; InaCs; dAs; InaCs; dTs; InaTs; dCs; InaAs; dG-Sup |
| 667 | SSPN-50 m02 | CGGCGCGGGTCCCTT | SSPN | 5' | human | dCs; InaGs; dGs; InaCs; dGs; InaCs; dGs; InaGs; dGs; InaTs; dCs; InaCs; dCs; InaTs; dT-Sup |
| 668 | SSPN-51 m02 | TGGTATTCGAATTAT | SSPN | 5' | human | dTs; InaGs; dGs; InaTs; dAs; InaTs; dTs; InaCs; dGs; InaAs; dAs; InaTs; dTs; InaAs; dT-Sup |
| 669 | SSPN-52 m02 | CGGCCTGCCCTGGTA | SSPN | 5' | human | dCs; InaGs; dGs; InaCs; dCs; InaTs; dGs; InaCs; dCs; InaCs; dTs; InaGs; dGs; InaTs; dA-Sup |
| 670 | SSPN-53 m02 | TCAGAGATTATGAAA | SSPN | 3' | human | dTs; InaCs; dAs; InaGs; dAs; InaGs; dAs; InaTs; dTs; InaAs; dTs; InaGs; dAs; InaAs; dA-Sup |
| 671 | SSPN-54 m02 | TGTTTTCAGAGATTA | SSPN | 3' | human | dTs; InaGs; dTs; InaTs; dTs; InaTs; dCs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | InaAs; dGs; InaAs; dGs; InaAs; dTs; InaTs; dA-Sup |
| 672 | SSPN-55 m02 | CATGTAGAAATGCTT | SSPN | 3' | human | dCs; InaAs; dTs; InaGs; dTs; InaAs; dGs; InaAs; dAs; InaAs; dTs; InaGs; dCs; InaTs; dT-Sup |
| 673 | SSPN-56 m02 | AAACATGTAGAAATG | SSPN | 3' | human | dAs; InaAs; dAs; InaCs; dAs; InaTs; dGs; InaTs; dAs; InaGs; dAs; InaAs; dAs; InaTs; dG-Sup |
| 674 | SSPN-57 m02 | TTGATACCATTTATG | SSPN | 3' | human | dTs; InaTs; dGs; InaAs; dTs; InaAs; dCs; InaCs; dAs; InaTs; dTs; InaTs; dAs; InaTs; dG-Sup |
| 675 | SSPN-58 m02 | GAACTCAATTATTAT | SSPN | 3' | human | dGs; InaAs; dAs; InaCs; dTs; InaCs; dAs; InaAs; dTs; InaTs; dAs; InaTs; dTs; InaAs; dT-Sup |
| 676 | UTRN-972 m02 | AAAACGACTCCACAA | UTRN | 5' | human | dAs; InaAs; dAs; InaAs; dCs; InaGs; dAs; InaCs; dTs; InaCs; dCs; InaAs; dCs; InaAs; dA-Sup |
| 677 | UTRN-312 m02 | CTCCGAGGAAAAACG | UTRN | 5' | human | dCs; InaTs; dCs; InaCs; dGs; InaAs; dGs; InaGs; dAs; InaAs; dAs; InaAs; dAs; InaCs; dG-Sup |
| 678 | UTRN-313 m02 | GCTCCGAGGAAAAAC | UTRN | 5' | human | dGs; InaCs; dTs; InaCs; dCs; InaGs; dAs; InaGs; dGs; InaAs; dAs; InaAs; dAs; InaAs; dC-Sup |
| 679 | UTRN-975 m02 | CTCGGCGGGAGAAAG | UTRN | 5' | human | dCs; InaTs; dCs; InaGs; dGs; InaCs; dGs; InaGs; dGs; InaAs; dGs; InaAs; dAs; InaAs; dG-Sup |
| 680 | UTRN-976 m02 | GAACCGAAATTTT | UTRN | 5' | human | dGs; InaAs; dAs; InaCs; dCs; InaGs; dAs; InaAs; dAs; InaTs; dTs; InaTs; dT-Sup |
| 681 | UTRN-977 m02 | GAGAAGGGTGCAGAT | UTRN | 5' | human | dGs; InaAs; dGs; InaAs; dAs; InaGs; dGs; InaGs; dTs; InaGs; dCs; InaAs; dGs; InaAs; dT-Sup |
| 682 | UTRN-978 m02 | CTCTCCAGATGAGAA | UTRN | 5' | human | dCs; InaTs; dCs; InaTs; dCs; InaCs; dAs; InaAs; dAs; InaTs; dGs; InaAs; dGs; InaAs; dA-Sup |
| 683 | UTRN-979 m02 | CAGGGGTCCGCTCTC | UTRN | 5' | human | dCs; InaAs; dGs; InaGs; dGs; InaGs; dTs; InaCs; dCs; InaGs; dCs; InaTs; dCs; InaTs; dC-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 684 | UTRN-980 m02 | TCCGGGCAGCCAGGG | UTRN | 5' | human | dTs; InaCs; dCs; InaGs; dGs; InaGs; dCs; InaAs; dGs; InaCs; dCs; InaAs; dGs; InaGs; dG-Sup |
| 685 | UTRN-981 m02 | GGGGCTCGCCTCCGG | UTRN | 5' | human | dGs; InaGs; dGs; InaGs; dCs; InaTs; dCs; InaGs; dCs; InaCs; dTs; InaCs; dCs; InaGs; dG-Sup |
| 686 | UTRN-982 m02 | CCCCCGGGAAGGGGC | UTRN | 5' | human | dCs; InaCs; dCs; InaCs; dCs; InaGs; dGs; InaGs; dAs; InaAs; dGs; InaGs; dGs; InaGs; dC-Sup |
| 687 | UTRN-983 m02 | CCCACCCCCCGGGAA | UTRN | 5' | human | dCs; InaCs; dCs; InaAs; dCs; InaCs; dCs; InaCs; dCs; InaCs; dGs; InaGs; dGs; InaAs; dA-Sup |
| 688 | UTRN-984 m02 | GCGTTGCCGCCCCCAC | UTRN | 5' | human | dGs; InaCs; dGs; InaTs; dTs; InaGs; dCs; InaCs; dGs; InaCs; dCs; InaCs; dCs; InaCs; dAs; dC-Sup |
| 689 | UTRN-985 m02 | GCTGGGTCGCGCGTT | UTRN | 5' | human | dGs; InaCs; dTs; InaGs; dGs; InaGs; dTs; InaCs; dGs; InaCs; dGs; InaCs; dGs; InaTs; dT-Sup |
| 690 | UTRN-986 m02 | GCGCAGGACCGCTGG | UTRN | 5' | human | dGs; InaCs; dGs; InaCs; dAs; InaGs; dGs; InaAs; dCs; InaCs; dGs; InaCs; dTs; InaGs; dG-Sup |
| 691 | UTRN-987 m02 | AGGAGGGAGGGTGGG | UTRN | 5' | human | dAs; InaGs; dGs; InaAs; dGs; InaGs; dGs; InaAs; dGs; InaGs; dGs; InaTs; dGs; InaGs; dG-Sup |
| 692 | UTRN-988 m02 | CGCTGGAGGCGGAGG | UTRN | 5' | human | dCs; InaGs; dCs; InaTs; dGs; InaGs; dAs; InaGs; dGs; InaCs; dGs; InaGs; dAs; InaGs; dG-Sup |
| 693 | UTRN-192 m02 | TGGAGCCGAGCGCTG | UTRN | 5' | human | dTs; InaGs; dGs; InaAs; dGs; InaCs; dCs; InaGs; dAs; InaGs; dCs; InaGs; dCs; InaTs; dG-Sup |
| 694 | UTRN-303 m02 | CTGCCCCTTTGTTGG | UTRN | 5' | human | dCs; InaTs; dGs; InaCs; dCs; InaCs; dCs; InaTs; dTs; InaTs; dGs; InaTs; dTs; InaGs; dG-Sup |
| 695 | UTRN-991 m02 | CTCCCCGCTGCGGGC | UTRN | 5' | human | dCs; InaTs; dCs; InaCs; dCs; InaCs; dGs; InaCs; dTs; InaGs; dCs; InaGs; dGs; InaGs; dC-Sup |
| 696 | UTRN-992 m02 | CGGCTCCTCCTCCTC | UTRN | 5' | human | dCs; InaGs; dGs; InaCs; dTs; InaCs; dCs; InaTs; dCs; InaCs; |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| | | | | | | dTs; InaCs; dCs; InaTs; dC-Sup |
| 697 | UTRN-993 m02 | GGCTCGCTCCTTCGG | UTRN | 5' | human | dGs; InaGs; dCs; InaTs; dCs; InaGs; dCs; InaTs; dCs; InaCs; dTs; InaTs; dCs; InaGs; dG-Sup |
| 698 | UTRN-994 m02 | TTTGTGCGCGAGAGA | UTRN | 5' | human | dTs; InaTs; dTs; InaGs; dTs; InaGs; dCs; InaGs; dCs; InaGs; dAs; InaGs; dAs; InaGs; dA-Sup |
| 699 | UTRN-995 m02 | ACGACTCCACAACTT | UTRN | 5' | human | dAs; InaCs; dGs; InaAs; dCs; InaTs; dCs; InaCs; dAs; InaCs; dAs; InaAs; dCs; InaTs; dT-Sup |
| 700 | UTRN-997 m02 | GCCCGCTTCCCTGCT | UTRN | 5' | human | dGs; InaCs; dCs; InaCs; dGs; InaCs; dTs; InaTs; dCs; InaCs; dCs; InaTs; dGs; InaCs; dT-Sup |
| 701 | UTRN-662 m02 | CGGCCGGCTGCTGCT | UTRN | 5' | human | dCs; InaGs; dGs; InaCs; dCs; InaGs; dGs; InaCs; dTs; InaGs; dCs; InaTs; dGs; InaCs; dT-Sup |
| 702 | UTRN-999 m02 | GCGGGAGAAAGCCCG | UTRN | 5' | human | dGs; InaCs; dGs; InaGs; dGs; InaAs; dGs; InaAs; dAs; InaAs; dGs; InaCs; dCs; InaCs; dG-Sup |
| 703 | UTRN-1000 m02 | CCTCCTCGCCCCTCG | UTRN | 5' | human | dCs; InaCs; dTs; InaCs; dCs; InaTs; dCs; InaGs; dCs; InaCs; dCs; InaCs; dTs; InaCs; dG-Sup |
| 704 | UTRN-1001 m02 | AGAGGCTCCTCCTCG | UTRN | 5' | human | dAs; InaGs; dAs; InaGs; dGs; InaCs; dTs; InaCs; dCs; InaTs; dCs; InaCs; dTs; InaCs; dG-Sup |
| 705 | UTRN-1002 m02 | TCGGCTTCTGGAGCC | UTRN | 5' | human | dTs; InaCs; dGs; InaGs; dCs; InaTs; dTs; InaCs; dTs; InaGs; dGs; InaAs; dGs; InaCs; dC-Sup |
| 706 | UTRN-1003 m02 | CCGTGATTCCCCAAT | UTRN | 5' | human | dCs; InaCs; dGs; InaTs; dGs; InaAs; dTs; InaTs; dCs; InaCs; dCs; InaCs; dAs; InaAs; dT-Sup |
| 707 | UTRN-1004 m02 | AGGGGGGCGCCGCTC | UTRN | 5' | human | dAs; InaGs; dGs; InaGs; dGs; InaGs; dGs; InaCs; dGs; InaCs; dCs; InaGs; dCs; InaTs; dC-Sup |
| 708 | UTRN-323 m02 | AAATGACCCAAAAGA | UTRN | 5' | human | dAs; InaAs; dAs; InaTs; dGs; InaAs; dCs; InaCs; dCs; InaAs; dAs; InaAs; dAs; InaGs; dA-Sup |

TABLE 9-continued

Oligonucleotides designed to target 5' and 3' ends of RNAs

| SEQ ID NO | Oligo Name | Base Sequence | Gene Name | Target Region | Organism | Formatted Sequence |
|---|---|---|---|---|---|---|
| 709 | UTRN-328 m02 | GTTTTCCGTTTGCAG | UTRN | 5' | human | dGs; InaTs; dTs; InaTs; dTs; InaCs; dCs; InaGs; dTs; InaTs; dTs; InaGs; dCs; InaAs; dG-Sup |
| 710 | UTRN-334 m02 | CCAAACGCTACAGAG | UTRN | 5' | human | dCs; InaCs; dAs; InaAs; dAs; InaCs; dGs; InaCs; dTs; InaAs; dCs; InaAs; dGs; InaAs; dG-Sup |
| 711 | UTRN-1008 m02 | CAGGCACCAACTTTG | UTRN | 5' | human | dCs; InaAs; dGs; InaGs; dCs; InaAs; dCs; InaCs; dAs; InaAs; dCs; InaTs; dTs; InaTs; dG-Sup |
| 712 | UTRN-1009 m02 | CCTGGAAGGGCGCG | UTRN | 5' | human | dCs; InaCs; dTs; InaGs; dGs; InaAs; dAs; InaGs; dGs; InaGs; dGs; InaCs; dGs; InaCs; dG-Sup |
| 713 | UTRN-345 m02 | CAGTCAAAGCGCAAA | UTRN | 5' | human | dCs; InaAs; dGs; InaTs; dCs; InaAs; dAs; InaAs; dGs; InaCs; dGs; InaCs; dAs; InaAs; dA-Sup |
| 714 | UTRN-1011 m02 | CCAAAAACAAAACAG | UTRN | 5' | human | dCs; InaCs; dAs; InaAs; dAs; InaAs; dAs; InaCs; dAs; InaAs; dAs; InaAs; dCs; InaAs; dG-Sup |
| 715 | UTRN-674 m02 | TTCCGCCAAAAACAA | UTRN | 5' | human | dTs; InaTs; dCs; InaCs; dGs; InaCs; dCs; InaAs; dAs; InaAs; dAs; InaAs; dCs; InaAs; dA-Sup |
| 716 | UTRN-1013 m02 | GGAGGAGGGAGGGTG | UTRN | 5' | human | dGs; InaGs; dAs; InaGs; dGs; InaAs; dGs; InaGs; dGs; InaAs; dGs; InaGs; dGs; InaTs; dG-Sup |
| 717 | UTRN-1014 m02 | CGAGCGCTGGAGGCG | UTRN | 5' | human | dCs; InaGs; dAs; InaGs; dCs; InaGs; dCs; InaTs; dGs; InaGs; dAs; InaGs; dGs; InaCs; dG-Sup |
| 718 | UTRN-1015 m02 | CCTGCCCCTTTGTTG | UTRN | 5' | human | dCs; InaCs; dTs; InaGs; dCs; InaCs; dCs; InaCs; dTs; InaTs; dTs; InaGs; dTs; InaTs; dG-Sup |
| 719 | UTRN-1016 m02 | GGCGGCTCCTCCTCC | UTRN | 5' | human | dGs; InaGs; dCs; InaGs; dGs; InaCs; dTs; InaCs; dCs; InaTs; dCs; InaCs; dTs; InaCs; dC-Sup |

Table 10 provides further exemplary non-coding RNA 5' and 3' end targeting oligos.

TABLE 10

Oligonucleotides designed to target 5' and 3' ends of non-coding RNAs

| SEQ ID NO | Oligo Name | Base Sequence | Gene Name | Target Region | Organism | Formatted Sequence |
|---|---|---|---|---|---|---|
| 720 | DINO-1 m02 | TAGACACTTCCAGAA | DINO | 3' | human | dTs; InaAs; dGs; InaAs; dCs; InaAs; dCs; InaTs; dTs; InaCs; dCs; InaAs; dGs; InaAs; dA-Sup |
| 721 | DINO-2 m02 | TTCCAGAATTGTCCT | DINO | 3' | human | dTs; InaTs; dCs; InaCs; dAs; InaGs; dAs; InaAs; dTs; InaTs; dGs; InaTs; dCs; InaCs; dT-Sup |
| 722 | DINO-3 m02 | CAGAATTGTCCTTTA | DINO | 3' | human | dCs; InaAs; dGs; InaAs; dAs; InaTs; dTs; InaGs; dTs; InaCs; dCs; InaTs; dTs; InaTs; dA-Sup |
| 723 | DINO-4 m02 | CTGCTGGAACTCGGC | DINO | 5' | human | dCs; InaTs; dGs; InaCs; dTs; InaGs; dGs; InaAs; dAs; InaCs; dTs; InaCs; dGs; InaGs; dC-Sup |
| 724 | DINO-5 m02 | GGCCAGGCTCAGCTG | DINO | 5' | human | dGs; InaGs; dCs; InaCs; dAs; InaGs; dGs; InaCs; dTs; InaCs; dAs; InaGs; dCs; InaTs; dG-Sup |
| 725 | DINO-6 m02 | GCAGCCAGGAGCCTG | DINO | 5' | human | dGs; InaCs; dAs; InaGs; dCs; InaCs; dAs; InaGs; dGs; InaAs; dGs; InaCs; dCs; InaTs; dG-Sup |
| 726 | DINO-7 m02 | ACTCGGCCAGGCTCA | DINO | 5' | human | dAs; InaCs; dTs; InaCs; dGs; InaGs; dCs; InaCs; dAs; InaGs; dGs; InaCs; dTs; InaCs; dA-Sup |
| 727 | DINO-8 m02 | GCTGGCCTGCTGGAA | DINO | 5' | human | dGs; InaCs; dTs; InaGs; dGs; InaCs; dCs; InaTs; dGs; InaCs; dTs; InaGs; dGs; InaAs; dA-Sup |
| 728 | HOTTIP-1 m02 | TTTAAATTGTATCGG | HOTTIP | 3' | human | dTs; InaTs; dTs; InaAs; dAs; InaAs; dTs; InaTs; dGs; InaTs; dAs; InaTs; dCs; InaGs; dG-Sup |
| 729 | HOTTIP-2 m02 | ATTGTATCGGGCAAA | HOTTIP | 3' | human | dAs; InaTs; dTs; InaGs; dTs; InaAs; dTs; InaCs; dGs; InaGs; dGs; InaCs; dAs; InaAs; dA-Sup |
| 730 | HOTTIP-3 m02 | GATTAAAACAAAAGA | HOTTIP | 3' | human | dGs; InaAs; dTs; InaTs; dAs; InaAs; dAs; InaAs; dCs; InaAs; dAs; InaAs; dAs; InaGs; dA-Sup |
| 731 | HOTTIP-4 m02 | AAAACAAAAGAAACC | HOTTIP | 3' | human | dAs; InaAs; dAs; InaAs; dCs; InaAs; dAs; InaAs; dAs; InaGs; dAs; InaAs; dAs; InaCs; dC-Sup |
| 732 | HOTTIP-5 m02 | GGGATAAAGGAAGGG | HOTTIP | 5' | human | dGs; InaGs; dGs; InaAs; dTs; InaAs; dAs; InaAs; dGs; InaGs; dAs; |

TABLE 10-continued

Oligonucleotides designed to target 5' and 3' ends of non-coding RNAs

| SEQ ID NO | Oligo Name | Base Sequence | Gene Name | Target Region | Organism | Formatted Sequence |
|---|---|---|---|---|---|---|
| | | | | | | InaAs; dGs; InaGs; dG-Sup |
| 733 | HOTTIP-6 m02 | CACTGGGATAAAGGA | HOTTIP | 5' | human | dCs; InaAs; dCs; InaTs; dGs; InaAs; dGs; InaAs; dTs; InaAs; dAs; InaAs; dGs; InaGs; dA-Sup |
| 734 | HOTTIP-7 m02 | GAGCCGCCCGCTTTG | HOTTIP | 5' | human | dGs; InaAs; dGs; InaCs; dCs; InaAs; dCs; InaCs; dCs; InaGs; dCs; InaTs; dTs; InaTs; dG-Sup |
| 735 | HOTTIP-8 m02 | TCTGGGCCCCACTG | HOTTIP | 5' | human | dTs; InaCs; dTs; InaGs; dGs; InaGs; dCs; InaCs; dCs; InaCs; dAs; InaCs; dTs; InaG-Sup |
| 736 | NEST-1 m02 | CAAAAGGTCTTAGCT | NEST | 3' | human | dCs; InaAs; dAs; InaAs; dAs; InaGs; dGs; InaTs; dCs; InaTs; dTs; InaAs; dGs; InaCs; dT-Sup |
| 737 | NEST-2 m02 | TAGCTATTATTACTG | NEST | 3' | human | dTs; InaAs; dGs; InaCs; dTs; InaAs; dTs; InaTs; dAs; InaTs; dTs; InaAs; dCs; InaTs; dG-Sup |
| 738 | NEST-3 m02 | ACTGTTGTTGTTTTA | NEST | 3' | human | dAs; InaCs; dTs; InaGs; dTs; InaTs; dGs; InaTs; dTs; InaGs; dTs; InaTs; dTs; InaTs; dA-Sup |
| 739 | NEST-4 m02 | ACCTTAGAGGTTGTA | NEST | 3' | human | dAs; InaCs; dCs; InaTs; dTs; InaAs; dGs; InaAs; dGs; InaGs; dTs; InaTs; dGs; InaTs; dA-Sup |
| 740 | NEST-5 m02 | TACCTGAAATTGCAG | NEST | 5' | human | dTs; InaAs; dCs; InaCs; dTs; InaGs; dAs; InaAs; dAs; InaTs; dTs; InaGs; dCs; InaAs; dG-Sup |
| 741 | NEST-6 m02 | GTCAGAAAAGCTACC | NEST | 5' | human | dGs; InaTs; dCs; InaAs; dGs; InaAs; dAs; InaAs; dAs; InaGs; dCs; InaTs; dAs; InaCs; dC-Sup |
| 742 | NEST-7 m02 | CACGCTTGGTGTGCA | NEST | 5' | human | dCs; InaAs; dCs; InaGs; dCs; InaTs; dTs; InaGs; dGs; InaTs; dGs; InaTs; dGs; InaCs; dA-Sup |
| 743 | NEST-8 m02 | CTGTGAATGTGTGAA | NEST | 5' | human | dCs; InaTs; dGs; InaTs; dGs; InaAs; dAs; InaTs; dGs; InaTs; dGs; InaTs; dGs; InaAs; dA-Sup |
| 744 | NEST-9 m02 | AACAGGAAGCACCTG | NEST | 5' | human | dAs; InaAs; dCs; InaAs; dGs; InaGs; dAs; InaAs; dGs; InaCs; dAs; InaCs; dCs; InaTs; dG-Sup |

TABLE 11

Sequences for FXN-434 and FXN-436

| SEQ ID NO | Oligo Name | Base Sequence | Gene Name | Target Region | Organism | Formatted Sequence |
|---|---|---|---|---|---|---|
| 745 | FXN-434 m02 | CGCTCCGCCCTCCAGTTT TTTTTTAGGAGGCAACA CATT | FXN | 5' and 3' | human | dCs; InaGs; dCs; InaTs; dCs; InaCs; dGs; InaCs; dCs; InaCs; dTs; InaCs; dCs; InaAs; dG; dT; dT; dT; dT; dTs; InaTs; dTs; InaTs; dTs; InaAs; dGs; InaGs; dAs; InaGs; dGs; InaCs; dAs; InaAs; dCs; InaAs; dCs; InaAs; dTs; InaT-Sup |
| 746 | FXN-436 m02 | CGCTCCGCCCTCCAGCC TTTTTTTTTAGGAGGCA ACACATT | FXN | 5' and 3' | human | dCs; InaGs; dCs; InaTs; dCs; InaCs; dGs; InaCs; dCs; InaCs; dTs; InaCs; dCs; InaAs; dGs; InaCs; dC; dT; dT; dT; dT; dTs; InaTs; dTs; InaTs; dTs; InaAs; dGs; InaGs; dAs; InaGs; dGs; InaCs; dAs; InaAs; dCs; InaAs; dCs; InaAs; dTs; InaT-Sup |

TABLE 12

Oligonucleotides targeting 5' and 3' ends of FXN, APOA1, THRB, HAMP and NR1H4

| Oligo Name | Gene | Organism | SEQ ID NO. | Base Sequence | Formatted Sequence |
|---|---|---|---|---|---|
| THRB-67 m01 | THRB | human | 747 | CTGTTATAAGCTTTT | InaCs; omeUs; InaGs; omeUs; InaTs; omeAs; InaTs; omeAs; InaAs; omeGs; InaCs; omeUs; InaTs; omeUs; InaT-Sup |
| THRB-68 m01 | THRB | human | 748 | GTTATAAGCTTTTTC | InaGs; omeUs; InaTs; omeAs; InaTs; omeAs; InaAs; omeGs; InaCs; omeUs; InaTs; omeUs; InaTs; omeUs; InaC-Sup |
| THRB-69 m01 | THRB | human | 749 | TATCTGTTATAAGCT | InaTs; omeAs; InaTs; omeCs; InaTs; omeGs; InaTs; omeUs; InaAs; omeUs; InaAs; omeAs; InaGs; omeCs; InaT-Sup |
| THRB-70 m01 | THRB | human | 750 | AGTAGATGTTTATTT | InaAs; omeGs; InaTs; omeAs; InaGs; omeAs; InaTs; omeGs; InaTs; omeUs; InaTs; omeAs; InaTs; omeUs; InaT-Sup |
| THRB-71 m01 | THRB | human | 751 | TAGGCAAAGGAATAG | InaTs; omeAs; InaGs; omeGs; InaCs; omeAs; InaAs; omeAs; InaGs; omeGs; InaAs; omeAs; InaTs; omeAs; InaG-Sup |
| THRB-72 m01 | THRB | human | 752 | GGTAGGCAAAGGAAT | InaGs; omeGs; InaTs; omeAs; InaGs; omeGs; InaCs; omeAs; InaAs; omeAs; InaGs; omeGs; InaAs; omeAs; InaT-Sup |
| THRB-73 m01 | THRB | human | 753 | GGCAAAGGAATAGTT | InaGs; omeGs; InaCs; omeAs; InaAs; omeAs; InaGs; omeGs; InaAs; omeAs; InaTs; omeAs; InaGs; omeUs; InaT-Sup |
| THRB-74 m01 | THRB | human | 754 | GAAATGACACCCAGT | InaGs; omeAs; InaAs; omeAs; InaTs; omeGs; InaAs; omeCs; InaAs; omeCs; InaCs; omeCs; InaAs; omeGs; InaT-Sup |
| THRB-75 m01 | THRB | human | 755 | AAATGACACCCAGTA | InaAs; omeAs; InaAs; omeUs; InaGs; omeAs; InaCs; omeAs; InaCs; omeCs; InaCs; omeAs; InaGs; omeUs; InaA-Sup |
| THRB-76 m01 | THRB | human | 756 | GGCAATGGAATGAAA | InaGs; omeGs; InaCs; omeAs; InaAs; omeUs; InaGs; omeGs; InaAs; omeAs; InaTs; omeGs; InaAs; omeAs; InaA-Sup |

TABLE 12-continued

Oligonucleotides targeting 5' and 3' ends of FXN, APOA1, THRB, HAMP and NR1H4

| Oligo Name | Gene | Organism | SEQ ID NO. | Base Sequence | Formatted Sequence |
|---|---|---|---|---|---|
| THRB-77 m01 | THRB | human | 757 | CAATGGAATGAAATG | InaCs; omeAs; InaAs; omeUs; InaGs; omeGs; InaAs; omeAs; InaTs; omeGs; InaAs; omeAs; InaAs; omeUs; InaG-Sup |
| THRB-78 m01 | THRB | human | 758 | ATGGAATGAAATGAC | InaAs; omeUs; InaGs; omeGs; InaAs; omeAs; InaTs; omeGs; InaAs; omeAs; InaAs; omeUs; InaGs; omeAs; InaC-Sup |
| THRB-79 m01 | THRB | human | 759 | GTTTCAAGTACCCGC | InaGs; omeUs; InaTs; omeUs; InaCs; omeAs; InaAs; omeGs; InaTs; omeAs; InaCs; omeCs; InaCs; omeGs; InaC-Sup |
| THRB-80 m01 | THRB | human | 760 | GACCGGAGAACGAAA | InaGs; omeAs; InaCs; omeCs; InaGs; omeGs; InaAs; omeGs; InaAs; omeAs; InaCs; omeGs; InaAs; omeAs; InaA-Sup |
| THRB-81 m01 | THRB | human | 761 | CTTTGGAAGGTGTTT | InaCs; omeUs; InaTs; omeUs; InaGs; omeGs; InaAs; omeAs; InaGs; omeGs; InaTs; omeGs; InaTs; omeUs; InaT-Sup |
| THRB-82 m01 | THRB | human | 762 | TTTCTTTGGAAGGTG | InaTs; omeUs; InaTs; omeCs; InaTs; omeUs; InaTs; omeGs; InaGs; omeAs; InaAs; omeGs; InaGs; omeUs; InaG-Sup |
| THRB-83 m01 | THRB | human | 763 | AGTTAATCCCCGCCG | InaAs; omeGs; InaTs; omeUs; InaAs; omeAs; InaTs; omeCs; InaCs; omeCs; InaCs; omeGs; InaCs; omeCs; InaG-Sup |
| THRB-84 m01 | THRB | human | 764 | TCCTGCAAAATGTCA | InaTs; omeCs; InaCs; omeUs; InaGs; omeCs; InaAs; omeAs; InaAs; omeAs; InaTs; omeGs; InaTs; omeCs; InaA-Sup |
| THRB-85 m01 | THRB | human | 765 | CCCCGCAGTCTCCAC | InaCs; omeCs; InaCs; omeCs; InaGs; omeCs; InaAs; omeGs; InaTs; omeCs; InaTs; omeCs; InaCs; omeAs; InaC-Sup |
| THRB-86 m01 | THRB | human | 766 | TCTCCACCCTCCTCC | InaTs; omeCs; InaTs; omeCs; InaCs; omeAs; InaCs; omeCs; InaCs; omeUs; InaCs; omeCs; InaTs; omeCs; InaC-Sup |
| THRB-87 m01 | THRB | human | 767 | GAGCGCCGGCGACTG | InaGs; omeAs; InaGs; omeCs; InaGs; omeCs; InaCs; omeGs; InaGs; omeCs; InaGs; omeAs; InaCs; omeUs; InaG-Sup |
| THRB-88 m01 | THRB | human | 768 | AGGATGTGCGCCTTC | InaAs; omeGs; InaGs; omeAs; InaTs; omeGs; InaTs; omeGs; InaCs; omeGs; InaCs; omeCs; InaTs; omeUs; InaC-Sup |
| THRB-89 m01 | THRB | human | 769 | GGCGCAGCGAGGAA | InaGs; omeGs; InaCs; omeGs; InaCs; omeAs; InaGs; omeCs; InaGs; omeAs; InaGs; omeGs; InaAs; InaA-Sup |
| THRB-90 m01 | THRB | human | 770 | TTTCACTGACATCTC | InaTs; omeUs; InaTs; omeCs; InaAs; omeCs; InaTs; omeGs; InaAs; omeCs; InaAs; omeUs; InaCs; omeUs; InaC-Sup |
| HAMP 01 m01 | HAMP | human | 771 | GGTGGTCTGAGCCCC | InaGs; omeGs; InaTs; omeGs; InaGs; omeUs; InaCs; omeUs; InaGs; omeAs; InaGs; omeCs; InaCs; omeCs; InaC-Sup |
| HAMP 02 m01 | HAMP | human | 772 | GGGCCTGCCAGGGGA | InaGs; omeGs; InaGs; omeCs; InaCs; omeUs; InaGs; omeCs; InaCs; omeAs; InaGs; omeGs; InaGs; omeGs; InaA-Sup |
| HAMP-03 m01 | HAMP | human | 773 | ACCGAGTGACAGTCG | InaAs; omeCs; InaCs; omeGs; InaAs; omeGs; InaTs; omeGs; InaAs; omeCs; InaAs; omeGs; InaTs; omeCs; InaG-Sup |
| HAMP-04 m01 | HAMP | human | 774 | GTCTGGGACCGAGTG | InaGs; omeUs; InaCs; omeUs; InaGs; omeGs; InaGs; omeAs; InaCs; omeCs; InaGs; omeAs; InaGs; omeUs; InaG-Sup |

TABLE 12-continued

Oligonucleotides targeting 5' and 3' ends of FXN, APOA1, THRB, HAMP and NR1H4

| Oligo Name | Gene | Organism | SEQ ID NO. | Base Sequence | Formatted Sequence |
|---|---|---|---|---|---|
| HAMP-05 m01 | HAMP | human | 775 | TGGGACCGAGTGACA | InaTs; omeGs; InaGs; omeGs; InaAs; omeCs; InaCs; omeGs; InaAs; omeGs; InaTs; omeGs; InaAs; omeCs; InaA-Sup |
| HAMP-06 m01 | HAMP | human | 776 | GCAGAGGTGTGTTCA | InaGs; omeCs; InaAs; omeGs; InaAs; omeGs; InaGs; omeGs; InaGs; omeUs; InaGs; omeUs; InaTs; omeCs; InaA-Sup |
| HAMP-07 m01 | HAMP | human | 777 | CGGCAGAGGTGTGTT | InaCs; omeGs; InaGs; omeCs; InaAs; omeGs; InaAs; omeGs; InaGs; omeUs; InaGs; omeUs; InaGs; omeUs; InaT-Sup |
| HAMP-08 m01 | HAMP | human | 778 | GGGCAGACGGGGTCA | InaGs; omeGs; InaGs; omeCs; InaAs; omeGs; InaAs; omeCs; InaGs; omeGs; InaGs; omeGs; InaTs; omeCs; InaA-Sup |
| HAMP-09 m01 | HAMP | human | 779 | CTCTGGTTTGGAAAA | InaCs; omeUs; InaCs; omeUs; InaGs; omeGs; InaTs; omeUs; InaTs; omeGs; InaGs; omeAs; InaAs; omeCs; InaA-Sup |
| HAMP-10 m01 | HAMP | human | 780 | CTGGTTTGGAAAACA | InaCs; omeUs; InaGs; omeGs; InaTs; omeUs; InaTs; omeUs; InaGs; omeAs; InaAs; omeAs; InaCs; InaA-Sup |
| HAMP-11 m01 | HAMP | human | 781 | GTTTGGAAAACAAAA | InaGs; omeUs; InaTs; omeUs; InaGs; omeGs; InaAs; omeAs; InaAs; omeAs; InaCs; omeAs; InaAs; omeAs; InaA-Sup |
| HAMP-12 m01 | HAMP | human | 782 | GGAAAACAAAGAAC | InaGs; omeGs; InaAs; omeAs; InaAs; omeAs; InaCs; omeAs; InaAs; omeAs; InaAs; omeGs; InaAs; omeAs; InaC-Sup |
| HAMP-13 m01 | HAMP | human | 783 | GAAAACAAAGAACC | InaGs; omeAs; InaAs; omeAs; InaAs; omeCs; InaAs; omeAs; InaAs; omeGs; InaAs; omeAs; InaAs; omeCs; InaC-Sup |
| HAMP-14 m01 | HAMP | human | 784 | TTTGGAAAACAAAG | InaTs; omeUs; InaTs; omeGs; InaGs; omeAs; InaAs; omeAs; InaAs; omeCs; InaAs; omeAs; InaAs; omeGs; InaG-Sup |
| HAMP-15 m01 | HAMP | human | 785 | TGGAAAACAAAAGAA | InaTs; omeGs; InaGs; omeAs; InaAs; omeAs; InaAs; omeCs; InaAs; omeAs; InaAs; omeGs; InaAs; omeAs; InaA-Sup |
| HAMP-16 m01 | HAMP | human | 786 | TCTGGGGCAGCAGGA | InaTs; omeCs; InaTs; omeGs; InaGs; omeGs; InaGs; omeCs; InaGs; omeCs; InaGs; omeGs; InaGs; omeGs; InaA-Sup |
| NR1H4-01 m01 | NR1H4 | human | 787 | ATAGAAAGGAACCTT | InaAs; omeUs; InaAs; omeGs; InaAs; omeAs; InaAs; omeGs; InaGs; omeAs; InaAs; omeCs; InaCs; omeUs; InaT-Sup |
| NR1H4-02 m01 | NR1H4 | human | 788 | TAGAAAGGAACCTTG | InaTs; omeAs; InaGs; omeAs; InaAs; omeAs; InaGs; omeGs; InaAs; omeAs; InaCs; omeCs; InaTs; omeUs; InaG-Sup |
| NR1H4-03 m01 | NR1H4 | human | 789 | ATTAACAATCCTTCC | InaAs; omeUs; InaTs; omeAs; InaAs; omeCs; InaAs; omeAs; InaTs; omeCs; InaCs; omeUs; InaTs; omeCs; InaC-Sup |
| NR1H4-04 m01 | NR1H4 | human | 790 | CTTCCCTGCTAAATG | InaCs; omeUs; InaTs; omeCs; InaCs; omeCs; InaTs; omeGs; InaCs; omeUs; InaAs; omeAs; InaAs; omeUs; InaG-Sup |
| NR1H4-05 m01 | NR1H4 | human | 791 | CCCTGCTAAATGATA | InaCs; omeCs; InaCs; omeUs; InaGs; omeCs; InaTs; omeAs; InaAs; omeAs; InaTs; omeGs; InaAs; omeUs; InaA-Sup |
| NR1H4-06 m01 | NR1H4 | human | 792 | TGATATAAACATAGA | InaTs; omeGs; InaAs; omeUs; InaAs; omeUs; InaAs; omeAs; omeCs; InaAs; omeUs; InaAs; omeGs; InaA-Sup |

TABLE 12-continued

Oligonucleotides targeting 5' and 3' ends of FXN, APOA1, THRB, HAMP and NR1H4

| Oligo Name | Gene Organism | SEQ ID NO. | Base Sequence | Formatted Sequence |
|---|---|---|---|---|
| NR1H4-07 m01 | NR1H4human | 793 | TCCCCGGGACTGAAC | InaTs; omeCs; InaCs; omeCs; InaCs; omeGs; InaGs; omeCs; InaAs; omeCs; InaTs; omeGs; InaAs; omeAs; InaC-Sup |
| NR1H4-08 m01 | NR1H4human | 794 | TACAACTTCTTTGAAT | InaTs; omeAs; InaCs; omeAs; InaAs; omeCs; InaTs; omeUs; InaCs; omeUs; InaTs; omeUs; InaGs; omeAs; InaAs; InaT-Sup |
| NR1H4-09 m01 | NR1H4human | 795 | TCTATCACTTCCCCG | InaTs; omeCs; InaTs; omeAs; InaTs; omeCs; InaAs; omeCs; InaTs; omeUs; InaCs; omeCs; InaCs; omeCs; InaG-Sup |
| NR1H4-10 m01 | NR1H4human | 796 | TCCTGGGCACCCGTA | InaTs; omeCs; InaCs; omeUs; InaGs; omeGs; InaGs; omeCs; InaAs; omeCs; InaCs; omeCs; InaGs; omeUs; InaA-Sup |
| NR1H4-11 m01 | NR1H4human | 797 | TTTCTGTACACATCA | InaTs; omeUs; InaTs; omeCs; InaTs; omeGs; InaTs; omeAs; InaCs; omeAs; InaCs; omeAs; InaTs; omeCs; InaA-Sup |
| NR1H4-12 m01 | NR1H4human | 798 | ACAGCCACTGAAAAT | InaAs; omeCs; InaAs; omeGs; InaCs; omeCs; InaAs; omeCs; InaTs; omeGs; InaAs; omeAs; InaAs; omeAs; InaT-Sup |
| NR1H4-13 m01 | NR1H4human | 799 | TTCACAGCCACTGAA | InaTs; omeUs; InaCs; omeAs; InaCs; omeAs; InaGs; omeCs; InaCs; omeAs; InaCs; omeUs; InaGs; omeAs; InaA-Sup |
| NR1H4-14 m01 | NR1H4human | 800 | TAAAGAAATGAGTTT | InaTs; omeAs; InaAs; omeGs; InaAs; omeAs; InaAs; omeAs; InaTs; omeGs; InaAs; omeGs; InaTs; omeUs; InaT-Sup |
| NR1H4-15 m01 | NR1H4human | 801 | ACATTTAAAGAAATG | InaAs; omeCs; InaAs; omeUs; InaTs; omeUs; InaAs; omeAs; InaAs; omeGs; InaAs; omeAs; InaAs; omeUs; InaG-Sup |
| NR1H4-16 m01 | NR1H4human | 802 | AAGAAATGAGTTTGT | InaAs; omeAs; InaGs; omeAs; InaAs; omeAs; InaTs; omeGs; InaAs; omeGs; InaTs; omeUs; InaTs; omeGs; InaT-Sup |
| NR1H4-17 m01 | NR1H4human | 803 | TGCCATTATGTTTGC | InaTs; omeGs; InaCs; omeCs; InaAs; omeUs; InaTs; omeAs; InaTs; omeGs; InaTs; omeUs; InaTs; omeGs; InaC-Sup |
| NR1H4-18 m01 | NR1H4human | 804 | TCCTGTTGCCATTAT | InaTs; omeCs; InaCs; omeUs; InaGs; omeUs; InaTs; omeGs; InaCs; omeCs; InaAs; omeUs; InaTs; omeAs; InaT-Sup |
| NR1H4-19 m01 | NR1H4human | 805 | GAAAATCCTGTTGCC | InaGs; omeAs; InaAs; omeAs; InaAs; omeUs; InaCs; omeCs; InaTs; omeGs; InaTs; omeUs; InaGs; omeCs; InaC-Sup |
| NR1H4-20 m01 | NR1H4human | 806 | CTGTTGCCATTATGT | InaCs; omeUs; InaGs; omeUs; InaTs; omeGs; InaCs; omeCs; InaAs; omeUs; InaTs; omeAs; InaTs; omeGs; InaT-Sup |
| NR1H4-21 m01 | NR1H4human | 807 | TAGAATTGAAGTAAC | InaTs; omeAs; InaGs; omeAs; InaAs; omeUs; InaTs; omeGs; InaAs; omeAs; InaGs; omeUs; InaAs; omeAs; InaC-Sup |
| NR1H4-22 m01 | NR1H4human | 808 | TGAAGTAACAATCAA | InaTs; omeGs; InaAs; omeAs; InaGs; omeUs; InaAs; omeAs; InaCs; omeAs; InaAs; omeUs; InaCs; omeAs; InaA-Sup |
| NR1H4-23 m01 | NR1H4human | 809 | AAGTAACAATCAATT | InaAs; omeAs; InaGs; omeUs; InaAs; omeAs; InaCs; omeAs; InaAs; omeUs; InaCs; omeAs; InaAs; omeUs; InaT-Sup |
| NR1H4-24 m01 | NR1H4human | 810 | TCATCAAGATTTCTT | InaTs; omeCs; InaAs; omeUs; InaCs; omeAs; InaAs; omeGs; InaAs; omeUs; InaTs; omeUs; InaCs; omeUs; InaT-Sup |

TABLE 12-continued

Oligonucleotides targeting 5' and 3' ends of FXN, APOA1, THRB, HAMP and NR1H4

| Oligo Name | Gene | Organism | SEQ ID NO. | Base Sequence | Formatted Sequence |
|---|---|---|---|---|---|
| NR1H4-25 m01 | NR1H4 | human | 811 | TATCTAGCCCAATAT | InaTs; omeAs; InaTs; omeCs; InaTs; omeAs; InaGs; omeCs; InaCs; omeCs; InaAs; omeAs; InaTs; omeAs; InaT-Sup |
| NR1H4-26 m01 | NR1H4 | human | 812 | TTCTATCTAGCCCAA | InaTs; omeUs; InaTs; omeUs; InaAs; omeUs; InaCs; omeUs; InaAs; omeGs; InaCs; omeCs; InaCs; omeAs; InaA-Sup |
| FXN-837 m1000 | FXN | human | 813 | CTCCGCCCTCCAGTTT TTATTATTTTGCTTTTT | InaCs; omeUs; omeCs; omeCs; InaGs; omeCs; omeCs; omeCs; InaTs; omeCs; omeCs; omeAs; InaGs; omeUs; omeUs; omeUs; InaTs; omeUs; omeAs; omeUs; InaTs; omeAs; omeUs; omeUs; InaTs; omeUs; omeGs; omeCs; InaTs; omeUs; omeUs; omeUs; InaT-Sup |
| FXN-838 m1000 | FXN | human | 814 | CCGCCCTCCAGTTTTT ATTATTTTGCTTTTT | InaCs; omeCs; omeGs; omeCs; InaCs; omeCs; omeCs; InaCs; omeAs; omeGs; omeUs; InaTs; omeUs; omeUs; omeUs; InaAs; omeUs; omeUs; omeAs; InaTs; omeUs; omeUs; omeUs; InaGs; omeCs; omeUs; omeUs; InaTs; omeUs; InaT-Sup |
| FXN-839 m1000 | FXN | human | 815 | GCCCTCCAGTTTTTAT TATTTTGCTTTTT | InaGs; omeCs; omeCs; omeCs; InaTs; omeCs; omeCs; omeAs; InaGs; omeUs; omeUs; omeUs; InaTs; omeUs; omeAs; omeUs; InaTs; omeAs; omeUs; omeUs; InaTs; omeUs; omeGs; omeCs; InaTs; omeUs; omeUs; omeUs; InaT-Sup |
| FXN-840 m1000 | FXN | human | 816 | CGCTCCGCCCTCCAGT TTTTATTATTTTGCTTT | InaCs; omeGs; omeCs; omeUs; InaCs; omeCs; omeGs; omeCs; InaCs; omeCs; omeUs; omeCs; InaCs; omeAs; omeGs; omeUs; InaTs; omeUs; omeUs; omeUs; InaAs; omeUs; omeUs; omeAs; InaTs; omeUs; omeUs; omeUs; InaGs; omeCs; omeUs; omeUs; InaT-Sup |
| FXN-841 m1000 | FXN | human | 817 | CGCTCCGCCCTCCAGT TTTTATTATTTTGCT | InaCs; omeGs; omeCs; omeUs; InaCs; omeCs; omeGs; omeCs; InaCs; omeCs; omeUs; omeCs; InaCs; omeAs; omeGs; omeUs; InaTs; omeUs; omeUs; omeUs; InaAs; omeUs; omeUs; omeAs; InaTs; omeUs; omeUs; omeGs; omeCs; InaT-Sup |
| FXN-842 m1000 | FXN | human | 818 | CGCTCCGCCCTCCAGT TTTTATTATTTTG | InaCs; omeGs; omeCs; omeUs; InaCs; omeCs; omeGs; omeCs; omeCs; InaCs; omeCs; omeUs; omeCs; InaCs; omeAs; omeGs; omeUs; InaTs; omeUs; omeUs; omeUs; InaAs; omeUs; omeUs; omeAs; InaTs; omeUs; omeUs; omeUs; InaG-Sup |
| FXN-843 m1000 | FXN | human | 819 | CTCCGCCCTCCAGTTT TTATTATTTTGCTTT | InaCs; omeUs; omeCs; omeCs; InaGs; omeCs; omeCs; omeCs; InaTs; omeCs; omeCs; omeAs; InaGs; omeUs; omeUs; omeUs; InaTs; omeUs; omeAs; InaTs; omeAs; omeUs; omeUs; InaTs; omeUs; omeGs; omeCs; InaTs; omeUs; InaT-Sup |
| FXN-844 m1000 | FXN | human | 820 | CCGCCCTCCAGTTTTT ATTATTTGCT | InaCs; omeCs; omeGs; InaCs; omeCs; omeCs; InaTs; omeCs; omeCs; InaAs; omeGs; omeUs; InaTs; omeUs; omeUs; InaTs; omeAs; omeUs; InaTs; omeAs; omeUs; InaTs; omeUs; omeUs; InaGs; omeCs; InaT-Sup |
| FXN-845 m1000 | FXN | human | 821 | GCCCTCCAGTTTTTAT TATTTGCT | InaGs; omeCs; omeCs; InaCs; omeUs; omeCs; InaCs; omeAs; omeGs; InaTs; omeUs; omeUs; InaTs; omeUs; omeAs; InaTs; omeUs; InaTs; omeUs; omeAs; InaTs; omeUs; InaTs; omeGs; omeCs; InaT-Sup |
| FXN-846 | FXN | human | 822 | CCCTCCAGTTTTTATT TTTGC | InaCs; omeCs; omeCs; InaTs; omeCs; omeCs; InaAs; omeGs; omeUs; InaTs; omeUs; |

TABLE 12-continued

Oligonucleotides targeting 5' and 3' ends of FXN, APOA1, THRB, HAMP and NR1H4

| Oligo Name | Gene | Organism | SEQ ID NO. | Base Sequence | Formatted Sequence |
|---|---|---|---|---|---|
| m1000 | | | | | omeUs; InaTs; omeAs; omeUs; InaTs; omeAs; omeUs; InaTs; omeUs; omeUs; InaGs; InaC-Sup |
| FXN-847 m1000 | FXN | human | 823 | CCTCCAGTTTTTATTAT TTTG | InaCs; omeCs; omeUs; InaCs; omeCs; omeAs; InaGs; omeUs; omeUs; InaTs; omeUs; omeUs; InaAs; omeGs; omeAs; InaAs; omeUs; omeUs; InaTs; omeUs; InaG-Sup |
| FXN-848 m1000 | FXN | human | 824 | GCTCCGCCCTCCAGAT TATTTTGCTTTTT | InaGs; omeCs; omeUs; InaCs; omeCs; omeGs; omeCs; omeCs; InaCs; omeUs; omeCs; omeCs; InaAs; omeGs; omeAs; omeUs; InaTs; omeAs; omeUs; omeUs; InaTs; omeUs; omeGs; omeCs; InaTs; omeUs; omeUs; omeUs; InaT-Sup |
| FXN-849 m1000 | FXN | human | 825 | TCCGCCCTCCAGATTA TTTTGCTTTTT | InaTs; omeCs; omeCs; InaGs; omeCs; omeCs; InaCs; omeUs; omeCs; InaCs; omeAs; omeGs; InaAs; omeUs; omeUs; InaAs; omeUs; omeUs; InaTs; omeUs; omeGs; InaCs; omeUs; omeUs; InaTs; omeUs; InaT-Sup |
| FXN-850 m1000 | FXN | human | 826 | CGCCCTCCAGATTATT TTGCTTTTT | InaCs; omeGs; omeCs; InaCs; omeCs; omeUs; InaCs; omeCs; omeAs; InaGs; omeAs; omeUs; InaTs; omeAs; omeUs; InaTs; omeUs; omeUs; InaGs; omeCs; omeUs; InaTs; omeUs; omeUs; InaT-Sup |
| FXN-851 m1000 | FXN | human | 827 | CCCTCCAGATTATTTT GCTTTTT | InaCs; omeCs; omeCs; InaTs; omeCs; omeCs; InaAs; omeGs; omeAs; InaTs; omeUs; omeAs; InaTs; omeUs; omeUs; InaTs; omeGs; omeCs; InaTs; omeUs; omeUs; InaTs; InaT-Sup |
| FXN-852 m1000 | FXN | human | 828 | GCTCCGCCCTCCAGAT TATTTTGCTTT | InaGs; omeCs; omeUs; InaCs; omeCs; omeGs; InaCs; omeCs; omeCs; InaTs; omeCs; omeCs; InaAs; omeGs; omeAs; InaTs; omeUs; omeAs; InaTs; omeUs; omeUs; InaTs; omeGs; omeCs; InaTs; omeUs; InaT-Sup |
| FXN-853 m1000 | FXN | human | 829 | GCTCCGCCCTCCAGAT TATTTTGCT | InaGs; omeCs; omeUs; InaCs; omeCs; omeGs; InaCs; omeCs; omeCs; InaTs; omeCs; omeCs; InaAs; omeGs; omeAs; InaTs; omeUs; omeAs; InaTs; omeUs; omeUs; InaTs; omeGs; omeCs; InaT-Sup |
| FXN-854 m1000 | FXN | human | 830 | GCTCCGCCCTCCAGAT TATTTTG | InaGs; omeCs; omeUs; InaCs; omeCs; omeGs; InaCs; omeCs; omeCs; InaTs; omeCs; omeCs; InaAs; omeGs; omeAs; InaTs; omeUs; omeAs; InaTs; omeUs; omeUs; InaTs; InaG-Sup |
| FXN-855 m1000 | FXN | human | 831 | TCCGCCCTCCAGATTA TTTTGCTTT | InaTs; omeCs; omeCs; InaGs; omeCs; omeCs; InaCs; omeUs; omeCs; InaCs; omeAs; omeGs; InaAs; omeUs; omeUs; InaAs; omeUs; InaTs; omeUs; omeGs; InaCs; omeUs; omeUs; InaT-Sup |
| FXN-856 m1000 | FXN | human | 832 | CGCCCTCCAGATTATT TTGCT | InaCs; omeGs; omeCs; InaCs; omeCs; omeUs; InaCs; omeCs; omeAs; InaGs; omeAs; omeUs; InaTs; omeAs; omeUs; omeUs; omeUs; InaGs; omeCs; InaT-Sup |
| FXN-857 m01 | FXN | human | 833 | GCCCTCCAGATTATTT TGC | InaGs; omeCs; InaCs; omeCs; InaTs; omeCs; InaCs; omeAs; InaGs; omeAs; InaTs; omeUs; InaAs; omeUs; InaTs; omeUs; InaTs; omeGs; InaC-Sup |
| FXN-858 m01 | FXN | human | 834 | CCCTCCAGATTATTTT G | InaCs; omeCs; InaCs; omeUs; InaCs; omeCs; InaAs; omeGs; InaAs; omeUs; InaTs; omeAs; InaTs; omeUs; InaTs; omeUs; InaG-Sup |

TABLE 12-continued

Oligonucleotides targeting 5' and 3' ends of FXN, APOA1, THRB, HAMP and NR1H4

| Oligo Name | Gene | Organism | SEQ ID NO. | Base Sequence | Formatted Sequence |
|---|---|---|---|---|---|
| FXN-859 m01 | FXN | human | 835 | CTCCAGATTATTTTG | InaCs; omeUs; InaCs; omeCs; InaAs; omeGs; InaAs; omeUs; InaTs; omeAs; InaTs; omeUs; InaTs; omeUs; InaG-Sup |
| FXN-461 m02 | FXN | human | 836 | CGCTCCGCCCTCCAGT TTTTATTATTTTGCTTT TT | dCs; InaGs; dCs; InaTs; dCs; InaCs; dGs; InaCs; dCs; InaCs; dTs; InaCs; dCs; InaAs; dGs; InaTs; dTs; InaTs; dTs; InaTs; dTs; InaTs; dTs; InaAs; dTs; InaTs; dTs; InaTs; dGs; InaCs; dTs; InaTs; dTs; InaTs; dT-Sup |
| Apoa1_mus-77 m1000 | APOA1 | mouse | 837 | AGTTCAAGGATCAGC CATTTTGGAAAGG | InaAs; dGs; dTs; InaTs; dCs; dAs; InaAs; dGs; dGs; InaAs; dTs; dCs; InaAs; dGs; dCs; InaCs; dAs; dTs; InaTs; dTs; dTs; InaGs; dGs; dAs; InaAs; dAs; dGs; InaG-Sup |
| Apoa1_mus-78 m1000 | APOA1 | mouse | 838 | TCAAGGATCAGCCATT TTGGAAAGG | InaTs; dCs; dAs; InaAs; dGs; InaAs; dTs; dCs; InaAs; dGs; dCs; InaCs; dAs; dTs; InaTs; dTs; dTs; InaGs; dGs; dAs; InaAs; dAs; dGs; InaG-Sup |
| Apoa1_mus-79 m1000 | APOA1 | mouse | 839 | AAGGATCAGCCATTTT GGAAAGG | InaAs; dAs; dGs; InaGs; dAs; dTs; InaCs; dAs; dGs; InaCs; dCs; dAs; InaTs; dTs; InaTs; dGs; dGs; InaAs; dAs; InaGs; InaG-Sup |
| Apoa1_mus-80 m1000 | APOA1 | mouse | 840 | GGATCAGCCATTTTG GAAAGG | InaGs; dGs; dAs; InaTs; dCs; InaAs; dGs; dCs; InaCs; dAs; dTs; dTs; InaTs; dTs; dGs; InaGs; dAs; dAs; InaAs; dGs; InaG-Sup |
| Apoa1_mus-81 m1000 | APOA1 | mouse | 841 | AGTTCAAGGATCAGC CATTTTGGAA | InaAs; dGs; dTs; InaTs; dCs; dAs; InaAs; dGs; dGs; InaAs; dTs; dCs; InaAs; dGs; dCs; InaCs; dAs; dTs; dTs; dTs; dTs; InaGs; dGs; dAs; InaA-Sup |
| Apoa1_mus-82 m1000 | APOA1 | mouse | 842 | AGTTCAAGGATCAGC CATTTTGG | InaAs; dGs; dTs; InaTs; dCs; dAs; InaAs; dGs; dGs; InaAs; dTs; dCs; InaAs; dGs; dCs; InaCs; dAs; dTs; dTs; dTs; dTs; InaGs; InaG-Sup |
| Apoa1_mus-83 m1000 | APOA1 | mouse | 843 | GTTCAAGGATCAGCC ATTTTGGAAAGG | InaGs; dTs; dTs; InaCs; dAs; dAs; InaGs; dGs; dAs; InaTs; dCs; dAs; InaGs; dCs; dCs; InaAs; dTs; dTs; InaTs; dTs; dGs; InaGs; dAs; dAs; InaAs; dGs; InaG-Sup |
| Apoa1_mus-84 m1000 | APOA1 | mouse | 844 | TCAAGGATCAGCCATT TTGGAAA | InaTs; dCs; dAs; InaAs; dGs; InaAs; dTs; dCs; InaAs; dGs; dCs; InaCs; dAs; dTs; InaTs; dTs; dTs; InaGs; dGs; dAs; InaAs; InaA-Sup |
| Apoa1_mus-85 m1000 | APOA1 | mouse | 845 | AAGGATCAGCCATTTT GGAAA | InaAs; dAs; dGs; InaGs; dAs; dTs; InaCs; dAs; dGs; InaCs; dCs; dAs; InaTs; dTs; dTs; dTs; dGs; dGs; InaAs; dAs; InaA-Sup |
| Apoa1_mus-86 m12 | APOA1 | mouse | 846 | AGGATCAGCCATTTTG GAA | InaAs; dGs; InaGs; dAs; InaTs; dCs; InaAs; dGs; dCs; dCs; InaAs; dTs; InaTs; dTs; InaTs; dGs; InaGs; dAs; InaA-Sup |
| Apoa1_mus-87 m12 | APOA1 | mouse | 847 | GGATCAGCCATTTTG GA | InaGs; dGs; InaAs; dTs; InaCs; dAs; InaGs; dCs; InaCs; dAs; InaTs; dTs; dTs; InaGs; dGs; InaA-Sup |
| Apoa1_mus-88 m1000 | APOA1 | mouse | 848 | CTCCGACAGTCTGCCA TTTTGGAAAGGT | InaCs; dTs; dCs; InaCs; dGs; InaCs; dAs; dGs; InaTs; dCs; dTs; InaGs; dCs; InaCs; dAs; InaAs; dTs; dTs; InaTs; dTs; dGs; InaGs; dAs; dAs; InaAs; dGs; dGs; InaT-Sup |
| Apoa1_mus-89 m1000 | APOA1 | mouse | 849 | CGACAGTCTGCCATTT TGGAAAGGT | InaCs; dGs; dAs; InaCs; dAs; InaTs; dCs; dTs; InaGs; dCs; dCs; InaAs; dTs; dTs; InaTs; dTs; dGs; InaGs; dAs; dAs; InaAs; dGs; dGs; InaT-Sup |

TABLE 12-continued

Oligonucleotides targeting 5' and 3' ends of FXN, APOA1, THRB, HAMP and NR1H4

| Oligo Name | Gene Organism | SEQ ID NO. | Base Sequence | Formatted Sequence |
|---|---|---|---|---|
| Apoa1_mus-90_m1000 | APOA1mouse | 850 | ACAGTCTGCCATTTTGGAAAGGT | InaAs; dCs; dAs; InaGs; dTs; dCs; InaTs; dGs; dCs; InaCs; dAs; dTs; InaTs; dTs; dTs; InaGs; dGs; dAs; InaAs; dAs; dGs; InaGs; InaT-Sup |
| Apoa1_mus-91_m1000 | APOA1mouse | 851 | CTCCGACAGTCTGCCATTTTGGAAA | InaCs; dTs; dCs; InaCs; dGs; dAs; InaCs; dAs; dGs; InaTs; dCs; dTs; InaGs; dCs; dCs; InaAs; dTs; dTs; InaTs; dTs; dGs; InaGs; dAs; dAs; InaA-Sup |
| Apoa1_mus-92_m1000 | APOA1mouse | 852 | CTCCGACAGTCTGCCATTTTGGA | InaCs; dTs; dCs; InaCs; dGs; dAs; InaCs; dAs; dGs; InaTs; dCs; dTs; InaGs; dCs; dCs; InaAs; dTs; dTs; InaTs; dTs; dGs; InaGs; InaA-Sup |
| Apoa1_mus-93_m1000 | APOA1mouse | 853 | CTCCGACAGTCTGCCATTTTG | InaCs; dTs; dCs; InaCs; dGs; dAs; InaCs; dAs; dGs; InaTs; dCs; dTs; InaGs; dCs; dCs; InaAs; dTs; dTs; InaTs; dTs; InaG-Sup |
| Apoa1_mus-94_m1000 | APOA1mouse | 854 | CTCCGACAGTCTGCCATTTTGGAAGG | InaCs; dTs; dCs; InaCs; dGs; dAs; InaCs; dAs; dGs; InaTs; dCs; dTs; InaGs; dCs; dCs; InaAs; dTs; dTs; InaTs; dTs; dGs; InaGs; dAs; dAs; InaAs; dGs; InaG-Sup |
| Apoa1_mus-95_m1000 | APOA1mouse | 855 | CCGACAGTCTGCCATTTTGGAAA | InaCs; dCs; dGs; InaAs; dCs; dAs; InaGs; dTs; dCs; InaTs; dGs; dCs; InaCs; dAs; dTs; InaTs; dTs; dTs; InaGs; dGs; dAs; InaAs; InaA-Sup |
| Apoa1_mus-96_m12 | APOA1mouse | 856 | GACAGTCTGCCATTTTGGA | InaGs; dAs; InaCs; dAs; InaGs; dTs; InaCs; dTs; InaGs; dCs; InaCs; dAs; InaTs; InaTs; dTs; InaGs; dGs; InaA-Sup |
| Apoa1_mus-97_m12 | APOA1mouse | 857 | ACAGTCTGCCATTTTGG | InaAs; dCs; InaAs; dGs; InaTs; dCs; InaTs; dGs; InaCs; dCs; InaAs; dTs; InaTs; dTs; InaTs; dGs; InaG-Sup |
| Apoa1_mus-98_m1000 | APOA1mouse | 858 | CGGAGCTCTCCGACACATTTTGGAAAGGTT | InaCs; dGs; dGs; InaAs; dGs; dCs; InaTs; dCs; dTs; InaCs; dCs; dGs; InaAs; dCs; dAs; InaCs; dAs; dTs; InaTs; dTs; dTs; InaGs; dGs; dAs; InaAs; dAs; dGs; InaGs; dTs; InaT-Sup |
| Apoa1_mus-99_m1000 | APOA1mouse | 859 | GGAGCTCTCCGACACATTTTGGAAAGGTT | InaGs; dGs; dAs; InaGs; dCs; dTs; InaCs; dTs; dCs; InaCs; dGs; dAs; InaCs; dAs; dCs; InaAs; dTs; dTs; InaTs; dTs; dGs; InaGs; dAs; dAs; InaAs; dGs; dGs; InaTs; InaT-Sup |
| Apoa1_mus-100_m1000 | APOA1mouse | 860 | AGCTCTCCGACACATTTTGGAAAGG | InaAs; dGs; dCs; InaTs; dCs; dTs; InaCs; dCs; dGs; InaAs; dCs; dAs; InaCs; dAs; dTs; InaTs; dTs; dTs; InaGs; dGs; dAs; InaAs; dAs; dGs; InaG-Sup |
| Apoa1_mus-101_m1000 | APOA1mouse | 861 | CTCTCCGACACATTTTGGAAA | InaCs; dTs; dCs; InaTs; dCs; dCs; InaGs; dAs; dCs; InaAs; dCs; dAs; InaTs; dTs; dTs; dTs; dGs; dGs; InaAs; dAs; InaA-Sup |
| Apoa1_mus-102_m12 | APOA1mouse | 862 | TCTCCGACACATTTTGGAA | InaTs; dCs; InaTs; dCs; InaCs; dGs; InaAs; dCs; InaAs; dCs; InaAs; dTs; InaTs; dTs; InaTs; dGs; dGs; dAs; InaA-Sup |
| Apoa1_mus- | APOA1mouse | 863 | CTCCGACACATTTTGGA | InaCs; dTs; dCs; InaCs; dGs; dAs; dCs; dAs; InaCs; dAs; InaTs; dTs; InaTs; dTs; InaGs; |

TABLE 12-continued

Oligonucleotides targeting 5' and 3' ends of FXN, APOA1, THRB, HAMP and NR1H4

| Oligo Name | Gene | Organism | SEQ ID NO. | Base Sequence | Formatted Sequence |
|---|---|---|---|---|---|
| 103 m12 | | | | | dGs; lnaA-Sup |
| Apoa1_mus-104 m12 | APOA1 | mouse | 864 | TCCGACACATTTTGG | lnaTs; dCs; lnaCs; dGs; lnaAs; dCs; lnaAs; dCs; lnaAs; dTs; lnaTs; dTs; lnaTs; dGs; lnaG-Sup |

TABLE 13

Other exemplary FXN oligos

| Oligo Name | Gene | Organism | SEQ ID NO. | Base Sequence | Formatted Sequence |
|---|---|---|---|---|---|
| FXN-375 | FXN | human | 865 | CGCTCCGCCCTCCAG | dCs; lnaGs; dCs; lnaTs; dCs; lnaCs; dGs; lnaCs; dCs; lnaCs; dTs; lnaCs; dCs; lnaAs; dG-Sup |
| FXN-390 | FXN | human | 866 | ATTATTTTGCTTTTT | dAs; lnaTs; dTs; lnaAs; dTs; lnaTs; dTs; lnaTs; dGs; lnaCs; dTs; lnaTs; dTs; lnaTs; dT-Sup |

TABLE 14

Oligonucleotide modifications

| Symbol | Feature Description |
|---|---|
| bio | 5' biotin |
| dAs | DNA w/3' thiophosphate |
| dCs | DNA w/3' thiophosphate |
| dGs | DNA w/3' thiophosphate |
| dTs | DNA w/3' thiophosphate |
| dG | DNA |
| enaAs | ENA w/3' thiophosphate |
| enaCs | ENA w/3' thiophosphate |
| enaGs | ENA w/3' thiophosphate |
| enaTs | ENA w/3' thiophosphate |
| fluAs | 2'-fluoro w/3' thiophosphate |
| fluCs | 2'-fluoro w/3' thiophosphate |
| fluGs | 2'-fluoro w/3' thiophosphate |
| fluUs | 2'-fluoro w/3' thiophosphate |
| lnaAs | LNA w/3' thiophosphate |
| lnaCs | LNA w/3' thiophosphate |
| lnaGs | LNA w/3' thiophosphate |
| lnaTs | LNA w/3' thiophosphate |
| omeAs | 2'-OMe w/3' thiophosphate |
| omeCs | 2'-OMe w/3' thiophosphate |
| omeGs | 2'-OMe w/3' thiophosphate |
| omeTs | 2'-OMe w/3' thiophosphate |
| lnaAs-Sup | LNA w/3' thiophosphate at 3' terminus |
| lnaCs-Sup | LNA w/3' thiophosphate at 3' terminus |
| lnaGs-Sup | LNA w/3' thiophosphate at 3' terminus |
| lnaTs-Sup | LNA w/3' thiophosphate at 3' terminus |
| lnaA-Sup | LNA w/3' OH at 3' terminus |
| lnaC-Sup | LNA w/3' OH at 3' terminus |
| lnaG-Sup | LNA w/3' OH at 3' terminus |
| lnaT-Sup | LNA w/3' OH at 3' terminus |
| omeA-Sup | 2'-OMe w/3' OH at 3' terminus |
| omeC-Sup | 2'-OMe w/3' OH at 3' terminus |
| omeG-Sup | 2'-OMe w/3' OH at 3' terminus |
| omeU-Sup | 2'-OMe w/3' OH at 3' terminus |
| dAs-Sup | DNA w/3' thiophosphate at 3' terminus |
| dCs-Sup | DNA w/3' thiophosphate at 3' terminus |
| dGs-Sup | DNA w/3' thiophosphate at 3' terminus |
| dTs-Sup | DNA w/3' thiophosphate at 3' terminus |
| dA-Sup | DNA w/3' OH at 3' terminus |
| dC-Sup | DNA w/3' OH at 3' terminus |
| dG-Sup | DNA w/3' OH at 3' terminus |
| dT-Sup | DNA w/3' OH at 3' terminus |

The suffix "Sup" in Table 14 indicates that a 3' end nucleotide may, for synthesis purposes, be conjugated to a solid support. It should be appreciated that in general when conjugated to a solid support for synthesis, the synthesized oligonucleotide is released such that the solid support is not part of the final oligonucleotide product.

Oligos targeting 3' and 5' ends of RNAs, as well as pseudocircularization oligos, can upregulate gene expression.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A formulation comprising:
a single stranded synthetic nucleic acid that is a synthetic mRNA, wherein the synthetic mRNA comprises one or more modified nucleotides;
one or more stabilizing oligonucleotides complementary with the single stranded synthetic nucleic acid; wherein the one or more stabilizing oligonucleotides are single stranded; further wherein the one or more stabilizing oligonucleotides are hybridized to the single stranded synthetic nucleic acid, and
a lipid nanoparticle, wherein the lipid nanoparticle comprises one or more cationic lipids and one or more non-cationic lipids.

2. The formulation of claim 1, wherein the lipid nanoparticle is conjugated to a targeting ligand.

3. The formulation of claim 2, wherein the targeting ligand targets a ligand receptor.

4. The formulation of claim 2, wherein the lipid nanoparticle is conjugated to a particle linker.

5. The formulation of claim 1, wherein the lipid nanoparticle comprises one or more conjugated lipids that inhibits aggregation of particles, or a combination thereof.

6. The formulation of claim 1 wherein:
(a) wherein the non-cationic lipid is an anionic lipid;
(b) wherein the non-cationic lipid is a neutral lipid; and/or
(c) the lipid nanoparticle comprises a conjugated lipid that inhibits aggregation of particles.

7. The formulation of claim 6, wherein:
(a) the anionic lipid is 1,2-dioleoyl-sn-glycero-3-phospho-(1'-rac-glycerol);
(b) the neutral lipid is 1,2-dioleoyl-sn-glycero-3-phosphatidylcholine; and/or
(c) the conjugated lipid is a PEG lipid.

8. The formulation of claim 7, wherein:
(a) the PEG lipid is a PEG-diacylglycerol (DAG), a PEG-dialkyloxypropyl (DAA), a PEG-phospholipid, a PEG-ceramide (Cer), or a mixture thereof;
(b) the PEG is a PEG-dilauryloxypropyl (C12), a PEG-dimyristyloxypropyl (C14), a PEG-dipalmityloxypropyl (C16), a PEG-distearyloxypropyl (C18), PEG-c-DOMG, PEG-DMG, or a mixture thereof;
(c) the conjugated PEG lipid is coupled to the surface of the lipid nanoparticle;
(d) the lipid nanoparticle comprises more than one cationic lipid, more than one non-cationic lipid, more than one conjugated lipid, or a combination thereof;
(e) the one or more stabilizing oligonucleotides are substantially encapsulated within an aqueous interior of the lipid nanoparticle;
(f) the lipid nanoparticle is about 50 to 150 nm in diameter;
(g) the lipid nanoparticle is about 20-50 nm in diameter; and/or
(h) the lipid to stabilizing oligonucleotide ratio (mass/mass ratio; w/w ratio) is from about 1:1 to about 50:1, from about 1:1 to about 25:1, from about 10:1 to about 14:1, from about 3:1 to about 15:1, from about 4:1 to about 10:1, from about 5:1 to about 9:1, or about 6:1 to about 9:1.

9. The formulation of claim 1, wherein;
(a) the stabilizing oligonucleotide is a modified oligonucleotide comprising a modified sugar moiety, a modified internucleoside linkage, a modified nucleotide, or a combination thereof; and/or
(b) the oligonucleotide is a mixmer or a morpholino.

10. The formulation of claim 1, wherein:
(a) the synthetic mRNA comprises a transcription start site; wherein
   (i) the one or more stabilizing oligonucleotides comprises an oligonucleotide of 8 to 50 nucleotides in length comprising a region of complementarity that is complementary with at least 5 contiguous nucleotides of the synthetic mRNA, wherein the nucleotide at the 3'-end of the region of complementarity is complementary with a nucleotide within 10 nucleotides of the transcription start site of the synthetic mRNA, wherein the oligonucleotide comprises nucleotides linked by at least one modified internucleoside linkage or at least one bridged nucleotide;
   (ii) the one or more stabilizing oligonucleotides comprises an oligonucleotide comprising two regions of complementarity each of which is complementary with at least 5 contiguous nucleotides of the synthetic mRNA, wherein the nucleotide at the 3'-end of the first region of complementarity is complementary with a nucleotide within 100 nucleotides of the transcription start site of the synthetic mRNA and wherein the second region of complementarity is complementary with a region of the synthetic mRNA that ends within 300 nucleotides of the 3'-end of the synthetic mRNA; and/or
   (iii) the one or more stabilizing oligonucleotides comprises an oligonucleotide comprising the general formula 5'-$X_1$-$X_2$-3', wherein $X_1$ comprises 5 to 20 nucleotides that have a region of complementarity that is complementary with at least 5 contiguous nucleotides of the synthetic mRNA, wherein the nucleotide at the 3'-end of the region of complementary of $X_1$ is complementary with the nucleotide at the transcription start site of the synthetic mRNA; and $X_2$ comprises 1 to 20 nucleotides; and/or
(b) wherein the synthetic mRNA has a 7-methylguanosine cap at its 5'-end.

11. The formulation of claim 10, wherein:
(a) $X_2$ comprises a region of complementarity that is complementary with at least 5 contiguous nucleotides in the 3'-UTR of the transcript;
(b) the one or more stabilizing oligonucleotides comprises an oligonucleotide of 10 to 50 nucleotides in length having a first region complementary with at least 5 consecutive nucleotides of the 5'-UTR of the synthetic mRNA, and a second region complementary with at least 5 consecutive nucleotides of the 3'-UTR, poly(A) tail, or overlapping the polyadenylation junction of the synthetic mRNA;
(c) the one or more stabilizing oligonucleotides comprises an oligonucleotide comprising the general formula 5'-$X_1$-$X_2$-3', wherein $X_1$ comprises 2 to 20 pyrimidine nucleotides that form base pairs with adenine; and $X_2$ comprises a region of complementarity that is complementary with at least 3 contiguous nucleotides of the synthetic mRNA, wherein the synthetic mRNA is polyadenylated, wherein the nucleotide at the 5'-end of the region of complementary of $X_2$ is complementary with the nucleotide of the synthetic mRNA that is immediately internal to the poly-adenylation junction of the synthetic mRNA; and/or
(d) the one or more stabilizing oligonucleotides comprises: a first oligonucleotide having 5 to 25 nucleotides linked through internucleoside linkages, and a second oligonucleotide having 5 to 25 nucleotides linked through internucleoside linkages, wherein the first oligonucleotide is complementary with at least 5 consecutive nucleotides within 100 nucleotides of the 5'-end of the synthetic mRNA and wherein the second oligonucleotide is complementary with at least 5 consecutive nucleotides within 100 nucleotides of the 3'-end of the synthetic mRNA.

12. The formulation of claim 10, wherein the first oligonucleotide and second oligonucleotide are joined by a linker that is not an oligonucleotide having a sequence complementary with the synthetic mRNA; wherein:
(a) the linker is an oligonucleotide; and/or
(b) the linker is a polypeptide.

13. The formulation of claim 1, wherein the formulation comprises a first and a second stabilizing oligonucleotide; wherein the first stabilizing oligonucleotide:
(a) comprises a region of complementarity to a 5' region of the synthetic mRNA and the second stabilizing oligonucleotide comprises a region of complementarity to a 3' region of the synthetic mRNA; and/or
(b) is covalently linked with the second stabilizing oligonucleotide through an internucleoside linkage, through an oligonucleotide, or through a linker.

14. The formulation of claim 13, wherein:
(a) the first stabilizing oligonucleotide comprises a region of complementarity that is complementary with the synthetic mRNA at a position within 10 nucleotides of the first nucleotide at the 5' end of the synthetic mRNA;
(b) the synthetic mRNA comprises a 5'-methylguanosine cap, and wherein the first stabilizing oligonucleotide comprises a region of complementarity that is complementary with the synthetic mRNA at a position within 10 nucleotides of the nucleotide immediately internal to the 5'-methylguanosine cap;
(c) the second stabilizing oligonucleotide comprises a region of complementarity that is complementary with the synthetic mRNA at a position within 250 nucleotides of the 3' end of the synthetic mRNA; and/or
(d) the synthetic mRNA comprises a 3'-poly(A) tail, and wherein the second stabilizing oligonucleotide comprises a region of complementarity that is complementary with the synthetic mRNA at a position within 100 nucleotides of the polyadenylation junction of the synthetic mRNA.

15. The formulation of claim 1, wherein the synthetic mRNA is circularized.

16. A method of delivering a synthetic mRNA to a cell, the method comprising delivering to a cell the formulation of claim 1, wherein delivery of the synthetic mRNA to the cell results in an increase in the level of gene expression of a protein encoded by the synthetic mRNA.

17. A method of treating a condition or disease associated with decreased levels of an RNA transcript in a subject, the method comprising administering a formulation of claim 1 to the subject.

18. The method of claim 17, wherein the formulation is administered via topical, oral, or parenteral administration.

* * * * *